United States Patent [19]
Demarest et al.

[11] Patent Number: 6,081,981
[45] Date of Patent: Jul. 4, 2000

[54] CONTROL SYSTEM FOR AN AUTOMATIC NEEDLE-SUTURE ASSEMBLY AND PACKAGING MACHINE

[75] Inventors: David D. Demarest, Parsippany; Robert A. Daniele, Flemington; Anthony Esteves, Somerville; Michael G. Hodulik, Dunellen; Teresa M. Shaw, Lawrenceville, all of N.J.; George Horst Reinemuth, Glen Mills; Richard Paul Branco, Collegeville, both of Pa.; Matthew Cafone, Edgewater Park, N.J.

[73] Assignee: Ethicon, Inc., Somerville, N.J.

[21] Appl. No.: 09/019,138

[22] Filed: Feb. 6, 1998

[51] Int. Cl.[7] ................................................. B23Q 17/00
[52] U.S. Cl. ................................. 29/407.08; 29/407.04; 29/407.09; 29/517; 29/712; 29/715; 29/430
[58] Field of Search .................................. 606/224, 225, 606/226; 163/1, 5; 53/118, 138.1, 244, 253, 329, 430; 83/151, 153, 950; 206/63.3, 227; 29/243.5, 243.517, 283.5, 515, 516, 517, 564.6, 705, 711, 715, 783, 785, 786, 788, 792, 793, 796, 818, 712, 407.01, 407.04, 407.05, 407.08, 407.09, 430

[56] References Cited

U.S. PATENT DOCUMENTS 5,473,810  12/1995  Demarest et al. .................... 29/712

*Primary Examiner*—David P. Bryant
*Attorney, Agent, or Firm*—Scully Scott Murphy & Presser

[57] ABSTRACT

A method for automatically forming armed surgical needles and for automatically packaging the same in a packaging tray, the automatic forming and packaging operating under control of a control computer, each armed surgical needle including a surgical needle having a suture receiving opening formed therein for attachment of a definite length suture material thereof. The method comprises the steps of sorting and depositing a plurality of needles on an indexing conveyor; enabling a robot gripper device to sequentially pick up the needles and place a picked needle in a precision conveyor device for automatic sequential conveyance to a first station; utilizing a first indexing device for sequentially indexing the needle from the first station to a second station to form the armed needle, the first indexing device being elevated in height; at the second station, automatically inserting a free end of a suture strand into the suture receiving opening of the needle, swaging the needle about the free end of the suture, and cutting the suture strand to a predetermined definite length to form the armed needle. The formed armed needle is then sequentially inserted into a respective single package tray indexed at a subsequent station that has been oriented in height with respect to the first indexing device in accordance with the size of the needle. At a further subsequent station the tray and parked armed needle therein is subject to at least one rapid winding operation to wind the suture around a peripheral channel of the tray.

57 Claims, 108 Drawing Sheets

| 881 | Pulling Forces | |
|---|---|---|
| | Pulling Forces used in the Two Pull Test | Pulling Forces used in the Five Pull Test |
| 887 | 883 | 885 |

FIG.6(u)

16.5 Degree Turn Station

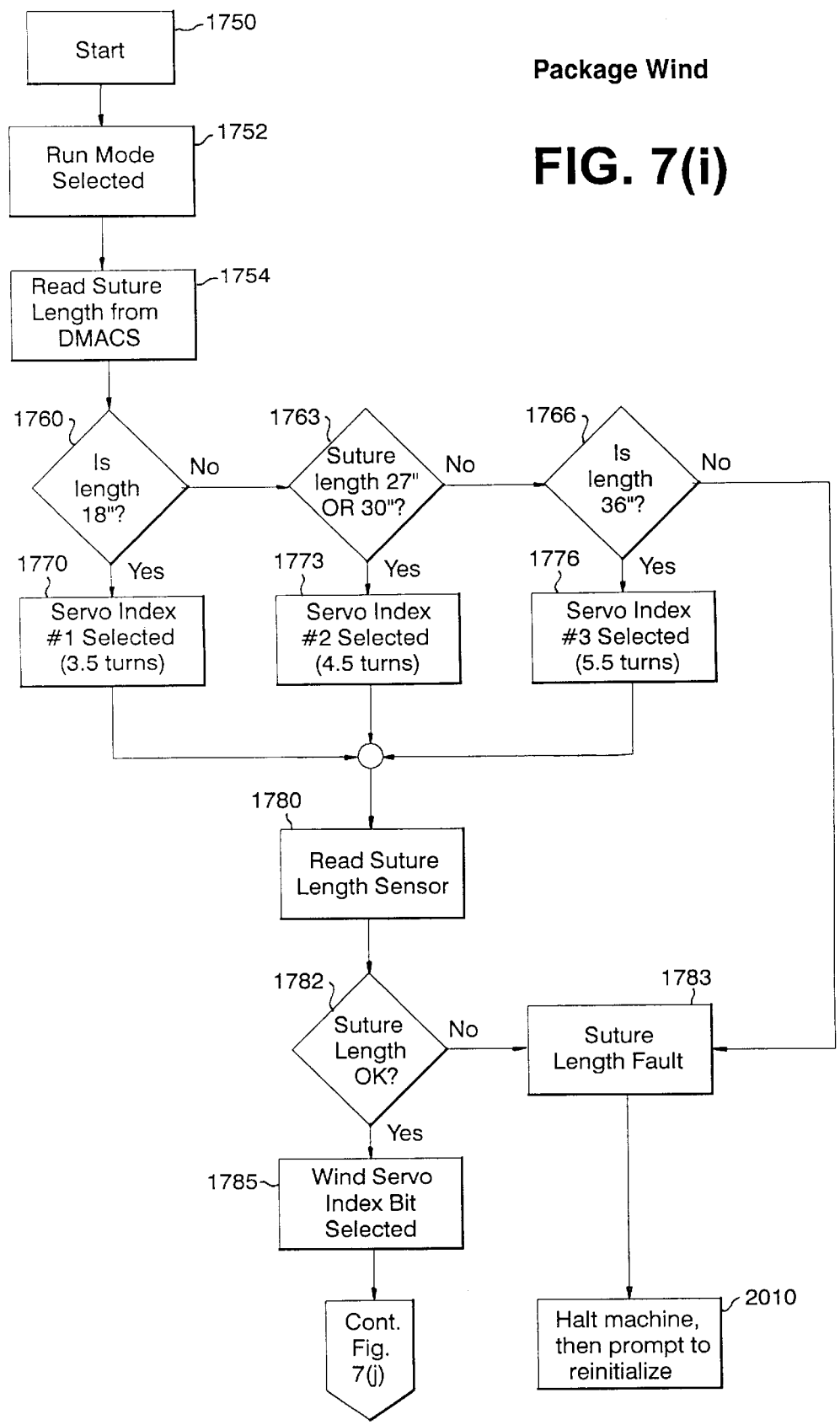
FIG. 7(i) Package Wind

Package Wind (continued)

Package Wind (continued)

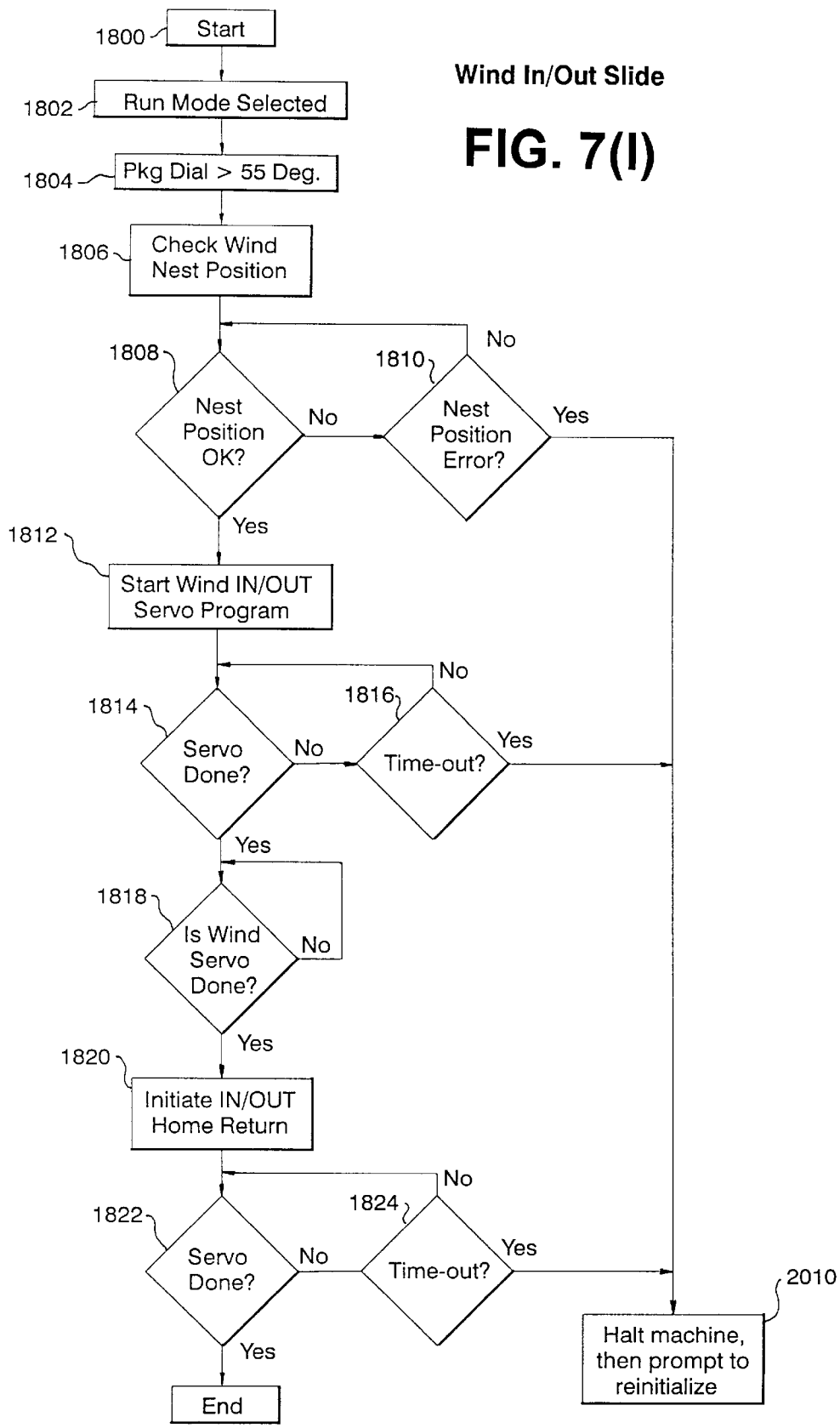

Package Unload (continued)

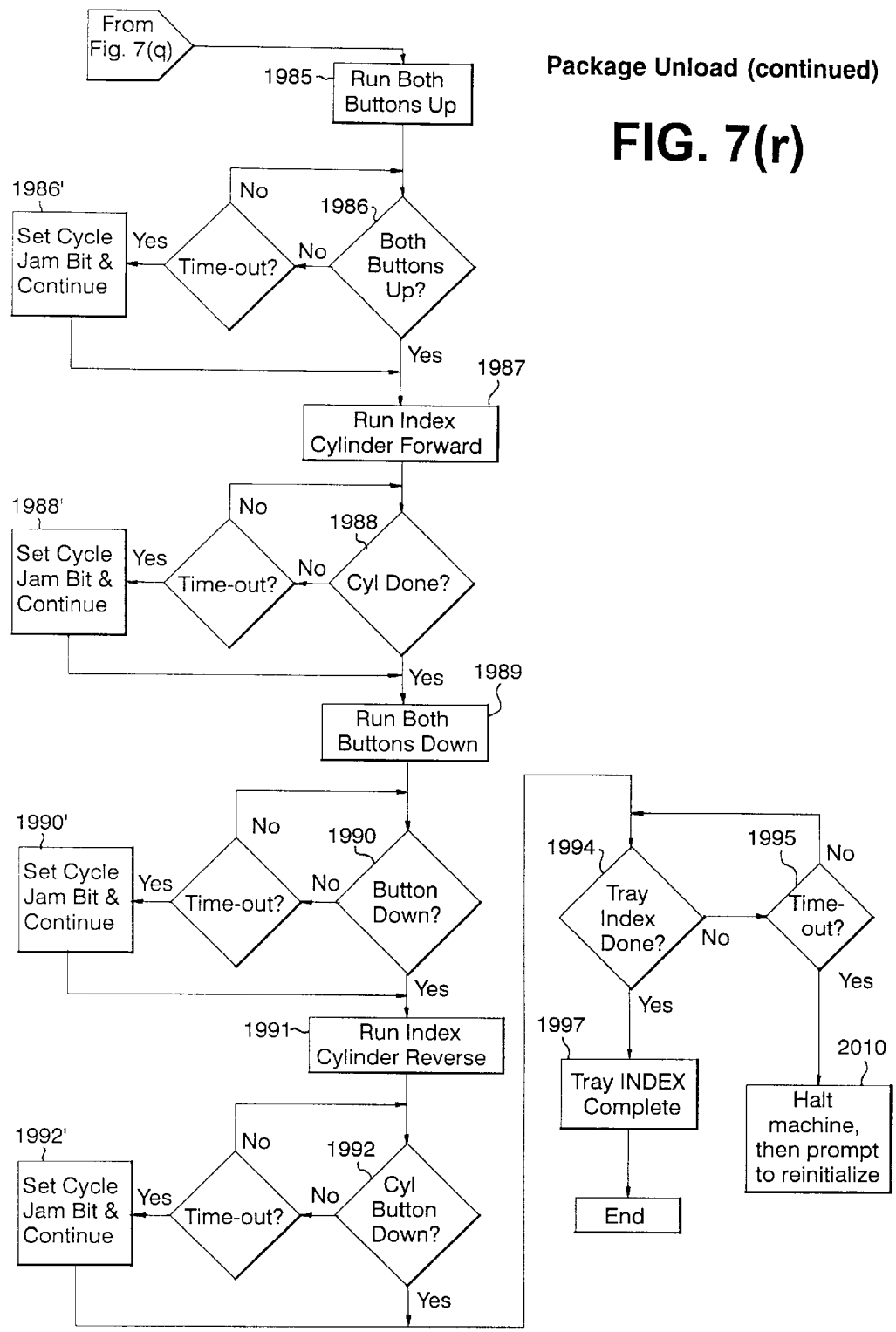
FIG. 7(r) Package Unload (continued)

Package Unload (continued)

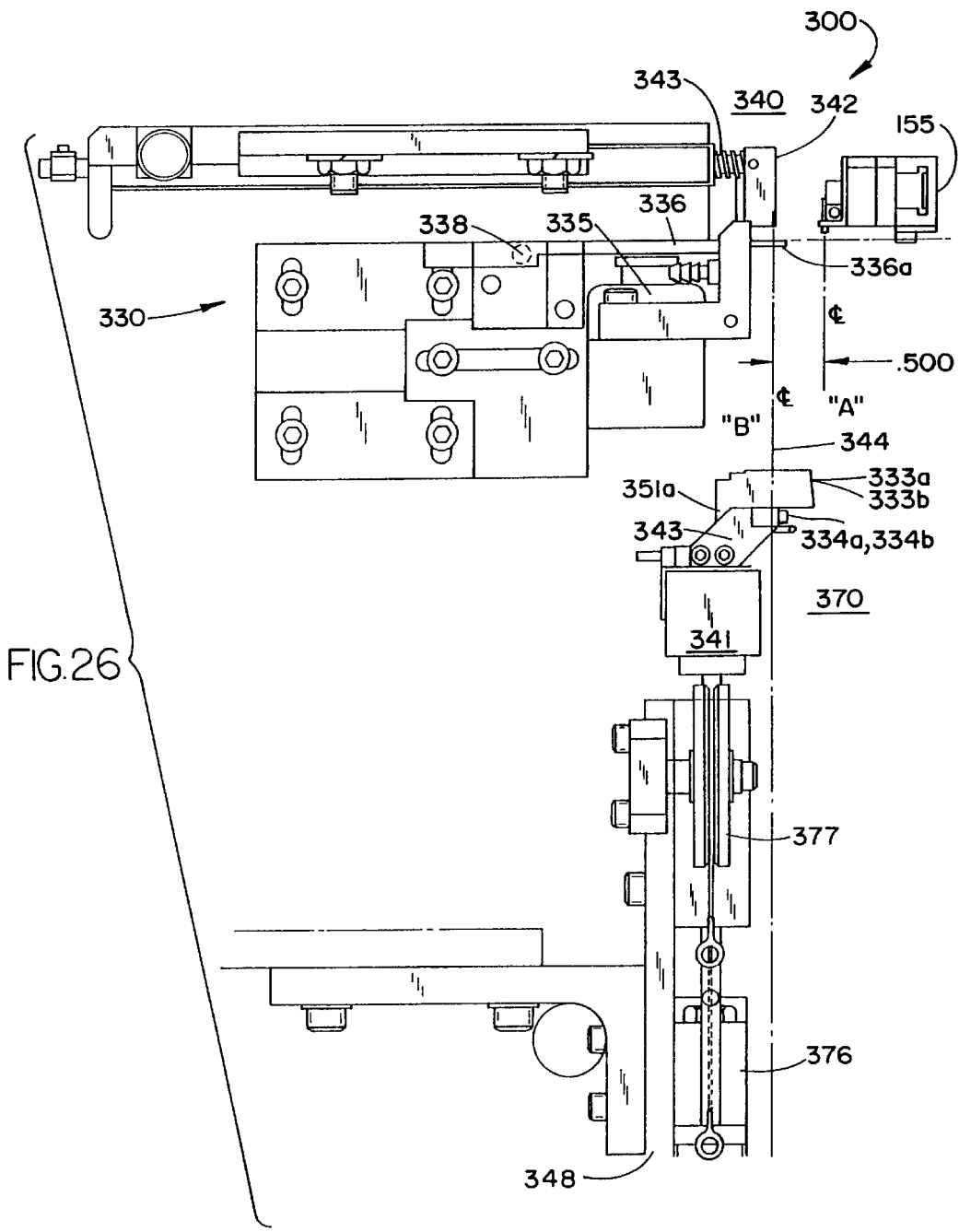

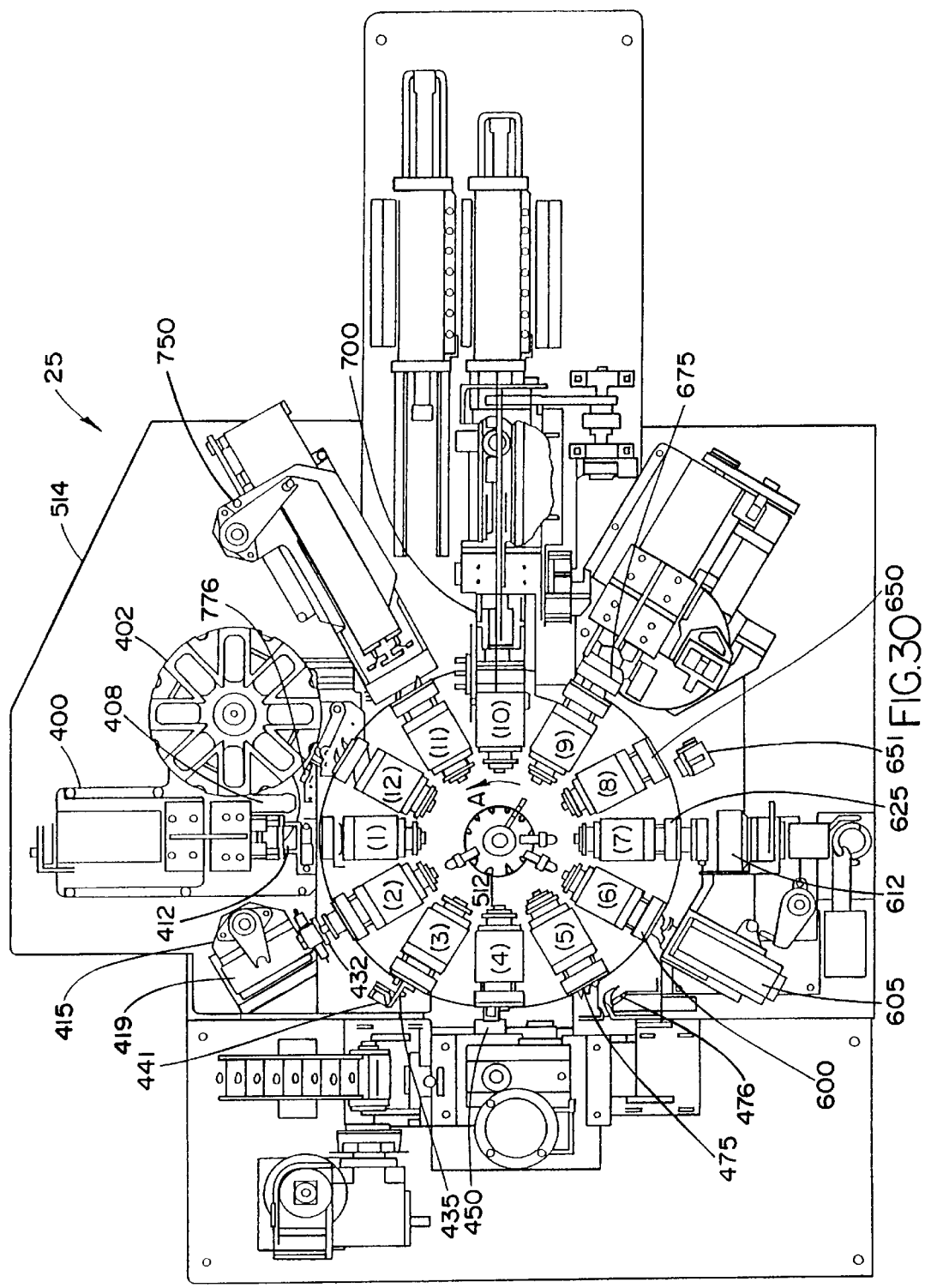

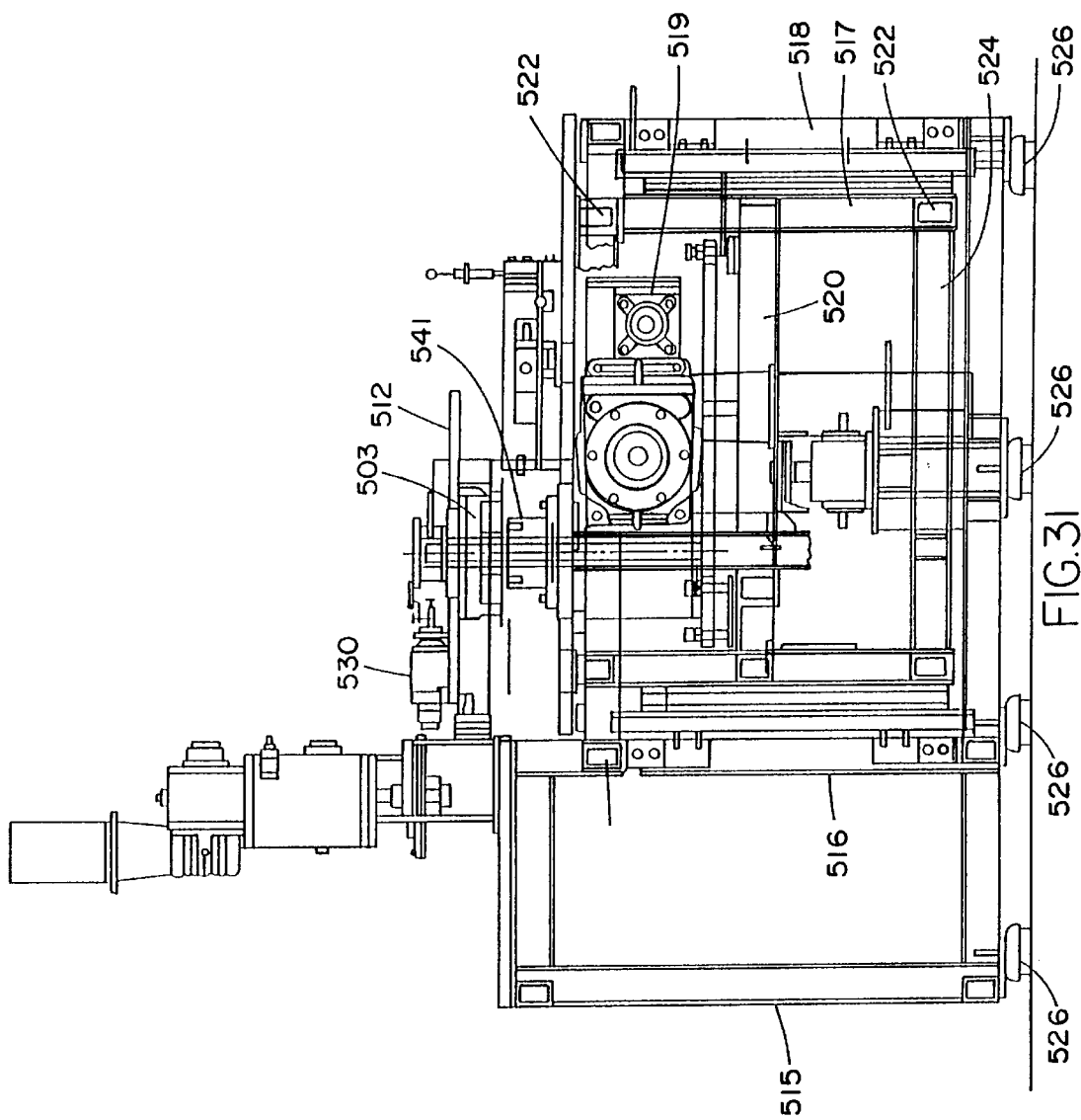

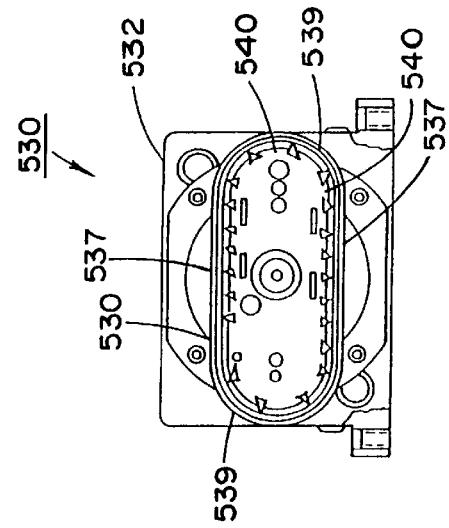
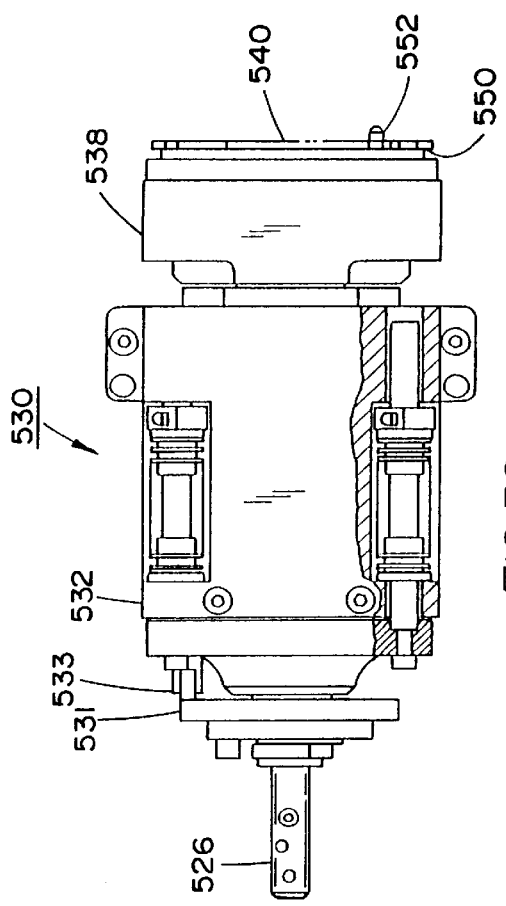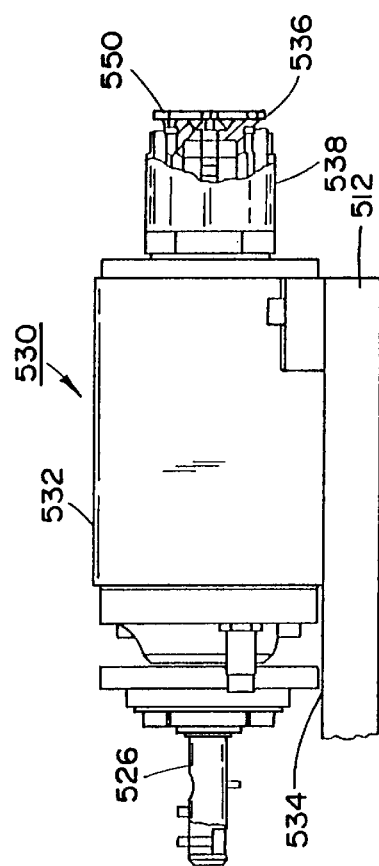

Initialize Or Re-Initialize (continued)

ific improvements to the
CONTROL SYSTEM FOR AN AUTOMATIC NEEDLE-SUTURE ASSEMBLY AND PACKAGING MACHINE

FIELD OF THE INVENTION

The present invention relates generally to machines for automatically producing armed surgical needles, i.e., needles having a suture strand of predetermined length attached at one end thereof, and automatically packaging the same, and more specifically, to a control system for controlling the processes involved in the automatic production, testing, and packaging of armed surgical needles.

DESCRIPTION OF THE PRIOR ART

This application describes in detail imporvements to the apparatus disclosed in a series of U.S. Patents, of which U.S. Pat. No. 5,487,216 entitled "Control System for an Automatic Needle-Suture Assembly and Packaging Machine"; and U.S. Pat. No. 5,473,810 entitled "Needle-Suture Assembly and Packaging System" are typical. All of these patents are assigned to the assignee of the present invention and incorporated by reference herein.

The automatic needle and suture threading machine described in the above referenced U.S. Patents is a highly automated machine intended for high volume production and packaging of needles and sutures wherein 20,000 to 40,000 needles and sutures are to be produced in a single run.

SUMMARY OF THE INVENTION

The present application describes a control system for an improved high-speed, automatic needle-suture assembly and packaging system.

It is another object of the instant invention to provide a control system for a cost-effective automatic needle threading and swaging system and automatic packaging system that virtually eliminates operator exposure to any repetitive manual operations.

It is still another object of the instant invention to provide a control system for an automatic needle-suture assembly and packaging system that incorporates a rotatable swage dial having a plurality of multi-axis grippers that automatically grip surgical needles for indexing to a plurality of processing stations that include: a loading station for transferring individual precisely oriented surgical needles from a precision conveyor to successively indexed multi-axis grippers; a swaging station that automatically draws an indefinite length strand of suture material, cuts the strand, inserts the free end of the definite length strand within the suture receiving end of the needle, and swages the suture strand to the surgical needle; a pull-test station that automatically performs minimum and n-count destructive pull-testing of the needle-suture combination; and finally, a needle-suture load to package station where armed, pull-tested needles are transferred to the automatic packaging station for packaging thereof.

Yet another object of the present invention is to provide a control system for an automatic needle-suture assembly and packaging system that incorporates a rotatable suture winding and packaging dial for automatically packaging armed surgical needles through several processing stations including: a package load station for loading an empty package tray onto a supporting structure of the tool nest; a package detect station for detecting the presence of an empty package tray; a needle-suture load to package station where an armed needle is transferred to the package from the multi-axis gripper; a needle check station where the presence or absence of an armed needle is checked; a winding station where the suture that depends from the surgical needle is wound around a peripheral channel located about the periphery of the package tray; a cover loading station where a cover is applied to the package; and finally, a package removal station where the completed package is removed from the machine, or rejected if the package is flawed.

Yet still another object of the present invention is to provide a control system for a needle threading and swaging system that can provide continuous on-line tool adjustments without unnecessary interruptions.

These and other objects of the present invention are attained with a method for automatically forming armed surgical needles and for automatically packaging the same in a packaging tray under control of a control computer, each armed surgical needle comprising a surgical needle having a suture receiving opening formed in a barrel end of the needle for semi-permanent attachment of a definite length suture material thereof at a needle-suture assembly machine, the method comprising the steps of: singulating a plurality of needles and depositing them on an indexing conveyor in random un-oriented positions; determining an acceptable needle location for picking up the needle, the acceptable needle location including location of a barrel end of the needle; enabling a robot gripper means to sequentially pick up the needles at the barrel end and place a picked needle in a precision conveyor device for automatic sequential conveyance to a first station, the needle being conveyed in an oriented position; utilizing a first indexing device for sequentially indexing the needle in the oriented position from the first station to a second station to form the armed needle, the first indexing device being elevated in height for movement along a first horizontal axis; at the second station, automatically inserting a free end of an indefinite length suture strand into the suture receiving opening of the needle, swaging the needle about the free end of the suture, and cutting the indefinite length suture strand to a predetermined definite length to form the armed needle; indexing the first indexing device to a subsequent station and sequentially inserting a single formed armed needle from the second station to a respective single packaging tray at said subsequent station; and, prior to inserting the armed needle in the packaging tray, the step of utilizing a second indexing device for sequentially indexing a single packaging tray at the third location for receiving a respective single armed needle, an elevation of the second indexing device being adjusted relative to the first horizontal axis so as to accommodate the transferring of differently sized surgical needles into the tray without substantially modifying any components of the machine.

Further benefits and advantages of the invention will become apparent from a consideration of the following detailed description given with reference to the accompanying drawings, which specify and show preferred embodiments of the invention.

BRIEF DESCRIPTION OF THE DRAWINGS

FIG. 12(b) is a detailed elevation view of the precision conveyor boat taken along line 12b—12b of the boat illustrated in FIG. 12a;

FIG. 26 is a diagrammatic side elevation view of the pull test apparatus of the present invention illustrating a load-cell assembly, the gripper assembly and a pull test assembly, and their relationship to the multi-axis gripper;

FIG. 30 illustrates generally diagrammatically, a plan view of the automated packaging station 25 for the automated packaging of individual surgical needles and attached sutures, pursuant to the present invention;

FIG. 31 illustrates a side elevational view of the machine frame of FIG. 30;

FIGS. 32, 33 and 34 illustrate, respectively, partially-sectional side and top plan views and a front end view of a tool nest utilized in the machine of FIG. 30;

DETAILED DESCRIPTION OF THE PREFERRED EMBODIMENT

Figure 1:
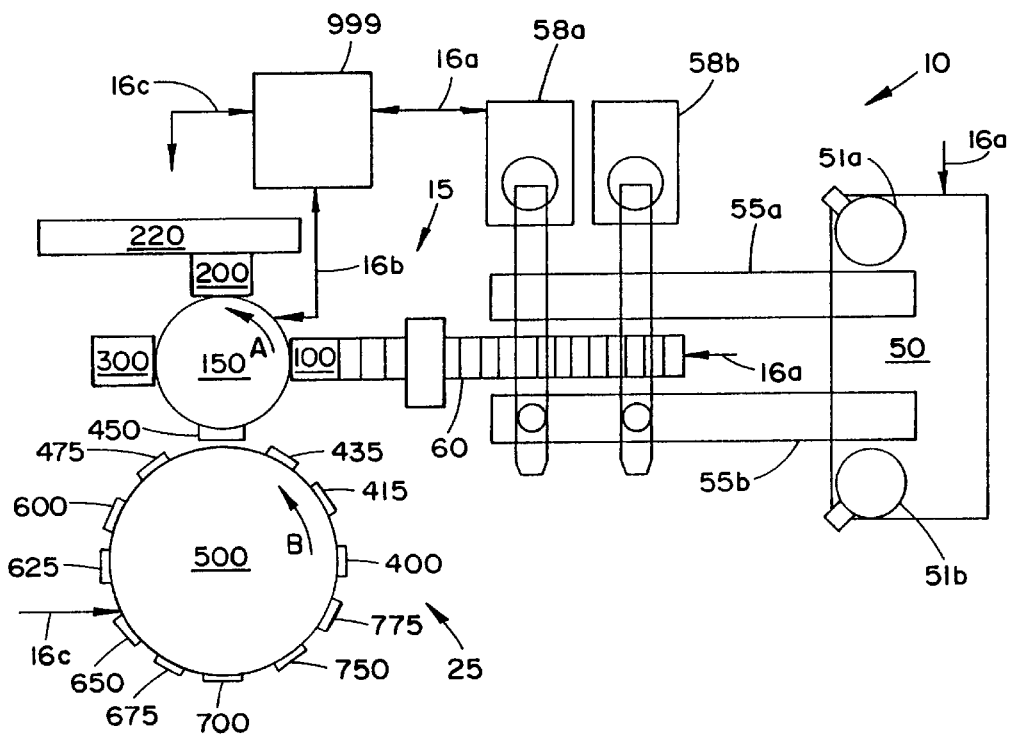
FIG. 1 is a conceptual top view of the needle threading and swaging machine and automatic packaging machine 10 operable under the control system of the instant invention.
Figure 8:
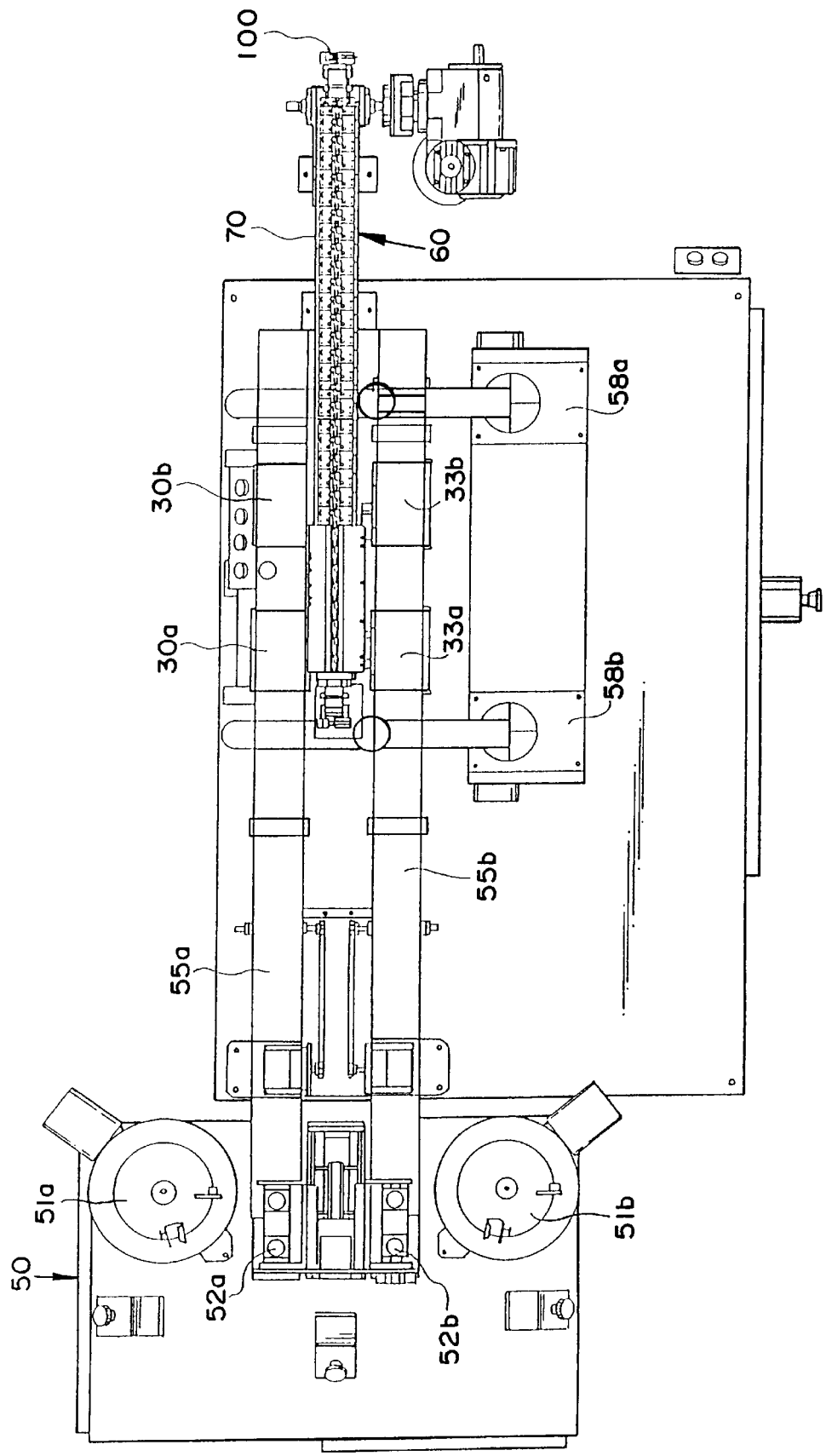
FIG. 8 is a top plan view of the needle infeed and singulation portion of the automatic needle suture-assembly machine controlled by the control system of the present invention.

Generally, FIGS. 1 and 8 illustrate respectively, a conceptual and detailed plan views of a machine 10 comprising an automatic surgical needle sorting/singulating and feeding apparatus 50, a needle-suture swaging and assembly apparatus 15, and an automatic needle-suture packaging machine 25. The combined machine 10 performs needle-suture assembly and needle-suture packaging operations under control of the control system of the invention implemented by control system computer 999. The needle-suture swaging and packaging machines are highly automated machines intended for high volume production and packaging of surgical needles and sutures as described in detail in co-pending U.S. patent application Ser. No. 09/020,085 and describes improvements to the needle suture assembly and packaging system disclosed in U.S. Pat. No. 5,473,810 and entitled "Needle-Suture Assembly and Packaging System" assigned to the assignee of the present invention. Correspondingly, the control system for the automatic needle-suture assembly and packaging machine of the invention is an improvement of the automatic needle-suture assembly and packaging machine control system described in U.S. Pat. No. 5,487,216 entitled "Control System for an Automatic Needle-Suture Assembly and Packaging Machine."

Figure 2:
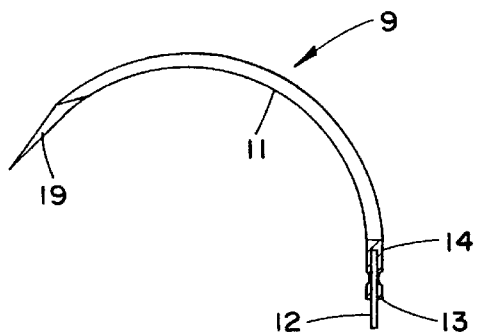
FIG. 2 is a detailed illustration of a typical surgical needle 9 having an arcuate portion 11 and suture receiving end 12.

Particularly, as described in the automatic needle threading and swaging system of co-pending U.S. patent application Ser. No. 09/020,085, parallel operations take place simultaneously at a plurality of different stations to ensure that approximately sixty (60) armed surgical needles are assembled and discharged for packaging per minute. As shown in FIGS. 1 and 8, an automated needle sorting and singulating station 50 assists in the sorting and singulating of individual surgical needles to a pair of translucent indexing conveyors 55a,b where the singulated needles are imaged by a vision system, selected by a computer, and transferred to a precision indexing conveyor 60 by robotic grippers of robot assemblies 58a and 58b. The precision indexing conveyor conveys precisely oriented surgical needles to a precise positioning station 100 to be sequentially received by a plurality of multi-axis grippers mounted on the rotary swage dial 150. The rotary swage dial 150 then rotates counter-clockwise as shown by the arrow in FIG. 1, to index each needle to the automatic swaging station 200 where the suture material is cut, inserted into the needle, and automatically swaged thereto. Particularly, the suture drawing and cutting tower 220 draws indefinite length of suture, tips, cuts and inserts the suture into the needle to be swaged. The needle is swaged at station 200 and then, the rotary swage dial 150 rotates to index the armed suture to the automatic pull-test station 300 where each armed needle is pull-tested to ensure that the minimum and/or destructive pull-test requirements of the medical profession, are met. As illustrated in FIG. 2, an armed needle 9 includes an arcuate blade portion 19 and a barrel portion 11 with an attached suture 12 which has been attached by swaging as indicated at 14 at the suture receiving end (or butt end) 13 of the needle 9. The suture 12 may be of any predefined length, but is commonly provided in lengths that are multiples of nine inches (18, 27 and 36 inch suture sizes are particularly common). Finally, the rotary swage dial 150 indexes the pull-tested armed needle to a needle-suture load to package station 450 where the armed surgical needles are handed-off to a package tray of unique construction at a suture winding and packaging dial 500 for automatic packaging thereof.

As described in the commonly assigned U.S. patent application Ser. No. 09/020,084 the contents and disclosure of which is incorporated by reference herein, the automatic packaging apparatus 25 shown in FIGS. 1 and 8 includes twelve (12) workstations located about the periphery of a forwardly indexing rotary suture wind and packaging dial 500 that are successively utilized to form a complete package of one or more armed surgical needles. As will be described, the automatic packaging apparatus 25 includes: a package load station 425 for successively feeding an empty package onto a support plate of a tool nest mounted on the suture wind packaging dial; a 16.5° turn workstation 435 for imparting angular movement to the tool nest portion having the tray supported thereon, to orient the tray for approximately 16.5° relative to the horizontal plane of rotation of a rotary turret to enable a subsequent "parking" of an armed surgical needle therein, at a further workstation; an optional package detect station 447 for checking the presence of the loaded empty package; the needle-suture to package load station 450 whereby the surgical needle with its attached suture is handed-off for retentive engagement with needle-engaging structure formed in the aligned tray so as to grip and park the needle therein, with the suture extending from the needle and depending downwardly therefrom outwardly of the tray; an optional needle check station 475 for detecting missing needles; a first suture winding station 600 containing structure operatively cooperating with the needle and suture-containing tray and the tool nest supporting the tray imparts an initial rotational movement to the tray about an axis perpendicular to the plane of the tray while maintaining the depending suture under tension; a second subsequent winding station 650 for imparting a rapid winding motion to the tray over multiple predetermined rotations so as to fully wind the downwardly depending suture into a peripheral tray channel extending within the perimeter of the tray; a workstation 700 containing a mechanism for separating a bottommost cover from a stack of covers and transferring the sliced cover to a rotatable platform whereby the cover is engaged by a robotically-controlled pivot arm which, under the action of a vacuum, pivots the cover into a vertical orientation and applies the cover onto the tray while concurrently imparting pressure to the cover to cause cooperating latching structure to clampingly fasten the cover to the needle and suture-containing tray; and, a package removal station 750 at which suitable vacuum grippers on a pivot arm mechanism engages the suture package, and the suture package is disengaged from the tool nest on which it is supported and transferred to and stacked in repository or receiving trays to be readied for further processing, such as sterilizing, overwrapping or the like, as may be required, or, if the package has been found defective during inspection, is scrapped.

Unlike the previous machines which packaged eight needles into a package in approximately eight seconds, the present needle-suture swaging machine has been improved to account for the higher packaging speeds. Thus, in order to provide for high production rates which are essentially compatible with those employed in the manufacture of suture packages each containing a plurality of armed sutures, the present invention contemplates the provision of a fully automated machine with a considerably increased rate of operating speed and production capability so as to render the machines economically viable in comparison with the previously described automated machines, while maintaining structural and functional reliability and ease of construction and maintenance.

Figure 5:
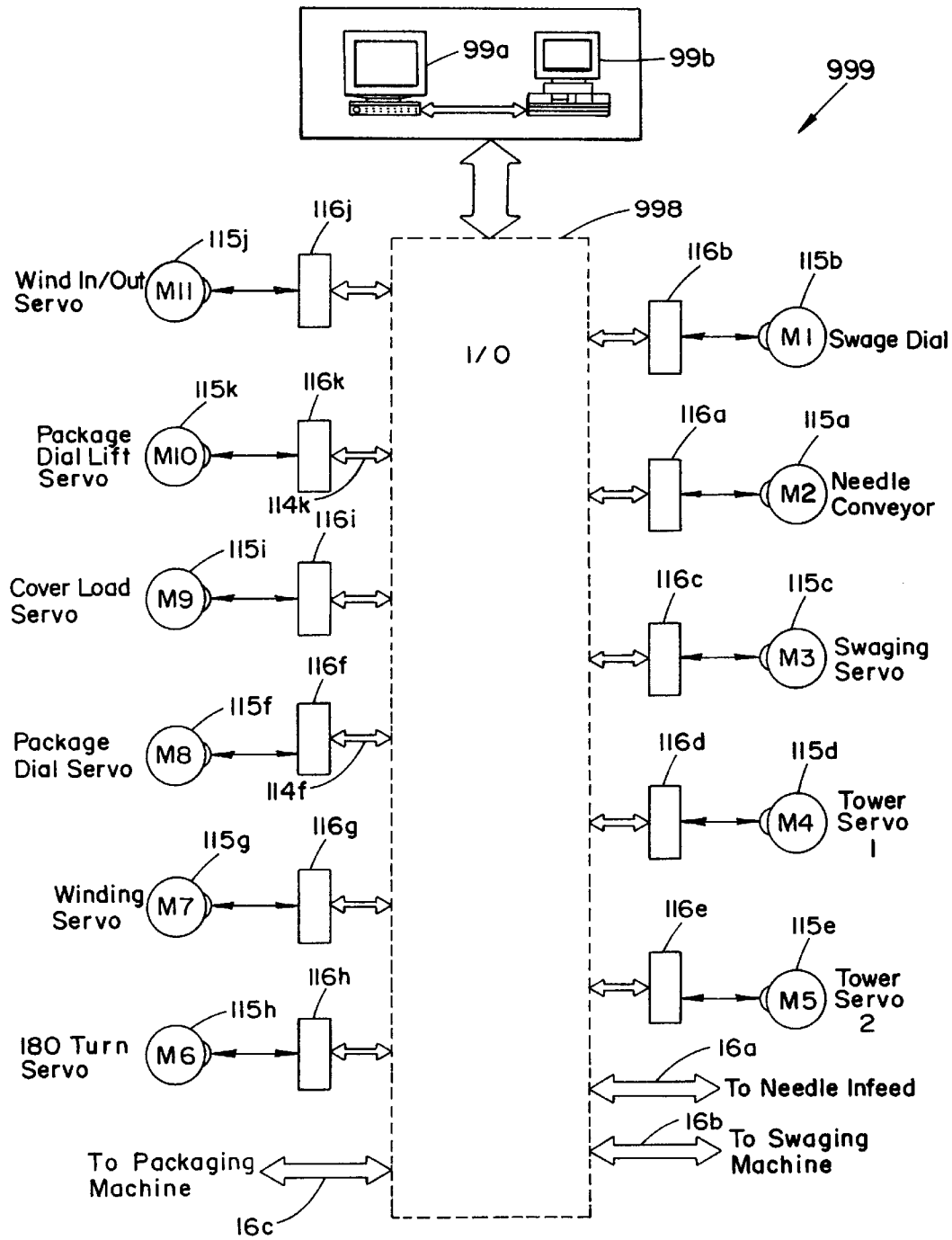
FIG. 5 is an illustration of the control computer 999 implementing control system 1000 of the invention and comprising an input/output means interfaced with first and second computers 99a, 99b, and a variety of servo drive motors and corresponding controls.
Figure 52A:
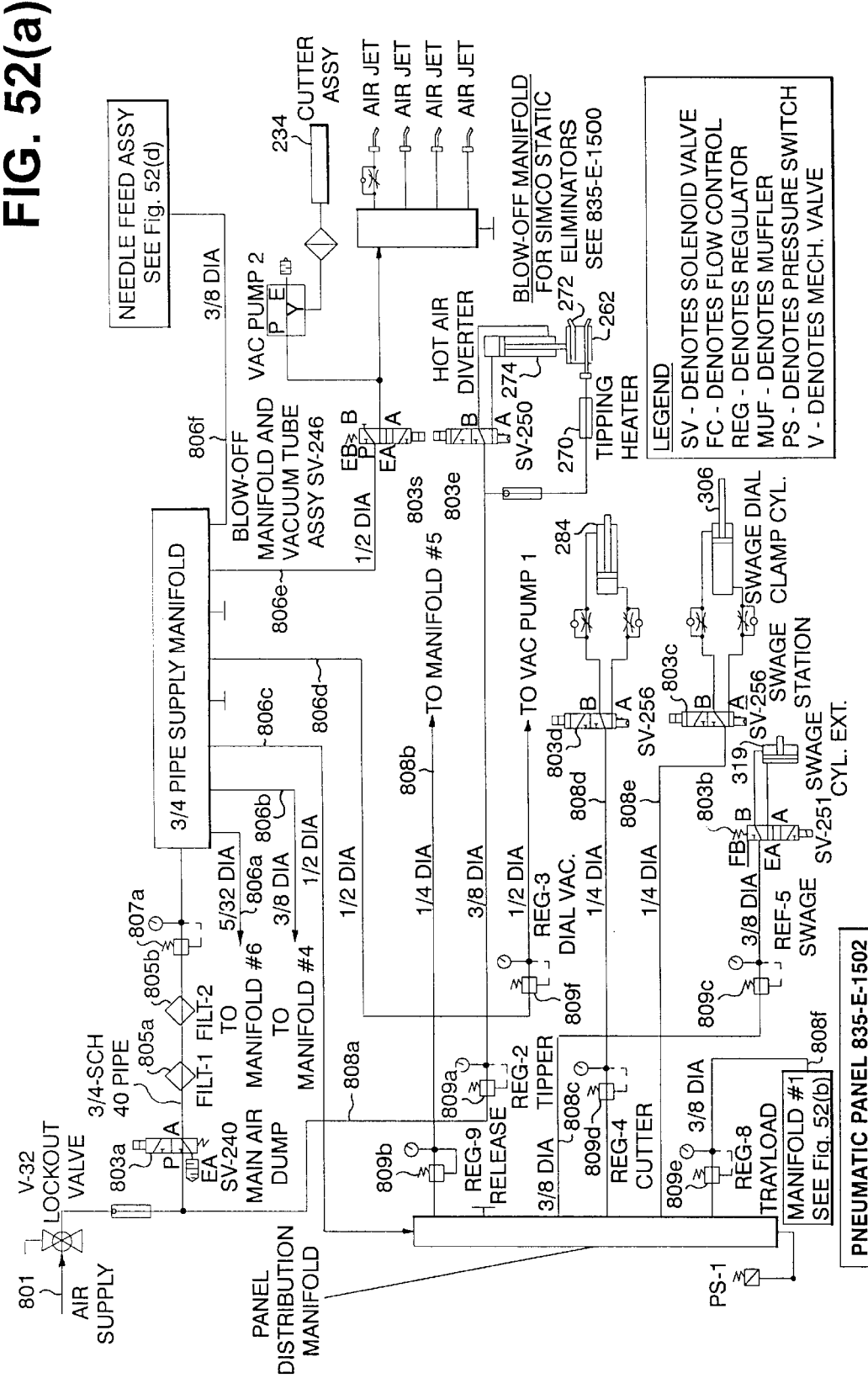
FIGS. 52(a)–52(e) illustrate the pneumatic control circuitry of the needle-suture assembly and suture wind and packaging systems as controlled by the control system of the present invention.
Figure 52B:
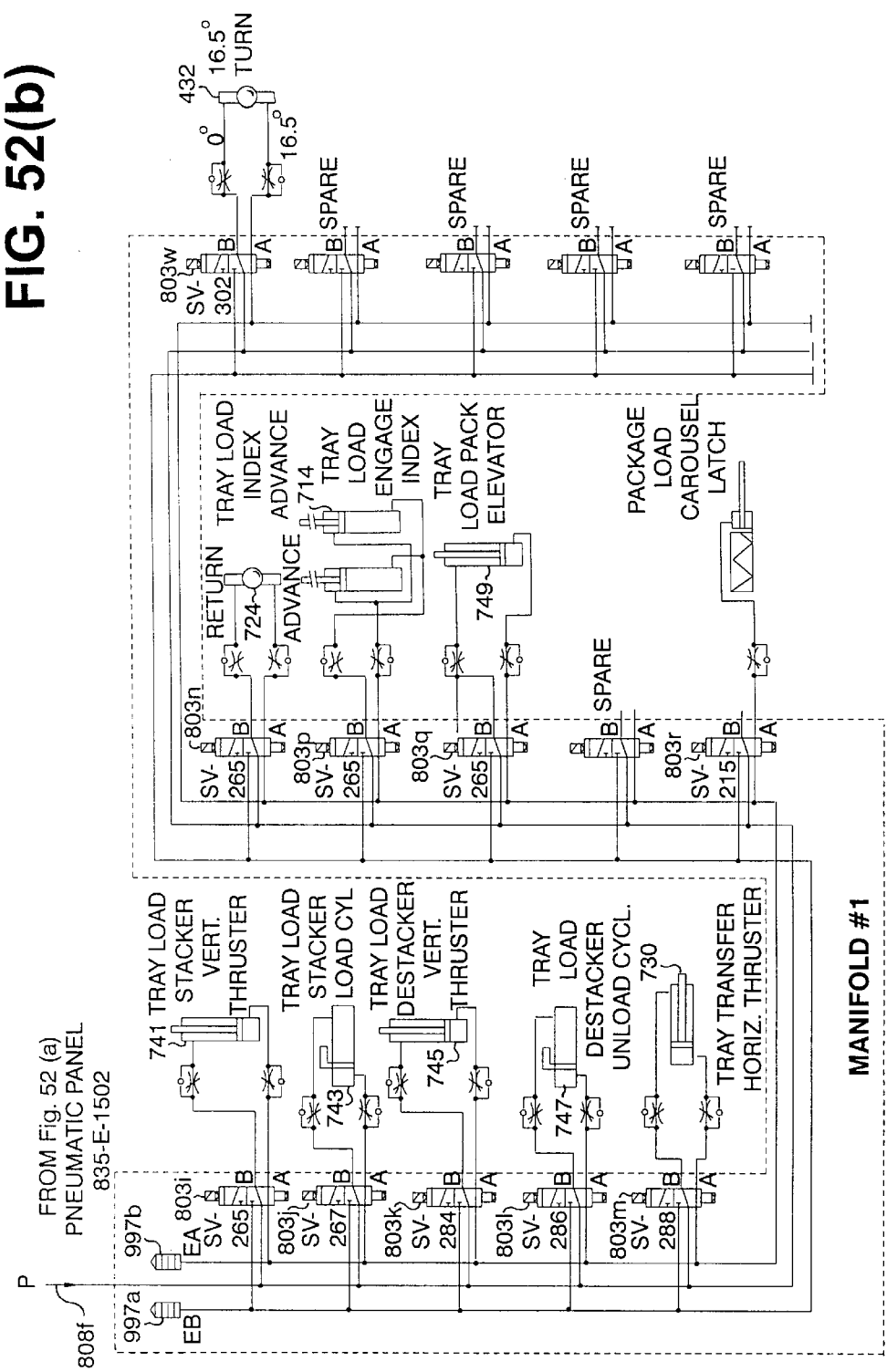
Figure 52C:
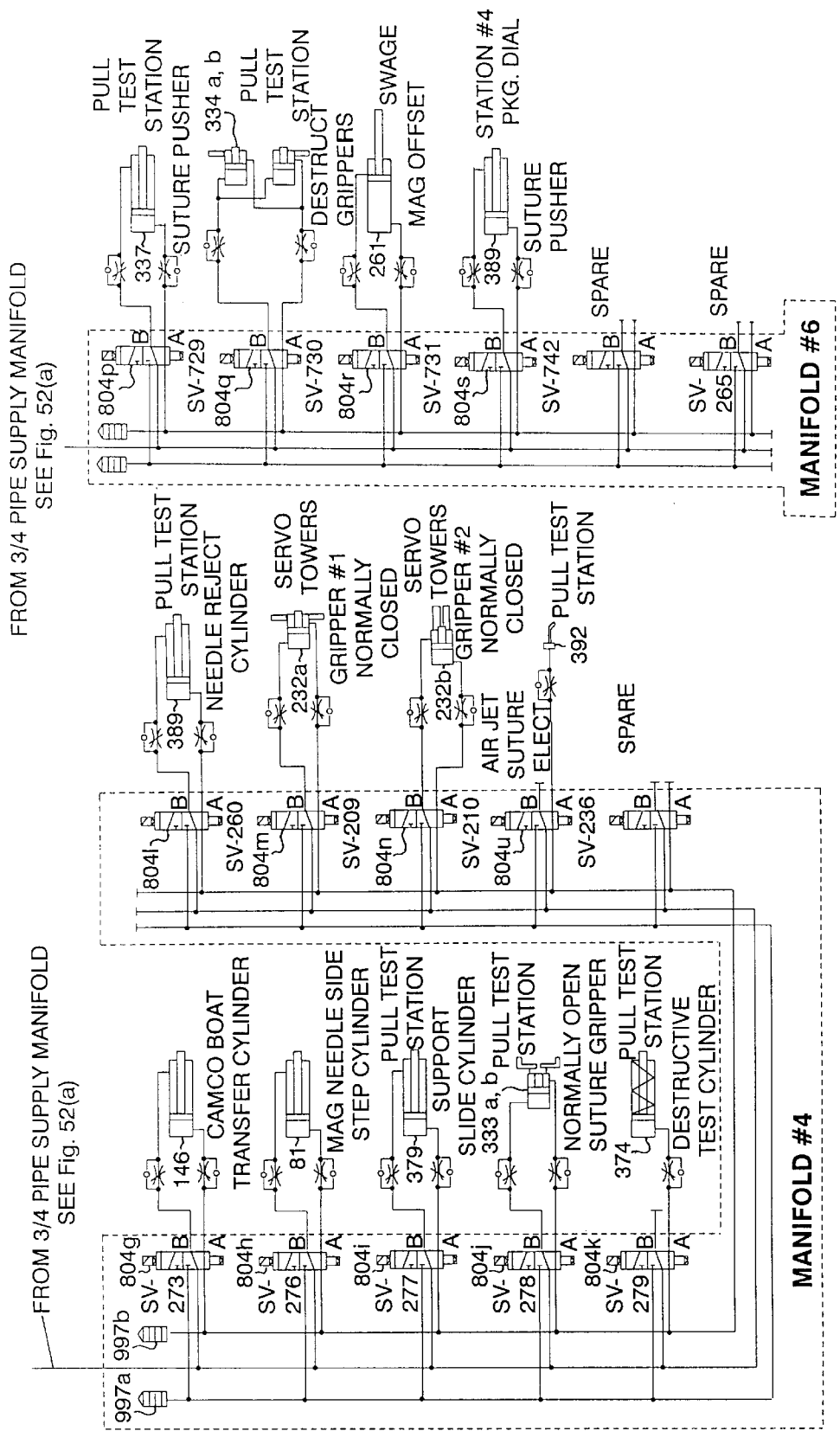
Figure 52D:
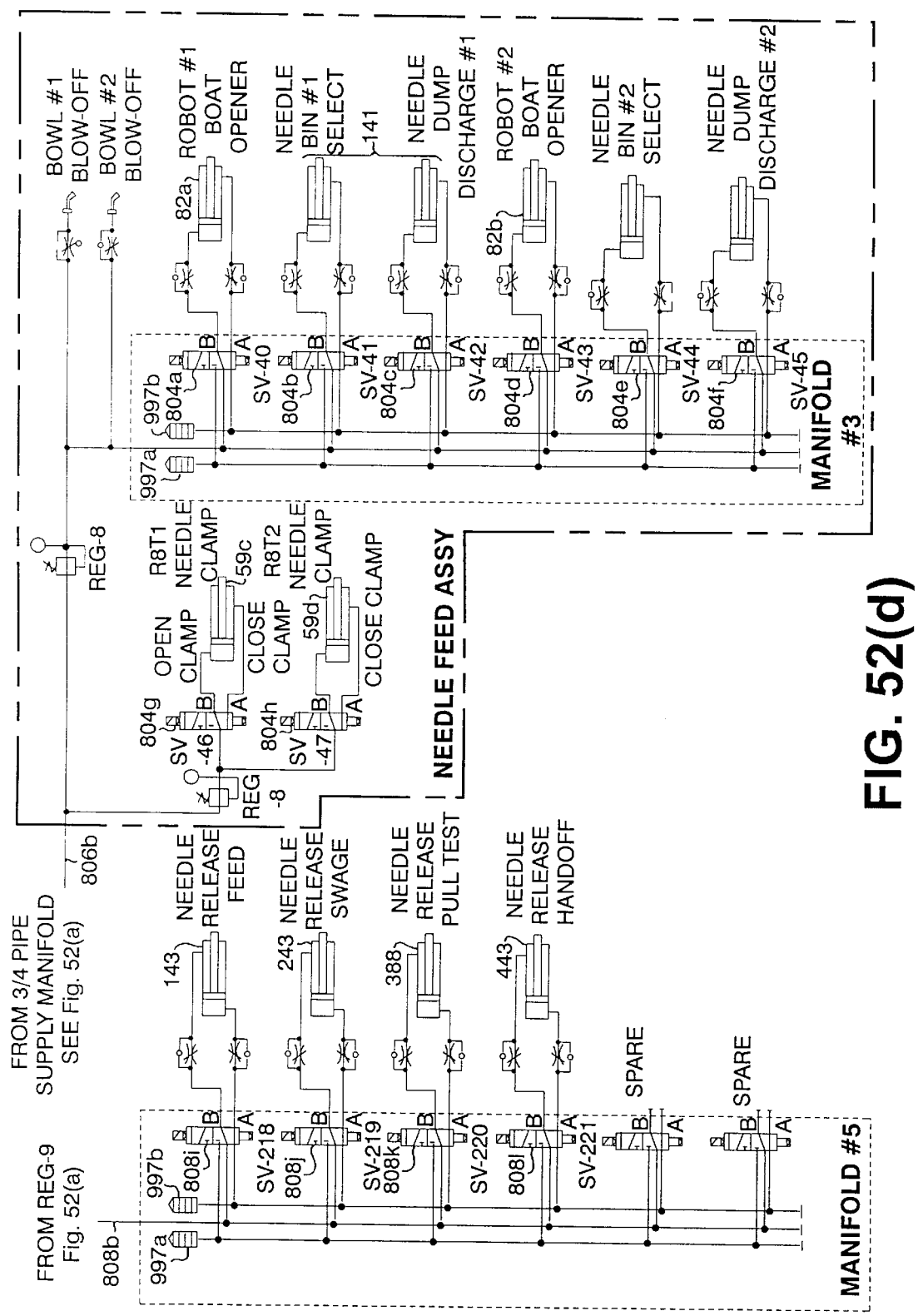
Figure 52:
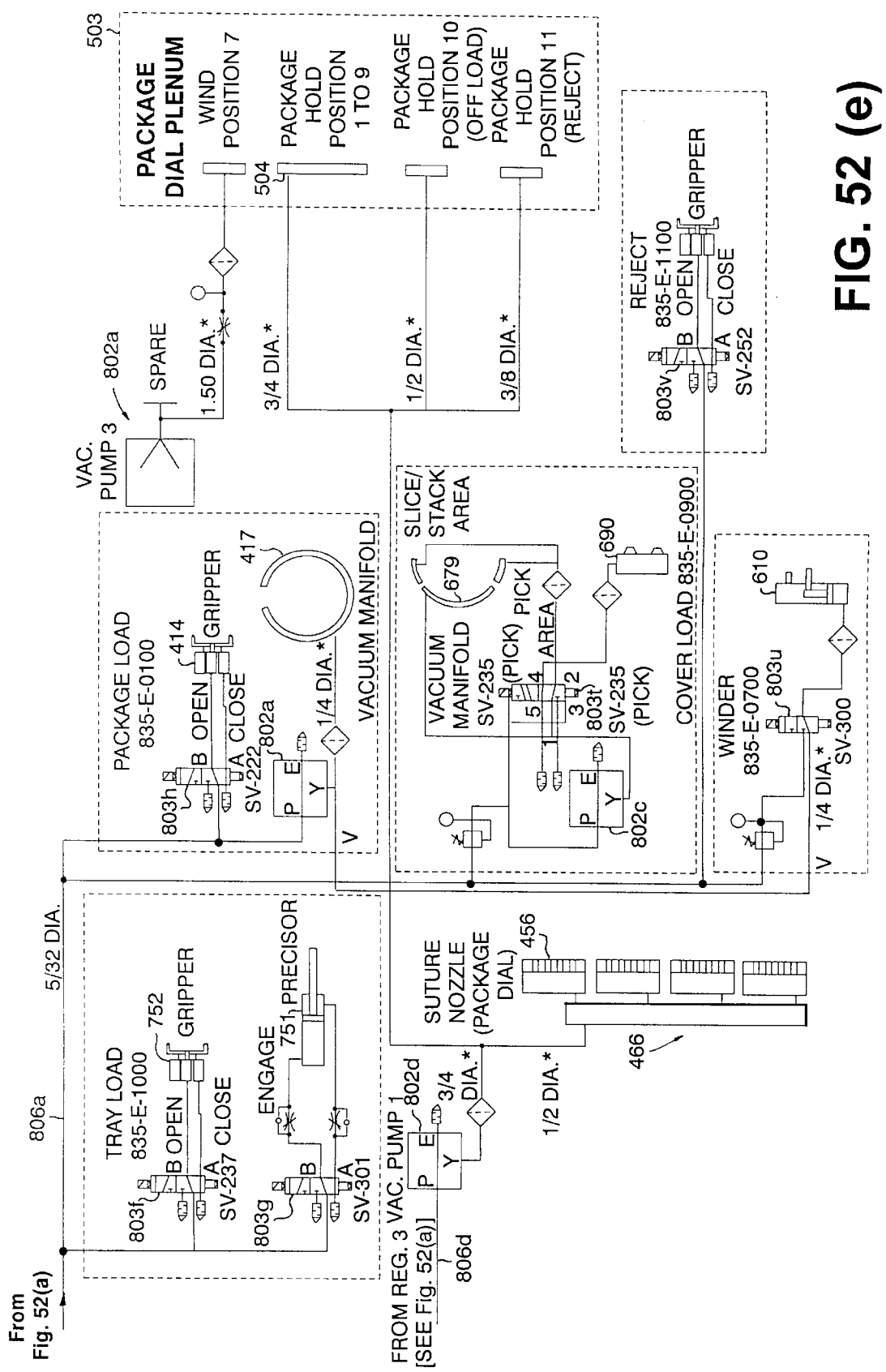
Figure 53A:
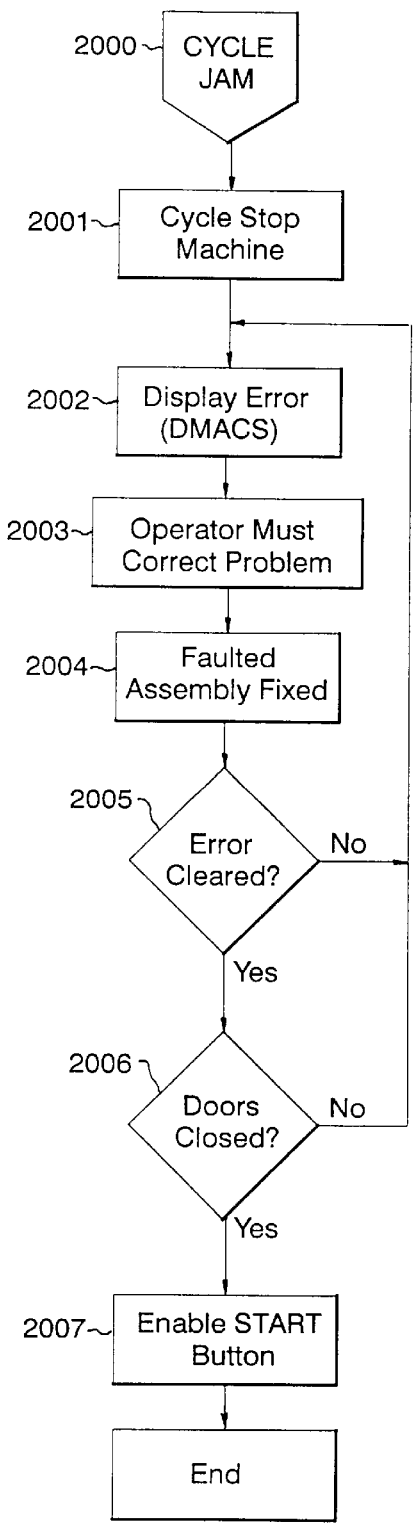
FIGS. 53(a)–53(i) illustrate the initialization or re-initialization routines utilized in the present invention.
Figure 53B:
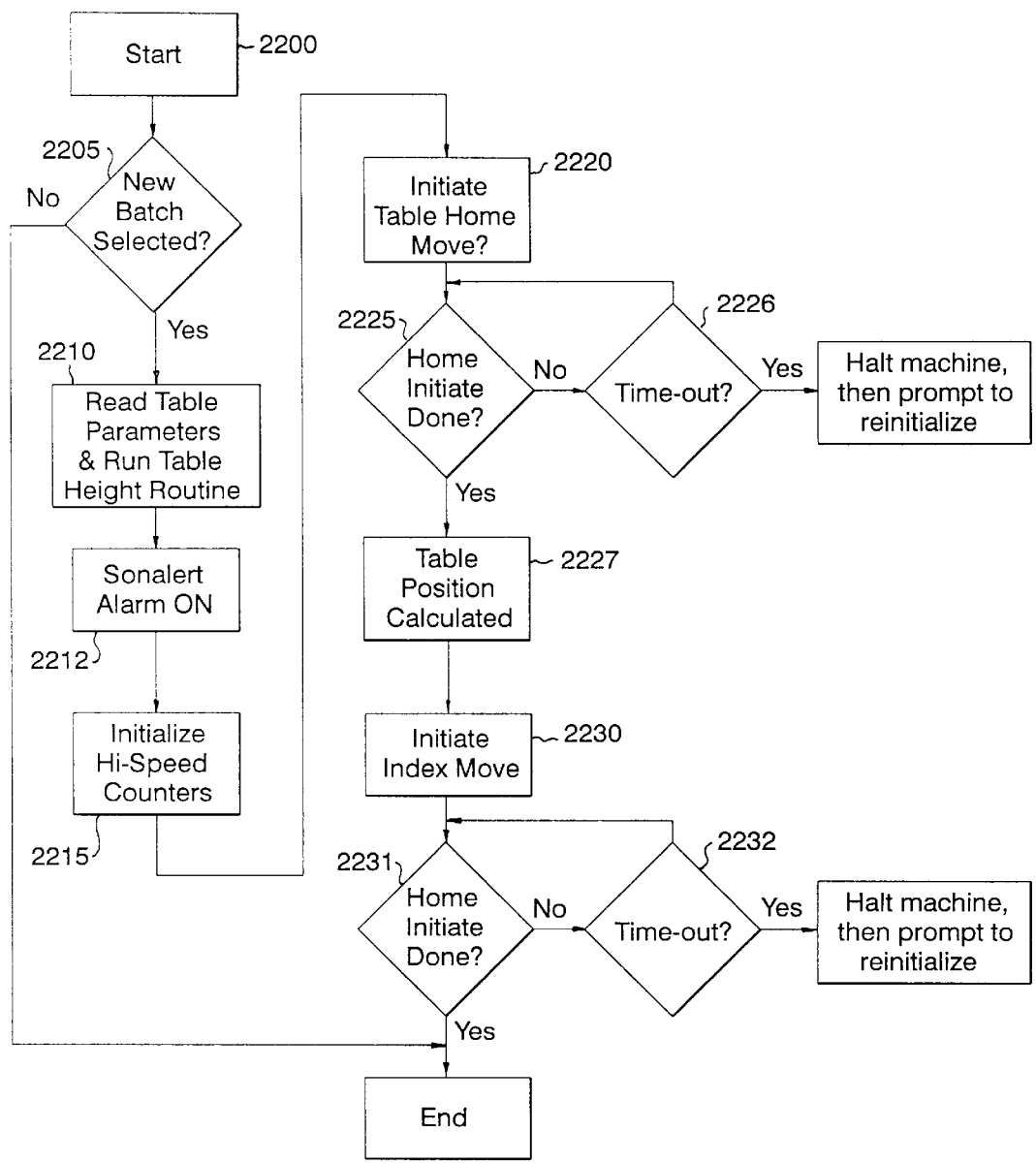
Figure 53C:
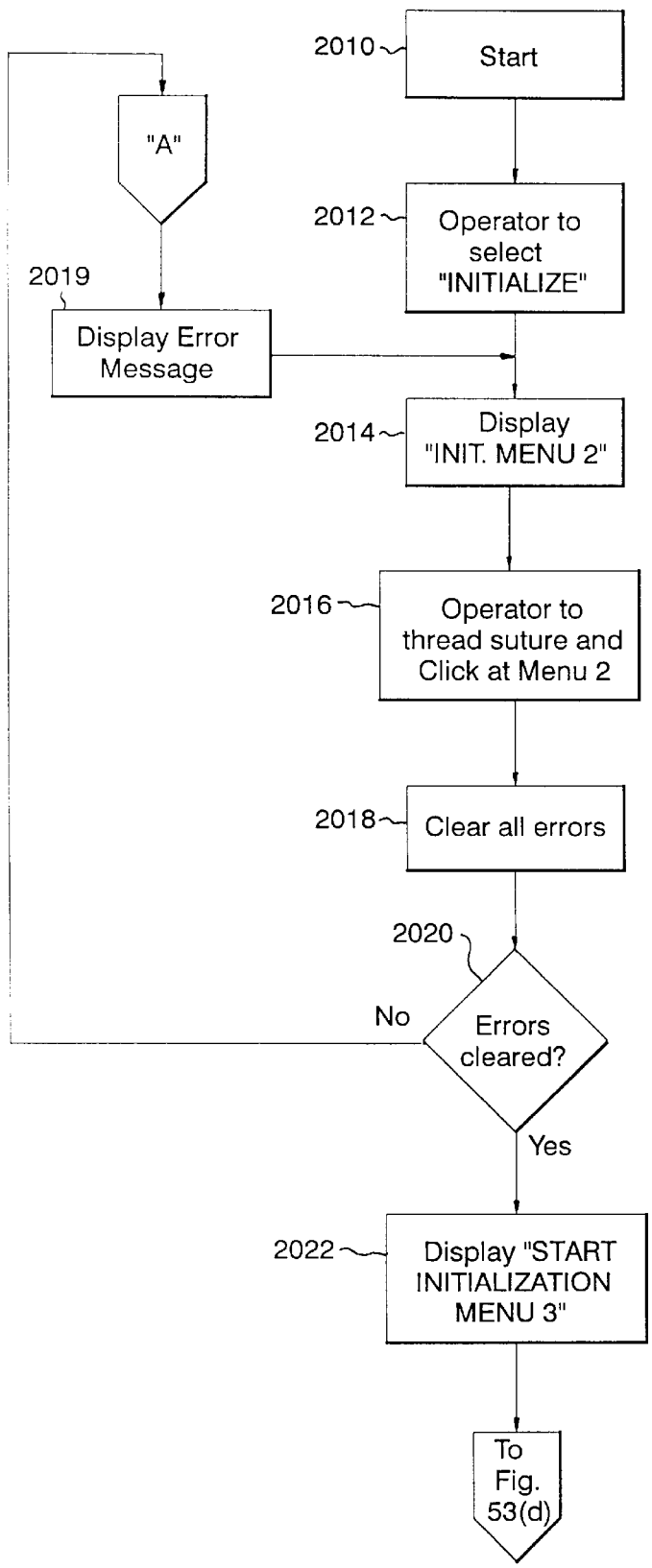
Figure 53D:
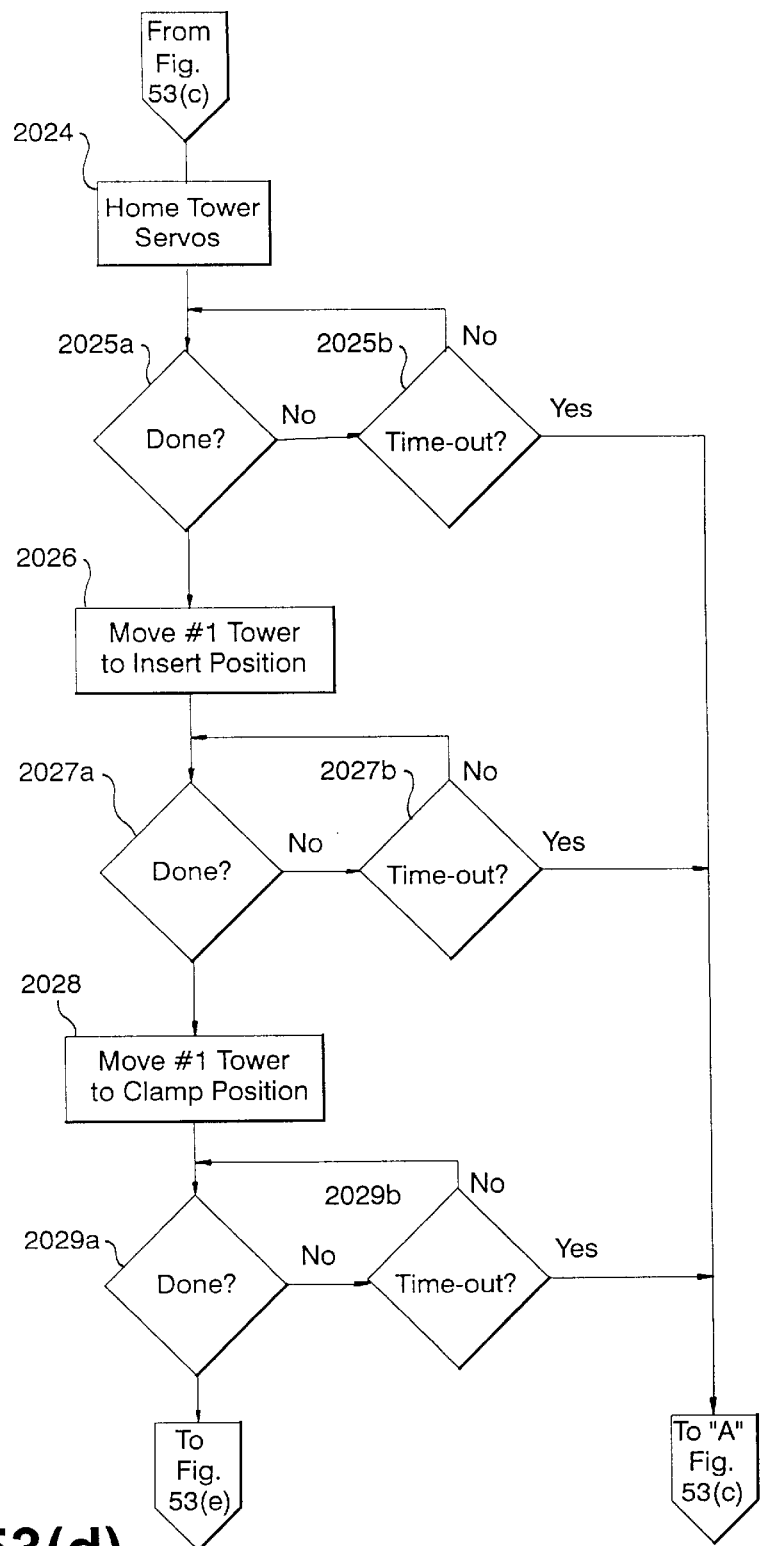
Figure 53E:
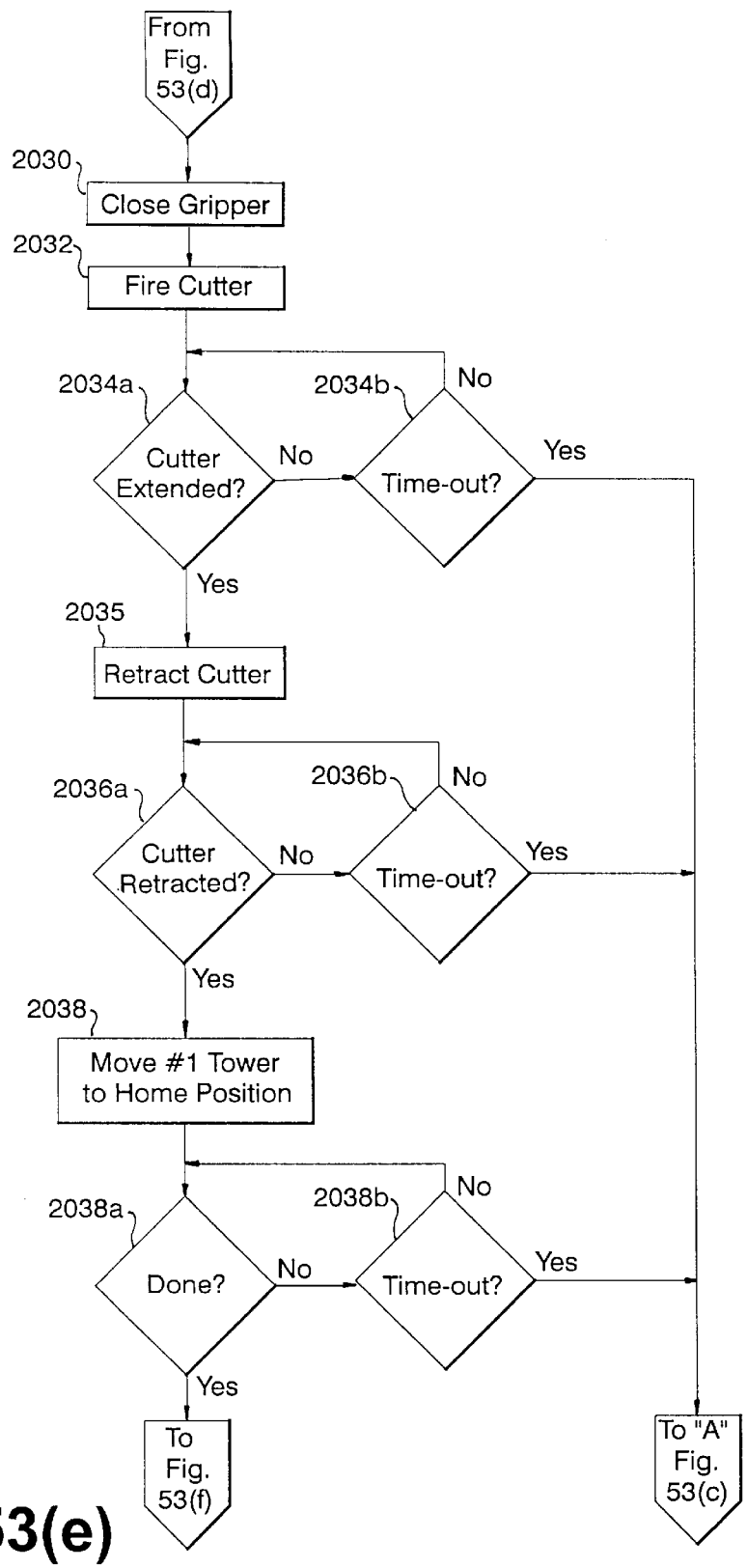
Figure 53F:
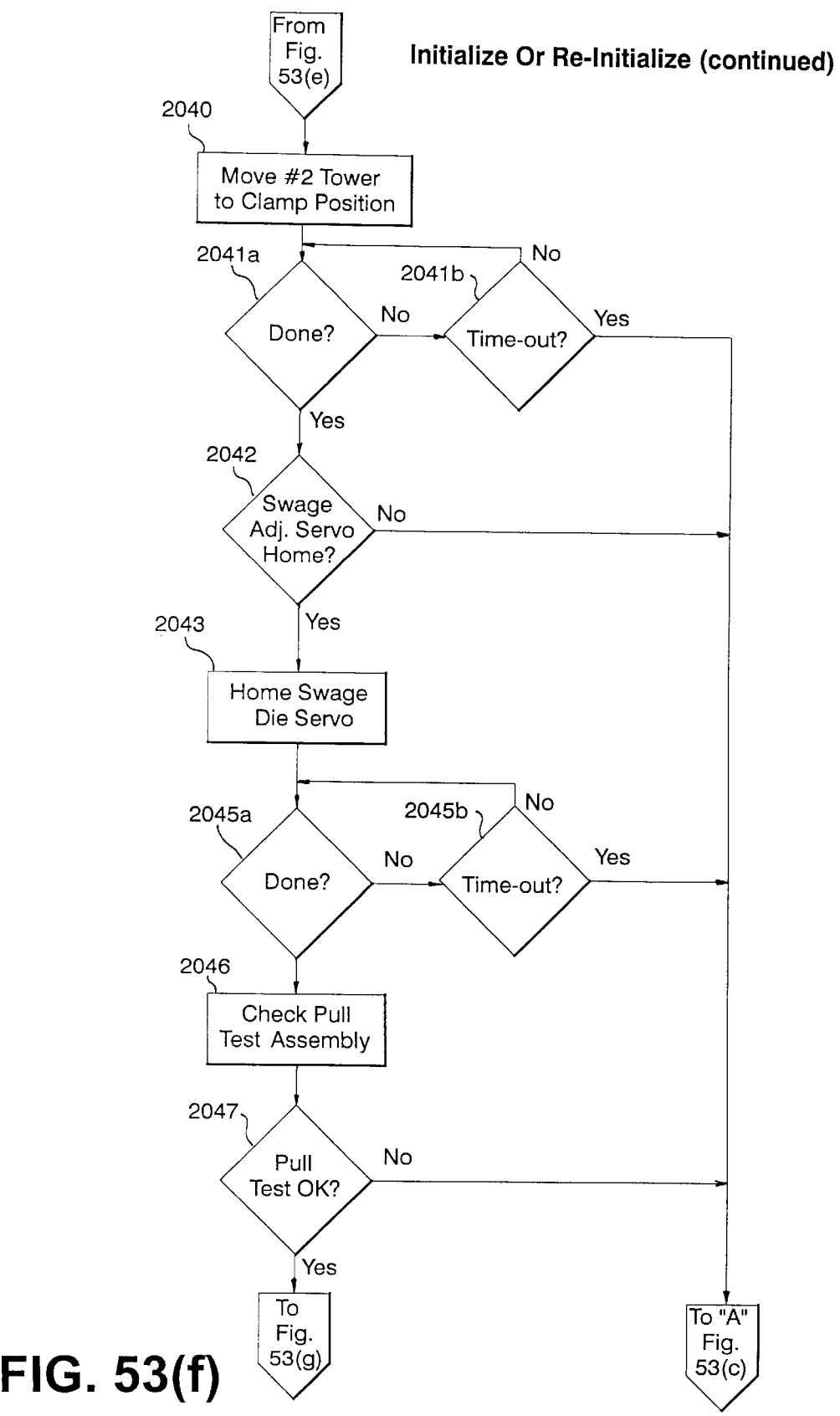
Figure 53G:
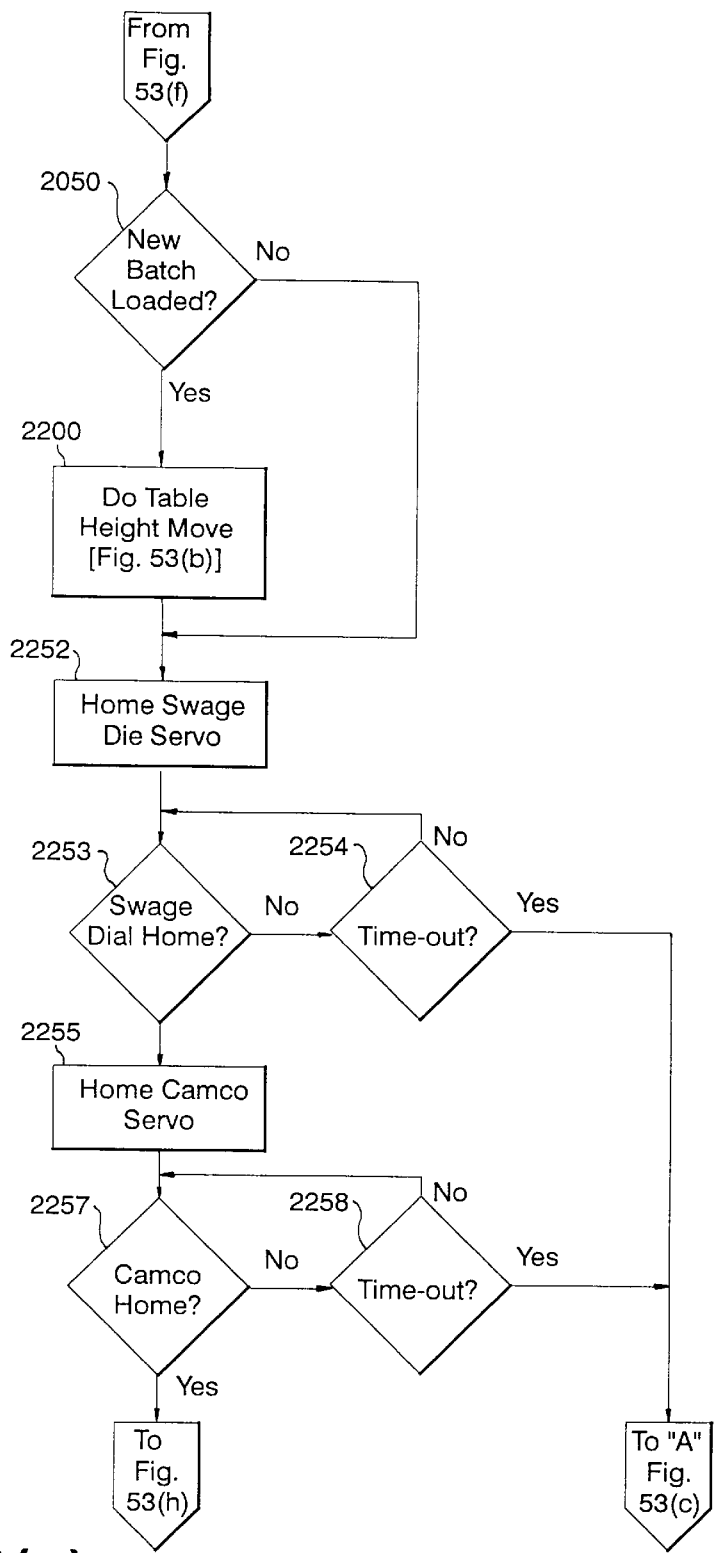
Figure 53H:
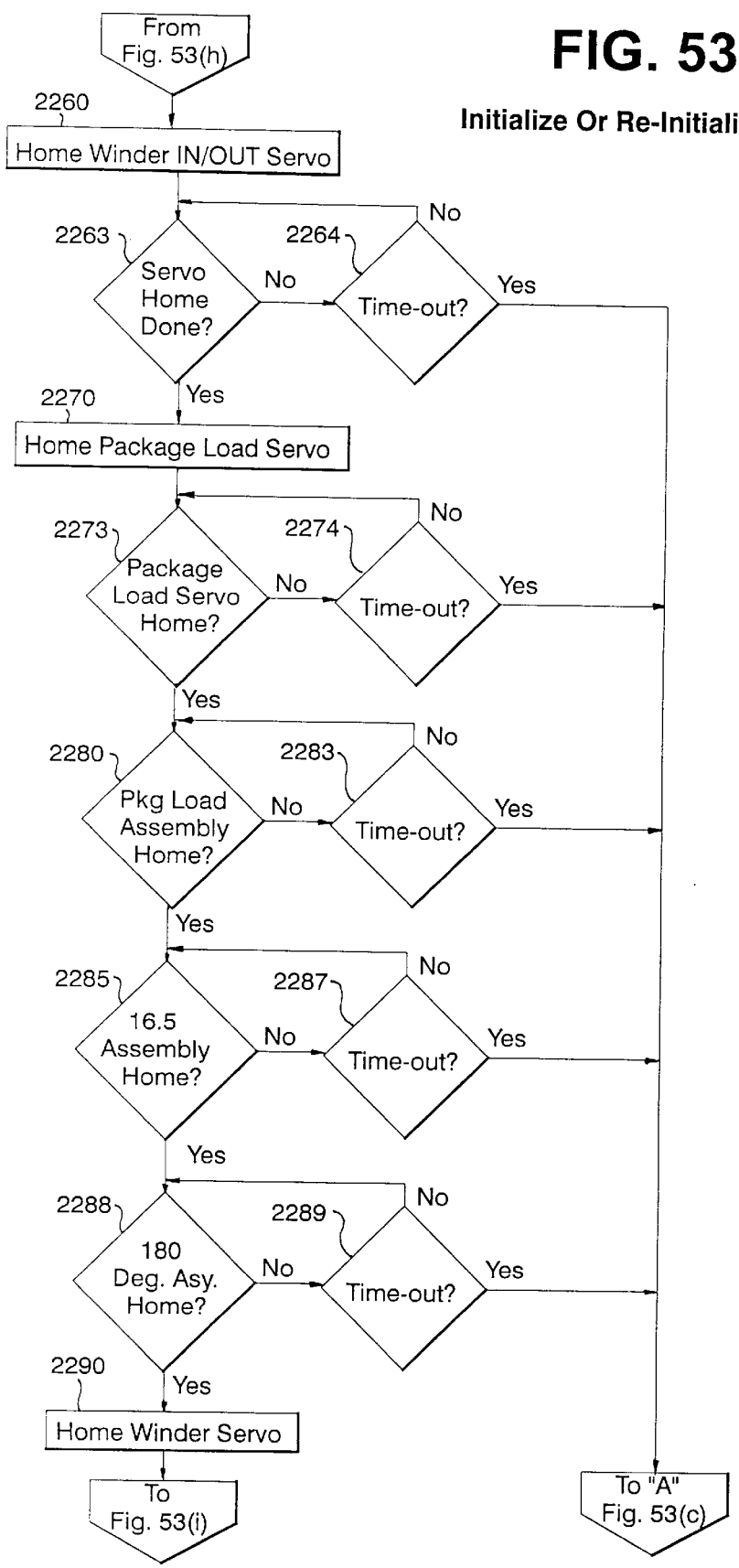
Figure 53I:
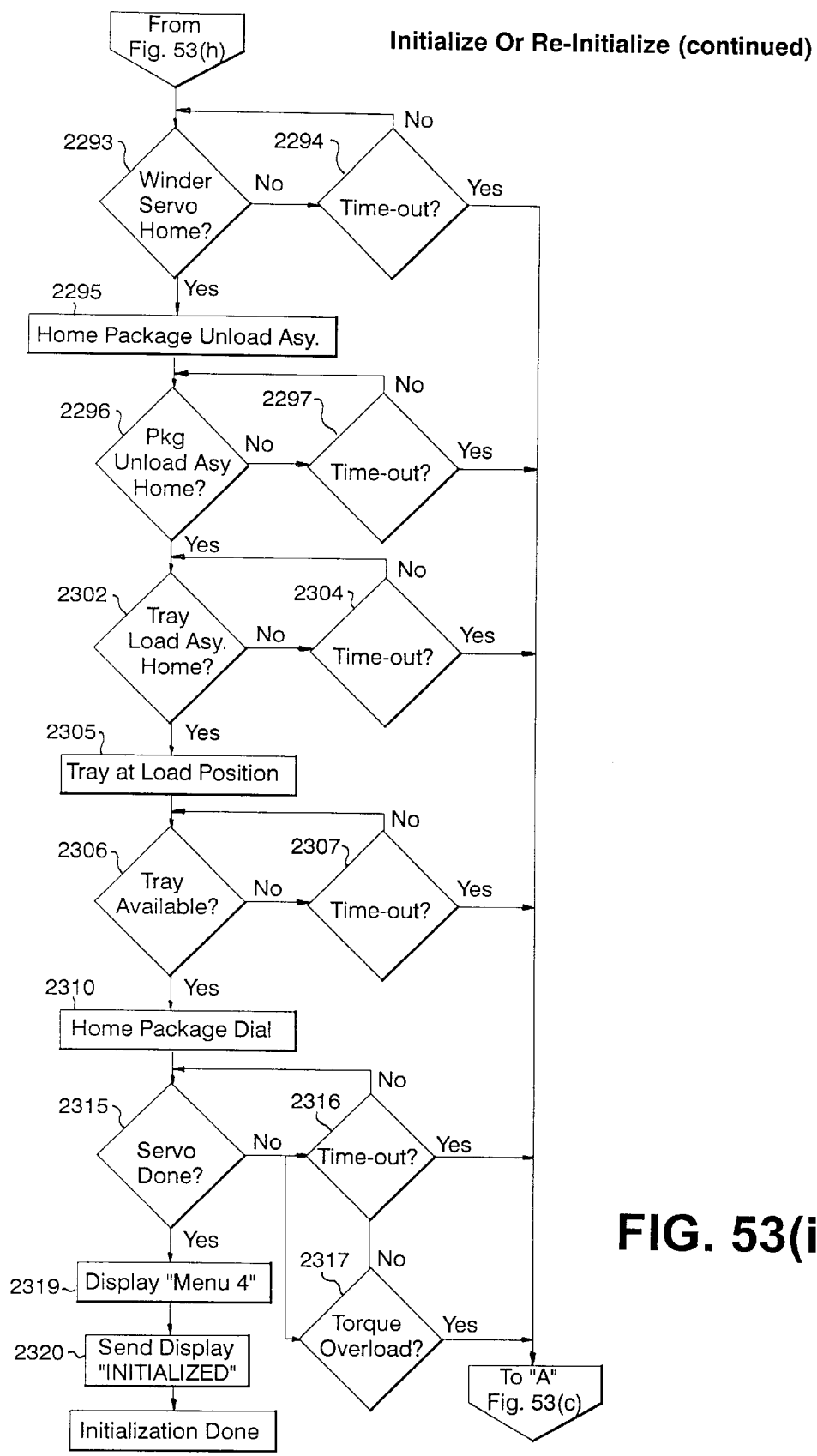

As described herein, and as shown in FIGS. 1, 5, and 52(*a*)–52(*e*), each station of the automatic needle threading and swaging apparatus and automatic packaging apparatus employs various types of pneumatic, electronic (digital and analog) and servo motor controls operable under a control system 1000 (FIG. 3) for controlling and monitoring every aspect of the armed surgical needle production and packaging processes. Alternatively, and, in addition, the control system implements a plurality of programmable logic controllers ("PLCs") or other such suitable control devices for controlling specialized production aspects, as will be described. The flow control system 1000 is implemented as computer programs and flow control modules resident on a first operator computer 99*a*, e.g., employing a Window's-based operating system, for instance, and a second supervisor computer 99*b*, both depicted as control system computer 999. The operator computer 99*a* preferably includes a display monitor and keyboard combination enabling manual entry of machine and die set-up parameters through a series of display menus, e.g., for initialization purposes, for initiating needle suture assembly and packaging run time operations, for real-time alarm monitoring, maintenance, etc. The supervisor or control system computer 99*b* can be an IBM PS/2 or one of equivalent processing power and may be provided with various data bases, referred to as batch recipes, containing lists of values for all production parameters on machine 10. Computer 99*b* may have a respective one batch recipe for each type of needle/suture combination that is to be processed by machine 10; and when needles of a given type are fed to the machine 10, the associated batch recipe is invoked to set parameters on the machine. Also, supervisor computer 99*b* may hold data or status words that in turn hold bits or flags describing various conditions on machine 10. Some of these status words may indicate conditions at each of the work stations and other status words that may describe the conditions of the needles at these stations, as will be hereinafter described. Thus, as shown in FIG. 5, operator computer 99*a* acts as an interface between an operator and supervisor computer 99*b* for receiving input data and commands from the operator and for displaying data and messages to the operator. Conceptually shown in FIGS. 1 and 5, control system computer 999 includes one or more I/O cards, depicted in FIG. 5 as I/O card 998, for routing various sensor and control signals to/from the computers 99*a*, 99*b* to the needle-feed apparatus 50 including robot apparatus and precision conveyor, via line 16*a*; to the automatic swage machine, via line 16*b*; and, to the automatic packaging machine 25, via line 16*c*.

In the pneumatic control system as shown in the pneumatic schematic diagram of FIGS. 52(*a*)–52(*e*), piping 801 supplies air through computer controlled solenoid valve 803*a*, suitable filters 805*a* and 805*b*, and through pressure regulator 807*a* to a pipe manifold which distributes pressurized air into several supply lines 806*a*–806*f* for operating the various pneumatic devices provided in the machine 10, as will be described. Many of these pneumatic devices are actuated by solenoid valves having control input lines 16*a,b* and *c* for actuating the various pneumatic components.

Figure 3:
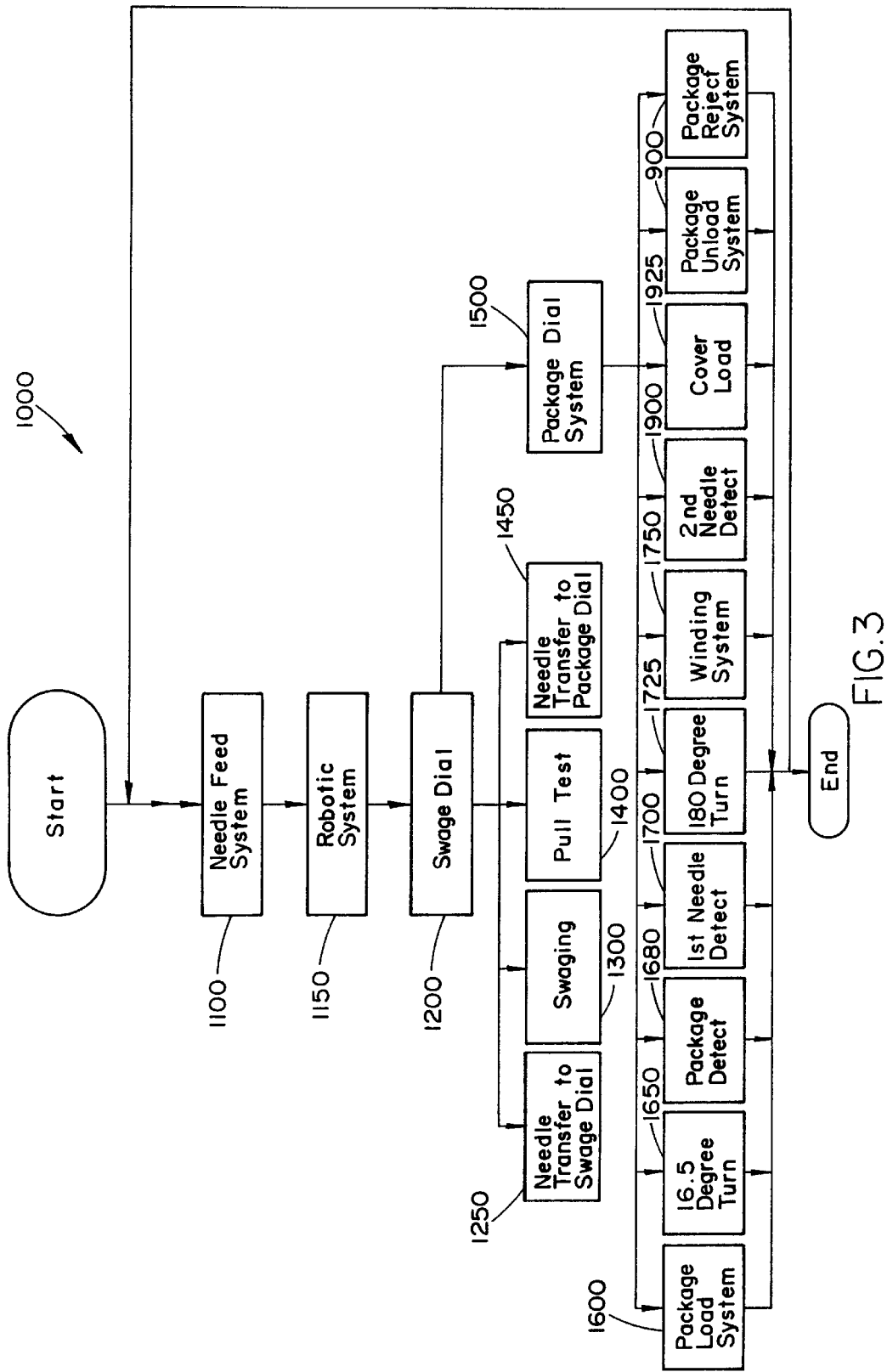
FIG. 3 is a general flow diagram illustrating the control system processes 1000 of the invention for controlling the needle threading and swaging machine and automatic packaging machine 10 of FIG. 1.

FIG. 3 illustrates a general overview of the control system 1000 of the invention. As shown in FIG. 3, the control system includes the following functional blocks: functional block 1100 for controlling all aspects of the needle sorting and singulating operations performed at the needle-feed station 50; functional block 1150 for controlling all aspects of the vision control, robotic pick and place, and indexing conveyor operations, and, a functional block 1200 for controlling the swage dial indexing operations. Particularly, swage dial functional block 1200 initiates the following four control system threads operating simultaneously for controlling each of the following automatic needle-suture assembly operations: a first thread 1250 for controlling the needle transfer to a multi-axis gripper at the swage dial at station 100 of machine 15; a second thread 1300 for controlling all of the operations relating to needle-suture swaging, e.g., suture draw, cut, tip, suture insertion, etc. at the suture tower and swaging stations; a third thread 1300 for controlling needle-suture pull-test operations at pull-test station 300; and a fourth thread 1450 for controlling the needle-suture handoff operation at the needle-load to package station 450.

As shown in FIG. 3, during indexing of the needle-suture swaging dial, the swage dial process automatically initiates flow control operations 1500 for the package dial indexing system, and, particularly, the following control system threads governing parallel needle-suture packaging assembly operations: a first control thread 1550 for controlling the tray (package) load operations at the package load station 425; a second control thread 1600 for controlling the 16.5° tray rotation operation at station 435; a control thread 1650 for controlling the package detect operation at station 447; a control thread 1700 for controlling a first needle detect operation at station 475; a control thread 1750 for controlling operations performed at the 180° degree package turn station 600; a control thread 1750 for controlling winding operations performed at the winding station 625; a control thread 1900 for controlling operations performed at a second needle detect station 650; a control thread 1925 for controlling operations performed at the package cover load station 675; a control thread 900 for controlling operations performed at the package unload station 700, including the package reject operations performed at the package unload station 750. During steady-state operation, each of the control system operations shown in FIG. 3 are performed concurrently in a machine cycle, barring the detection of any critical faults that would prompt machine termination during a machine cycle and necessitate machine reinitialization, or non-critical faults, hereinafter referred to as "cycle jams" which may necessitate termination of the current machine cycle to alert an operator for possible corrective action, however, would not prompt re-initialization.

Figure 4:
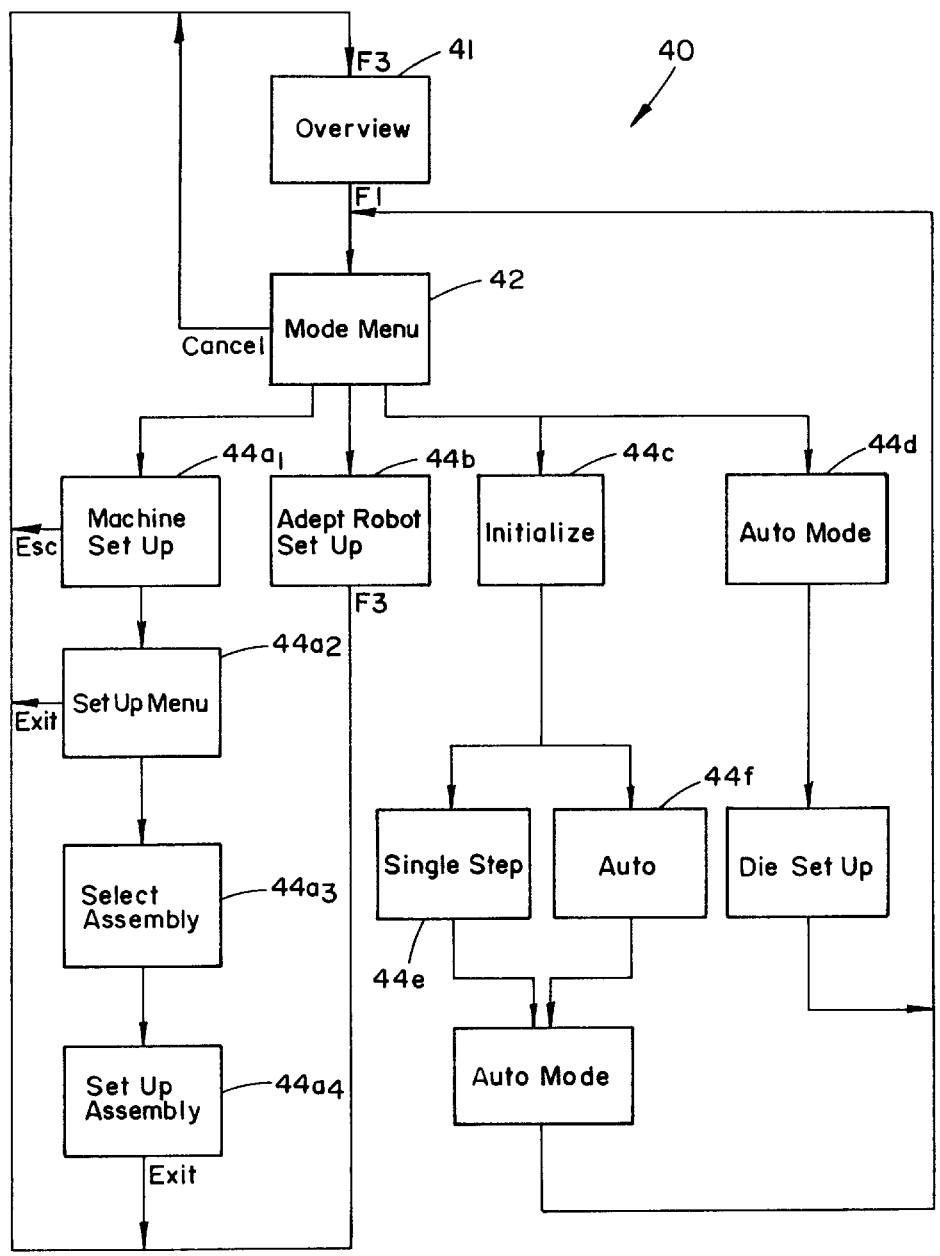
FIG. 4 is a general block diagram illustrating generally the menu choices for initiating various needle-suture assembly and packaging operations.

As shown in FIG. 4, a variety of operator menu choices 40 is first provided on the computer display 98 to enable operator view of the whole assembly and packaging system 10 as indicated at block 41, and a mode menu 42 providing the operator with the following menu choices: a selection for implementing machine/assembly set-up $44a_{1-4}$; a selection for Adept Robot Setup 44b at the needle infeed station; an initialization 44c routine for powering up all the various assemblies and bringing all functional components to their initial state; and, automatic die set-up changes 44d for changing the swage dies in accordance with the size of the needles and sutures to be swaged for the current batch, as will be described. Additionally, as part of the display, an operator can be prompted to choose between initialization in the normal, fully automatic mode 44e, or, in a single step mode 44f, for diagnostic or trouble-shooting purposes. The initialization (or reinitialization) routine is discussed below in greater detail with respect to FIGS. 53(*a*) through 53(*i*).

Overview of the Needle-Swaging Apparatus

FIG. 8 shows a top plan view of the needle-suture swage apparatus 15 constructed according to the teachings as described in co-pending U.S. patent application Ser. No. 09/020,085 and is used in the following descriptive overview of the apparatus. Further details regarding the mechanical operations performed at the needle-suture apparatus can be found in co-pending U.S. patent application Ser. No. 09/020,085 the disclosure of which is incorporated by reference herein by reference thereto.

Needle Infeed

This apparatus includes an automatic needle singulation and transfer station 50 for automatically sorting and singulating needles and preparing them for automatic swaging and packaging. Particularly, as shown in FIG. 8, a batch of unoriented needles of uniform size are first loaded into vibratory bowls 51*a,b*, automatically sorted and linearly deposited by singulating devices 54*a,b* to each of two translucent indexing conveyors 55*a,b*, respectively, which provide a moving line of singulated needles for further imaging, manipulation and handling.

Figure 9:
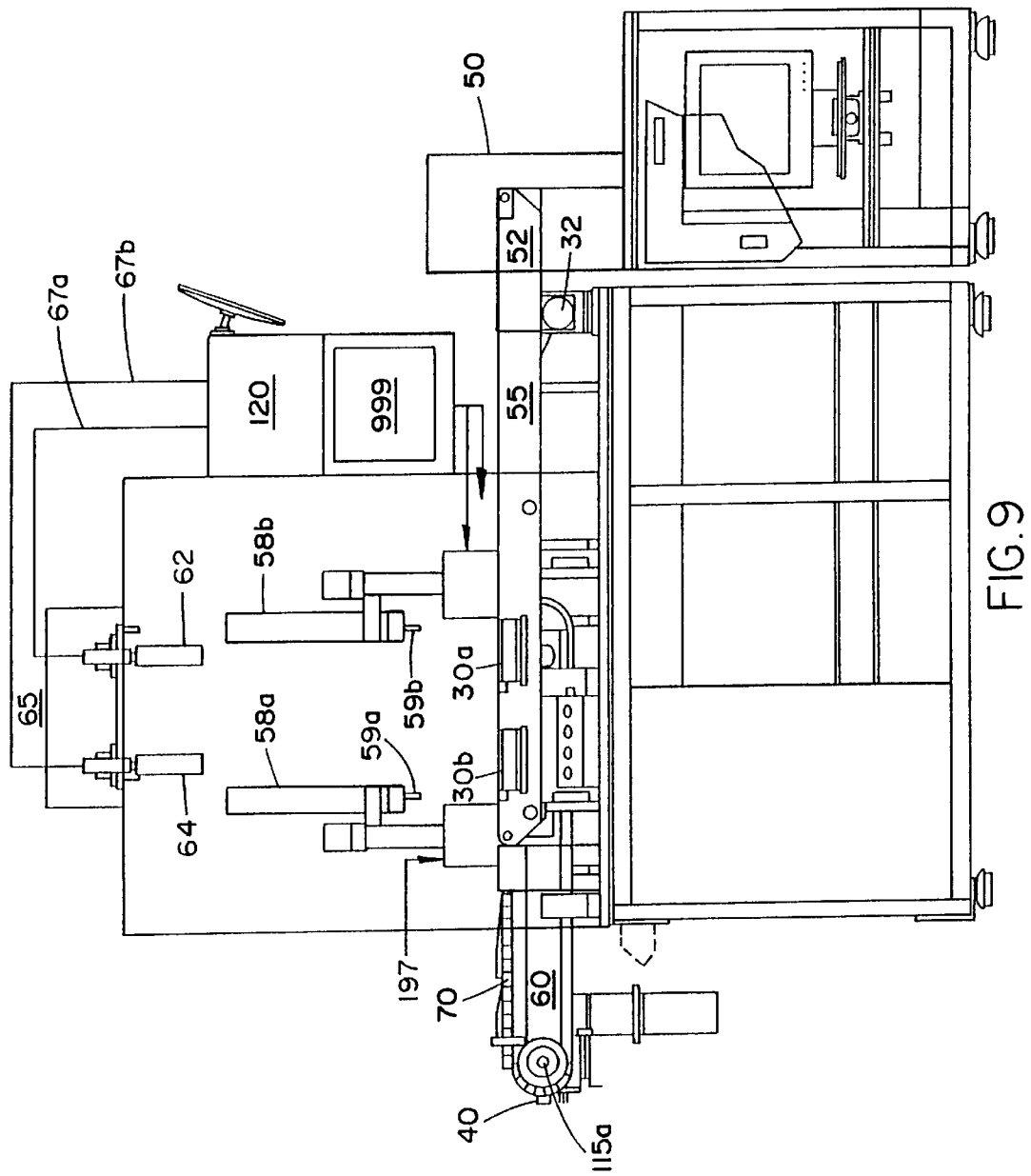
FIG. 9 is a side elevational view of the needle sorting device and infeed apparatus 50 showing the robot assembly above the first conveyor means and the vision tracking means comprising two video cameras for obtaining images of the needles and the control system means for processing the image data.

The preferred embodiment of the needle sorting and infeed apparatus 50 is illustrated in the top view of the system in FIG. 8 and the side view of FIG. 9. As shown therein, needles 9 are delivered in bulk to each of two vibratory bowls or hoppers 51*a,b* where they are singulated by the vibratory bowls into a single file of needles, and intermittently fed to the linear slide discharge assemblies 52*a,b* where they are individually deposited upon each of two translucent conveyors 55*a,b*. The two translucent conveyors 55*a,b* carry the singulated and deposited needles 9 in the direction indicated by the arrow A in FIG. 8 where their position and orientation are evaluated by a remotely located vision tracking system that will be discussed in detail below with respect to FIG. 9.

The tracking system evaluates the position and orientation of each available needles on the translucent conveyors 55*a,b* as it forwardly conveys the needles over illuminated (backlit) platforms 30*a* and 33*b* and further evaluates the position and orientation of the each available needle upon translucent conveyor 55*b* as it forwardly conveys the needles over illuminated (backlit) platforms 33*a* and 33*b*.

The orientation and positional information obtained from the vision tracking system is processed and converted to coordinates usable by each of two robot assemblies 58*a,b*, for instructing respective robot grippers 59*a,b*, to pick up and transfer identified needles from one of the translucent conveyors to individual engagement boats 70, located on a precision conveyor 60 that is also being indexed in the same direction as the translucent conveyors as shown in FIG. 8.

The control system computer 999 instructs a robot gripper, e.g., gripper 59*a* of the robot assembly 58*a*, to grab the tracked needle from one of the two conveyors 55*a,b*, for a dwell cycle of the system, i.e., when the respective conveyor has paused. If the singulated needles 9 are oriented such that neither of the robot grippers 55*a,b*, are able to pick one of them up or place a needle onto the precision conveyor because of its limited range of motion, a recovery procedure will be executed to ensure that there are no shortages of needles 9 to be fed by the precision conveyor 60 to the automatic high-speed swaging workstation (not shown) which can achieve up to 60 needle swages per minute.

In the preferred embodiment, the timing of each conveyor 55*a,b*, is identical, but the dwell periods are out of phase. Because of the phased timing, the vision tracking system will be identifying needles on one indexing conveyor, for e.g.,55*a*, while both robots are picking needles from the other indexing conveyor 55*b* and placing each needle in an individual engagement boat of the precision conveyor. Similarly, while both robots are picking needles from the indexing conveyor 55*a*, the vision tracking system will be identifying needles on the other indexing conveyor 25*b*.

The first step of the automatic swage/wind process 10 involves introducing a predetermined amount of needles 9 from an infeed device, such as a vibratory bowl or hopper, which serves as the first component in the needle singulating assembly. This first step in singulating needles for the automatic swage/wind process 10 involves singulating individual needles from a bulk supply of needles for introduction to the vision inspection system. The singulating apparatus includes a vibrating hopper assembly which singulates the needles into a single file, and a linear discharge slide mechanism which provides for timed and positioned placement of individual needles on the translucent indexing conveyor.

Figure 10A:
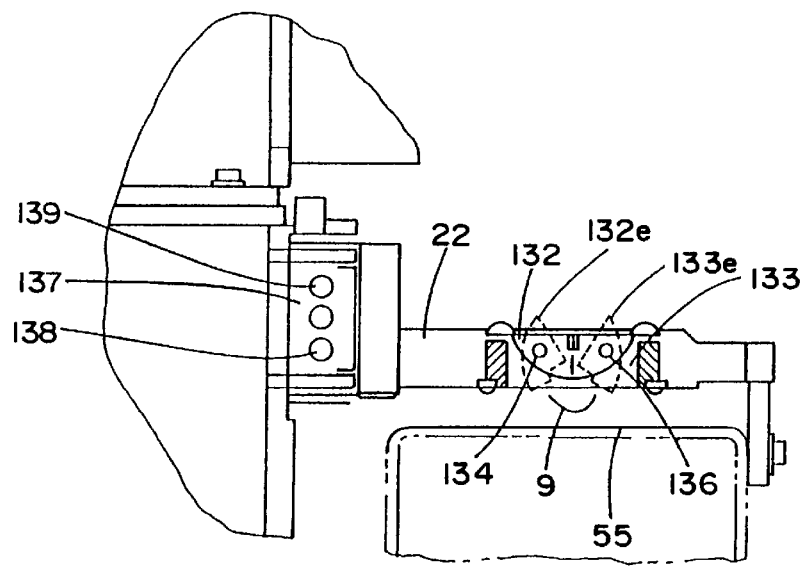
FIG. 10(a) is a detailed cross-sectioned view of the linear slide mechanism used to singulate and deposit individual needles onto one of the translucent conveyors.

Two separate needle feed mechanisms are illustrated in FIG. 8 to feed two separate translucent indexing conveyors. In FIGS. 10(*a*)–10(*c*), the linear slide mechanisms 52*a,b* are illustrated in greater detail, and the vibrating bowl assembly is illustrated in greater detail in FIG. 10(*c*). Parts that are substantially identical in the two separate feed mechanisms are identified with the same reference numeral with an (a) or (b) suffix, depending on which feed mechanism they are associated with. When a part is referred to without the suffix, it is understood the description applies equally to both needle feed mechanisms.

As illustrated in FIG. 10(*c*), a vibrating bowl assembly receives a plurality of needles in bulk on a central floor area 121. The vibrating bowl is capable of providing between 60 and 100 parts per minute. The track assembly 122 is a continuous spiral track which begins at the bottom of the bowl at 122(*a*) and ends at the linear discharge point 122(*b*). The track includes along virtually all of its entirety a vertical rib 122(*c*) which supports the needle during the vibratory transport as illustrated by the needle 123 at position C. The needles are transported from the floor 121 at position A to the discharge point 122(*b*) by pulsed vibration from vibratory unit 24 controlled by a control system 1000. The vibrations supplied by the unit 24 are both vertical and horizontal and are timed to coincide to provide a maximum rate of movement for the needles 9. Track member 122 begins at the floor of the unit 121 and winds upwardly to the top of the vibrating bowl wherein the vertical portion 122*c* is interrupted for a pair of vertical gates 126 and 127 which redirect overlapping needles and nested needles back into the vibrating bowl 51. A secondary track and dam 127 is used to catch overlapping needles screened by the first dam 126 and return them to the floor of the hopper 21 with minimal damage to the points of the needle. Each of the vertical dams 126, 127 include adjustable knock off screws 126*a,b*, and 127*a,b*, which are used to provide precise adjustment of dams 126 and 127 for various needle sizes. Thumb screws 126*c,d* and 127*c,d* provide coarse adjustment of the gates 126,127 while knock off screws 126*a,b*, and 127*a,b*, provide for fine adjustment thereof.

The pulsed vibration of vibrating unit 24 provides a single file stream of needles oriented on trackway 122 as illustrated at position B and C by needles 9. As they reach the end of the track 122*b*, they are first detected by an optical sensor 128 which is activated by the reflection of the needle on the trackway 122. When the needle has fallen from the trackway at 122(*b*), a second detector signal is generated by a second optical detector 29. The electrical signals from optical detectors 28, 29 are provided to control means 999 for use in controlling the vibratory motor 24 as will be hereinafter described in greater detail.

Vibrating bowls 51*a,b* provide a serial single line output of needles, dispensed one at a time to the needle feed stations 22*a,b* which are more fully illustrated and described with respect to FIGS. 10(*a*)–10(*b*).

Figure 10B:
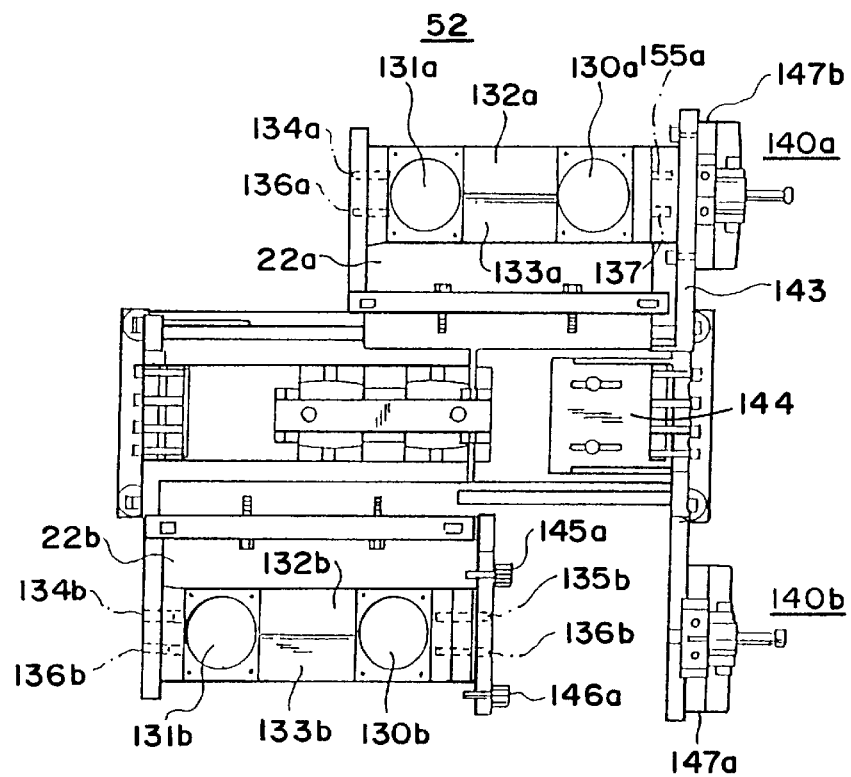
FIG. 10(b) is a detailed plan view of the linear slide mechanism 52.
Figure 10C:
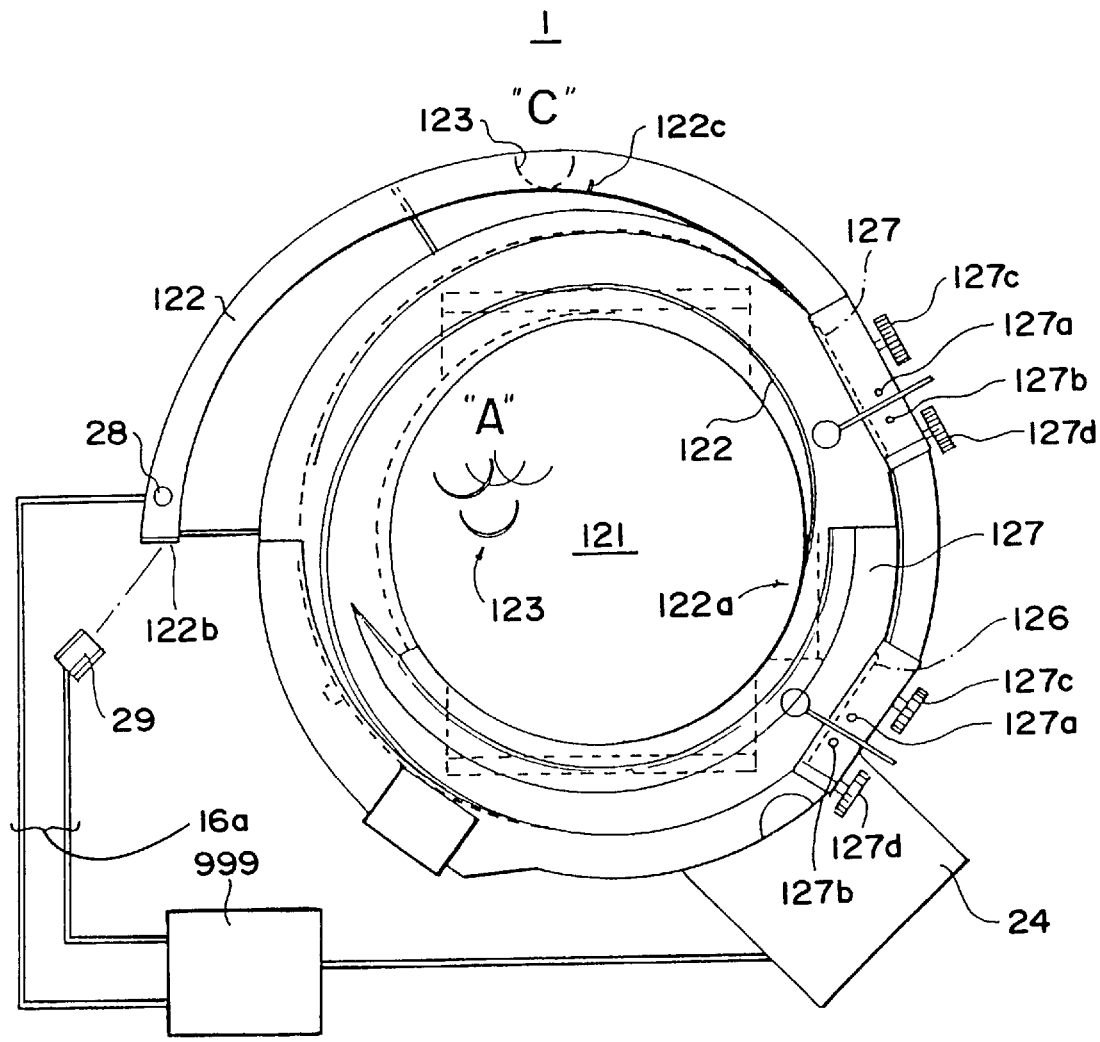
FIG. 10(c) is a detailed top plan view of one of the vibratory conveyor bowls and the needle trackway used to feed the linear slide mechanisms.

As illustrated in FIG. 10*b*, the needle feed stations include a first linear slide 52*a* and a second linear slide 52*b* which are reciprocated between the two positions illustrated in FIG. 10(*b*) by slides 52*a* and 52*b*. In a first position, as illustrated by the linear discharge slide 52*b*, a first needle pocket 130 is arranged under the drop point 122*b* of the trackway 122*a* leading from the vibrating bowl members 51*a,b*. After sensor means 29 has detected a falling needle from the end of trackway 122, the linear slide is reciprocated to its second position illustrated by slide 122*a* in FIG. 10*b*. In this position, the second needle cup 31*a* is now positioned below the end of a trackway 122*b* formed on the vibrator bowl assembly 51*a*. The pulsing vibrator unit 24 is then energized until a second needle is detected by optical sensor 29 as it falls into needle pocket 31*a*.

The needle pockets 130 and 131 are formed in a pair of pivoting blocks 132,133 which are mounted for pivotal movement on the slide mechanism 22*a,b*. As illustrated in FIG. 10(*a*), block member 132*a* pivots on pins 134,135 while block member 133 pivots on pins 136, 137. The pivotal movement is illustrated in FIG. 10(*a*) wherein block members 132, 133 pivot around pivot points 134,136 to the position illustrated at 132(*e*) and 133(*e*). As the block members 132,133 pivot, the needle pockets are opened as illustrated in FIG. 10(*a*) to deposit the needle 9 on the translucent indexing conveyor 55. An air slide mechanism 137 and guide rails 138, 139 which provide the reciprocal movement of the slide mechanisms 52*a,b* are also illustrated in cross-section in FIG. 10(*a*). Further details on the singulation operation may be found in commonly assigned co-pending U.S. Pat. application No. 08/804,039, the contents and disclosure of which are incorporated by reference herein.

In the sequence of operation under control system thread 1100 (FIG. 3), the control computer 999 energizes the vibratory motor 24 to vibrate the bowl in a pulsed manner, with the amplitude of the pulses controlled by an adjustable rheostat. The adjustable amplitude setting varies depending upon the size and mass of the needle to be transported along the trackway 122. The needles are then singulated in single file along the entire length of the track 122 from the floor of the vibratory bowl 121 to the discharge point 122*b*. When optical sensor 28 senses the presence of a needle at the end of the trackway, vibrating motor 24 is stopped until the reciprocating slide 122 is reciprocated to its most rearward position as illustrated in by slide 52*b* in FIG. 10(*c*). After linear slide 52*b* is in position, control means 999 energizes the motor 24 and the needle is vibrated from trackway 122 into needle pocket 130*b*. As the needle falls from the trackway to the pocket, its presence is detected by optical sensor 29. Control circuit 999 keeps motor 24 vibrating until another needle is sensed on track 122 by sensor 28. After receiving a needle, the linear slide 52*b* is then advanced to the forward position as illustrated by slide 52*a* in FIG. 10(*c*). In the event a second needle is detected by optical detector 28 before slide member 52*b* has reached its forward position, the drive motor 24 is stopped until slide member 52*b* is in position to receive the second needle. Thus there are two control situations for the deposit of a needle into the second pocket 131*b*. If a needle was detected at sensor 28, then the vibrating motor 24 is reenergized to vibrate that needle off the end of track 122 and into needle pocket 131*b*. If a needle has not been detected by optical sensor 28, the control means will keep vibrator 24 running following the first drop, and the vibrator will continue to run until sensor 129 detects a dropping needle. After each drop, the control means 999 keeps the vibrating motor 24 running until a needle is detected at optical sensor 28. After both needle pockets 130b, 131b have received a single needle, the air slide 141 is actuated opening the needle cups and depositing the needles therein in a singulated and spaced relationship on the translucent conveyor 25 for imaging by the optical system and further handling by the robotic tracking system. Actuation of the air slides is controlled by solenoid valves 804b,c and 804e,f as shown in FIG. 52(d).

It should be understood that while the needles 19 deposited on translucent conveyor 55a,b, are singulated and spaced apart, they will be randomly positioned and unoriented. In the preferred embodiment, each translucent conveyor 55a,b, is an endless loop conveyor that is driven at a rate of four inches per sec (4 in./sec) and runs parallel to a precision conveyor 60 as shown in FIG. 3(a).

As described above, and in view of FIG. 9, the robot assembly comprises two robots 58a,b, located downstream from each needle singulating assembly 52a,b and proximate both the precision and translucent indexing conveyors. In the preferred embodiment described herein, each robot assembly 58a,b, is an Adept® 604-S robot capable of accomplishing needle transfers at a rate of approximately 40 transfers per minute as controlled by each robot's corresponding Adept® CC controller. Each robot is a four-axis SCARA (Selective Compliance Assembly Robot Arm) robot comprising four joints. Robot grippers 59a,b, are attached to the quill of each respective robot assembly 58a,b, and are enabled to provide gripping action by pressure supplied from respective air cylinders 59c,d as respectively shown in FIG. 52(d) actuated by solenoid valves 804g and 804h under control of the control system computer 999.

Referring now to FIG. 9, there is illustrated the precision conveyor 60 which is driven by drive motor assembly 115a at a rate sufficient to index and transfer one oriented surgical needle per second (1 needle/sec) to the automatic swaging machine. A similar drive motor assembly 32 is provided for driving the indexing conveyors 55a,b. As will be explained in detail below, each drive motor assembly is interfaced with and operates under the control of the control system 999 to cause the indexing motion to enable the pick-up and transfer of a needle from the indexing conveyor to the precision conveyor.

FIGS. 8 and 12(a)–12(c) illustrates in detail the precision conveyor 60 and the plurality of engagement boats 70 located thereon for engaging respective individual surgical needles 9. Motion of the precision conveyor 60 is also paused periodically at the desired cycle rate to allow for the transfer of the needles 9 thereto from the robots 58a,b. The precision conveyor receives needles 9 with rough positioning from the robotic assemblies 58a,b, in boats 70 as will hereinafter be described. The needles when received in boats 70 are orientated as to point and butt end, but not orientated with respect to the direction of curvature of the needles.

As further described in co-pending U.S. patent application Ser. No. 09/020,085, needle orientation devices such as a needle plow mechanism to further orient the curvature of the needles while engaged in the conveyor boat and needle pre-positioner for prepositioning the butt end of each needle, are provided. The needles are finally precisely positioned by a moveable hard stop mechanism. The individual needles are then removed and held for swaging to a suture by a multi-axis gripper 155, which gripper is described in greater detail in FIGS. 14(a)–(b).

In the preferred embodiment, the control system 1000 includes a programmable logic controller (PLC) that is in digital communication with the Adept® robot controllers and the vision tracking system components to control the infeed system.

As shown in FIG. 9, the vision tracking system comprises a camera assembly 65 having two video cameras 62 and 64, one located overhead each respective illuminated platform portion, 30a and 30b, for its indexing conveyor 55a. As will be explained in detail below, the video images of the needles obtained from each camera 62,64 are bit-mapped or suitably digitized and transmitted via suitable transmission media, such as communication lines 67a,b, shown in FIG. 9, to the remotely located control system computer 999 where a Vision Control task processes the video images and inputs the data to each robot 58a,b, via communication line 67c. Preferably, the conveyors 55a and 55b are translucent and are backlit at the respective portions 30a,b and 33a,b, so that a sharp video image may be obtained by the overhead camera assembly for processing. It is understood that for descriptive purposes, only two video cameras 62,64 corresponding to the two illuminated platforms 30a, 30b are shown in FIG. 9. However, the invention includes a second set of video cameras (not shown) corresponding to illuminated platforms 33a and 33b for conveyor 55b so that, as mentioned above, binary images of needles on conveyor 55b may be obtained while the robots are picking and placing needles from conveyor 55a. The redundancy designed into this system ensures that there will be no momentary shortage of needles fed to the swaging station and that maximum throughput of oriented needles for input to the swaging station is achieved.

In the event the state of robotics technology improves, and as the robot assemblies achieve greater degrees of movement at faster speeds, the second set of cameras and a second robot assembly may no longer be required. Furthermore, a robotic assembly of sufficient speed and precision may be able to pick up randomly deposited needles from a moving conveyor and lace them directly in an oriented position at the waging station.

In the preferred embodiment, each camera 62,64 is mounted approximately one (1) meter above each backlit indexing conveyor 25a,b, and utilizes an electrically controlled telephoto lens with a focal distance ranging from 10 mm to 140 mm that may be changed with suitable adaptors. Suitable lens controllers are used to establish lighting/iris, focus, and field of view for each camera lens, and, are interfaced with the Adept® controller via an RS-232 link.

A further component of the control system for the needle sorting and infeed apparatus includes an SCADA Node which is used to oversee and direct the infeed system. This node interfaces with each of the Adept® controllers via discrete RS-232 links which are used to download data information, such as needle parameters, error messages, and status messages, to the Adept® controllers during run-time. The SCADA node may comprise a personal computer or such suitable device, running commercially available FIXD-MACS® software. Serial communication is used to exchange the needle parameters entered at the FIX/DMACS "Adept® Setup" screen during a needle changeover procedure which is used to inform the infeed system of the size and type of needles to be processed. After an operator enters the needle parameters and initiates a changeover, the FIX/DMACS Node will transmit these parameters to the robot controller(s).

Figure 11:
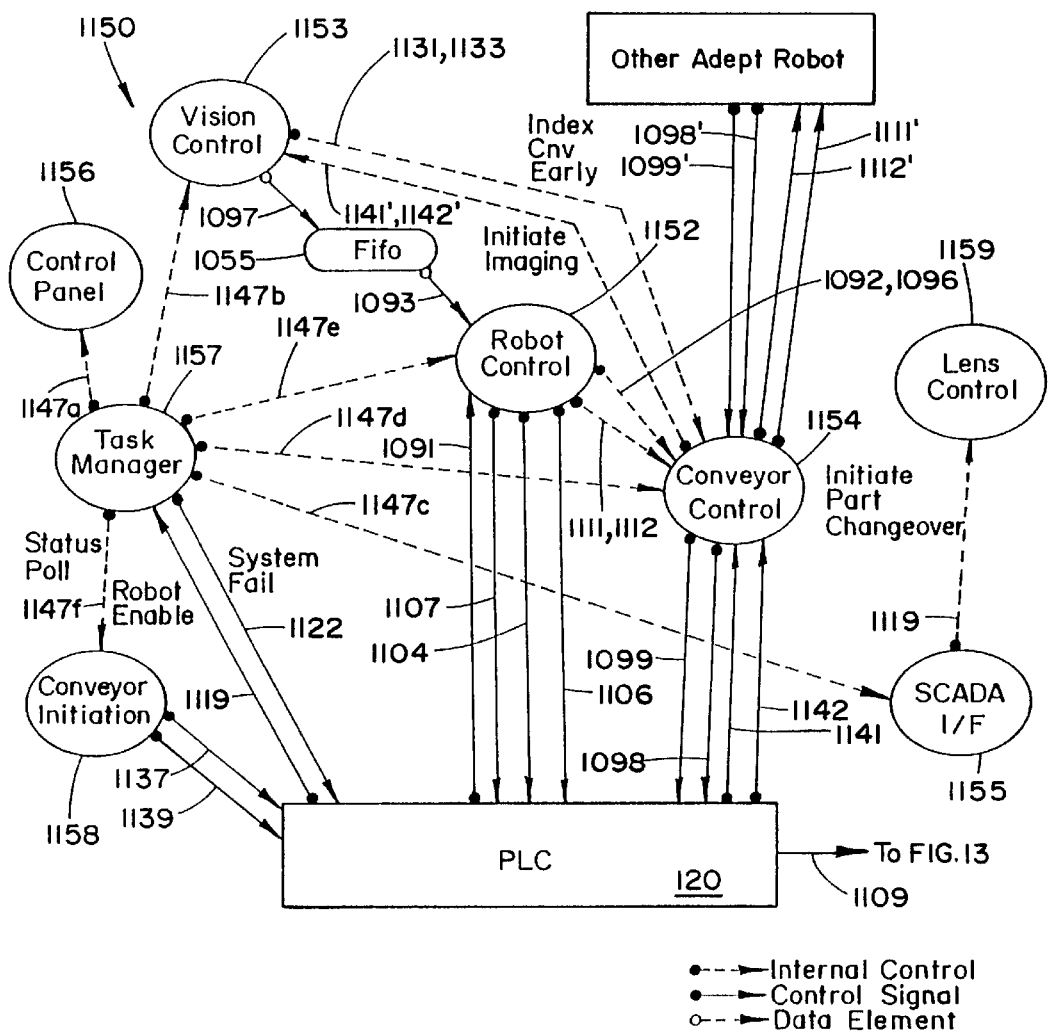
FIG. 11 is a schematic representation of the control and data flow for each of the control tasks of the needle sorting apparatus of the present invention.

The robotic/vision control system 1150 is shown conceptually in FIG. 11 as a state task diagram as comprising individual computer software programs, each associated with a particular task to be performed by the needle infeed system 50 and executed under the control of the Adept CC controller depicted as PLC 120. As shown in FIG. 11, the software architecture for controlling the needle sorting apparatus of the instant invention performs eight (8) main tasks: a Robot Control task 1152; a Vision Control task 1153; a Conveyor Indexing Control task 1154; a SCADA Node Interface task 1155; A Control Panel task 1156; a Task Manager 1157; a Conveyor Initiation task 1158; and, a Lens Control task 1159. Of these eight tasks mentioned above, the first six are active during the needle infeed steady state operation as will be explained below. FIG. 11 additionally shows the data flow among the tasks and the signals which initiate the tasks. It is understood that the software language used in the preferred embodiment, is Adept's V/V+ language, which supports both vision and robotic control in a multitasking environment. Each of the tasks will be generally described below with respect to FIG. 11. A more detailed description of the following tasks can be found in the above-mentioned U.S. Pat. No. 5,568,593.

It should be understood to those skilled in the art that each robot assembly, controllers, and camera vision tracking system requires careful calibration and configuration procedures for the infeed system to properly function. For instance, each robot assembly requires that joint positions be set and joint limits be configured to ensure that the robots avoid structural damage when enabled. Furthermore, a camera-to-robot calibration is required so that the vision system may accurately compute the positional coordinates of the needle so that the robot may move to the pick position. This procedure provides a translation matrix between the camera's field-of-view and each robot base position.

The PLC 120 is responsible for initially powering the robot controllers and robots. A robot calibration procedure may be initiated after power-up to move the robot joints to known "home" positions to synchronize the digital encoders (not shown).

The process of starting the PLC 120, robot controllers, and conveyors 55a,b, and 60 is time-critical. From the robot controller perspective, when a ROBOT ENABLE signal 1119 is raised by PLC 120, it begins its normal cycle by executing the Robot Control Task 1152, the Vision Control Task 1153, the Conveyor Indexing Control Task 1154, and the Conveyor Initiation Task 1158; which initiates the movement of conveyor 55a, waits approximately up to two (2) seconds, and then initiates the movement of second conveyor 55b as will be described in detail below. The PLC simultaneously raises the ROBOT ENABLE signal on the other Adept robot, shown in FIG. 11. Under this scenario, the PLC integrates the startup of the Bulk Feeding Device System, the Indexing Conveyors, and swaging machine with the raising of the ROBOT ENABLE signal 1119. As will be explained in further detail below, when the ROBOT ENABLE signal goes low, the Adept robot halts its standard processing and responds to requests from the SCADA node.
Robot Control Task There is a single Robot Control task associated with each Adept® controller for each robot assembly 58a,b, although only one is indicated as element 1152 in FIG. 11. The control system software for the Robot Control task 1152 manages the respective robot assembly 58a or 58b as a resource, reads a FIFO buffer 1055 of identified needle locations which are produced by and input from the Vision Control Task 1153, interfaces with the programmable logic controller (PLC) 120 of control system 999 for needle placement handshaking, and, initiates the indexing of the conveyor belts 55a,b.

The steady state operation of the Robot Control task 1152 for each robot assembly 50a, (50b) is as follows:

First, the respective robot controller continuously polls its input FIFO 1055 via data line 1093 to obtain positional coordinate data for the identified needle locations on a respective translucent conveyor 55a or 55b. The data for the needle locations are provided to the FIFO buffer from the Vision Control task 1153 via respective data lines 1097 as will be explained in further detail below. When an acceptable (recognizable) needle position is entered into the FIFO buffer 1055, the robot controller will remove the needle position from the buffer and direct the robot gripper arm 55a, (55b) to move to that location on the conveyor belt. Next, for each recognized needle, the Robot Control task 1152 will signal the robot gripper 55a, (55b) to close on the needle barrel portion 7 and to depart from the conveyor to an approach location proximate the precision conveyor 35. The robot control task then generates a NEEDLE IN GRIPPER signal 1107 to the PLC as indicated and waits for a response from the PLC 120. As shown in FIG. 11, when the PLC receives a Robot task generated NEEDLE IN GRIPPER signal 1107, the PLC 120 will generate a SAFE TO PLACE signal 1091 for receipt by each of the robots 50a,b. The purpose of the SAFE TO PLACE signal 1091 is to inform the respective robot assembly 50a,b that a needle may be placed onto a precision conveyor boat 70 of conveyor 35. As a response to the receipt of the SAFE TO PLACE signal 1091, the Robot Control task 1152 will generate a DON'T INDEX PRECISION CONVEYOR signal 1104 for receipt by the PLC 120 immediately before it places the needle on the precision conveyor 35. While this signal remains high, for e.g., at a logic "1" state, the Adept® robot 50a or 50b will attempt to place a needle onto a boat 70 of precision conveyor 60. This involves initiating the engagement jaws 77,79 of the precision conveyor engagement boat 70 to retract to allow the placement of the needle therebetween, as will be explained below. Once the movement of the robot has settled and a needle is placed, the Robot task 1152 will generate a NEEDLE PLACE COMPLETE signal 1106 for receipt by the PLC 120 and, the PLC will generate a suitable control signal 1109 to enable the engagement jaws of the precision conveyor engagement boat 70 to engage the needle. In the preferred embodiment, the dwell time of the NEEDLE PLACE COMPLETE signal 1106 is approximately 48–64 milliseconds. After activating this signal, the robot assembly 50a,b will hold the needle in place for the same time period. (48–64 msec.) Immediately thereafter, the robot will open its grippers and move back to its approach location away from the engagement boat 70. Finally, the DON'T INDEX PRECISION CONVEYOR signal 1104 is removed indicating that it is now clear for the precision conveyor 35 to index which is performed at the command of the PLC 120.

As a safety interlock for conveyor index initiation, the Robot Control Task 1152 will signal the Conveyor Indexing Control Task 1154 with an internal control respective LAST PICK signal 1092, 1096 indicating that the robot assembly, 50a or 50b, has picked up the last needle from the current conveyor as indicated in FIG. 11. If the maximum number of needles expected per current camera field-of-view (hereinafter "FOV") is not picked from the respective current infeed conveyor belt 55a, (b), the Robot Control Task 1152 will request the Conveyor Control task 1154 to index that conveyor belt "early" via the INDEX CONVEYOR 1 EARLY or the INDEX CONVEYOR 2 EARLY signals 1111,1112 as shown in FIG. 11. Since all signals affecting the motion of the conveyors are routed through the Conveyor Control task 1154, this task will generate a corresponding INDEX CONVEYOR 1 EARLY, signal 1111' or INDEX CONVEYOR 2 EARLY, signal 1112', for receipt by the other adept robot. If during normal operation a Robot Control Task receives either Index Conveyor 1 Early or the Index Conveyor 2 Early signal, it will flush the contents of its FIFO buffer 1055 and continue as if the last needle has been picked from the conveyor.

The control software must take into account the floating 16–32 ms duration of a digital output based on the time slicing of V/V+. This will affect the calculation for minimum time required for placement in conjunction with setting and resetting the Don't Index Precision conveyor signal 1104.

The Robot Control Task 1152 performs error recovery on two type of errors. These errors are grouped as indexing errors and gross errors. As in all other tasks, gross errors cause the Task Manager 1157 error recovery to respond and stop the Robot Control Task immediately. An indexing error occurs if a robot is waiting for a needle to be placed in its parts FIFO and both conveyor belts have not indexed within an appropriate amount of time. The Robot Control Task 1152 recovers from this type of error by requesting the other robot to index early via signals INDEX CONVEYOR 1 EARLY and INDEX CONVEYOR 2 EARLY signals 1111,1112 respectively. This forces both vision/robot control systems to flush the contents of its current parts FIFO and index the conveyor belts.

Conveyor Indexing Control Task

The Conveyor Indexing Control Task 1154 initiates the indexing of each respective translucent indexing conveyor 55a,b, and the task is initiated by the Conveyor Initiation task 190. All signals affecting the motion of the conveyors are routed through the Conveyor Control task 1154. As shown in FIG. 5, the precision conveyor is controlled by needle conveyor servo motor 115a and servo controller 116a shown which receives commands from the control system computer and PLC 120, e.g., for indexing control, as now described.

As shown in FIG. 11, the first step of the Conveyor Indexing Control task 1154 is to check for the LAST PICK signal 1092,1096 internally generated from the Robot Control Task 1152 and indicating that the last needle pick-up from the respective infeed translucent conveyor 55a,55b has been completed by one of the Adept® robots 50a,b. Alternatively, the Conveyor Indexing Control task 1154 awaits for the INDEX CONVEYOR EARLY (1 and 2) signals 1131,1132 internally generated from the Vision Control task 1153 when no needles are recognized in the current camera FOV. As a result of receiving the LAST PICK signals 1092,1096 from the robot task, the Conveyor Control task will generate a corresponding INDEX CONVEYOR 1 signal 1098, or, an INDEX CONVEYOR 2 signal 1099, for receipt by the PLC 120. It is understood that each Adept® robot controller must request the PLC 120 to index a translucent indexing conveyor 55a(,b) after picking up the last needle from the respective conveyor. Therefor, the other Adept® robot must generate its corresponding INDEX CONVEYOR 1 (or INDEX CONVEYOR 2) signal for receipt by the PLC before it can command the current translucent conveyor 55a, (55b) to index. As a result of receiving the INDEX CONVEYOR 1 EARLY, signal 1111' or INDEX CONVEYOR 2 EARLY, signal 1113' from the Conveyor Control task 1154 indicating that the maximum number of needles have not been picked up or that there are no or insufficient needles in the respective camera's FOV, the other Adept robot will generate a corresponding CONVEYOR 1 INDEXED EARLY signal 1098', or CONVEYOR 2 INDEXED EARLY signal 1099' for receipt by the Conveyor Control task 1154, as shown in FIG. 11. These signals will cause the corresponding conveyor 55a, (b) to abort processing and initiate indexing of the belt.

After receipt of both INDEX CONVEYOR 1 or INDEX CONVEYOR 2 signals 1098,1099 from each of the robot assemblies, the PLC 120 commands the translucent indexing conveyor 55a to index and generates a corresponding CONVEYOR 1 SETTLED signal 1141 or, a CONVEYOR 2 SETTLED signal 1142 for receipt by the Conveyor Control Task 1154. Note that the CONVEYOR 1 SETTLED signal 1141 and the CONVEYOR 2 SETTLED signal 1142 are raised approximately 2 seconds after the PLC has been requested by the robot control task 1152 to index conveyor 55a, (55b). The Conveyor Control Task 1154 then informs the Vision Control task 1153 to begin needle imaging upon receipt of internal control signals 1141',1142' that correspond to the respective CONVEYOR 1 SETTLED and the CONVEYOR 2 SETTLED signals 1141,1142. Once the indexing conveyor 55a (55b) has been indexed and the corresponding CONVEYOR SETTLED signal 1141,1142 has been received, the Vision Control Task 1153 may begin needle recognition in the corresponding cameras's FOV. Specifically, as will be explained below, the cameras 62,64 above conveyor 55a,b, each take a snapshot of the respective field of views at respective illuminated portions 30a,b of the translucent conveyor and the Vision Control task 1153 will control the processing of the image to make a determination of whether a recognizable needle is present each camera's field of view.

At this point, a distinction must be made between the mere presence or detection of a needle in the field of view and the presence of a "recognizable" needle. A needle may be present, but, for a variety of reasons, the Vision Task 1153 may not be able to determine its positional coordinates until the camera vision parameters are changed by the execution of an auto-imaging algorithm which automatically adjusts the iris and vision system lighting parameters of each camera so that the cameras may subsequently obtain enhanced images that may be processed. During steady state, when the vision task has already "recognized" a needle in its respective field of view, the auto-imaging algorithm is not repeated.

Vision Control Task

The Vision Control Task 1153 controls and processes the images taken by each of the two camera assemblies 62,64. Since the timing of the two translucent conveyors are phased, only one camera is operating at one time.

Specifically, as shown in FIG. 9, the Vision Control task 1153 interfaces with each respective camera 62,64 to identify the needle locations of recognizable needles in that camera lens's respective field of view encompassing an area located at respective illuminated platforms 30a,30b. The Vision Task 1153 then processes the positional and orientation information of the identified needle locations and writes those locations to the Robot Task FIFO 1055 via data lines 1097. As mentioned above, the Vision Control task is additionally responsible for initiating an early conveyor index if no needles were imaged in a camera field of view.

As described briefly above, the Vision Control task runs each time either conveyor 55a,55b completes indexing. It is initiated to begin needle recognition upon receipt of either a CONVEYOR 1 SETTLED signal 1141' or CONVEYOR 2 SETTLED signal 1142' which is generated by the PLC 120 and routed through the Conveyor Control task 1154 each time respective translucent indexing conveyor 55a,55b has ceased indexing, as commanded by the Adepts. Each CONVEYOR SETTLED signal 1141,1142 goes high (logic "1") approximately two (2) seconds after the PLC has been requested by the Adept® robot to index a translucent indexing conveyor. Each of the CONVEYOR SETTLED signals 1 and 2 (1141,1142) remain high until the PLC 120 receives the next respective INDEX CONVEYOR 1 or 2 signal 1098,1099 from the Adept robots.

The Vision Task 1153 activates that camera which is associated with the conveyor settled signal. When activated, the camera 62,64 takes a picture of the backlit areas 30a,b of the conveyor belt 55a,(55b). Any image obtained is preferably converted to binary image data for subsequent digital processing. The Vision Control task 1153 utilizes "vision tools" to detect acceptable needles, and places the coordinates of acceptable needle pick-up points in the FIFO buffer 1055 for the Robot task. An "acceptable" needle in the backlit areas is a needle that measures within the tolerances of the needle parameters that have been previously accepted during the needle changeover procedure. The needle changeover procedure is a procedure to inform the infeed system software of the type and size of the needles in the current batch to be processed and must be executed before making needle batch changes as to be discussed below. Specified needle tolerances are for the needle radius, barrel width, angular characteristics of the needle with respect to the robots, and the calculated area as computed from the needle parameters.

Auto-Imaging Algorithm

As mentioned above, if a detected needle is unrecognizable, the auto-imaging algorithm is invoked to change the camera vision parameters. Thus, after the binary image data is processed, a determination is made as to whether the needle image is of the specified radius, whether the needle image is of the specified barrel width, whether the needle image has the specified angular characteristics, and, whether the needle image area is within the specified tolerance. If any of these criteria are out of specification, then an auto-imaging algorithm is executed which functions to take a series of pictures of the same needle image at the respective camera's field of view to thereby enhance the needle image for better needle recognition by improving the vision parameters between pictures. Thus, after each of the series of pictures is taken, the auto-imaging algorithm will automatically adjust the camera's iris and vision system lighting parameters to enable the vision system to image the needles properly within the camera's field of view. For example, when adjusting the lighting of the fields of view, certain camera vision parameters such as the gain, offset, and binary threshold may be modified. The auto-imaging algorithm is executed until a needle is recognized in each camera's field of view and is not repeated until a needle changeover is executed.

Even when the cameras of the Vision Control task 1153 are adjusted, needle images may still not be imaged properly. This is because each camera's field of view utilizes a backlighting source and needles that overlap, touch with each other, or, are clipped by field of view edge boundaries will not be considered for recognition. Thus, the Vision Control task will make a determination of whether the needles overlap or touch each other, and, will determine whether the needles are too close to the edge of the field of view.

After all of the possible needles are recognized, the Vision Control task will calculate the needle pick-up coordinates of the acceptable needles and place them in the Robot Control task FIFO buffer 1055 to enable the robot to pick and place the acceptable needle onto the precision conveyor. In the preferred embodiment, the maximum number of needles that can be recognized during each dwell cycle of each translucent indexing conveyor is three (3). If less than this maximum or if no needles are recognized, a robot may be signaled to index the corresponding conveyor early, causing the vision system to abort its processing as described above.

Vision Task 1153 is responsible for limiting the number of needle locations written to the FIFO to three, since the Robot Control Task will pick and place a needle for every needle location passed to the FIFO 1055. In the preferred embodiment, the Vision Task is limited to operate for five seconds per indexing conveyor cycle.

The Vision Control Task 1153 performs error recovery on three types of errors. These errors are grouped as imaging errors, processing errors, and gross errors. The gross errors cause the Task Manager error recovery to respond and stops the Vision Control Task 1153 immediately. When an imaging error occurs, the Vision Control Task 1153 suspends all execution on the current FOV and requests an early index of the conveyor belt by generating either INDEX CONVEYOR 1 EARLY or INDEX CONVEYOR 2 EARLY signals 1131, 1133 as discussed above. Receipt of these signals causes no needles to be placed in the parts FIFO and forces both vision/robot systems to pass on the current FOV of needles. If a processing error occurs, the Vision Control Task suspends all processing on the current needle and begins processing a new needle in the same FOV if another needle is available. As a result, the Vision Task does not insert the needle into the parts FIFO.

Conveyor Initiation Task

The Conveyor Initiation Task 1158 functions to initiate the Conveyor Indexing Control task 1154 and is started whenever the ROBOT ENABLE signal 1119 is raised from the PLC 120. Once started, this task requests an INDEX INFEED CONVEYOR 1 (55a), signal 1137, then waits approximately two (2) seconds, and requests an INDEX INFEED CONVEYOR 2 (55b) signal 1139, as shown in FIG. 11. The task 1158 is then terminated and is not restarted again until the ROBOT ENABLE signal 1119 is lowered and raised again.

Task Manaaer

The Task Manager 1157 initializes the software and hardware I/O signals, the global variables, and the vision/robot system tasks. Once the vision/robot system tasks are running, the task manager monitors the integrity and status of each task currently running and the resources that are controlled by these tasks. The status poll signals 1147a–1147f are indicated in FIG. 11. The resources are the robot, communication ports, and the I/O signal lines. The Task Manager reports any errors to the PLC, via the SYSTEM FAIL signal 1122, and the SCADA node, via the SCADA Node Interface Task 1155. The SYSTEM FAIL signal 1122 is generated whenever a robot (as detected by the Task Manager) has recognized a gross error which prevents it from continuing operation. This signal is active-low and remains low until the Adept robot is reset. Thus, the PLC must lower the ROBOT ENABLE signal 1119 immediately upon receiving this signal.

For gross errors occurring with the vision/robot control software, the Task Manager 1157 is utilized to detect and recover from these errors by continuously polling the status and integrity of all steady-state tasks and resources during program execution. If it is determined that a gross error has occurred, the SYSTEM FAIL signal 1122 will be raised to the PLC 120 and all tasks except the SCADA Node Interface Task, the Control Panel Task and the Task Manager will be stopped. A code indicating the reason for the last unrecoverable error will be available to the SCADA Node through the SCADA Node Interface Task. In some cases, an error message will be displayed in the Monitor Window of the Adept robot controller. After the SYSTEM FAIL signal is raised, the Task Manager will attempt to correct any problems detected on the robot and notify the operator through the Monitor Window. In most cases, the operator will only need to raise the ROBOT ENABLE signal again to re-set the vision/robot control software.

The Precision Conveyor

Figure 12A:
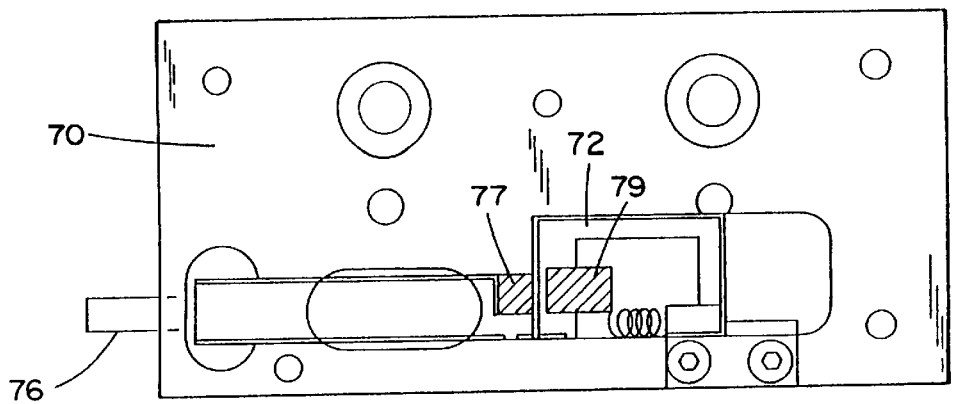
FIG. 12(a) is a detailed view of the precision conveyor boat having jaws for engaging and retaining an oriented needle for subsequent swaging.
Figure 12B:
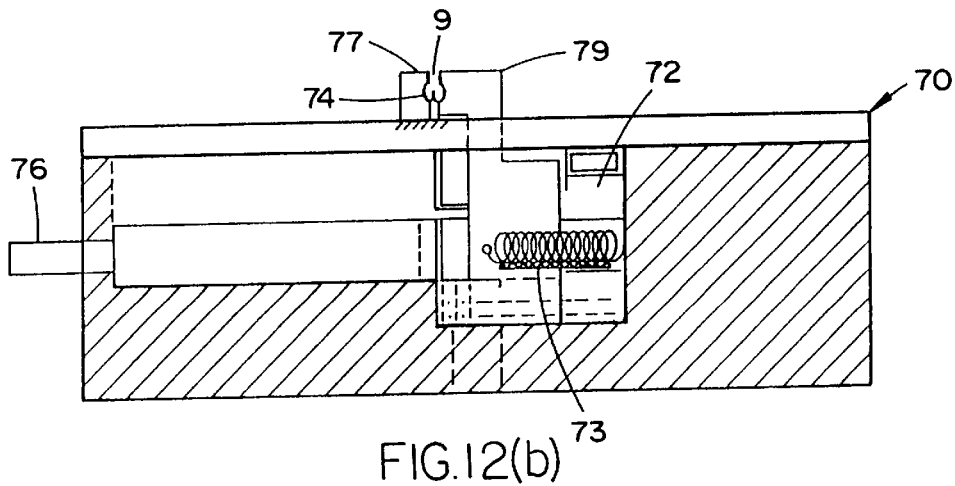
Figure 12C:
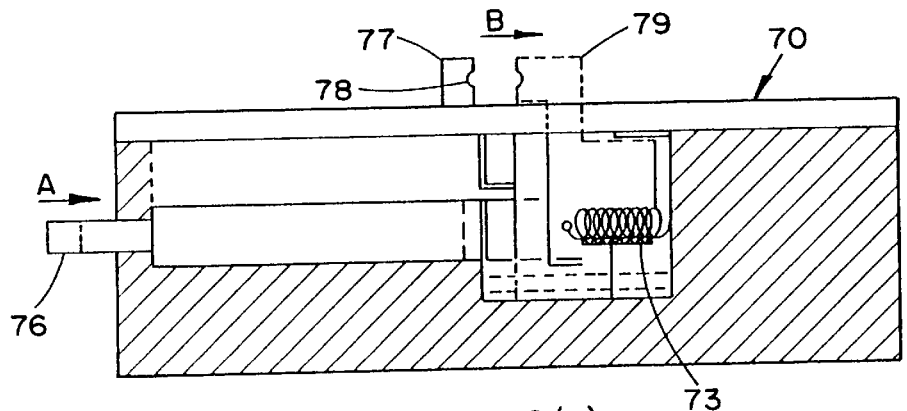
FIG. 12(c) is a detailed view of the precision conveyor boat with movable jaw extended for placement of needle oriented for automatic swaging.

FIGS. 12(a)–12(c) illustrate the precision conveyor boat 70 to which each needle 9 is transferred. Each boat 70 is preferably provided with a pair of jaws; one jaw 77 being fixedly mounted, and the second jaw 79 being slidable within pocket 72. In operation, a push rod 76 associated with each boat is pushed in the direction of the arrow "A" shown in FIG. 12(c) to compress spring 73 which retracts the position of the movable jaw 79 in the direction indicated by the arrow "B" to allow the robot gripper to place needle 9 within the notch 78 formed by the opening of the jaws in a manner such that the butt end of the needle 9 is engaged by gripping jaws. After deactuation of push rod 76, spring 73, and hence movable jaw 79, are biased back to their initial position, as shown in FIG. 12(b), with both jaws 77 and 79 engaging needle 9 in the notch 78. It should be understood that any type of releasable engaging mechanism may be provided for releasably retaining a needle 9 on conveyor boat 70, provided that each needle be correctly oriented on its respective boat for subsequent swaging to take place.

Figure 13:
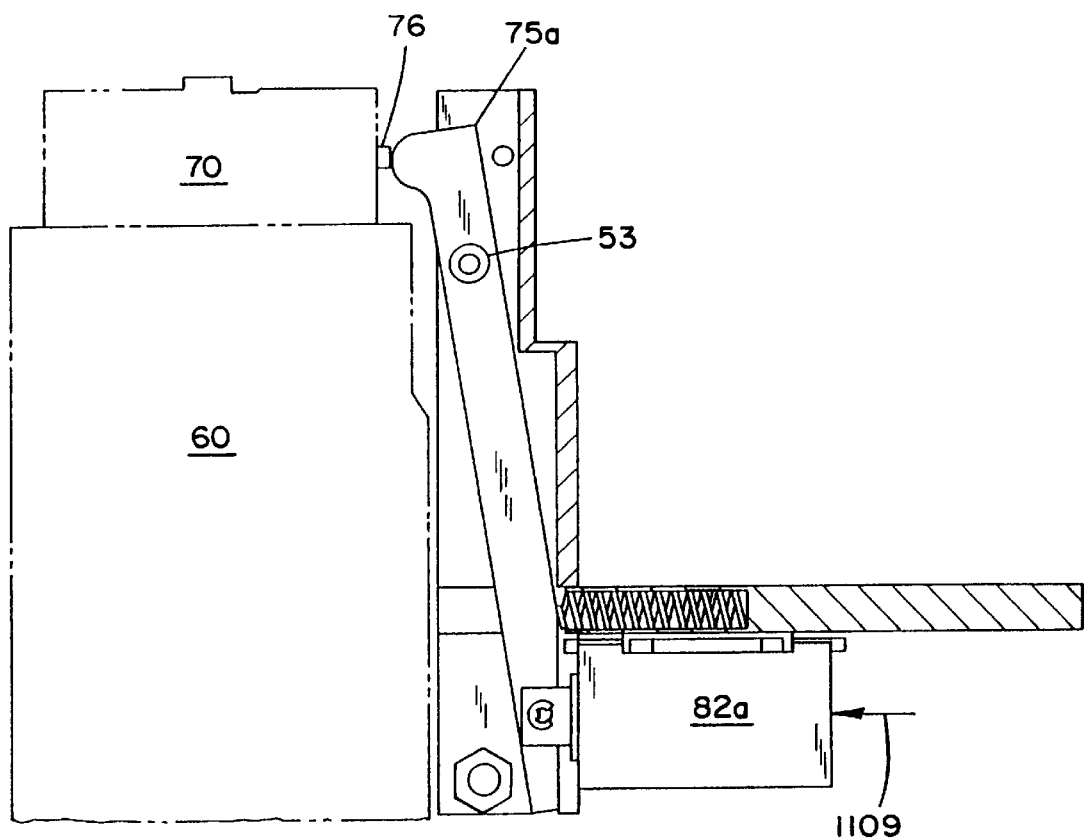
FIG. 13 is a side view of the robot load solenoid that actuates the jaws of the precision conveyor boat.

FIG. 52(d) illustrates the pneumatic operated boat opener cylinders 82a,b actuated by respective solenoid valve 804a, 804d under the control of control system 1000 each time a needle 9 is being placed on a precision conveyor boat 70 by a respective robot assembly 58a,b. FIG. 13 illustrates one boat opener cylinder, e.g., cylinder 82a, that is activated by signal line 1109 from the PLC 120 each time a needle 9 is being transferred to a precision conveyor boat 70 by the robot as described above. The robot load cylinder 82a may be mounted to the precision conveyor by an appropriate mounting plate. A sensor mounted on the precision conveyor, is provided to sense the proximity of the precision conveyor boat 70. At such time a conveyor boat is dwelled for transference of a needle 9 thereto, the cylinder 82a is actuated to enable corresponding release arm 75a of to pivot about pin 53 to depress push rod 76 and retract the movable jaw 79 to the position illustrated in FIG. 12(c). The robot arm 59a then positions the needle 9 between the jaws 77,79 of conveyor boat 70 for engagement thereof. The release arm 75a is then retracted by spring 78 as the conveyor boat 70 resumes movement. It is understood that a like control mechanism is provided for release arm 75b (not shown) associated with robot assembly 58b.

As will be described, the boats 70 of precision conveyor 60 are adapted to sequentially hand-off a needle to a multi-axis gripper (hereinafter "MAG") mounted on the swage dial 150 and indexed thereto in an extended position. Each MAG is adapted to receive the needle from the precision conveyor boat for subsequent transfer to the automatic swaging station 200. For automatic swaging to take place at the swaging station 200, it is necessary that the needle be precisely positioned within the notch 78 of engagement jaws 77, 79 of the boat 70. This is because the multi-axis gripper must receive a precisely positioned needle for a suture to be placed within the suture receiving end 13 of needle 9. To ensure that each needle is uniformly oriented for transference to the multi-axis gripper of the automatic swaging station, a needle orientation device, e.g., a "plow" can be provided as shown in FIG. 13(a) to orient each needle while engaged between jaws 76,77 on conveyor boat 56. Alternatively, or in addition, other orientation devices such as a fixed post, or a prepositioner assembly, such as described in co-pending U.S. patent application Ser. No. 09/025,085, can be used to facilitate the needle hand-off at the needle hand-off station 100. Such a prepositioner device (not shown) is adapted to approximately locate the butt end of the needle and a moveable hard stop assembly at needle-handoff station 100 to precisely register the butt end of the needle engaged by gripping jaws on the conveyor boats 70 of the precision conveyor 60 to an accuracy of 0.001 inches.

Precise Positioning and the Moveable Hard Stop Assembly

After the needle 9 has been plow oriented in the conveyor boat 70 and pre-positioned as previously described, it is conveyed to a precision positioning station 100 for precise placement before hand-off to the automatic swaging system 200. The precise positioning station includes a reciprocable hard stop assembly 120 illustrated conceptually in FIG. 14(a). As described in detail in co-pending U.S. patent application Ser. No. 09/020,085, the reciprocable hard stop assembly enables a precise positioning surface for the needle in boat 70, typically, to within an accuracy of 0.001 inches of a denoted reference position subsequently used for swaging.

After the needle has been conveyed to the precise positioning station 100 (FIG. 1) by the precision conveyor, it is fed to and gripped by one of the multi-axis grippers positioned on the rotary swage dial mechanism 150 to be indexed through a plurality of stations including a swage station 200 wherein a suture of definite length is cut from a suture spool of indefinite length at tower 220 and inserted into the needle at swage station 200 for permanent assembly thereto in the next machine cycle. After swaging, the needle is advanced to the pull-test station 300 for testing of the needle suture bond, and then indexed to the packaging station 450, under control of control system thread 1000 as shown in FIG. 4.

Multi-Axis Gripper

Figure 14A:
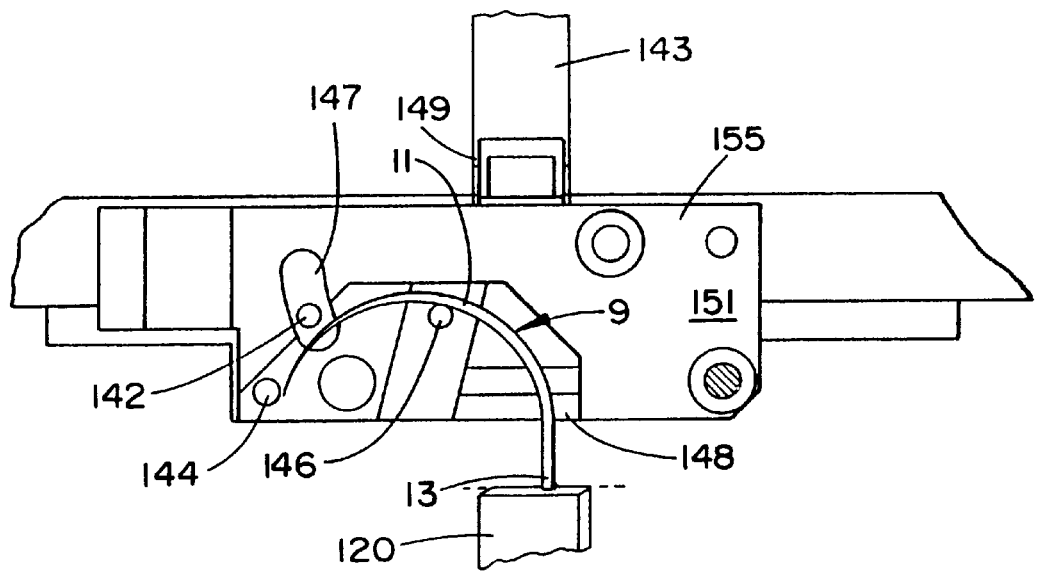
FIG. 14(a) is front face view of the multi-axis gripper 155 showing a surgical needle 9 in a relaxed engagement thereby, and additionally showing pin 142 in a retracted position.
Figure 14B:
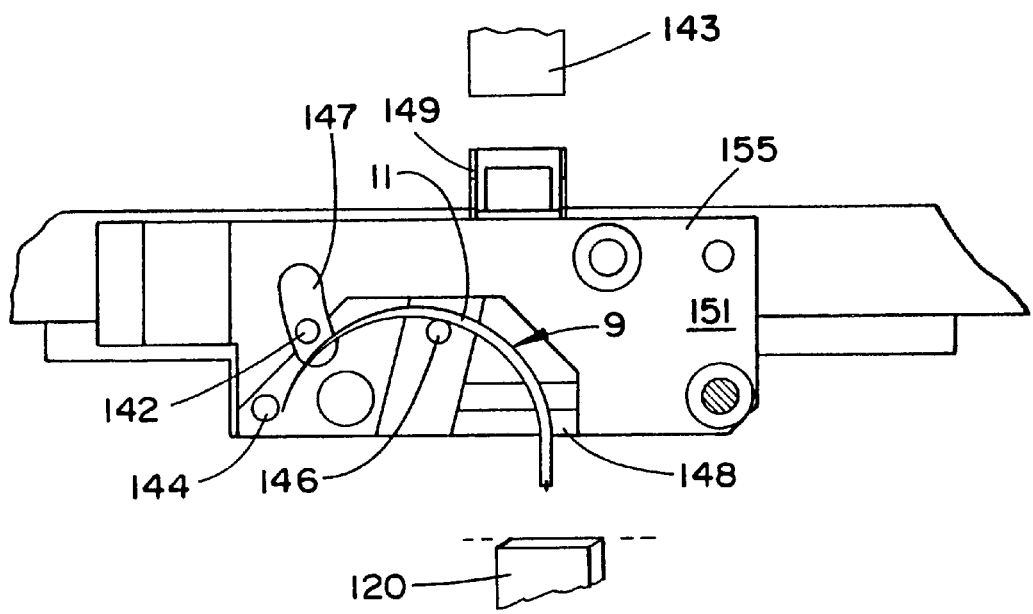
FIG. 14(b) is front face view of the multi-axis gripper 155 showing a surgical needle 9 in an engaged position therein.

Referring now to FIGS. 14(a) and 14(b), the multi-axis gripper 155 of the present invention receives the needle from the precision conveyor boat 70 and moveable hard stop mechanism 120, and transports the needle through the swage operation 200 in which a suture is automatically inserted into the barrel end of the needle, and the metal of the needle swaged about the suture. As can be appreciated, when the opening in the barrel is only 0.0106 and the suture diameter is 0.0088, a high degree of precision handling is required, particularly so when the insertion and swage operation need to be completed in less than 0.5 seconds in order to maintain an 60 needle per minute cycle rate. The multi-axis gripper 155 also transports the needle through the pull test station 300 in which the suture bond is tested and to the packaging area 500, where the armed suture (needle and suture) is automatically packaged.

As illustrated in FIGS. 14(a) and (b), the gripper portion of the multi-axis gripper is illustrated, with three needle gripping pins 142,146,148, that extend outward from the gripper to engage a portion of the needle 9 therein. Pins 146 and 148 are fixed and pin 142 is reciprocable along channel 147 to grip the needle 9 in a three point gripping engagement. The moveable hard stop 120 provides a precise positioning point for the butt end of the needle 9, and the pins 144, 146 of the multi-axis gripper provide precise arcuate placement for the needle. It should be understood that the MAG gripper structure 155 may be simply interchanged with other similar structures which are modified with respect to the engagement points 142, 146 and 148 and related aspects so as to be able to accommodate differently sized and/or curved surgical needles, while the remaining structure is maintained.

In operation, a plurality of multi-axis grippers are employed, each of which grips a single needle for swaging, pull-testing and packaging. Referring to FIG. 14(a), as the multi-axis gripper is moved into position toward the needle, the pin 142 is retracted out of position so that open pins are presented on each side of the needle. The jaws 77,79 of the precision conveyor boat are then opened, and during transfer, the needle rests on the moveable hard stop 120. Pin 142 of the multi-axis gripper is then closed to force the needle into engagement with registration pin 148 to grip the needle and the moveable hard stop is reciprocated out of engagement with the needle, as shown in FIG. 14(b), and away from the jaws 77,79 of the precision conveyor to allow the precision conveyor to advance the next needle into the needle transfer position.

Figure 40:
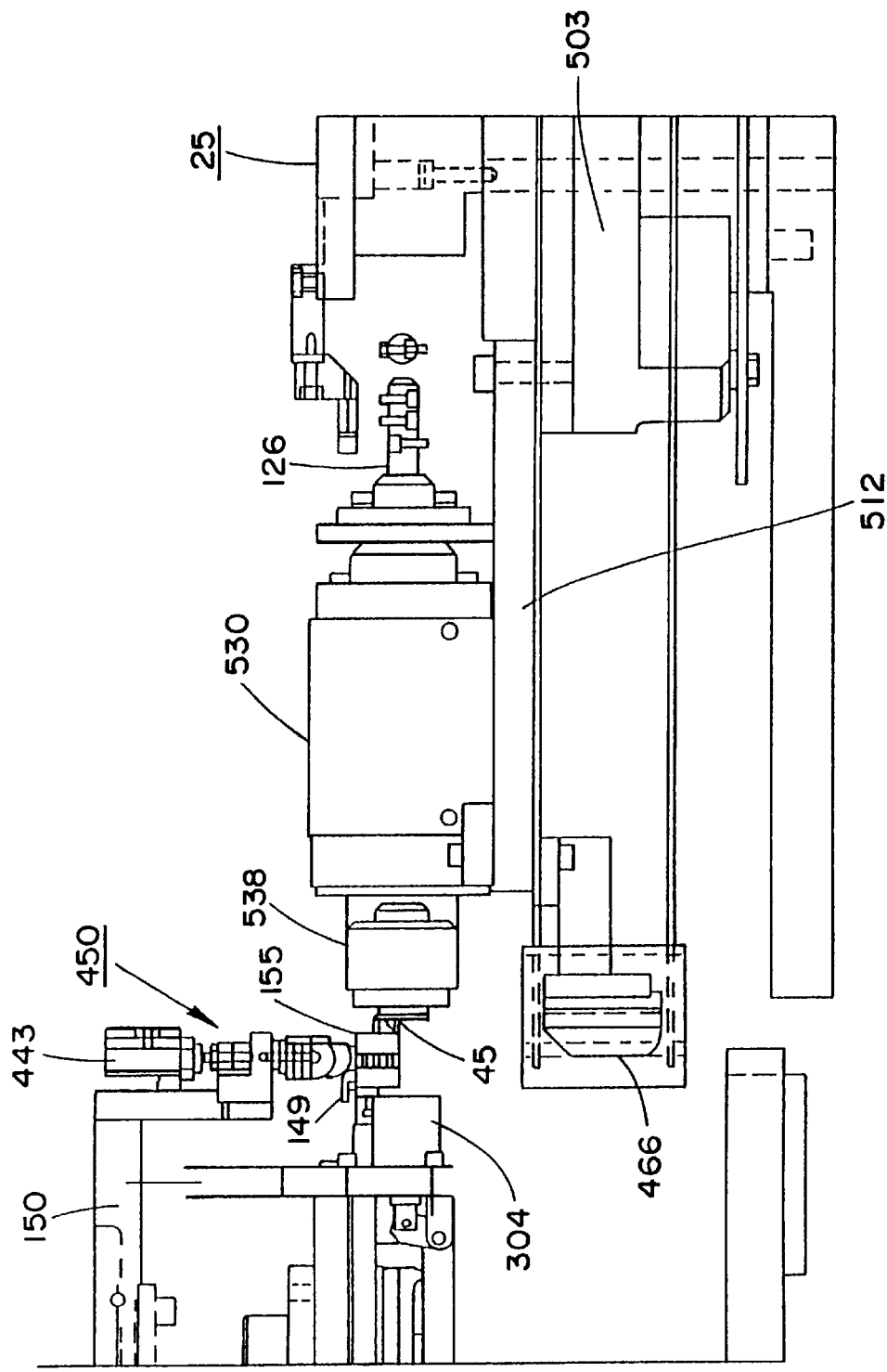
FIG. 40 illustrates the multi-axis gripper 155 of the rotary swage dial 150 extended to insert an armed suture into the suture tray 45 indexed at the needle-suture to package load station 450.

To accomplish the transfer of the needle to the MAG, it must be registered at station 100 so that the gripper pins 144, 146, 148 are confronting the needle precision conveyor boat 70 as shown in FIG. 40. As described in further detail below with respect to FIG. 14(a), the MAG is extended at the needle-transfer station so that gripper pins 144 and 146 penetrate a plane formed by the curvature of needle 9. As the MAG is reciprocated into the plane of the needle, the control system 1000 initiates the command for a solenoid-actuated cylinder 143 to depress a needle release plunger 149 to retract engagement pin 142 to enable feeding of the needle from the conveyor boat 70 to between pins 146 and 148 of the multi-axis gripper 155. As shown in FIG. 52(d), needle release feed cylinder 143 is operated under timing and control of the control system 1000 by actuating solenoid valve 808i. Simultaneously therewith, the control system 1000 initiates the command for a push cylinder or a like device to open engagement jaws 77,79 of the precision conveyor boat 70 (not shown) to release the needle 9 and effectuate the transfer of the needle to the pin assembly of the multi-axis gripper.

Figure 6A:
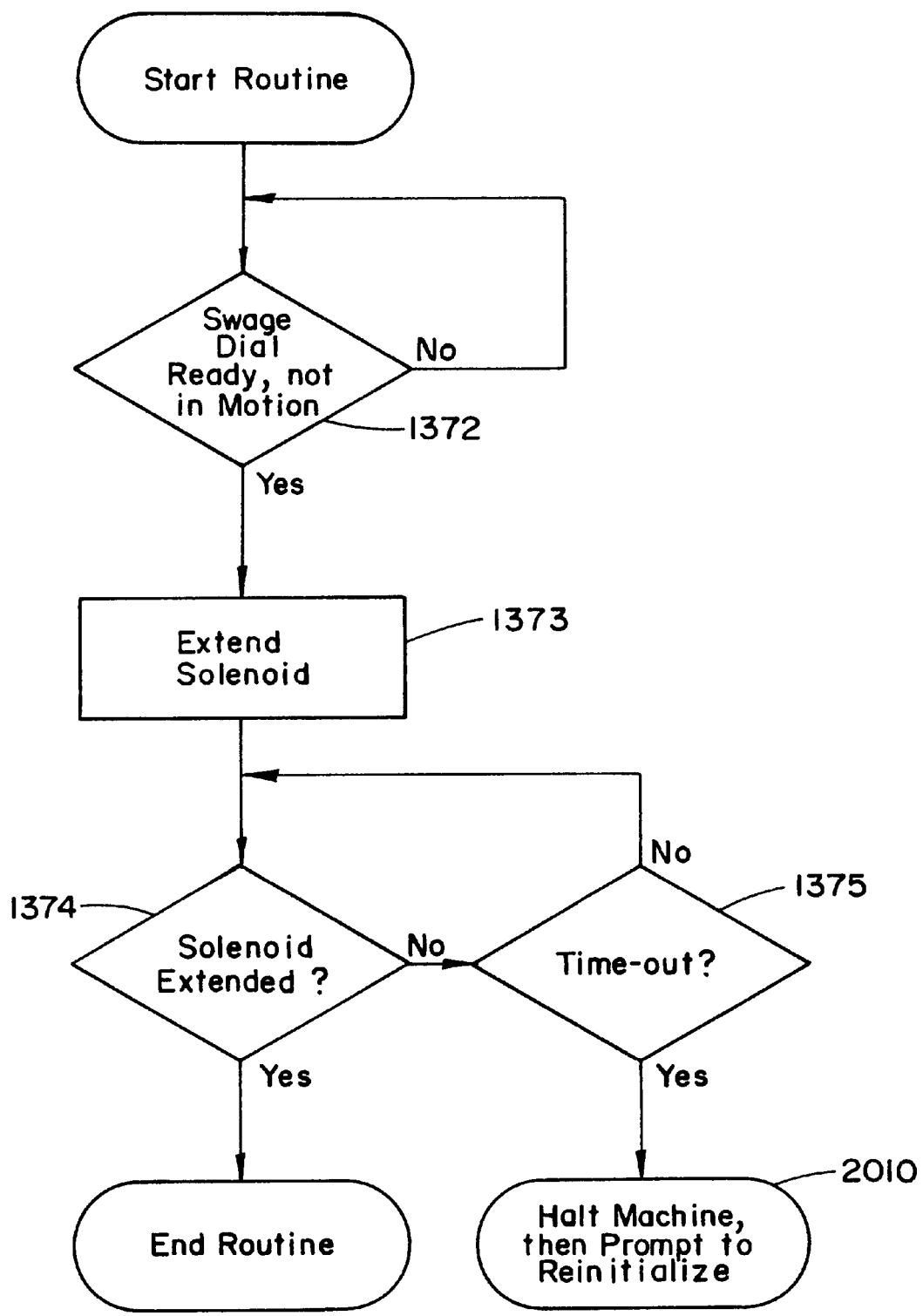
FIGS. 6(a)–6(o) are flow diagrams illustrating the control processes for controlling the rotary swage dial 150 and the needle-suture assembly operations performed at each of the needle-suture assembly stations at the swage dial 150.

As described herein, after indexing of the multi-axis gripper at each of respective stations 100, 200, 300 and 450, it is required that the multi-axis gripper relaxes its grip of the needle while certain operations, e.g., swaging, pull-test, etc., are performed. Releasing of the needle involves controlling a solenoid-actuated cylinder at the various stations to depress the plunger 149 located on the MAG in the manner heretofore described. Thus, as shown in FIG. 6(a), the control system process first waits for the swage dial to stop its motion after an index, as shown at step 1372. Then, at step 1373, the control system generates an extend cylinder signal for extending the solenoid to activate the needle release plunger 149. The system then performs a check at steps 1374 and 1375 to determine whether the suture gripper has closed within the allotted time of the current cycle. If a time-out flag has been generated by the control system indicating a time-out error, the process will be terminated and prompted for reinitialization at step 2010. As shown in FIG. 52(d), the needle release cylinder 243 at the swage station is operated under timing and control of the control system 1000 by actuating solenoid valve 808j. Likewise, the needle release pull-test cylinder 388 at the pull-test station 300 is operated under timing and control of the control system 1000 by actuating solenoid valve 808k, and the needle release hand-off cylinder 443 at the needle-suture load to package station 450 is operated by actuating solenoid valve 8081 as shown in as shown in FIG. 52(d).

Additionally, provided at precision positioning station 100 and is a pneumatically operated side step cylinder shown in FIG. 52(c) as MAG needle side step cylinder 81 operating under control of solenoid valve 804h and control computer 999. This side step cylinder functions to bias the MAG gripper transversely as it moves to its extended position for a more accurate orientation and will be described with respect to the MAG offset cylinder shown in FIGS. 16(d) and (e).

The Swage Dial Drive Assembly

Figure 15:
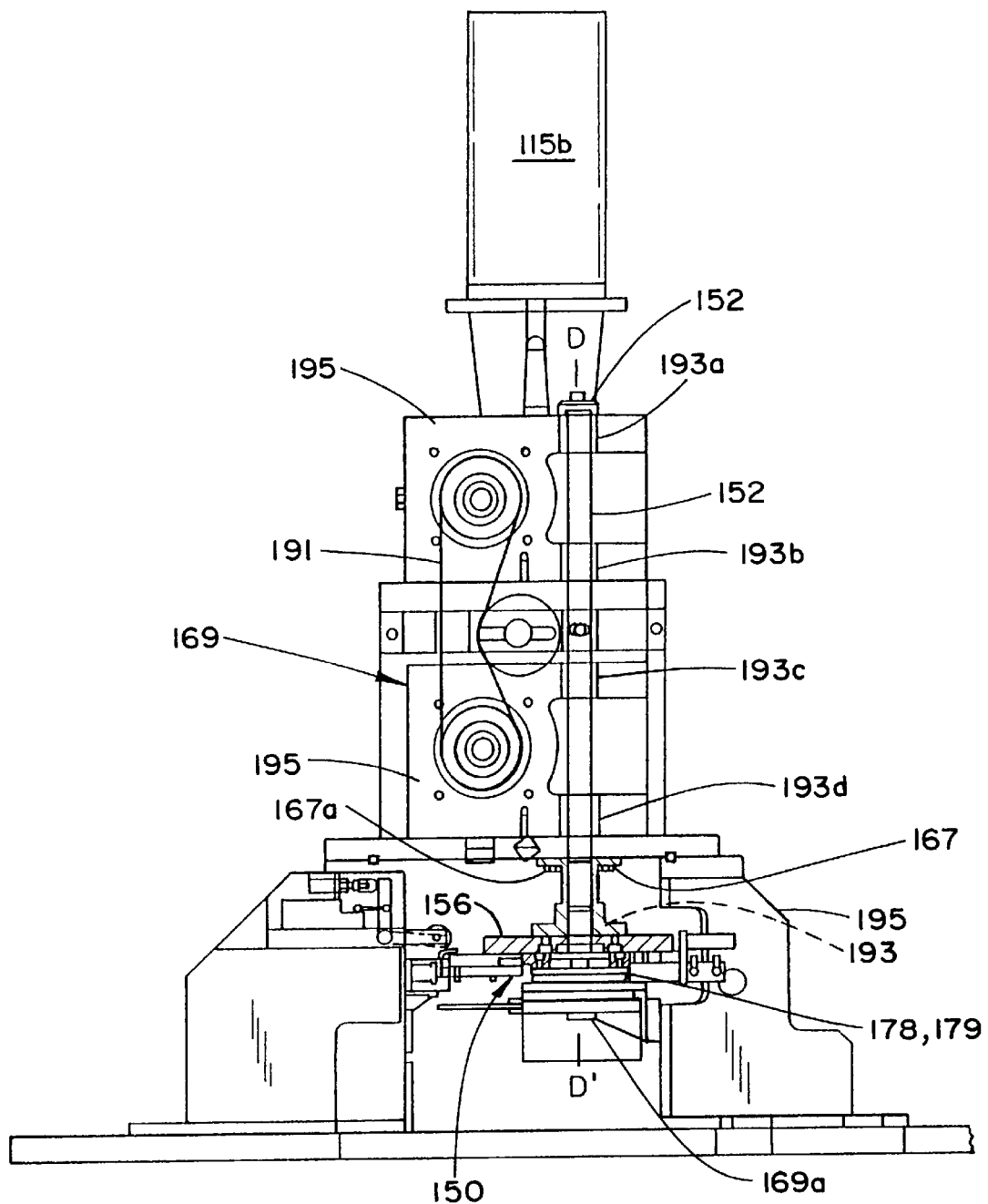
FIG. 15 is an elevation view of a portion the apparatus illustrating the drive for the cam dial and swage dial of the present invention.

The drive assembly for the swage dial 150 is illustrated in FIG. 15. As illustrated in FIG. 15, the swage dial assembly 150 includes a swage dial 150 and a cam dial assembly 156 both of which are independently driven by swage dial drive motor 115b and servo controller 115b as shown in FIG. 5 under control of control system thread 1200, as will be explained. The drive motor 115b drives both of these dials through first and second indexing, drive transmissions and are coupled together with a timing belt 191 in the manner described in co-pending U.S. application Ser. No. 09/020, 085.

The cam dial assembly 156 is mounted on an annular drive collar 167 which connects the output of the second indexing drive 169 to the cam dial plate 156 as more fully illustrated in FIG. 15. The annular drive 167 is journaled for rotation on drive shaft 152 by means of needle bearings 193 to provide a single drive access D–D' for rotation of the swage dial assembly 150. The annular drive collar provides suspension support and rotational drive for the cam dial assembly 156. The use of this annular collar also separates the cam dial and swage dial from the drive apparatus and enables operator workspace for alignment of the apparatus and for part changes when necessary.

The swage dial 150 is mounted for rotation on a ball detent clutch 169a which is fixably attached to shaft 152 and enables breakaway rotation between clutch drive plates 178 and 179 in the event of a catastrophic jam. The clutch 179 and shaft 152 also provide suspension support and rotational drive for the swage dial 150.

The annular cam drive 167 is bolted to the output rive flange of the second indexing drive 169 as illustrated at 167a and provides for both suspension support and rotation of the cam dial assembly 156. Likewise, the breakaway clutch 179 provides physical support and rotational drive for the swage dial 150 by virtue of its fixed mounting on shaft 152 at 169a.

The Swage Dial

Figure 16A:
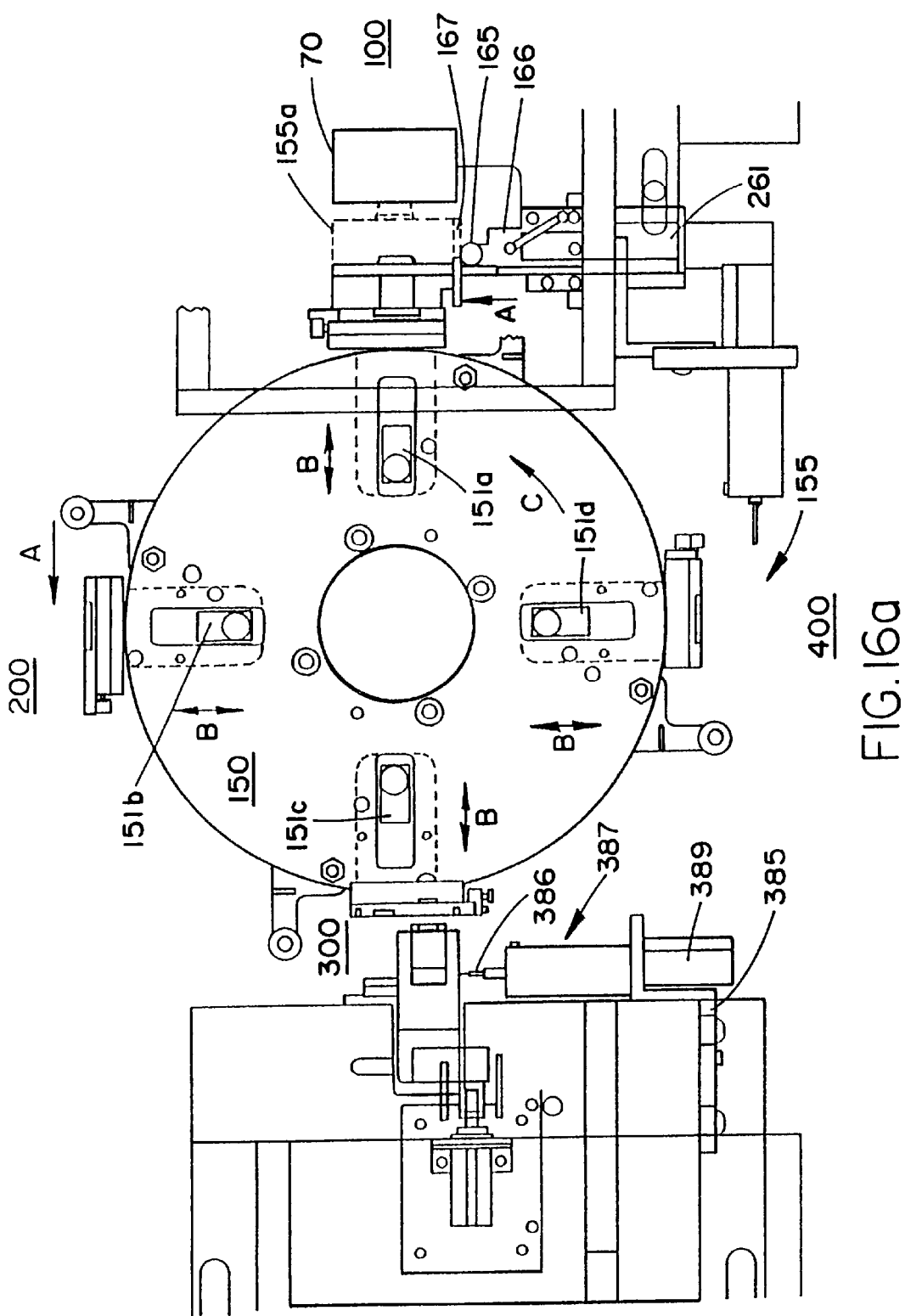
FIG. 16(a) is a top view of the swage dial assembly comprising a swage dial plate having four multi-axis gripper stations mounted thereon.
Figure 16B:
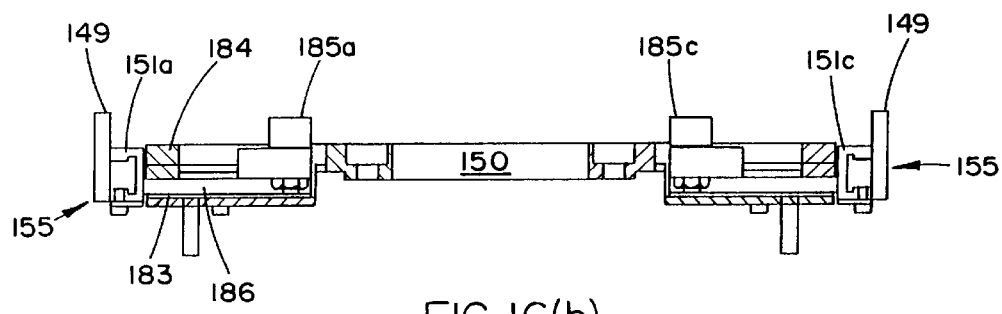
FIG. 16(b) is cross-sectional view of the four station swage dial assembly showing two multi-axis grippers in a retracted position.
Figure 16C:
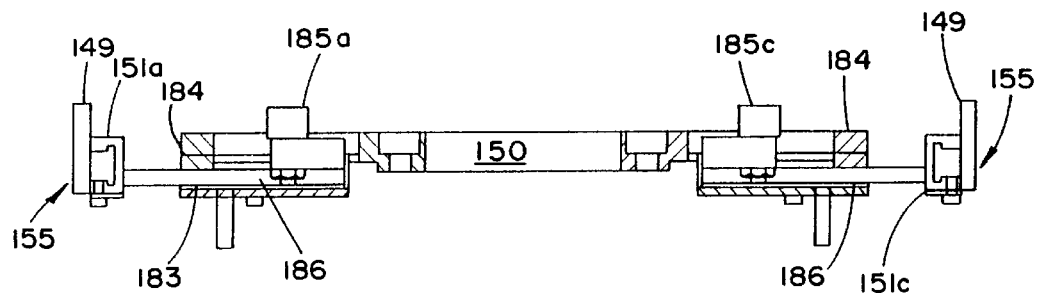
FIG. 16(c) is cross-sectional view of the four station swage dial assembly showing two multi-axis grippers in an extended position.
Figure 16D:
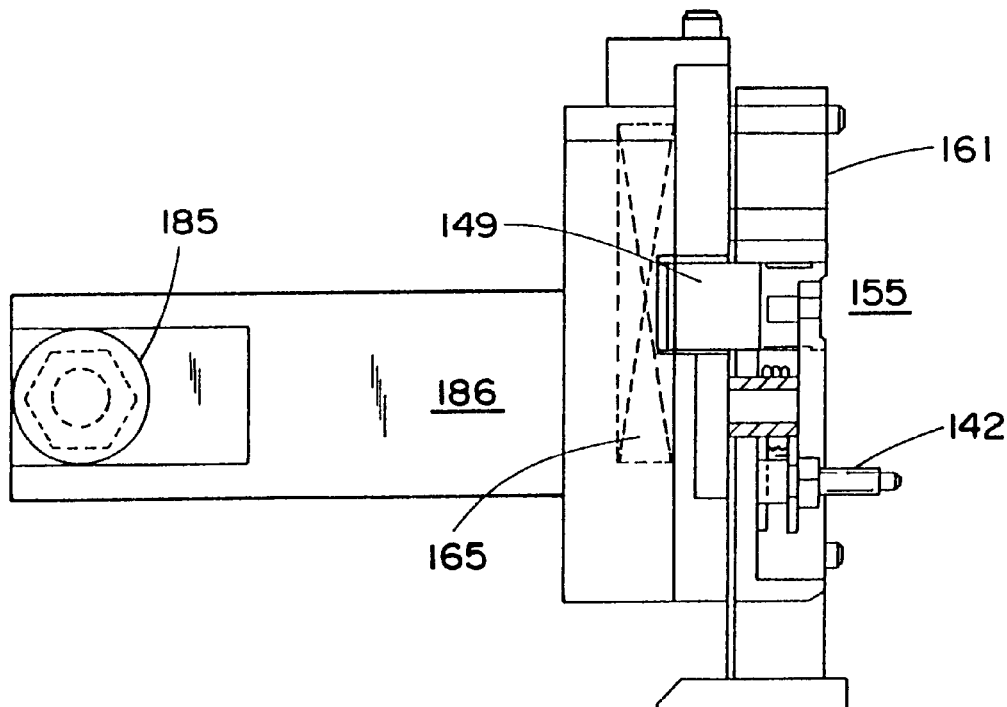
FIG. 16(d) is top plan view of the multi-axis gripper and slide assembly used in the present invention, illustrating in dotted lines the various operating components thereof.
Figure 16E:
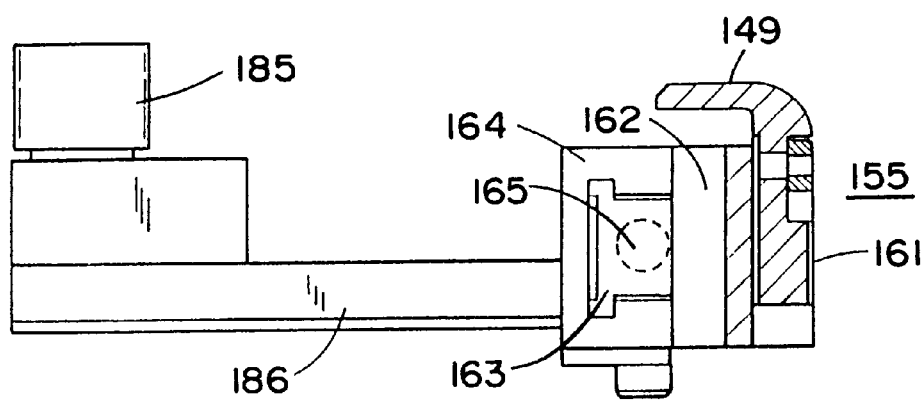
FIG. 16(e) is partially cross-sectioned side view of the multi-axis gripper and slide assembly illustrated in FIG. 16(d).
Figure 17A:
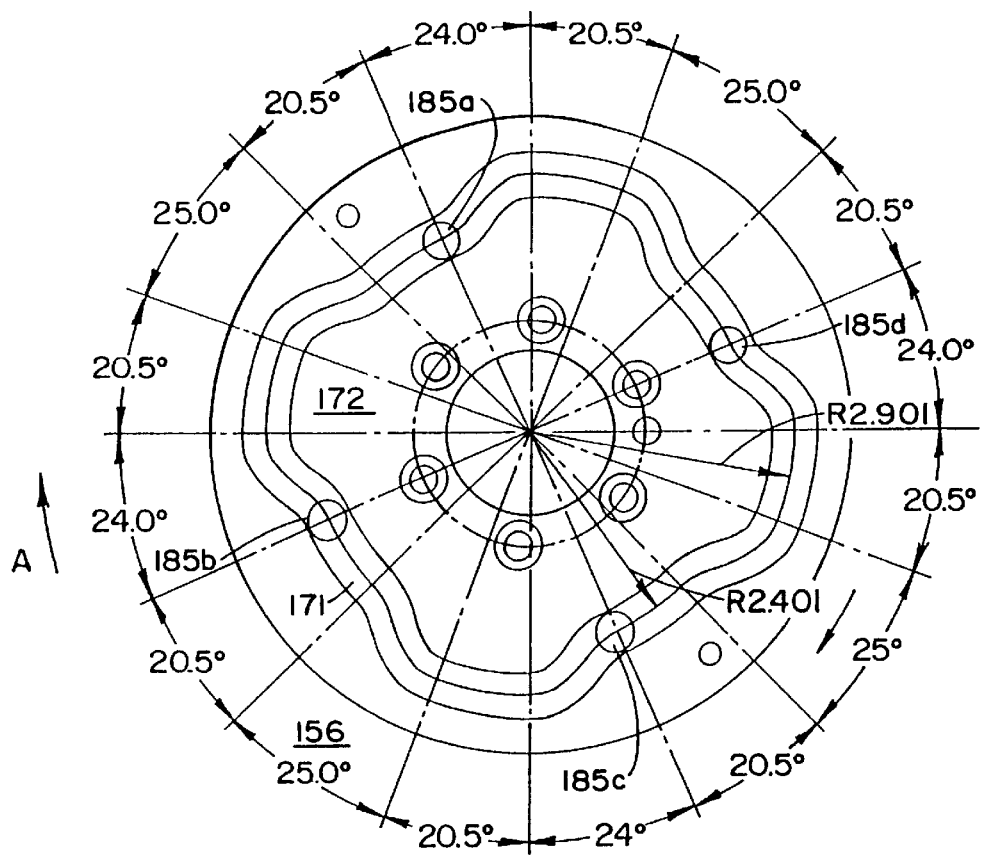
FIG. 17(a) is detailed top view of the cam dial assembly having cam dial plate with a cam follower in a retracted position within a cam track.

The process for extending each multi-axis gripper 155 for needle processing at each of the stations 100, 200, 300, and 400 will now be explained. As shown in FIGS. 16(a), 16(b) and 16(c), each multi-axis gripper 155 is connected to a reciprocating carriage 151 and a cam slide 186. Cam followers 185(a), (b), (c) and (d) are mounted to a cam slide 186 at one end thereof with the multi-axis gripper at the other end. Cam slide 186 is slidable within stationary guides 184,183 and is adapted for reciprocal movement when the cam follower 185 is actuated. In the preferred embodiment shown in FIG. 17(a), cam followers 185(a)–(d) are rollers that fit within the cam track of a rotatable cam dial assembly 156. Cam dial assembly 156 is shown in FIG. 17(a) as comprising a cam dial plate 172 having a continuous cam track 171 which receives cam followers 185(a)–(d) attached to multi-axis grippers 155a,b,c and 155d, respectively. Each cam follower 185 is positioned within the cam track at each station for movement therein.

Figure 17B:
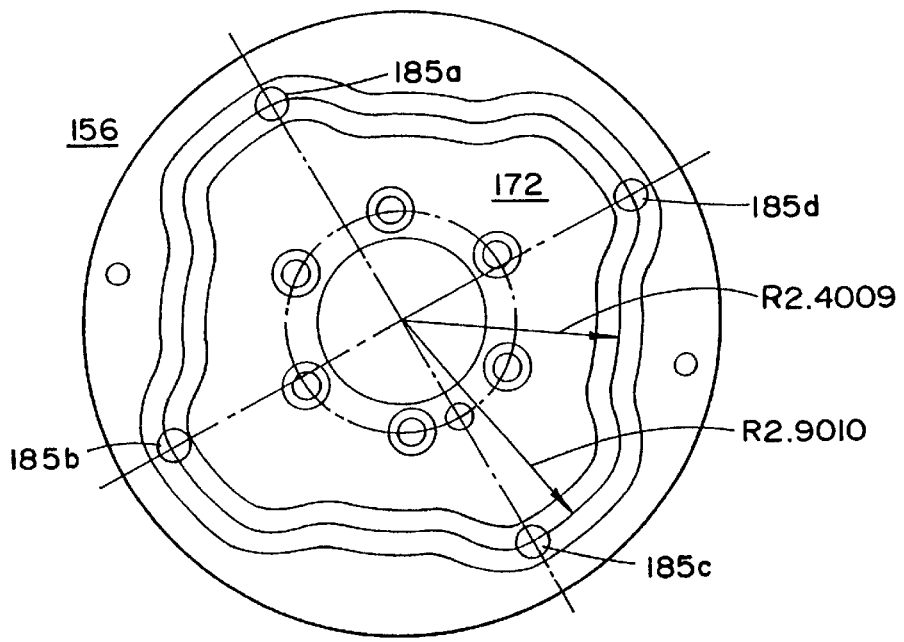
FIG. 17(b) is top view of the cam dial plate showing a cam follower in an extended position within the cam track.

As illustrated in FIG. 17(a), cam dial 172 is positioned above swage dial 150 and mounted coaxial therewith. The cam dial 172 is rotatable about a central axis and controlled by a separate rotary indexing transmission as described previously so that it may rotate separately from the swage dial plate 150. The cam dial is driven in multiple drive and dwell cycles as explained in co-pending U.S. patent application Ser. No. 09/020,085 with the degrees of each phase diagrammatically illustrated in FIG. 17(*a*). FIG. 17(*a*) also shows cam followers 185*a–d* in a first retracted position within the cam track 171. When the dials are in this position, each of the reciprocating carriages and consequently multi-axis grippers 155 are in their retracted position as shown in FIGS. 16(*a*) and 16(*b*) discussed above.

To extend the multi-axis grippers 155 in place at their respective stations, the cam dial plate 172 is rotated in the clockwise direction, as indicated by the arrow A in FIG. 17(*a*), with respect to the swage dial plate 150 held stationary, for approximately 25–45 degrees, forcing cam followers 185*a–d* in cam track 171 to move toward the periphery of the dial as shown in FIG. 17(*b*). Consequently, each of the cam slides 186, reciprocating carriages 151*a*, and the multi-axis grippers 155 move to the extended position as shown in FIG. 16(*c*) enabling simultaneous processing, e.g., swaging, pull-testing, etc. at the assembly stations.

To move the MAG grippers back to their retracted positions, the cam dial plate 172 is rotated in the counter clockwise direction with respect to the swage dial plate 150 for approximately 20 to 30 degrees, forcing cam followers 295*a–d* in the cam track 292 to move to their retracted position (FIG. 16(*b*)). Consequently, the cam slide 186, reciprocating carriage 187*a*, and the multi-axis grippers 155 each move back to their retracted position as shown in FIG. 16(*c*) and discussed above.

When cam dial plate 172 rotates with respect to swage dial 150, each multi-axis gripper 155 is either extended or retracted by the cam track. Thus, the system is designed so that all processes performed at each station occur simultaneously and for approximately the same duration of time when the multi-axis grippers are in their extended position, for e.g., for needle pick-up, for needle swaging, for needle pull-testing, or needle packaging.

When the multi-axis gripper 155 is retracted, the needle engaged thereby may then be indexed to a different station for further processing. To index the needle to another station, both swage dial plate 150 and cam dial plate 172 are rotated together for approximately 90 degrees to position the multi-axis gripper at the next station. For example, when the cam dial plate 172 and the swage dial plate 150 are simultaneously rotated 90 degrees counterclockwise in FIG. 16, the gripper 155 that had received the needle at station 100 is now indexed to station 200 for swaging a suture thereto. Similarly, after swaging, and after the cam dial plate 172 has rotated with respect to the swage dial to retract the MAG gripper, the cam dial plate 172 and the swage dial plate 150 are simultaneously rotated counterclockwise to index the armed needle to the pull-testing station 300 for pull-testing thereof. The operations performed concurrently at each station about the swage dial increases throughput to provide an output of pull-tested armed surgical needles at a rate of approximately 80 per minute in the preferred embodiment.

FIG. 16(*a*) also illustrates roller cam surface 157 which acts on the multi-axis gripper to provide a compound off-set movement of the multi-axis gripper as it is reciprocated outwardly by the swage dial cam plate 172. Each of the multi-axis grippers 155 is mounted for linear movement with respect to the cam slide 186 by means of an off-set slide assembly, the details of which will be.explained as with respect to FIGS. 16(*d*) and (*e*). As indicated therein, the housing 161 of the multi-axis gripper 155 is mounted on a mounting block 162 and slide 163, where slide 163 is spring biased to a home position during reciprocation within slide carriage 164 by spring member 165. This second reciprocal movement is transverse to the reciprocal movement imparted by cam slide 186.

FIG. 16(*a*) illustrates a typical positioning for the off-set drive used to drive cam roller 165 at the precise positioning station 100. Roller cam 165 is mounted on a linear slide 166, which is driven by a pneumatic MAG offset cylinder 261, mounted on the swage dial frame, such as shown in FIG. 52(*c*) actuated by solenoid valve 804*r* under control of control system computer 999. FIG. 16(*a*) also illustrates the relative motions of the multi-axis gripper 155, with arrow A indicating the off-set movement, arrow B indicating the reciprocal movement which results in the radial reciprocation of the multi-axis gripper 155 to 155*a* in FIG. 16(*a*), and arrow C indicating the rotary motion of the swage dial 150.

Indexing of the swage dial 150 is controlled by control system thread 1200 (FIG. 3) for controlling the swage dial servo motor 115*b* as now explained with reference to FIGS. 6(*b*)–6(*c*). As indicated at step 1205, FIG. 6(*b*), a run mode operation is assumed. At step 1210, the swage dial is indexed and simultaneously, by virtue of the cam mechanism described, each of the four multi-axis grippers at each station is extended. At steps 1220 and 1221, a decision is made as to whether the MAGs have been extended within the time period allotted for the current index cycle. If, the MAGs have been extended the process continues to initiate concurrent needle-suture swage processing operations at stations 110, 200, 300 and 450 as indicated at step 1225 and described above with respect to FIGS. 6(*a*), 6(*e*) 6(*f*), 6(*g*), 6(*h*), 6(*l*), 6(*m*), 6(*n*), and 6(*o*). If the MAGs have riot been extended then a time-out flag is generated by the control system indicating a time-out error and the process will be terminated and prompted for reinitialization at step 2010.

Figure 6B:
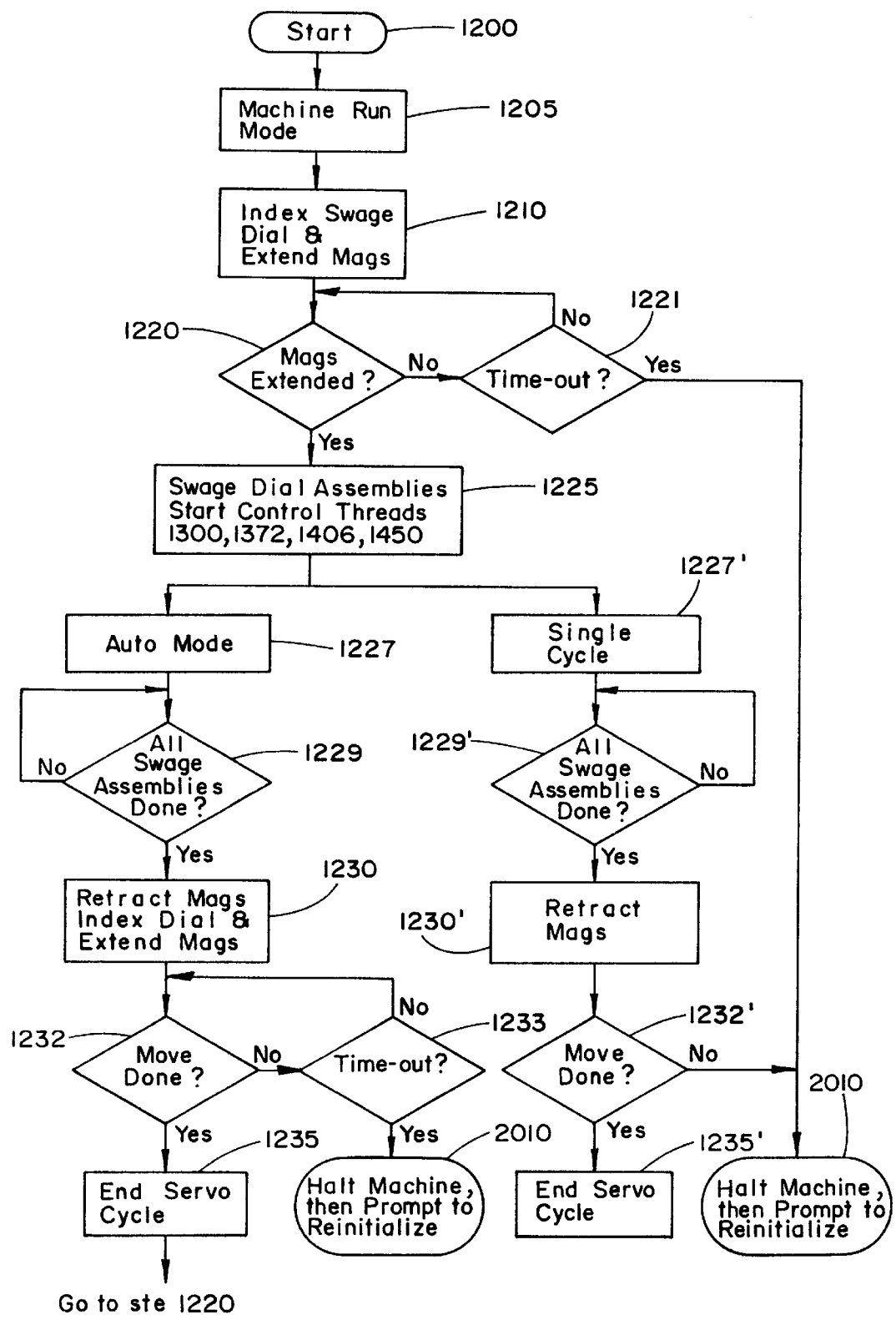
FIGS. 6(p)–6(s) are flow charts showing a procedure 810 for analyzing and using the information obtained during the destructive pull tests, with FIG. 6(q) illustrating a swage die setup routine.
FIG. 6(t) is a chart illustrating the accept and reject ranges for pull-test values.
FIG. 6(u) is a table showing recordation of destructive pull-test measurement values for various pull-tests hperformed in procedures of FIG. 6(p)–6(s).
Figure 6C:
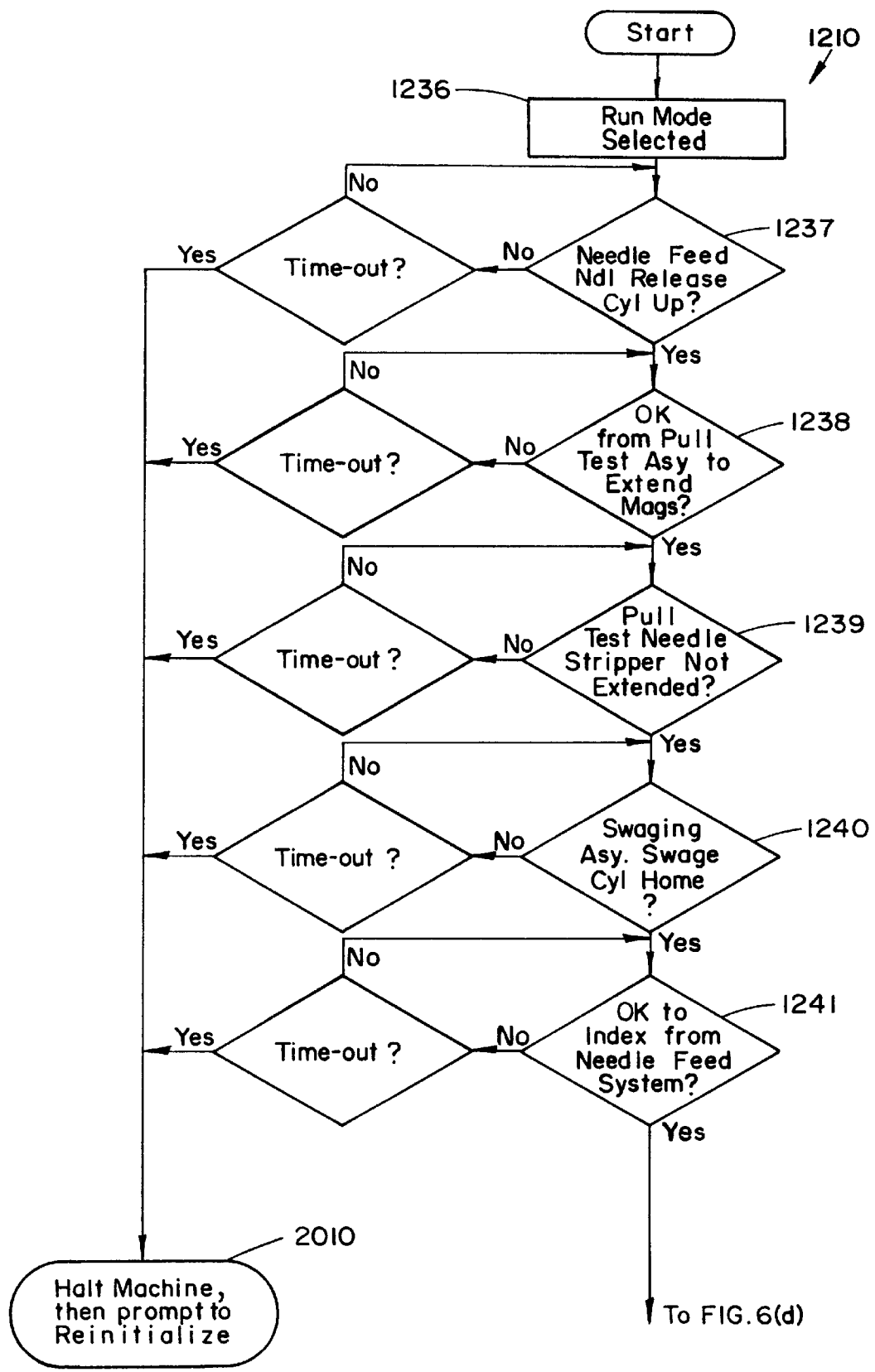
Figure 6D:
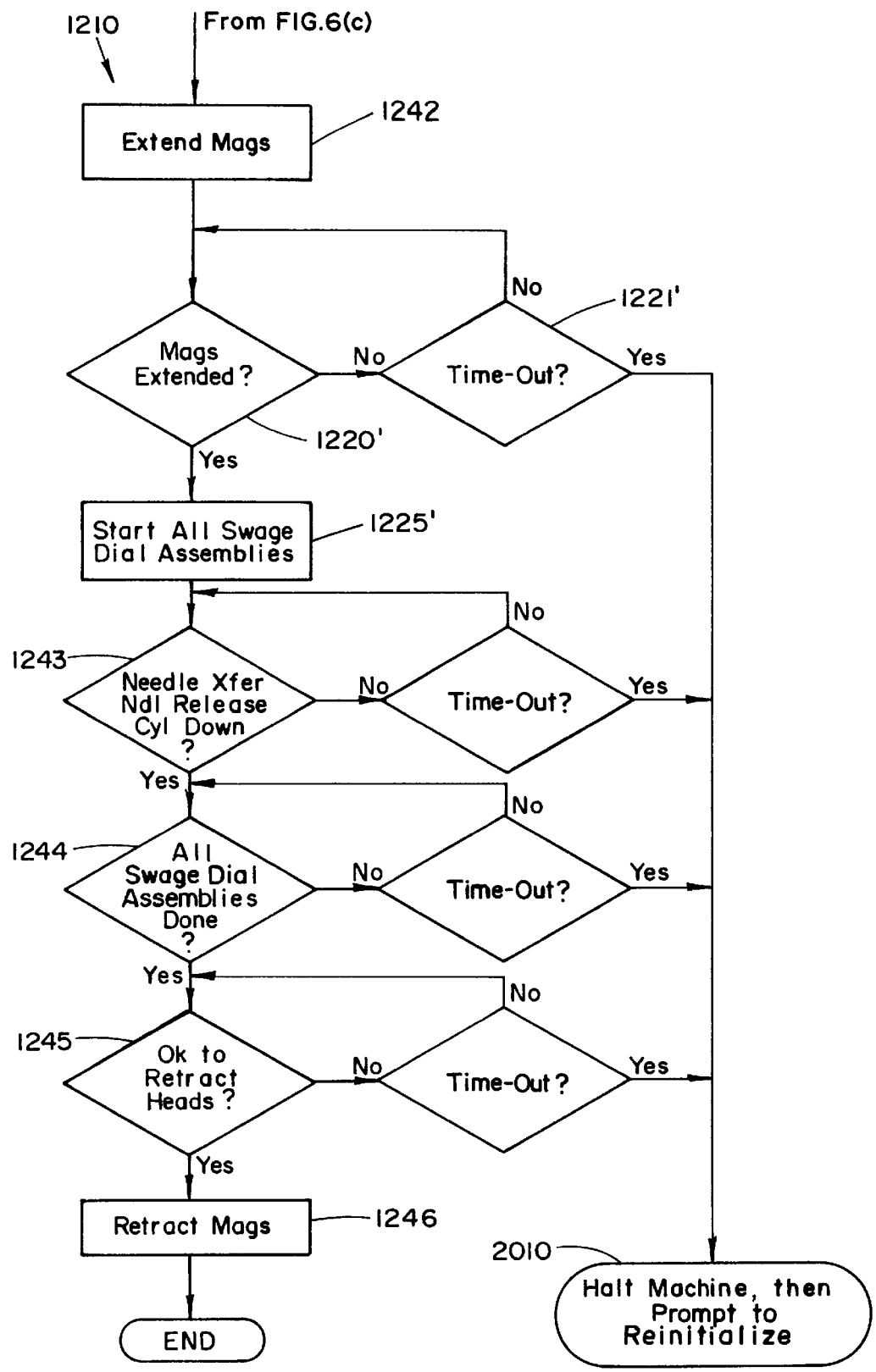
Figure 6E:
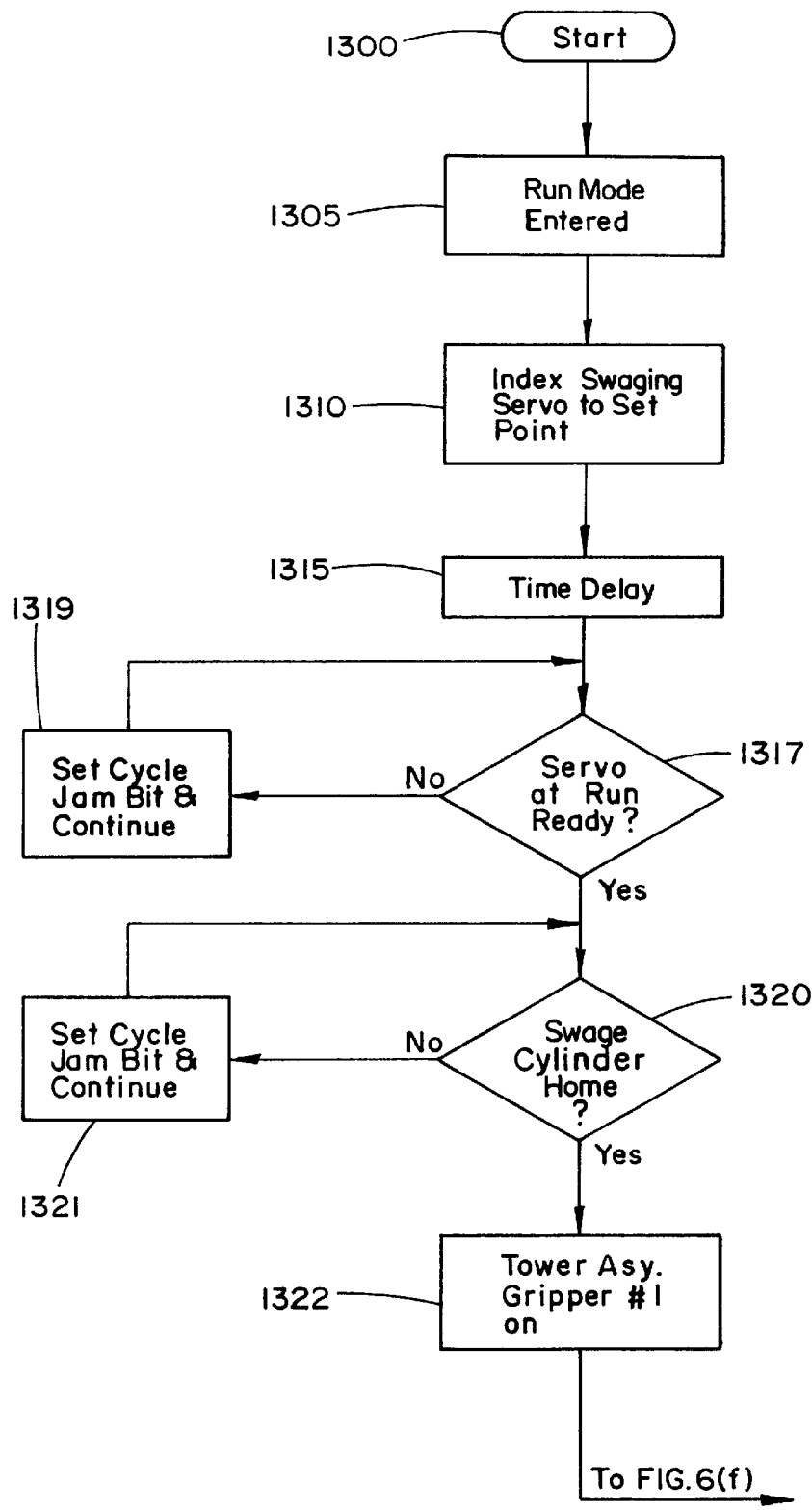
Figure 6F:
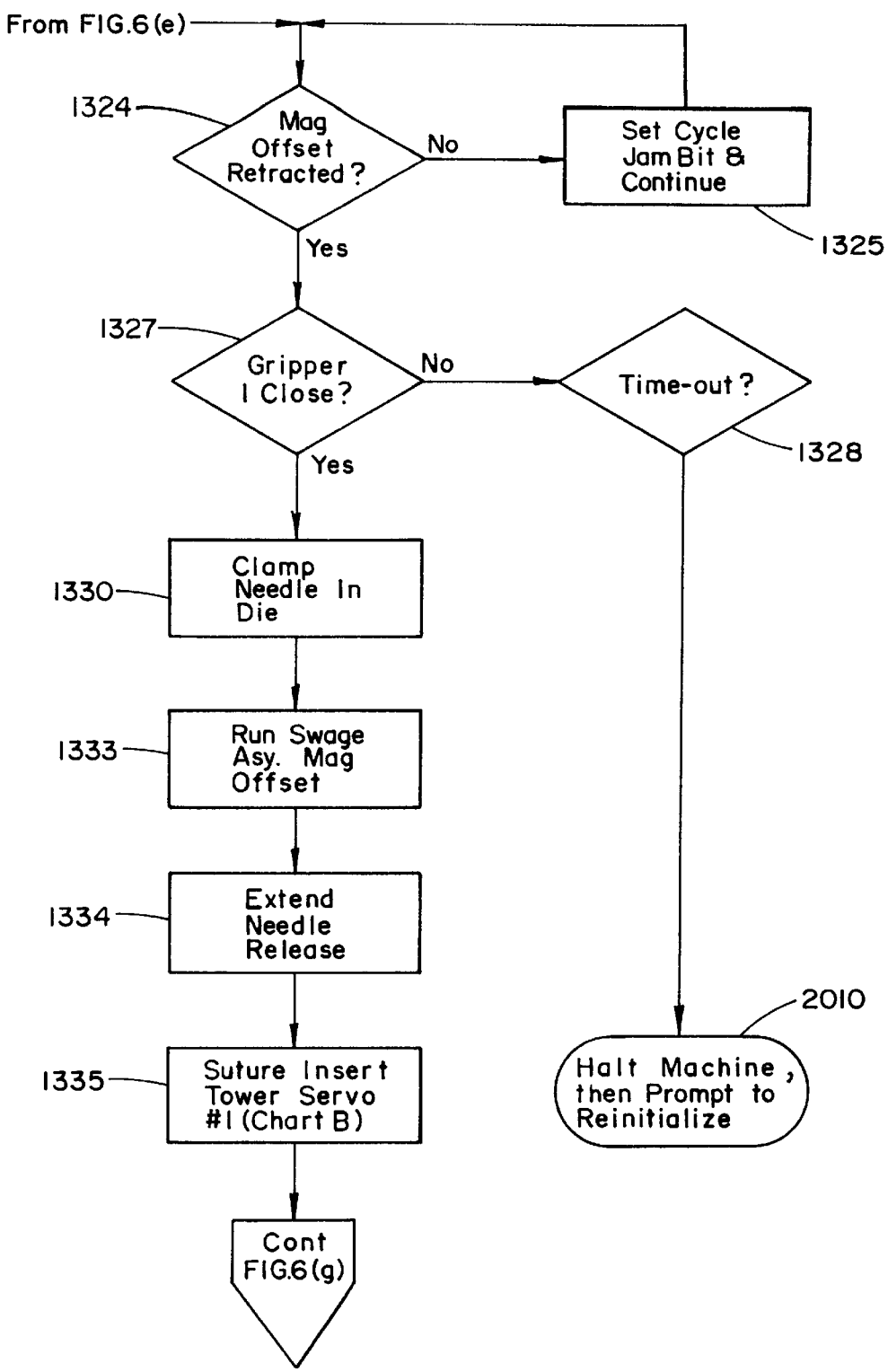
Figure 6G:
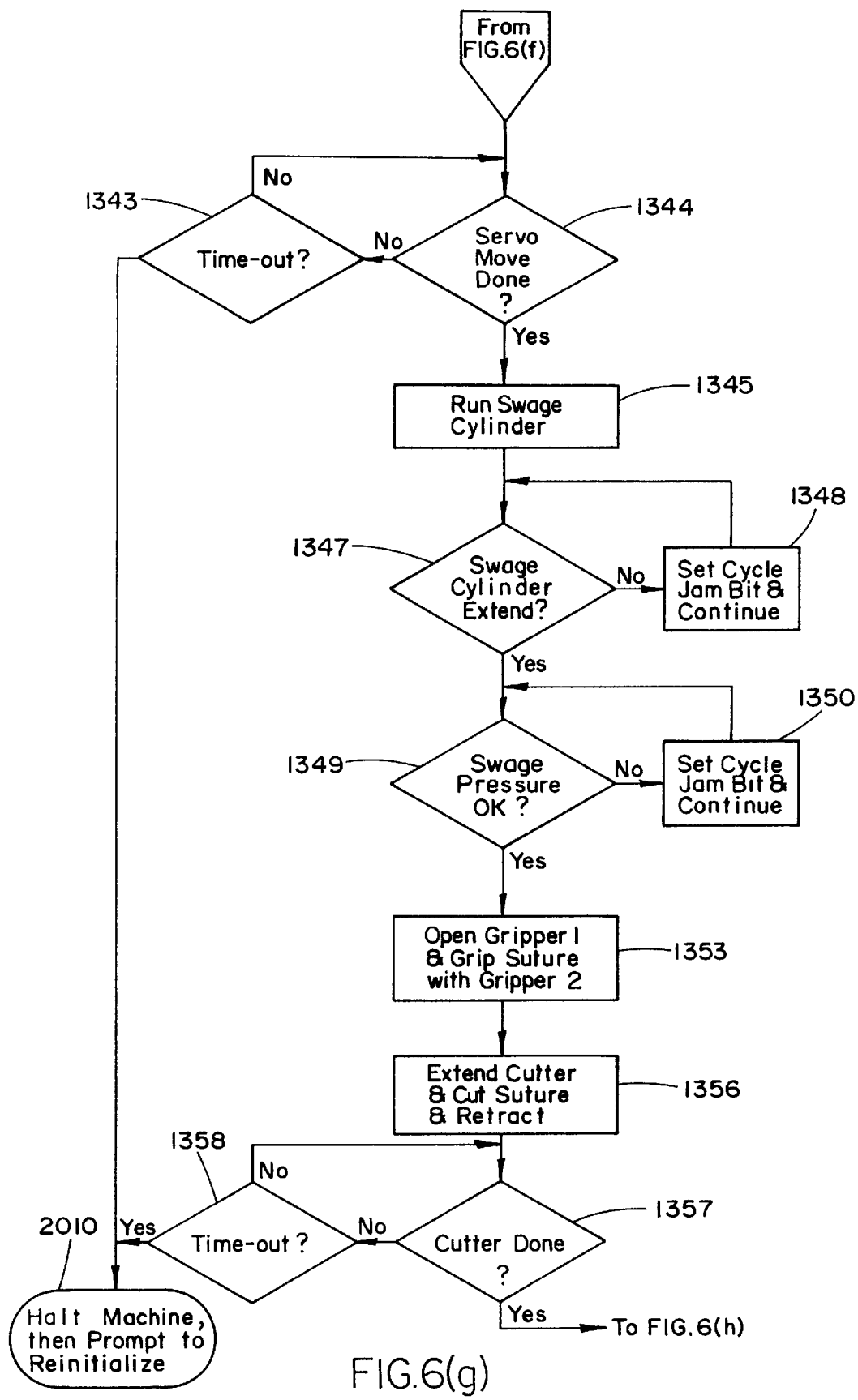
Figure 6H:
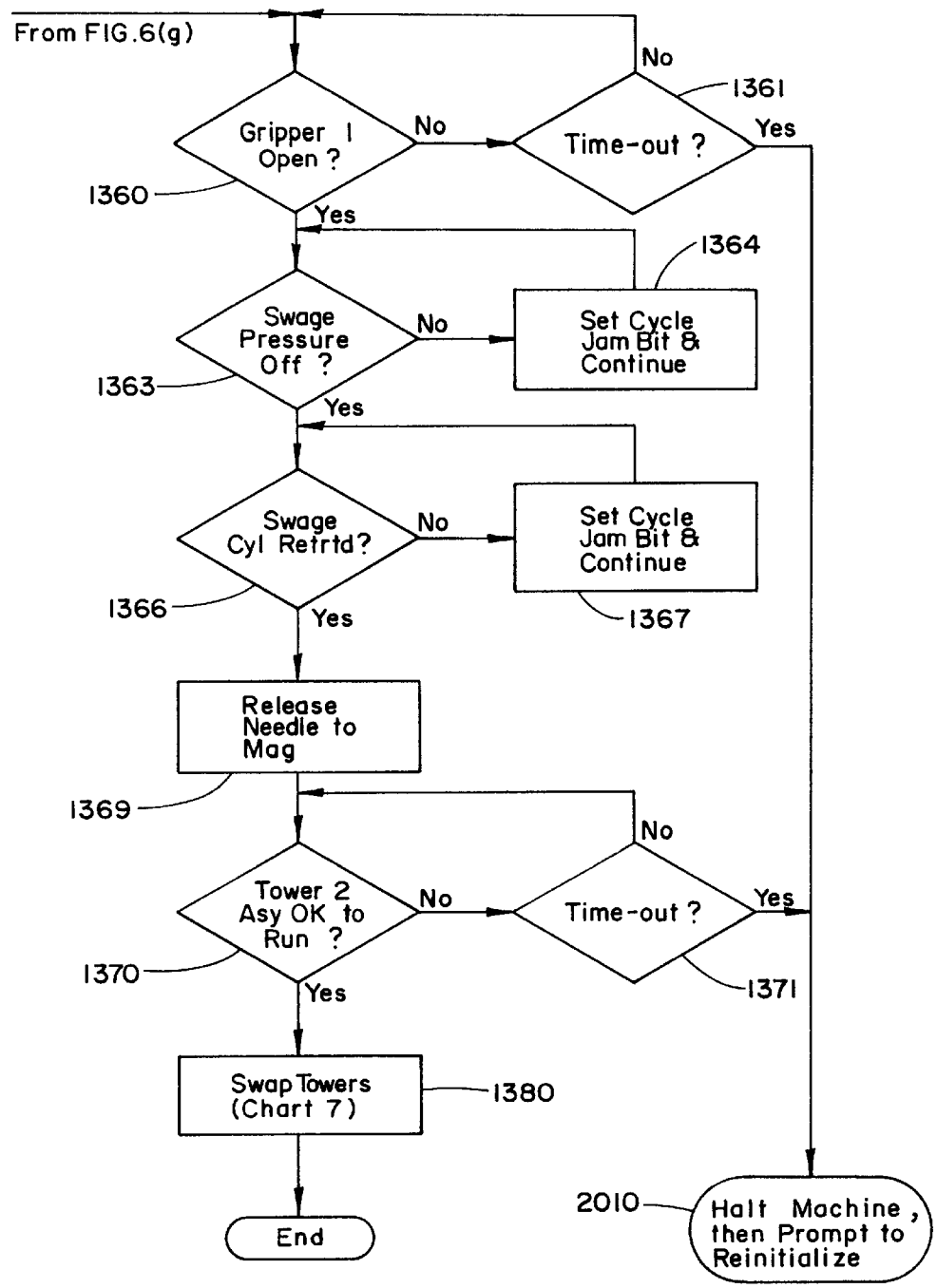
Figure 6I:
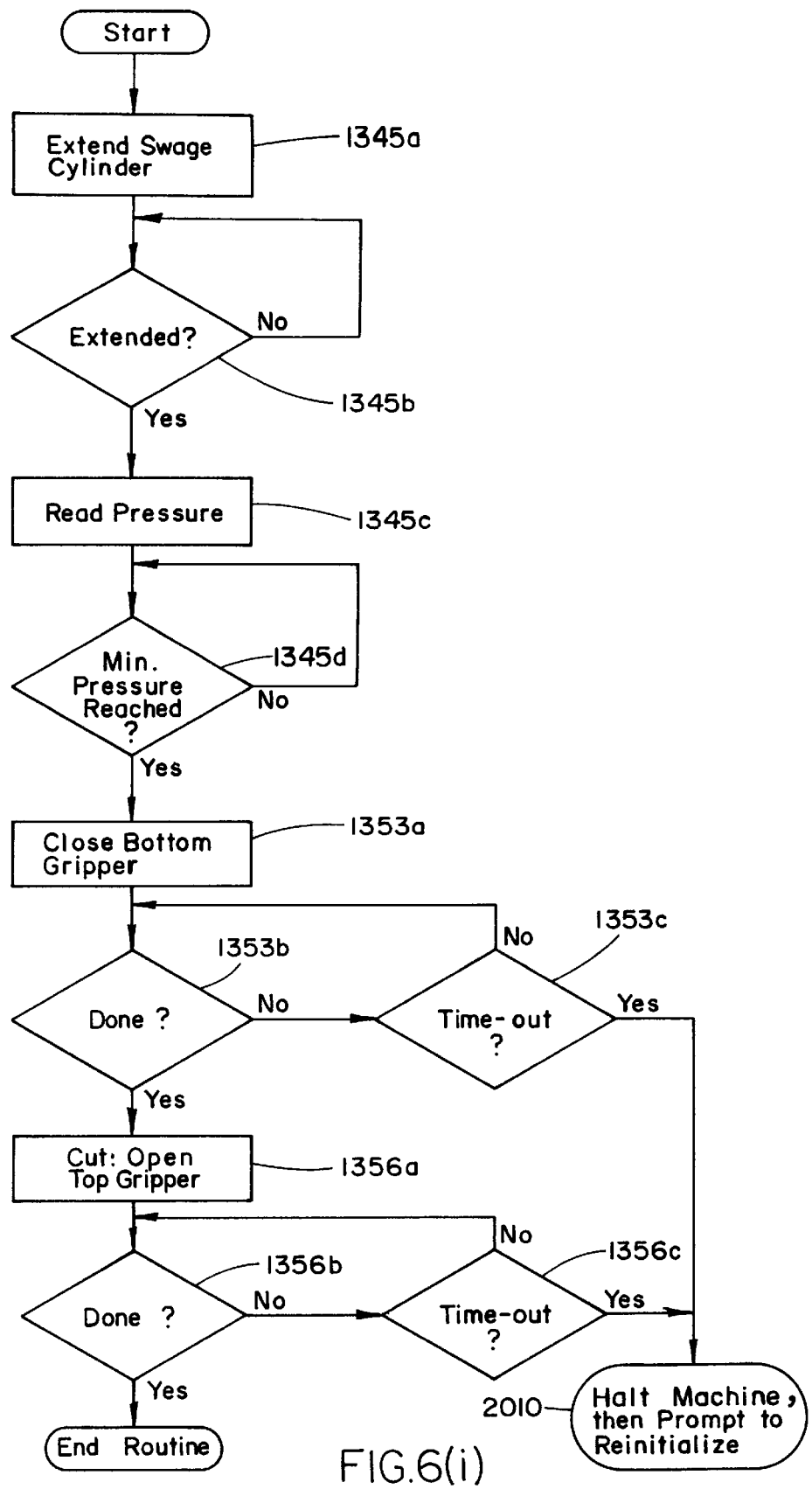
Figure 6J:
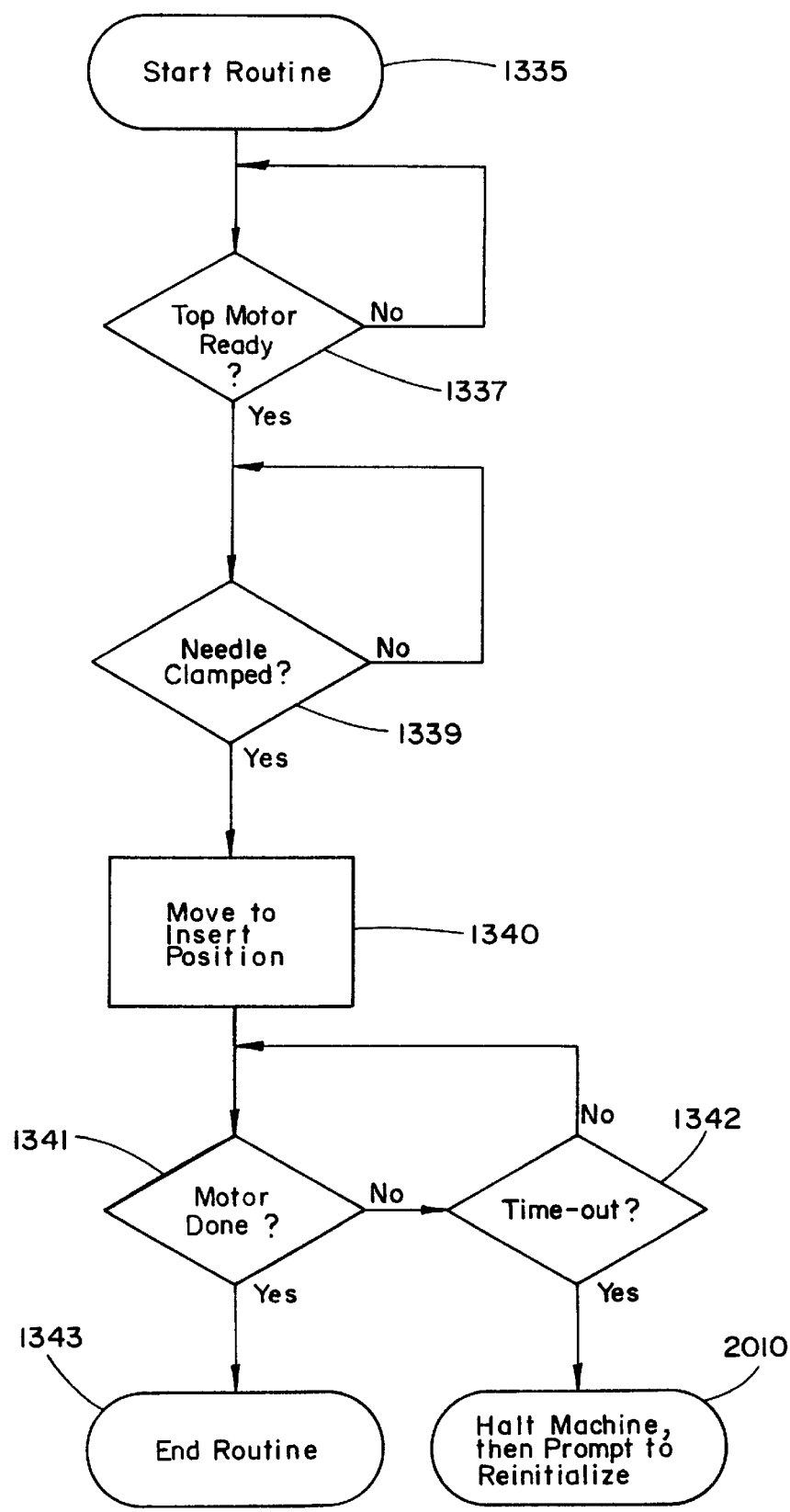
Figure 6K:
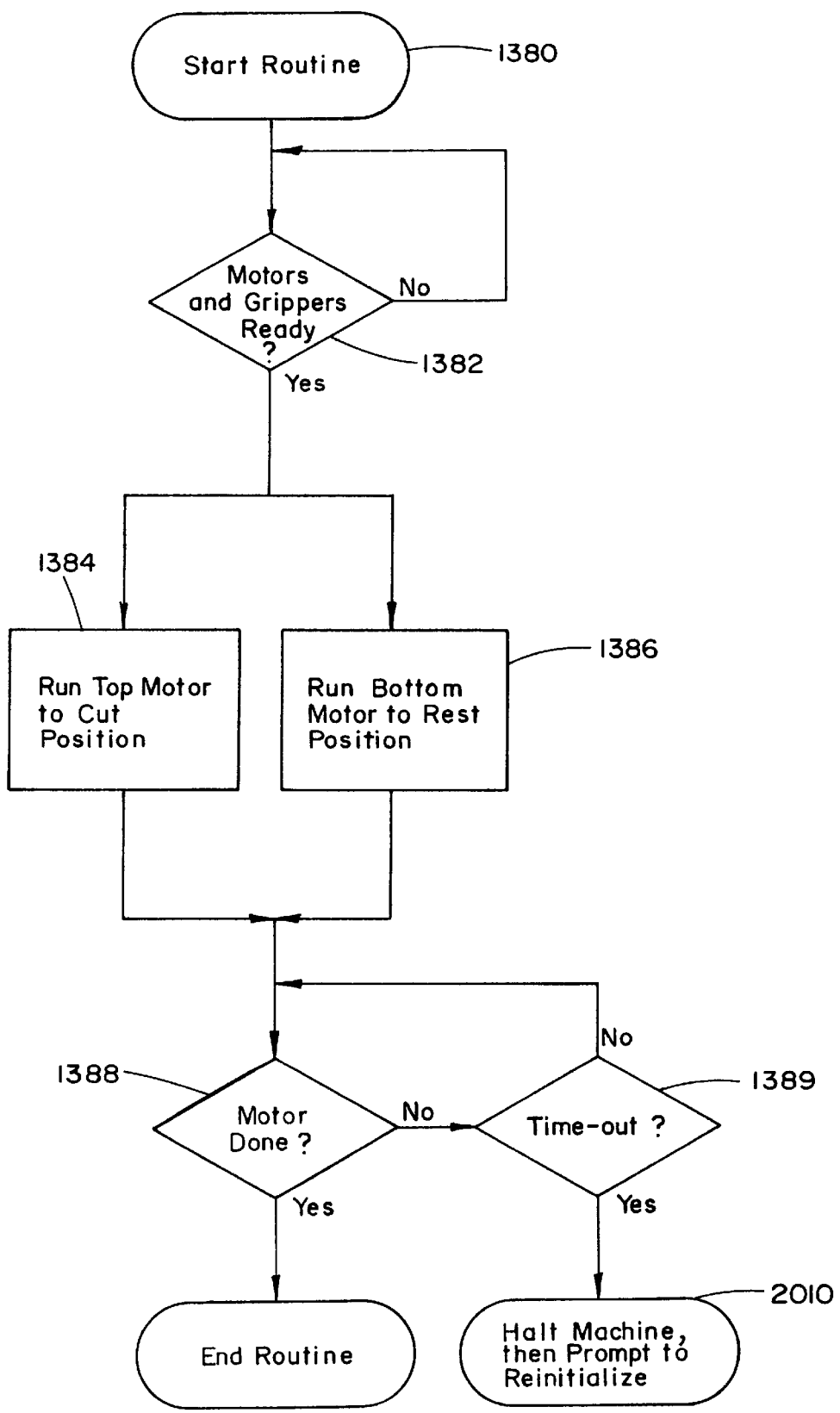
Figure 6:
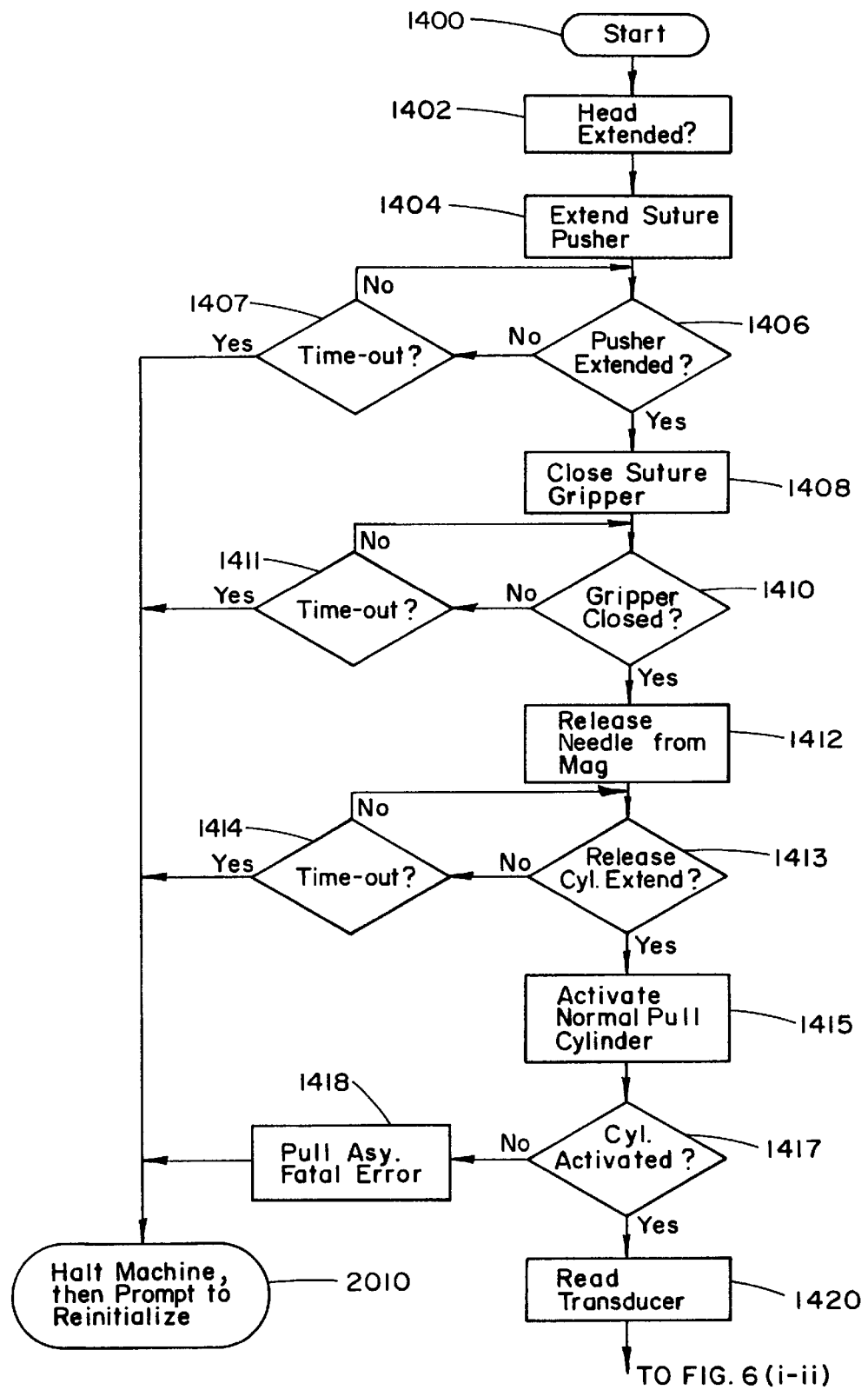

If the auto-run mode had been selected, as indicated at step 1227, FIG. 6(*b*), the process continues at step 1229 to ensure that the various system interlock signals, indicating that all of the swaging operations have been performed, are received. Then, at step 1230, the MAGs are retracted, the swage dial is indexed forward, and the MAGs are extended again for the next cycle. A decision is made at steps 1232, 1233 to determine whether the swage dial has been indexed within the time period allotted for the index cycle. If the swage index is accomplished within the allotted time, then the current servo cycle ends as indicated at step 1235. The swage dial servo process repeats for each subsequent cycle by returning to step 1220. If the swage dial has been indexed within the time period allotted for the index cycle, then a time-out flag is generated by the control system indicating a time-out error and the process will be terminated and prompted for reinitialization at step 2010. It should be understood that if the single cycle mode had been selected, as indicated at step 1227', the same process steps 1229'–1235' are performed as in auto-mode, however, at step 1230', only the MAGs are retracted and the dial is not indexed, thus obviating the need for a time-out determination.

FIGS. 6(*c*) and 6(*d*) particularly relates to the control system process relating to the reception of the various system interlock signals in the current indexing cycle, prior to initiating extension of the swage dial MAGs of swage dial 150, indicated as step 1210 in FIG. 6(*b*). These signals must be received to ensure that the MAGs have sufficient time and clearance to extend within each of the processing stations. As shown in FIG. 6(*c*), assuming run mode operation indicated at step 1236, a determination is made as to whether the following control system signals have been received: 1) the Needle feed needle release cylinder is up, as indicated at step 1237; 2) a signal indicating whether the Pull-test assembly is ready, as indicated at step 1238; 3) a signal indicating whether the pull-test needle stripper is not extended, as indicated at step 1239, and as will be described with respect to the automatic pull-test; 4) a signal indicating whether the swaging assembly swage cylinder is home, as indicated at step 1240; and 5) a signal indicating whether the OK to Index from the needle feed system, as indicated at step 1241. If any one of these signals are not received within the time period allotted, then a time-out flag is generated by the control system indicating a time-out error and the process will be terminated and prompted for reinitialization at step 2010. If all of these signals are received within the time period allotted, the Extend MAGs signal is initiated and the MAGs will be extended at each of the stations, as indicated at step 1242. The next steps 1220', 1221' and 1225' are performed as described above with respect to FIG. 6(*b*). Particularly, at steps 1220' and 1221', a decision is made as to whether the MAGs have been extended within the time period allotted for the current index cycle. If, the MAGs have been extended the process continues to initiate concurrent needle-suture swage processing operations at stations 100, 200, 300 and 450 as indicated at step 1225' and described above with respect to FIGS. 6(*a*), 6(*e*), 6(*f*), 6*l*), 6(*m*), 6(*n*), and 6(*o*). If the MAGs have not been extended then a time-out flag is generated by the control system indicating a time-out error and the process will be terminated and prompted for reinitialization at step 2010.

As further shown in FIGS. 6(*c*) and 6(*d*), after the all of the needle-suture swage processing operations at stations 100, 200, 300 and 450 are performed, the control system 999 waits for the various system interlock signals in the current indexing cycle, prior to initiating MAG retraction. Specifically, a determination is made as to whether the following control system signals have been received: 1) a control system signal indicating whether the Needle transfer needle release cylinder is down, as indicated at step 1243; 2) control system signals indicating whether all of the swage dial assemblies are done, as indicated at step 1244; and 3) a control system signal indicating whether it is OK to retract the Mag heads, as indicated at step 1245. If any one of these signals are not received within the time period allotted, then a time-out flag is generated by the control system indicating a time-out error and the process will be terminated and prompted for reinitialization at step 2010. If all of these signals are received within the time period allotted, the Retract MAGs signal is initiated and the MAGs will be retracted at each of the stations, as indicated at step 1246.

Suture Drawing and Cutting

Simultaneously with the positioning and transfer of the surgical needles to the multi-axis gripper on the swage dial, predetermined lengths of suture are being drawn, tipped and cut by the suture drawing and cutting tower 220. An overview of the suture drawing and cutting tower 220 will now be discussed.

Figure 18:
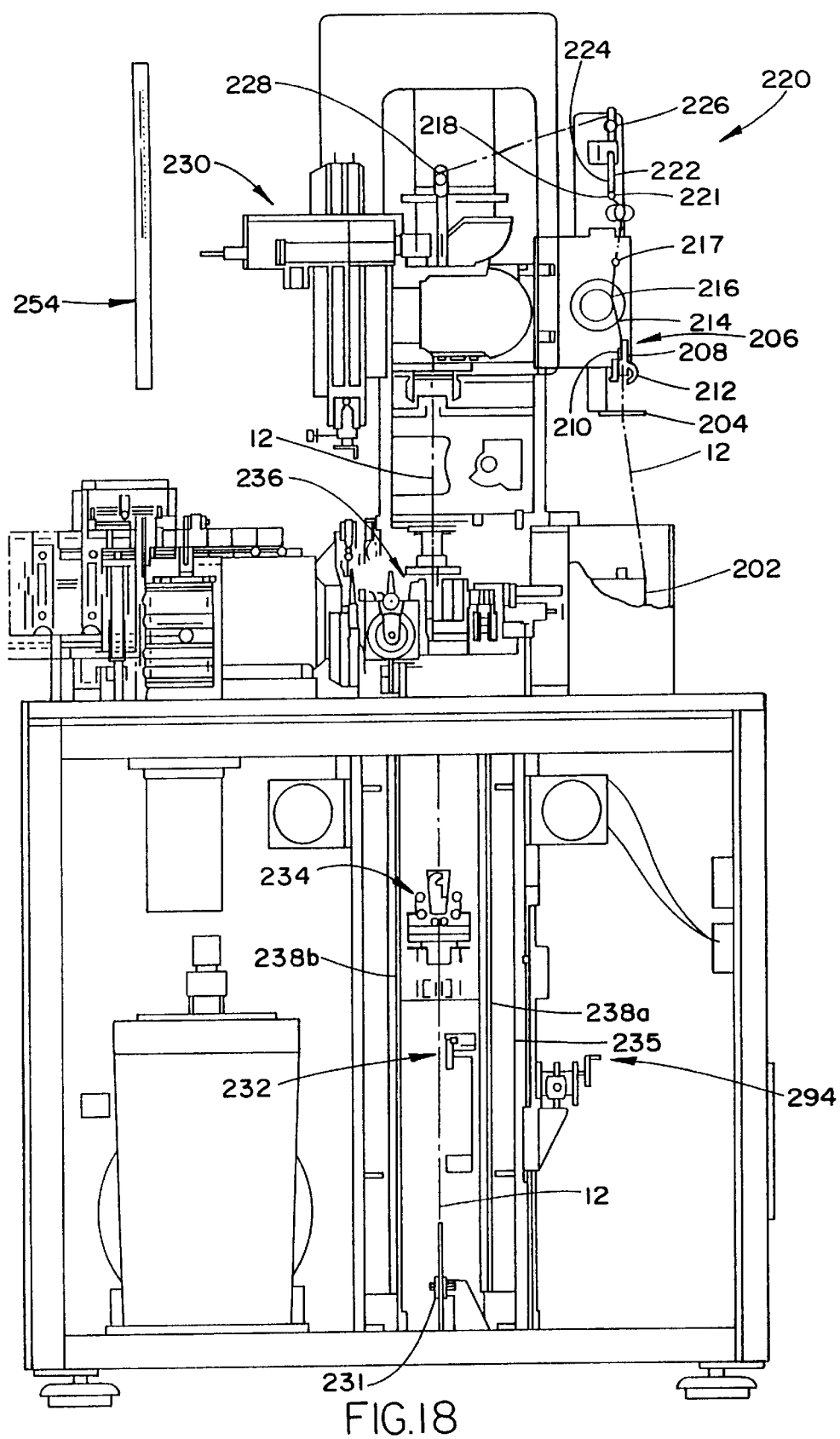
FIG. 18 illustrates a front elevational view of the servo tower 220 showing the suture path herethrough and the locations of the major assemblies hereof.

FIG. 18 illustrates a front elevational view of one designed embodiment of a servo tower 220, and shows the suture drawing path therethrough. Suture 12 is pulled off one end of a supply roll 202 mounted to one side of the servo tower, through the center of an annular guide disc 204, and into a mechanical tensioner 206. The mechanical tensioner 206 can comprise a stationary guide frame 208 and a pivotally mounted guide frame 210, pivotally mounted about a pin 212 at the lower end of the stationary guide frame. The pivotally mounted guide frame 210 is spring biased about the mounting pin 212 to rotate the top thereof away from the top of the stationary guide frame, such that the suture extending between alternating stationary guide frame elements and the pivoted guide frame elements is placed under tension while being pulled therethrough.

The suture then extends to and is wrapped twice around a tension roller 214 which is mounted on one end of a torque motor 216, which applies a given tension to the suture 12 as it is pulled through the servo tower by first and second gripper assemblies 232*a*, 232*b*. Each different suture size and material should have a different tension applied thereto as it is drawn through the apparatus. The torque motor 216 provides a different tension force for each different suture size and type, and the specific tension force (in grams per volt to be applied by the torque motor) is downloaded from supervisor computer 99*b* at each suture batch changeover. The proper tension is important for several operations described herein, and is particularly important for the cutter assembly to operate while providing a clean neat cut without a broom effect, to be described.

The suture then extends to an out-of-suture sensor positioned at 217, and then through a pair of opposed rollers 218, 221 of a knot detector. One of the pair of rollers is 218 mounted on one end of a lever arm 222, and if a knot travels between the pair of opposed rollers, it pushes the lever arm away, and the movement of the lever arm is detected by a photodetector 224 which transmits a control signal to the control computer 999 for appropriate action. The suture 12 then travels around an idler roller 226 to change direction, to a further idler roller 228 to change direction again, from which the suture 12 extends vertically downwardly through a heated tipping assembly 230, which heats and ultimately stiffens a mall length of the suture, at which the suture is subsequently cut and the cut tip is inserted into and swaged to a needle. The suture 12 then extends downwardly from the tipping assembly to a large idler roller 231, at which the suture reverses direction and travels vertically upwardly as gripped by one of two gripper assemblies 232*a*, 232*b*, one of which is shown in FIG. 18.

Figure 22:
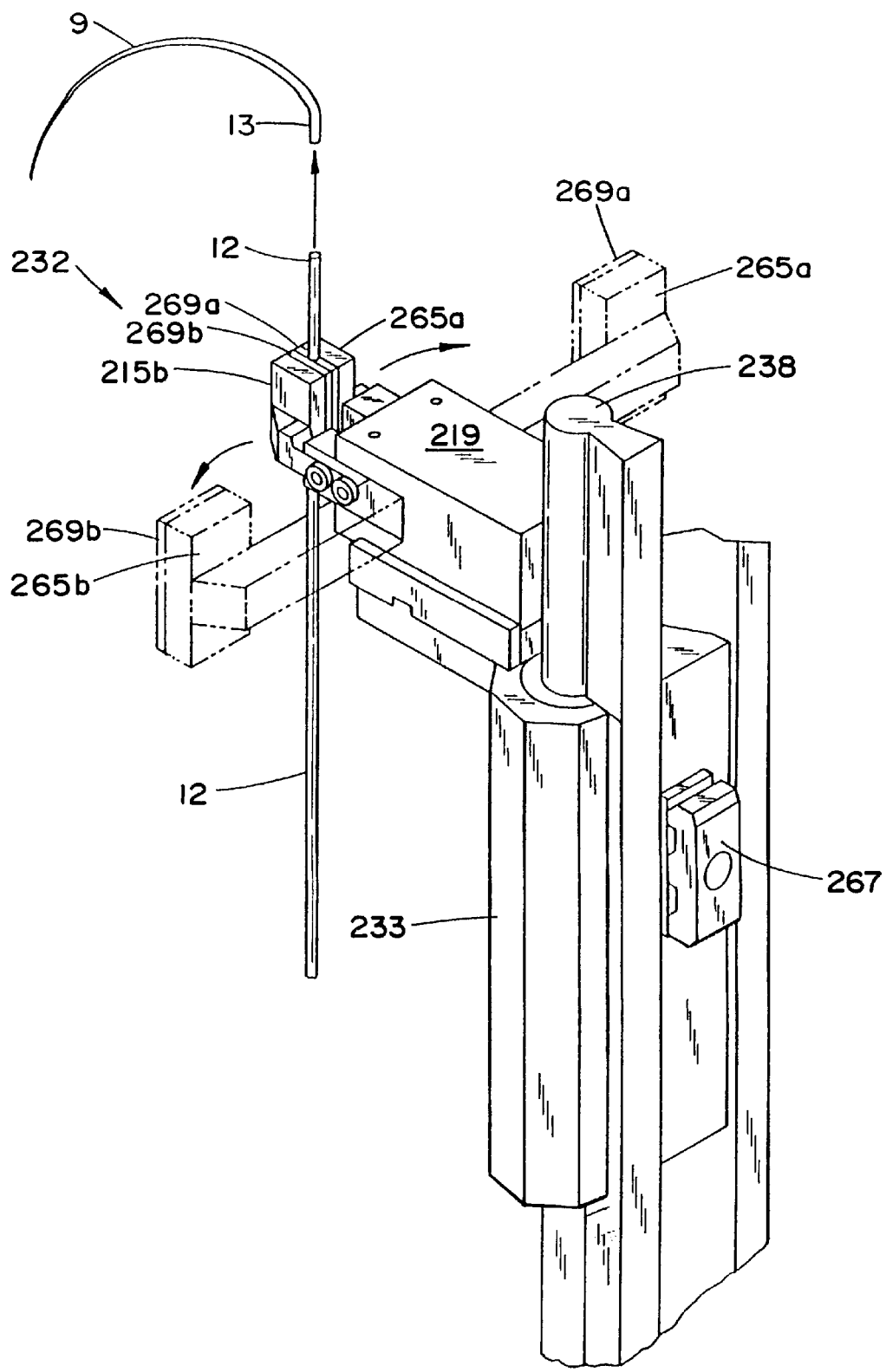
FIG. 22 is an enlarged isometric view of a suture gripper assembly having gripper arms shown in their open (dotted lines) and closed (suture gripping) positions.

As illustrated in FIG. 22, suture draw gripper 232 includes a traveling carriage 233 which reciprocates up and down frame member 238 by means of a timing belt which is secured to the carriage at 267. A pneumatic actuator 219 includes first and second clamps 265*a*,265*b* having respective first and second gripping surfaces 269*a*,269*b* which clamp the suture material therebetween. As shown in FIG. 18, each gripper, e.g., gripper 232*a* (232*b*) includes a traveling carriage 233*a* (233*b*) that reciprocates up and down respective frame members 238*a* (238*b*) as controlled by respective servomotors and connected by means of a timing belt which is secured to the carriage at 267. As shown in FIG. 5, servomotors 115*d* and 115*e* and respective servo controllers 116*d* and 116*e* control reciprocating movement of respective first and second gripper carriages 233*a,b*, while pneumatic solenoids, shown in FIG. 52(*c*) as solenoid valves 804*m* and 804*n* control gripping action for first and second grippers 232*a*; 232*b*, respectively. As will be explained, control system thread 1300 generates various actuating signals to advance the suture material up the tower in a coordinated hand-over-hand manner, while controlling suture heat tipping, suture insertion, swaging and suture cutting operations.

Generally, in a first cycle of operation, top gripper 232*a* draws the suture of indefinite length to a suture insertion point under control of control system computer 999 immediately adjacent the swage plates of the swaging station and then dwells while a second suture gripper 232*b* clamps the indefinite suture length below the suture cutter 234 (illustrated in FIG. 18). After the second suture gripper has engaged the suture, the cutter 234 is actuated to cut the suture while the tipped end of the suture 12 carried by the first suture gripper 232*a* is inserted into the barrel end of the needle in the manner as discussed below. The tip end of the suture 12*a* is positioned below a funnel dye formed in suture alignment plates 311,313 which reciprocate immediately below swage plates 301,302. After the suture tip end 12*a* has been inserted into the barrel end 13 of needle 9, the swage station is actuated driving the swage plate 302 against swage plate 301 to swage the suture tip 12*a* in the surgical needle 9.

Figure 19:
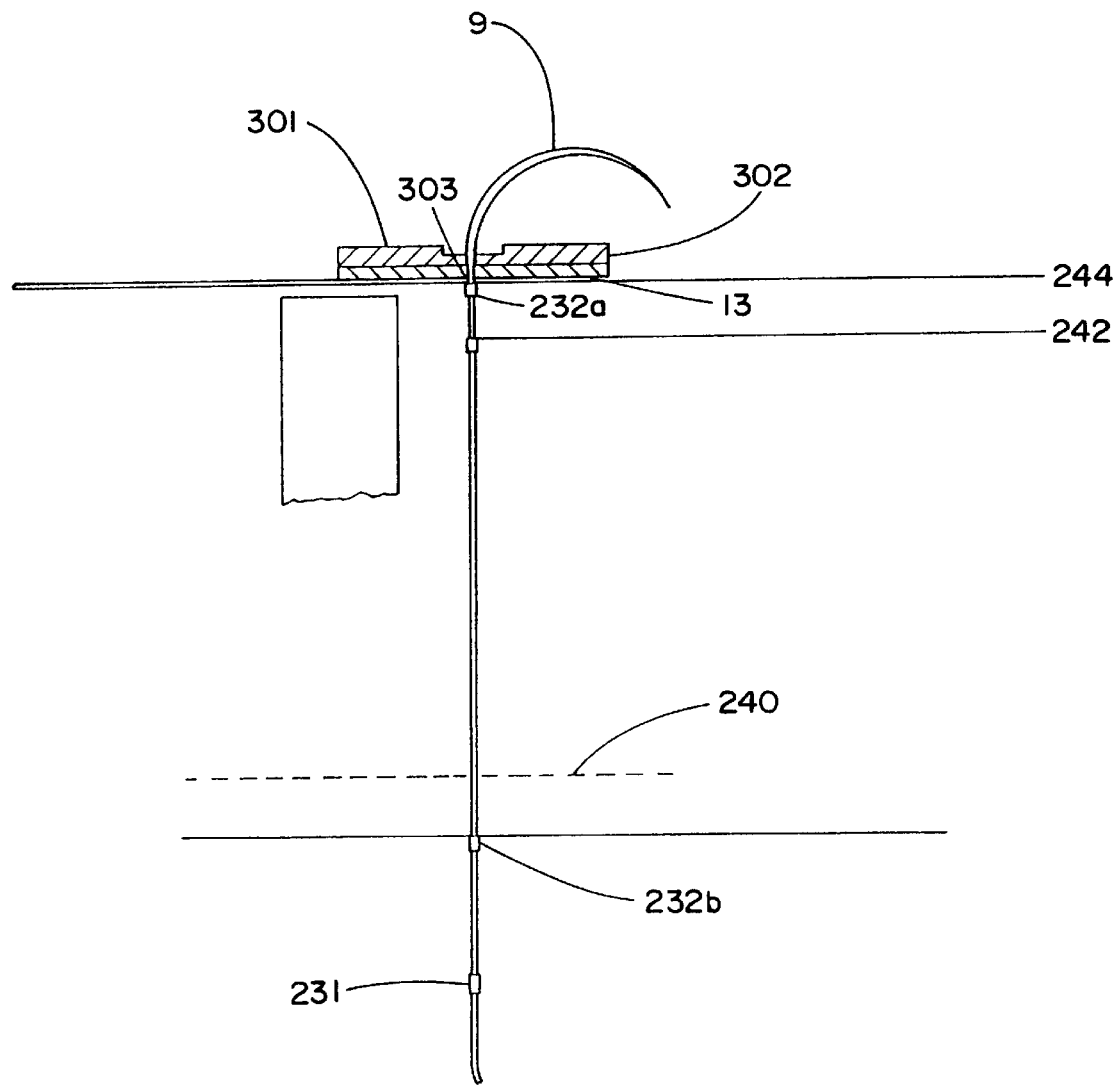
FIG. 19 is a schematic illustration of the different positions in the servo tower including from the bottom, the large idler roller, the bottom servo gripper position, the cut blade position, the home position of the servo gripper, and the final insertion position of the servo gripper.

FIG. 19 is a schematic illustration of the different positions in the servo tower including, from the bottom, the large idler roller 231, the bottom suture draw gripper position 232, the position 240 of the cutting blade, the home position 242 of the servo gripper, and the final insertion position 244 of the servo gripper. During the insertion operation, the cut suture end is guided by a funnel shaped aperture 303 in a funnel element 313 into the aperture in the end of a needle, after which a moving anvil 302 is moved relative to a stationary anvil 301, of a swage die, to swage and attach the needle to the suture.

In this embodiment, after initialization, one gripper assembly will be in a home position, 2.000" below the face of the swage die mounting surface, allowing a 2.030" movement from the home position to an insert position. A proximity switch is located on each tower at 2.000" below the face of the swage die mounting surface to set the home position during an initialization procedure.

Assuming that the machine is being initially set up to cut a desired length of suture, the cutter assembly 234 will be moved to a predetermined vertical position in the swaging machine by operation of the handcrank 294. This is done by aligning a pointer for the cutter assembly with a vertical scale positioned on the side of the swaging machine at 235.

The cutter assembly includes a proximity switch thereon, and during an initialization procedure, the position of a gripper assembly is detected by the proximity switch, and that position is set in memory to set the servo gripper bottom position 238 during subsequent normal operation of the machine. The tipping assembly is also moved to an appropriate position in the machine as described hereinbelow. Details of the cyclic operation for drawing suture, inserting tipped suture end, swaging the suture to the tip, and cutting the suture to a definite length is described hereinbelow with respect to FIG. 6(*i*).

As the silk suture may be subject to shrinkage at a later downstream sterilization operation, the cutter assembly position must be adjusted along the length of the suture tower to account for any shrinkage. Accordingly, the cut lengths of suture must be cut to lengths slightly longer than their desired (or label) final lengths to compensate for such shrinkage. The following table gives, for silk suture, in the left column the commercial (or label) suture length, in the middle column the low servo position of the low gripper assembly below the face of the swage die mounting surface, and in the right column the cut length of suture prior to shrinkage. VICRYL shrinkage during sterilization is approximately 3% of the table values for silk.

18" servo—16.51 allowed for 18.380"
27" servo—25.51 allowed for 27.380"
30" servo—28.51 allowed for 30.380"
36" servo—34.51 allowed for 36.380"

As described above, after heating of a predetermined length of suture at the tipping assembly, the suture must cool to allow setting and hardening of the suture material prior to cutting of the suture at the hardened length and insertion of the cut stiffened end into a needle. This cooling of the suture is provided in this embodiment by allowing a discrete number of machine cutting cycles to occur between tipping of the suture and cutting of the suture. This is provided by allowing a predetermined long length of suture travel between the tipping assembly and the cutter assembly. Hence, the suture tipping assembly 230 is positioned near the top of the servo tower, and after heating thereat, the suture travels to the bottom of the machine, around the large idler roller 231 thereat, and then back upwardly to the cutter assembly 234. The large diameter of the idler roller 231, relative to the other idler rollers 226, 228, is provided because the small length of suture which has been heated at the tipping assembly 230, has begun to harden and set by the time the heated section reaches the large idler roller. The large diameter thereof facilitates the suture to travel therearound without picking up a permanent curved set from the large idler roller, as it is desirable for the suture to be straight, without any curve, when it is subsequently cut and inserted into a needle.

The operation of the machine depends upon a discrete whole number of machine cycle operations to be performed between the tipping and cutting operations. Accordingly, for each different length of cut suture, both the cutting assembly 234 and the tipping assembly 230 must be positioned at a different predetermined position within the machine for the tipped section of suture to be precisely and correctly positioned at the cutter assembly 234 after a given number of machine cycles.

The following table gives in its columns, proceeding from left to right, the label suture length, the actual cut suture length, the number of machine cycles or increments provided between tipping and cutting, the total travel length of the suture between tipping and cutting, the tipping assembly vertical position above the table top, and the tipping assembly scale pointer position above the table top (explained in greater detail hereinbelow). The values provided in these tables may be stored in the supervisor control computer 99*b* and down-loaded with each batch changeover or set-up procedure.

| SUTURE LENGTH | | | | ABOVE TABLE TOP | |
|---|---|---|---|---|---|
| LABEL | ACTUAL | INCREMENTS | TOTAL | TIPPER C | POINTER |
| 18 IN. | 19 IN. | 6 | 114 IN. | 27.64 IN. | 25.89 IN. |
| 27 IN. | 28 IN. | 4 | 112 IN. | 25.64 IN. | 23.89 IN. |
| 30 IN. | 31 IN. | 4 | 124 IN. | 37.64 IN. | 35.89 IN. |
| 36 IN. | 36.25 IN. | 3 | 108.75 IN | 22.39 IN. | 20.64 IN. |

Figure 20:
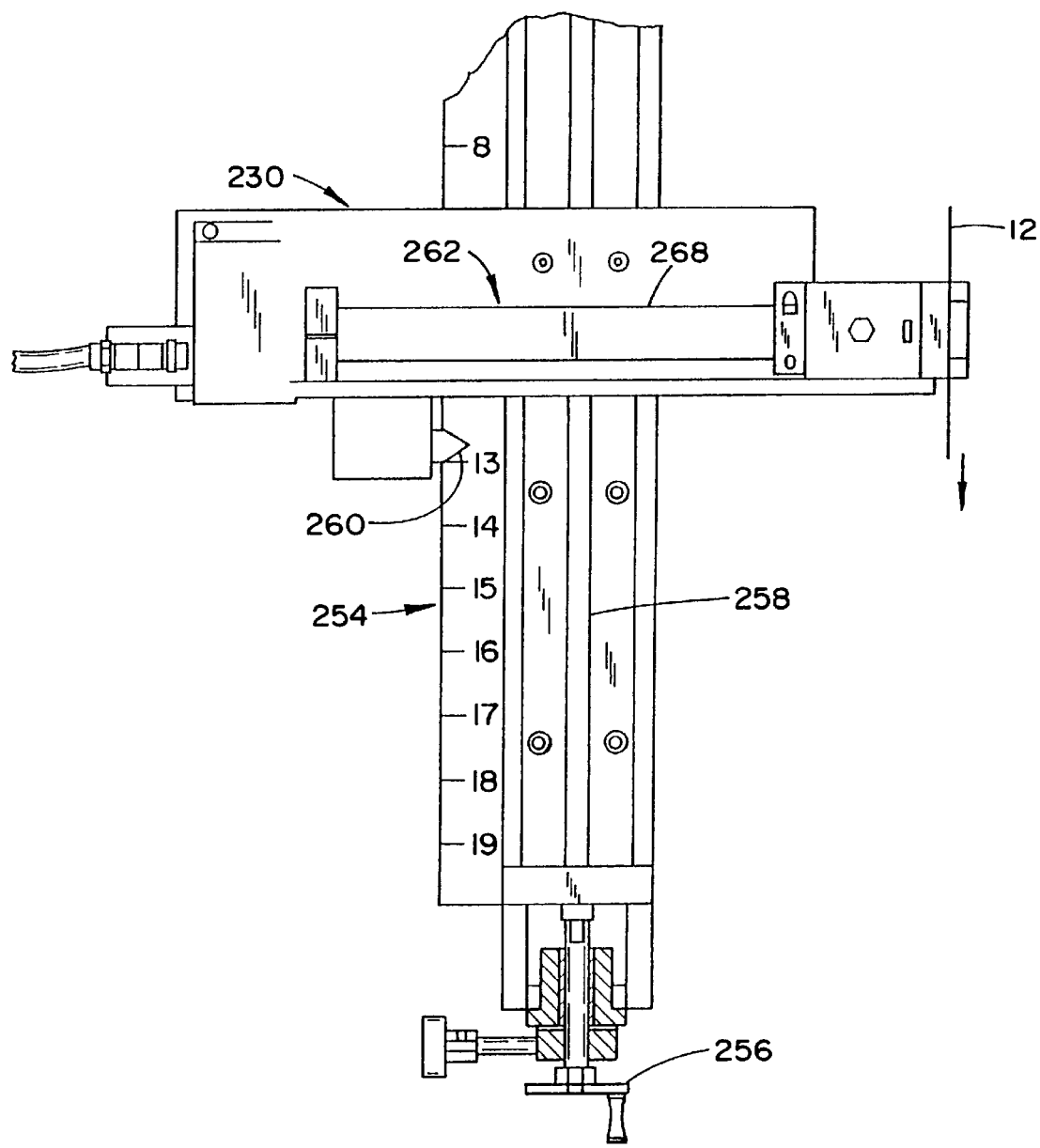
FIG. 20 illustrates an enlarged front elevational view of the suture tipping assembly at which a small length of the suture is heated to stiffen the suture material after subsequent cooling thereof, and also illustrates the adjustable movement thereof along a vertical scale provided adjacent to the tipping assembly.

FIG. 20 illustrates an enlarged front elevational view of the suture tipping assembly at which a small length of the suture is heated to stiffen the suture material after subsequent cooling thereof, in preparation for cutting a given length of the suture and inserting the lead cut end of the suture into the end of a needle for swaging thereto. FIG. 20 illustrates the movement of the tipping assembly 230 along a vertical scale 254 provided adjacent to the tipping assembly 230. The vertical position of the tipping assembly in the machine is adjustable by a handcrank 256 and precision leadscrew 258, similar to the positioning mechanism for the cutter assembly as described hereinabove. As the handcrank is rotated, the vertical position of the tipping assembly 230 in the machine is changed, and is precisely positioned by reading a pointer 260 attached to the tipping assembly on the scale 254. A chart is provided for the machine which gives, for each desired length of suture, the appropriate position for pointer 260 of the tipper assembly 230 on the vertical scale 254, and a similar position for the cutter mechanism 234 on the vertical scale 235.

In this embodiment, the position of the cutting mechanism along the drawing axis is continuously adjustable to provide an infinite number of possible different lengths of cut suture. For each different cutting position of the cutting mechanism, the tipping mechanism is adjustably positioned at a different predetermined position in the apparatus to provide for the tipped section of suture to be precisely positioned at the cutter mechanism after a discrete number of machine cycles.

In an alternative embodiment which does not have this infinite adjustment feature, several standard lengths of suture are accommodated by several standard positions which are fixed in the machine by pins which secure the cutter mechanism to the machine frame by pin receiving holes in the machine at the standard positions. For example, the cutter mechanism might be moved to a position for cutting 18" sutures and be secured to the frame by the placement pins being inserted into the pin receiving holes in the machine for 18" sutures. The cutter mechanism might also be moved to positions for cutting 27", 30", or 36" sutures by moving the placement pins to the pin receiving holes in the machine provided for those length sutures. Each different position can have a separate proximity switch provided therefor, which indicates the cutting mechanism position to the controller, which then downloads the appropriate servo gripper bottom position. The appropriate tipping mechanism position is then adjusted for each different cutter mechanism position.

Figure 21:
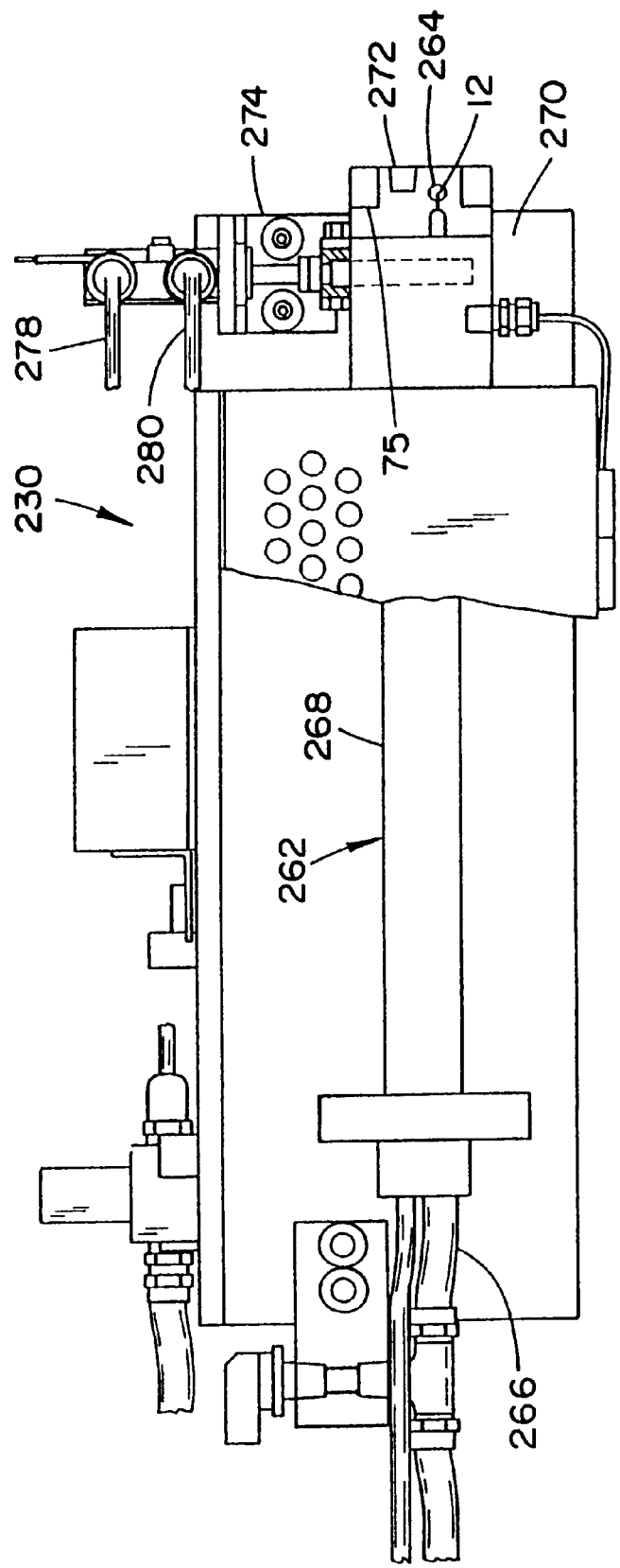
FIG. 21 is an enlarged top plan view of the tipping assembly shown in FIG. 20, and illustrates further details of the flow of heated air through the tipping assembly and its control to selectively heat and tip a small length of the suture.

FIGS. 20 and 21 illustrate the heater 262 in the tipping assembly 230 and the vertical movement of the suture 12 down (front view, FIG. 20) and through (top view, FIG. 21) a suture tipping aperture 264, FIG. 21, positioned on the right side of the tipping assembly. FIG. 21 illustrates further details of the flow of heated air through the tipping assembly and its control to selectively heat and tip the suture. As described previously, the tipping assembly 230 is mounted near the top of the machine so that it takes a discrete number of machine cycles for the suture to reach the cut position. This gives the tipped area time to cool down before the cutting and insertion operations. The tipping assembly operates by flowing air supplied at a regulated pressure through an inlet air duct 266 at a regulated flow rate, in one embodiment 195 CFH (Cubic Feet per Hour), over a heater coil mounted within an outer heater casing 268. As shown in FIG. 52(a), air is supplied to a flowmeter 809a at a regulated pressure required to maintain 195 CFH of air flowing over the heater coil. A thermocouple 270 is positioned in the air flow at the discharge end of the heater casing 268, to monitor and control the air temperature through a controller in a programmable logic controller (PLC). The tipping assembly 230 is operated at various temperatures between 200° F. and 550° F. depending upon the particular suture material to be run. The particular temperature is a down loaded parameter from the control system computer 999 at each suture batch changeover. The tipping assembly guides the suture and provides a 2.000" long heating aperture 264 for the tipping length.

In further view of FIGS. 52(a) and 21, the constant flow of heated air at the outlet of 268 flows either 1) through the heating aperture 264 in which the suture 12 is intermittently stopped and positioned during a tipping operation, or 2) alternatively the heated air is dumped into the surrounding atmosphere through a diverter channel 272, FIG. 21. The flow of hot air is controlled by an air cylinder 274, under control of a solenoid 803(e), which controls the flow of actuating air through air tubes 278, 280. The air cylinder 274 controls the position of a retractable slide element having a flow aperture therein which is selectively positioned in front of either 1) a channel into the heating aperture 264 or 2) the diverter channel 272, depending upon the position of the slider element which is controlled by an air cylinder.

As an example, the following control parameters have been established for heat tipping of Braided VICRYL sutures sizes 1, 0, 2/0, 3/0 and 4/0. The suture tension refers to the tension force in grams which the tension roller 214 and torque motor 216 apply to the suture as it is being drawn through the machine by the grippers.

| Suture Size | Tipping Temp. +/− 25 deg. | Tipping Time +/− 25 Ms | Suture Tension +/− 25 Grams |
|---|---|---|---|
| 4/0 | 375 F. | 380 | 275 |
| 3/0 | 395 F. | 380 | 275 |
| 2/0 | 410 F. | 380 | 275 |
| 0 | 425 F. | 380 | 275 |
| 1 | 435 F. | 380 | 275 |

As a further example, the following control parameters have been established for suture tension and heat tipping of silk sutures sizes 2/0, 3/0 and 4/0. In the following table the left column lists commercial needle types, the next column needle sizes, the next column suture sizes, the next column suture tension in grams applied by the tension roller 214, the next column tipping dwell time, the next column tipping heated air flow in standard cubic feet per minute, and the right column suture tipping temperature. The control system of the invention ensures that the temperature time and suture tensioning criteria are met at the tipping assembly.

| | SILK SUTURE AND TIPPING PARAMETERS | | | | | |
|---|---|---|---|---|---|---|
| Needle type | Wire Size (0.000") | Size Size | Suture Tension (grams) | Tipping Dwell (seconds) | Tipping Air Flow (SCFM) | Tipping Temperature (° F.) |
| Tolerance | N/A | N/A | (±10 grams) | (±0.020) | (±5) | (±15) |
| CT-1 | 39 | 2-0 | 275 | 0.380 | 190 | 300 |
| CT-2 | 39 | 2-0 | 275 | 0.380 | 190 | 300 |
| SH | 26 | 2-0 | 275 | 0.380 | 190 | 300 |
| SH | 24 | 3-0 | 275 | 0.380 | 190 | 300 |
| SH | 22 | 4-0 | 275 | 0.380 | 190 | 300 |

-continued

SILK SUTURE AND TIPPING PARAMETERS

| Needle type | Wire Size (0.000") | Size Size | Suture Tension (grams) | Tipping Dwell (seconds) | Tipping Air Flow (SCFM) | Tipping Temperature (° F.) |
|---|---|---|---|---|---|---|
| SH-1 | 22 | 3-0 | 275 | 0.380 | 190 | 300 |
| SH-1 | 18 | 4-0 | 275 | 0.380 | 190 | 300 |

The previous tables are for braided VICRYL suture and silk suture, and similar tables could be developed for other suture materials such as Ethibond (braided polyester) and monofilament and braided nylon.

Figure 23A:
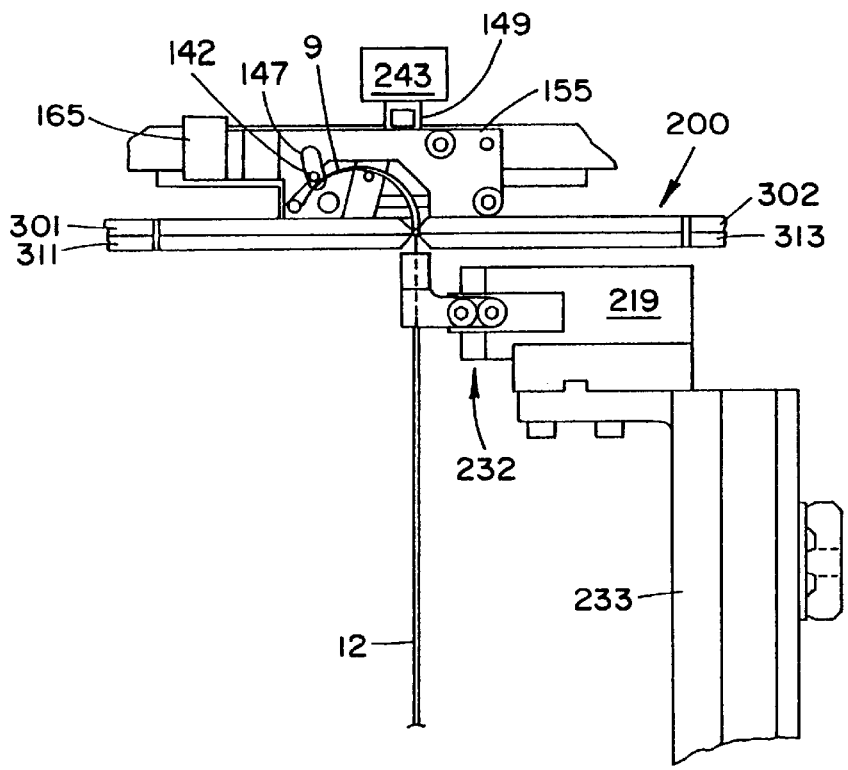
FIG. 23(a) is a detailed view of the gripper shown inserting the suture tip within the confines of the suture receiving end of the surgical needle.
Figure 23B:
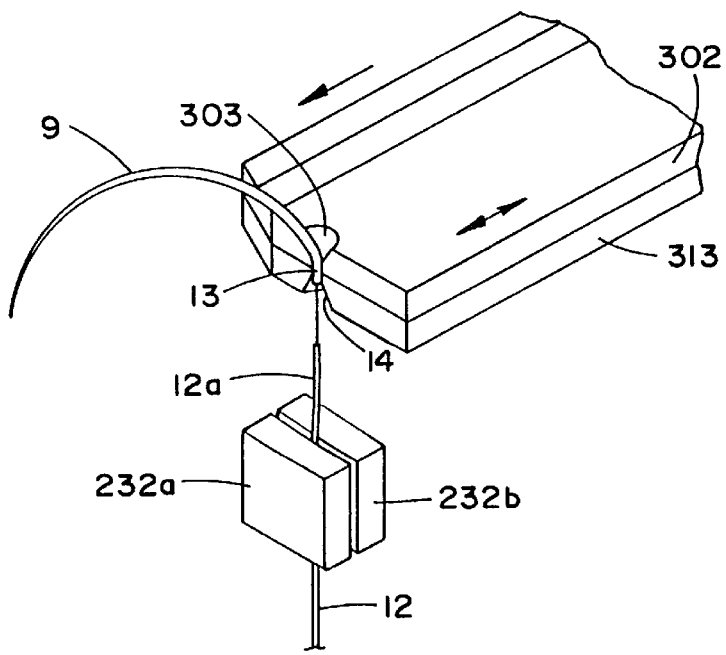
FIGS. 23(b)–23(f) illustrate the multi-axis gripper and swaging and suture alignment dies shown in various stages of the suture insertion and needle swaging sequence.
Figure 24A:
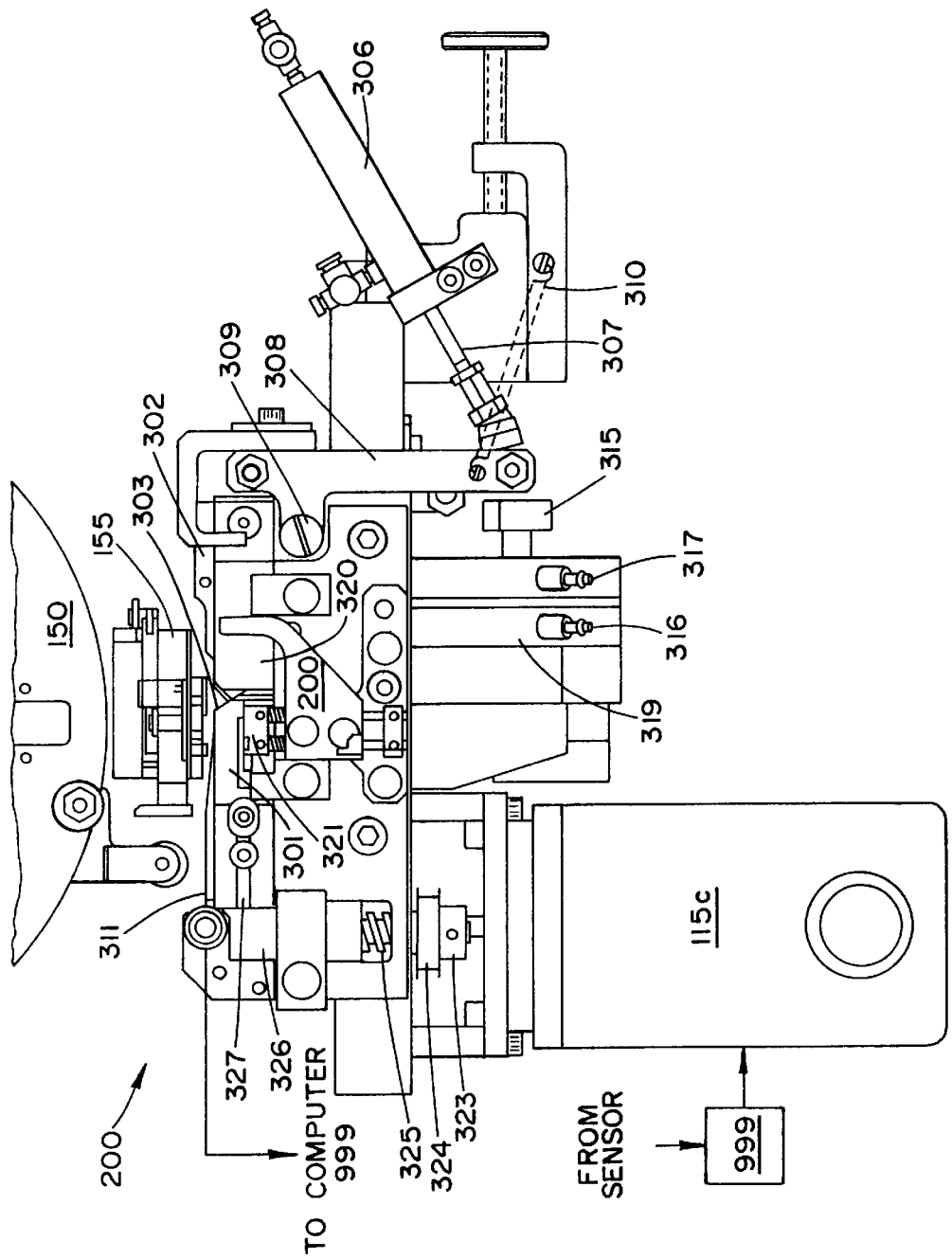
FIG. 24(a) is a top view of the swage assembly of the present invention with the multi-axis gripper indexed thereat.
Figure 24B:
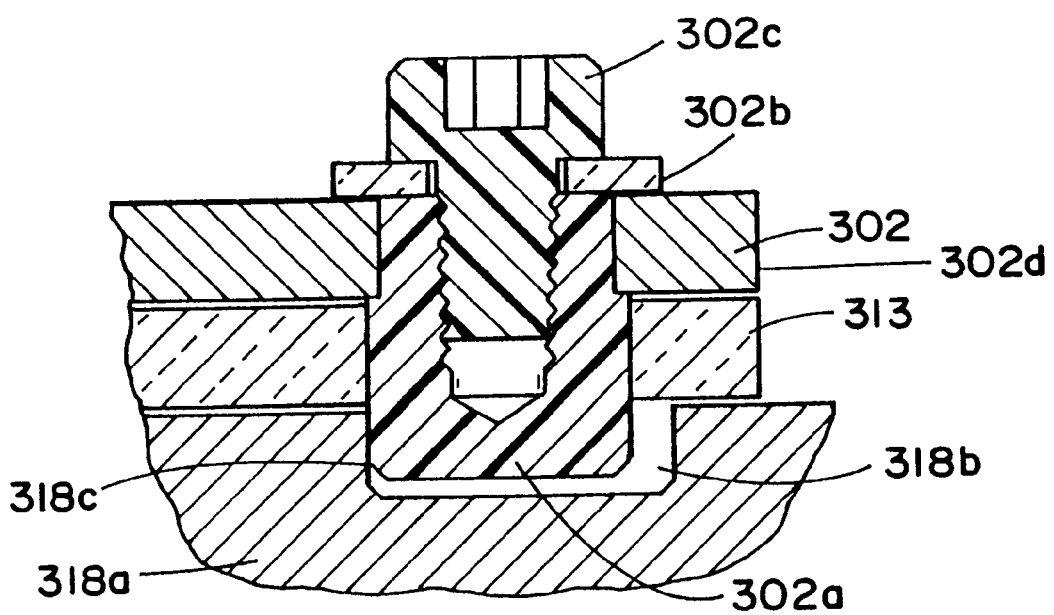
FIG. 24(b) is a detailed view of the swage stop mechanism for the swage assembly.
Figure 25A:
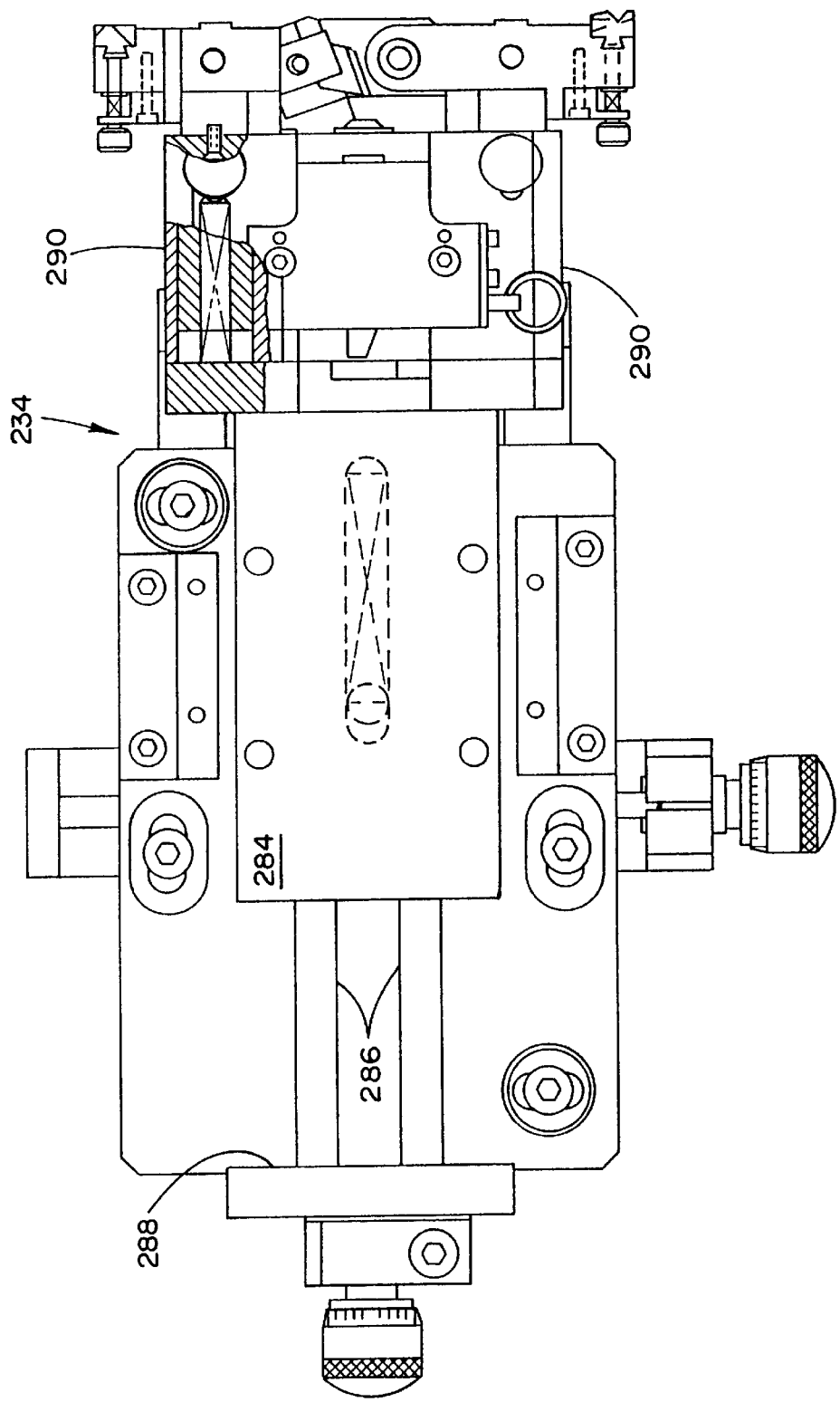
FIG. 25a illustrates a top plan view of a cutter assembly shown in a retracted position.
Figure 25B:
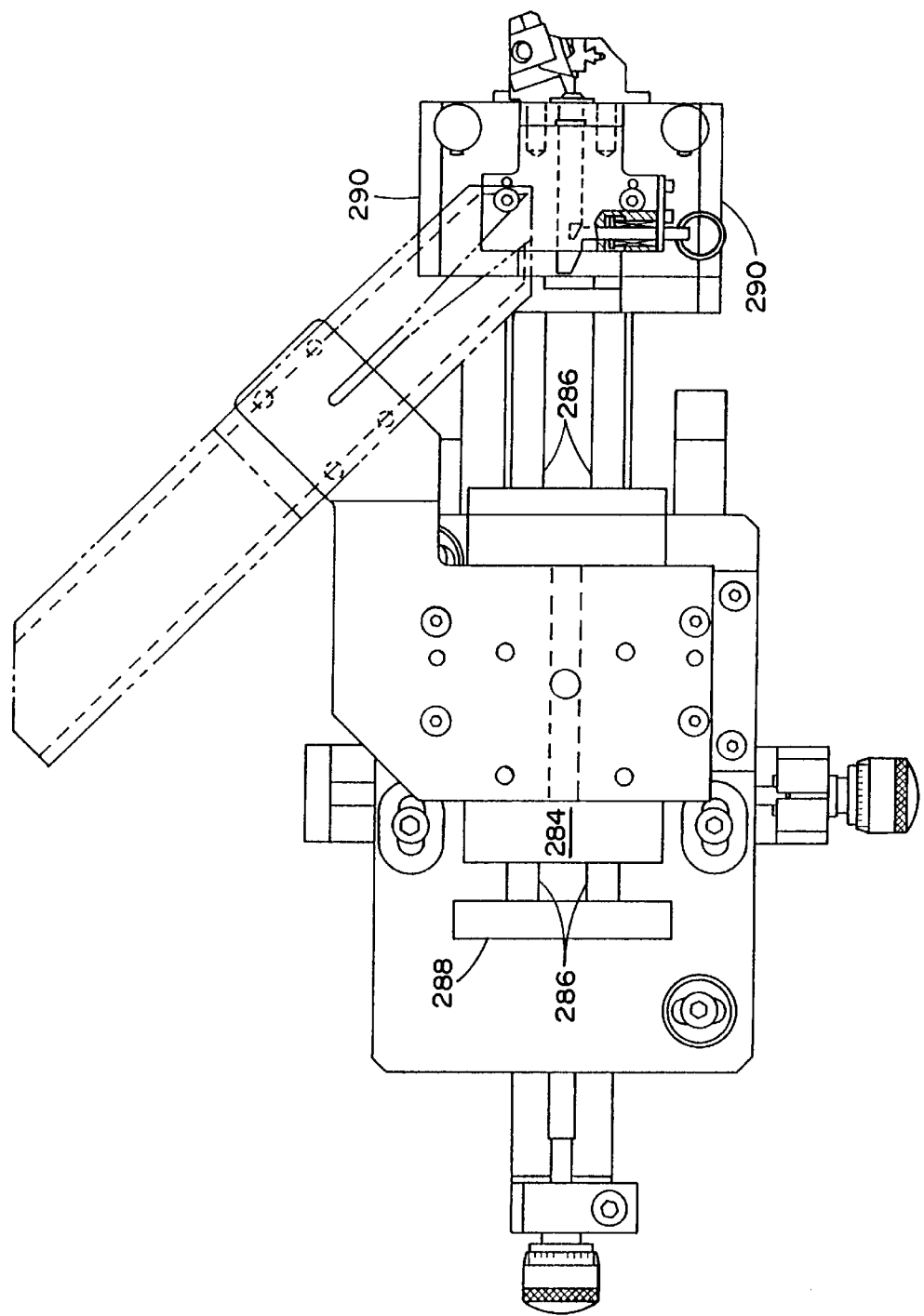
FIG. 25b is a top plan view of the cutter assembly of FIG. 25a, shown in an extended cutting position.

FIG. 25 illustrates a top plan view of a cutter assembly pursuant to the present invention, shown in a retracted position and FIG. 24 is a top plan view of the cutter assembly of FIG. 23, shown in an extended cutting position. Operational details of the cutting mechanism 234 of the preferred embodiments can be found in detail in co-pending U.S. patent application Ser. No. 09/020,085. Basically, the cutter assembly is actuated by an air cylinder 284 which during a cutting operation drives a slide mechanism (blade overtravel block) 286 from the retracted position of FIG. 23 to the extended position of FIG. 24. The air cylinder 284 mounts two drive rods 286 which extend therethrough and which the air cylinder translates back and forth to extend and retract the cutter assembly. A transverse bar 288 connects the two drive rods 286 at their ends remote from the cutter mechanism. The other ends of the two drive rods 286 are connected to the slide mechanism (blade overtravel block) 290, on which the knife blade 292 is mounted by a suitable mounting structure for movement therewith. FIG. 52(a) illustrates solenoid valve 803d operating under control of the control system 999 for controlling the extension and retraction of the cutter assembly for cutting the suture.

The suture drawing, tipping and cutting is more completely described in U.S. Ser. No. 08/804,477, U.S. Ser. No. 08/803,573, and U.S. Ser. No. 08/804,478, all of which are entitled "Suture Cutting System," the disclosures of which are incorporated herein by reference thereto.

Needle Threading and Swaging Station

The swaging operation taking place at the swaging station will now be described. FIGS. 23a–23f illustrate the multi-axis needle gripper 184 and swaging and suture alignment dies shown in various stages of the suture insertion and needle swaging sequence. This sequence, and the interaction of the dies in relation to each other, the needle and the insertion of the suture are performed with minimal parts and simple motions.

After conveying the needle to swaging assembly 200 shown in FIG. 24a and 24b, the multi-axis gripper 155 is radially extended from the swage dial to position the suture receiving end 13 of needle 9 between the funnel shaped die opening formed at the ends of two swage dies 301, 302, as shown in FIG. 31a, and the partial perspective view of FIG. 31b. As will be explained, swage die 301 is fixed in position, and swage die 302 is movable laterally toward the fixed swage die 301, as indicated by the arrow, to accomplish swaging of the suture receiving end of a needle placed therebetween. A funnel shaped die opening 303 having an exit diameter slightly larger than the diameter of the suture receiving end 13 of the needle 9 is formed when the two swage dies 301, 302 are positioned adjacent each other, as shown in FIGS. 23e and 23f. Note that different sets of swage dies may be provided during swage die set-up (FIG. 4), depending upon the size (diameters) of the needles and sutures to be swaged.

To precisely position the suture receiving end 13 of needle 9 between the swage die opening 303 formed at the ends of two swaging dies 301, 302, the movable swage die 302 is temporarily moved apart. In the illustration of the swaging assembly 200 shown in FIG. 24a, swage die 302 is moved apart from the fixed swage die 301 by actuating air cylinder 306 to provide a force to cylinder rod 307 to enable swage die operating lever 308 to pivot about screw 309 and pull movable swage die 302 a predetermined distance away from the fixed swage die 301. In the preferred embodiment, lever 308 is biased by spring 310 so that the movable swage die 302 will return toward the fixed swage die by the spring restoring force when the pressure provided by the air cylinder 306 is terminated.

Figure 23C:
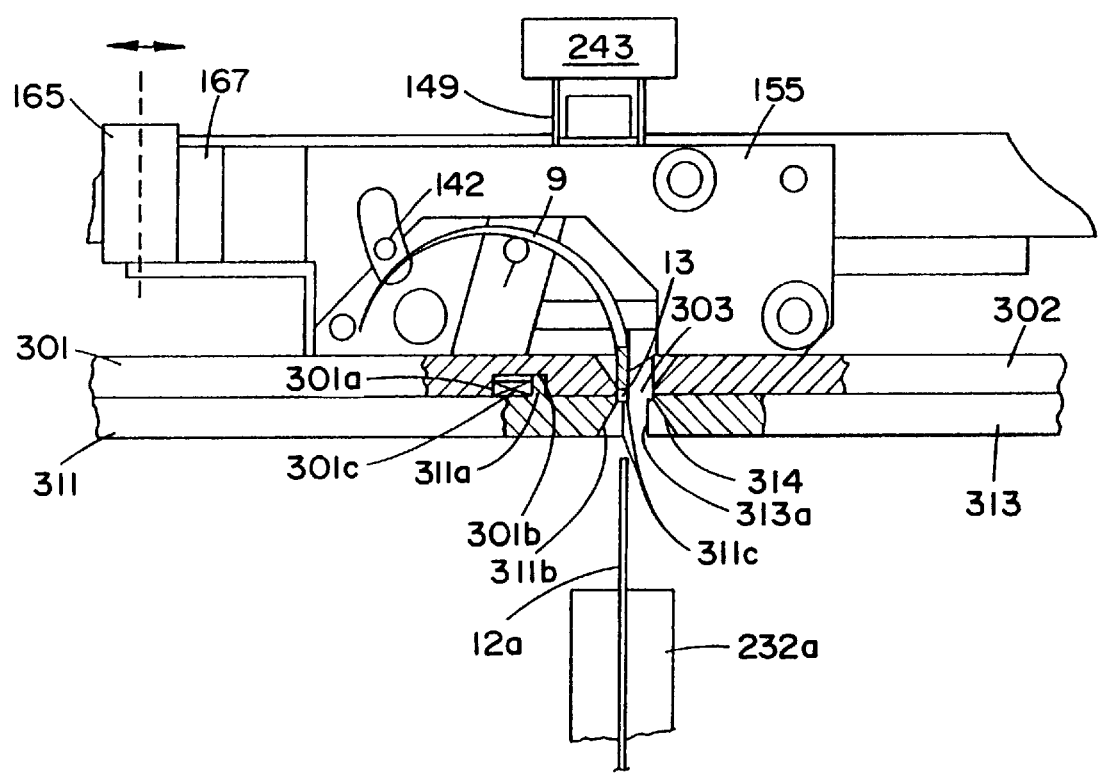

FIG. 23c shows die 301 in its fixed position, and movable die 302 in its spaced apart position prior to receiving the surgical needle 9 presented by multi-axis gripper 155. Suture alignment die 311, containing suture guide funnel half 311b is positioned under swage die 301, and free to slide laterally within limits. Alignment die 311 has a tang 311a that protrudes into cavity 301a formed within swage die 301. Compression spring 301c bears against the back wall of cavity 301a and tang 311a such that funnel die 311 slides forward until it is constrained by cavity wall 301b. In this position, it is forward of the center axis defined by the suture receiving end of the needle, and serves as a shelf 311c that helps assure suture receiving end 13 of needle 9 is in position for swaging. In this stage of the cycle, the parts are not positioned for suture insertion, and suture gripper 232a gripping suture 12 and stiffened end 12a, are in dwell. Suture alignment die 313, containing funnel half 314, is fastened to swage die 302 by suitable fastening means, and travels with it to the open position shown.

Figure 23D:
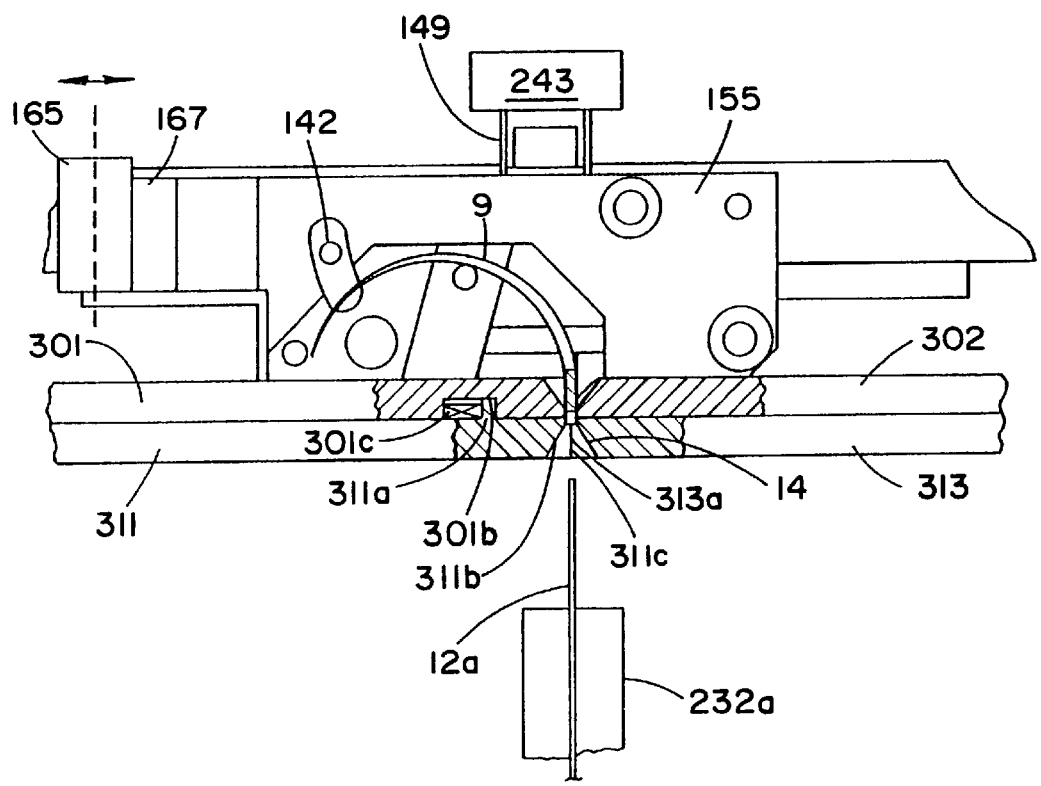
Figure 23E:
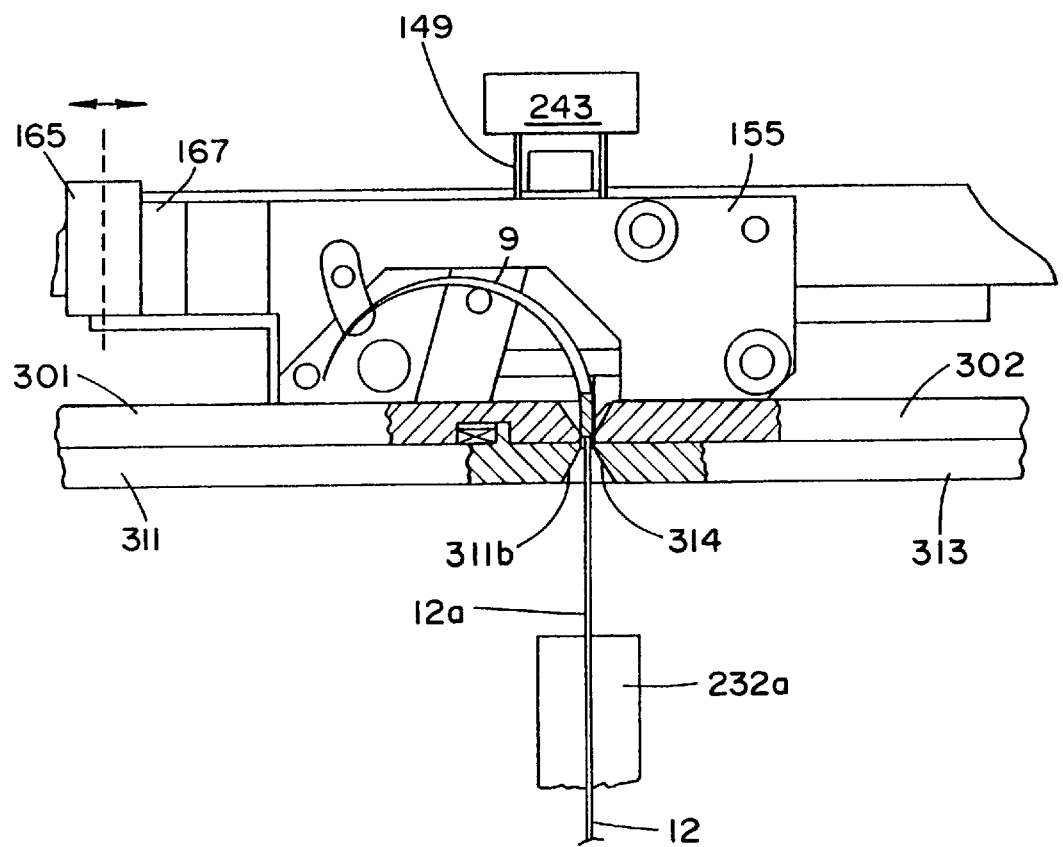
Figure 23F:
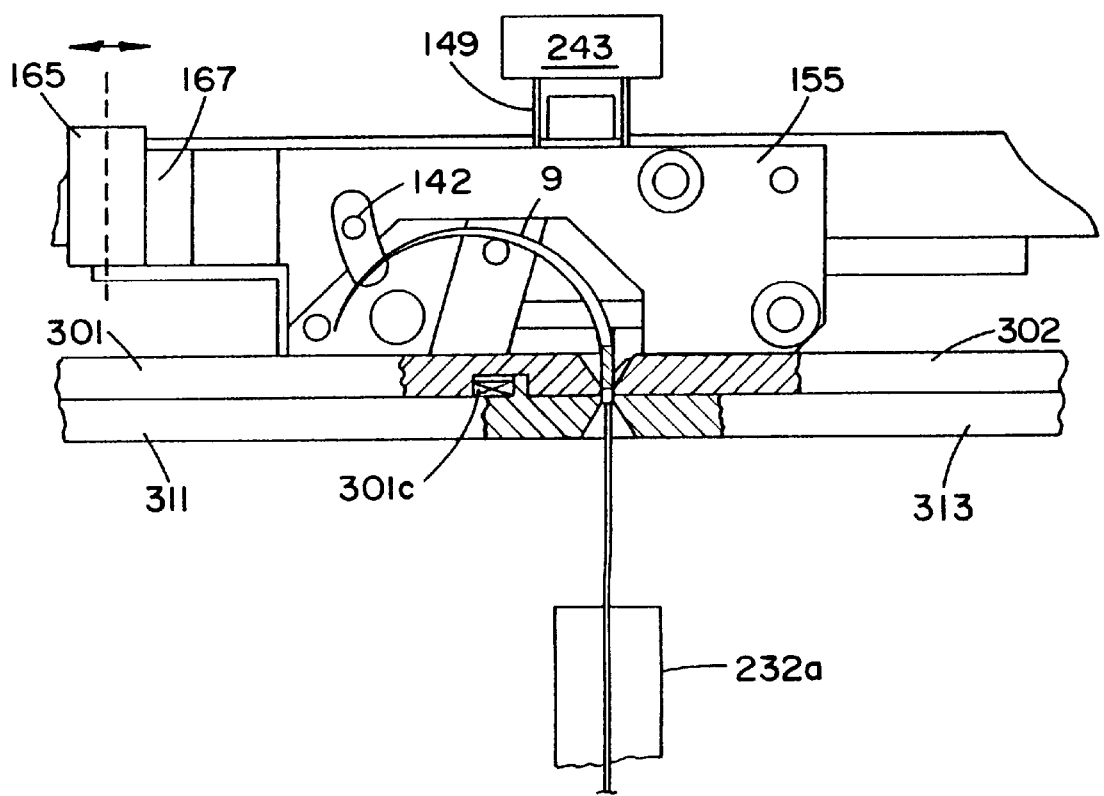

While the swage dies are apart, the multi-axis gripper 155 is extended to position the suture receiving end 13 of needle 9 within the opening 303, as shown in FIG. 23c and FIG. 24a. After positioning the suture receiving end 13 of needle 9 at the swage die opening 303, the swage die 302 and suture alignment die 313 are moved toward needle 9 with the resilient spring force present in spring 310 (FIG. 33a) that is sufficient to enable the die 302 to grip and locate the suture receiving end 13 precisely against fixed swage die 301 without deforming the cavity of the suture receiving end 13 formed therein. Concurrently, needle retaining pin 142 in multi-axis gripper 155 is raised by downward external force on plunger 149 by cylinder 243, as described above, and as shown in FIG. 52(d) activated by control system solenoid valve 808j, thereby releasing the needle so that its position is determined by the grip of swaging dies 301 and 302. Referring back to FIGS. 23c and 23d, the motion of dies 313 and 302 cause the face 313a of suture alignment die 313 to come in contact with the corresponding face 311c of suture alignment die 311. The resilient force causing this motion is forceful enough to compress spring 301c and move funnel die 311b to the left, such that tang 311a is no longer in contact with cavity wall 301b. Dimensioning of dies 302 and 313 is such that this motion results in the formation of two funnel halves 311b and 314 defining a smooth conical shape that is coaxial with the suture receiving end 13 of needle 9. FIG. 23d shows the suture receiving end 13 being gripped by the swage dies 301, 302 prior to suture insertion. Note that the exit diameter of the conically shaped funnel guide formed of funnel halves 311b and 314 is preferably equal to or greater than the diameter of the suture tipped end 12a and smaller than the diameter of the suture receiving end 13 of the needle 9, as shown in FIG. 23e, so that the tipped end 12a of the suture strand may be easily inserted therein.

FIG. 23e shows suture gripper 232a moved vertically to the insertion position, which causes stiffened suture end 12a to enter funnel 311b and 314, and be guided into the suture receiving cavity 13 of needle 9 axially aligned therewith. Once the strand is inserted into the suture receiving end 13 of the needle, as discussed above, the automatic swaging of the suture receiving cavity occurs. In the preferred embodiment of the swaging assembly 200 shown in FIG. 24a, a pneumatic air cylinder 319 provides air pressure to actuate cam 315 that bears on lever 308 to thrust movable swage die 302 toward the fixed swage die to accomplish the swaging of the suture receiving end of the needle placed therebetween. Air pressure is supplied to the swage cylinder 319 via ports 316, 317 under the control of the control system computer 99b and air flow regulator 809c and solenoid valve 803(b), as shown in FIG. 52(a).

FIG. 23f shows the completed swage stroke. The swage die 302 has been driven to a fixed stop by the swage cylinder, which exerted sufficient force to deform the suture receiving end 13 of needle 9. As deformation takes place, suture alignment die 313 further displaces funnel die 311, causing additional compression of spring 301c. In the preferred embodiment, the movable swage die 302 comes to an automatic stop by a swage stop mechanism herein described.

As shown in FIG. 24b, movable swage die 302 and suture alignment die 313 are mechanically held coincident to each other by shouldered post 302a, the smaller diameter of which is a light press fit into the mating hold die 302. Cap screw 302c with washer 302b retain the post in die 302. The larger diameter of post 302a, below die 302, extends through a light press fit hole in funnel die 313, so that the right hand swage and funnel dies are linked to move together laterally during the swaging cycle. The lower portion of shouldered post 302a extends through funnel die 313 into groove 318b, which is cross milled into swage assembly frame 318a. When the swage stroke is performed, the swage cylinder drives this die assembly to the left until it is positively stopped by the lower portion of post 302a, striking wall 318c of groove 318b. This stalls air cylinder 319, so that the stroke of the movable right hand die assembly shown is always the same for repeating cycles of the machine.

In an alternative embodiment, both swage dies 301, 302 may be movable towards each other to accomplish swaging. Furthermore, an adjustable swage stop mechanism for changing the swage stroke distance of one of the movable dies may be provided to further control the swaging pressure applied to the suture receiving opening and obviate the need for a fine-tuning positioning adjustment for a fixed swage die.

As shown in the top view of FIG. 24a, a needle fence assembly 321 is provided to ensure that the needle 9 does not tip or become misaligned when the end 13 of the relaxed needle is positioned between the swage dies. The needle fence assembly 321 comprises a needle fence plate whose distance from the tapered swage die opening 303 is adjustable depending upon the size of the surgical needle to be swaged.

In the preferred embodiment, the degree of swage compression imparted on the needle and resulting strength of grip by the needle on the suture is adjusted by precise positioning of the fixed die 301. As shown in FIGS. 24a and 5, servomotor 115c, operating under control of servo controller 116c, drives pulley 323 via timing belt 324, which rotates the swage adjust screw 325. The pitch of the swage adjust screw 325 is selected to move sliding wedge 326 a small distance. The swage die 301 has a complementary ramp angle 327 at the opposite end, which bears on the wedge 326 to retract or advance the position of the swage die 301 a precise distance proportional to the movement of the sliding wedge. Thus, the rotation of the swage adjust screw 325 and motion of the sliding wedge 326 results in transverse movement of the swage die 301 to thereby finely adjust its fixed position. For example, when a larger suture is to be swaged to a needle, the position of the fixed die 301 may be moved further away from the suture drawing axis so as to provide the desired amount of deformation when the swaging pressure is applied to the needle by the movable swage die 302. In the preferred embodiment shown in FIG. 33a, the control system computer 999 will send the approximate signals to automatically direct the servomotor 115c to adjust the position of the swage adjust screw 325, and hence, the position of the fixed die 301, in accordance with the pull-out test values of the needle-suture bond as measured by automatic pull-test system, as explained in further detail below. Specifically, appropriate control signals may be generated to direct the servomotor 115c to adjust the rotational position of the swage adjust screw 325 in accordance with stored statistical results of the pull-testing occurring at the pull-test station. Automatic pull-testing of the armed needle is desirable to ensure that the upstream swaging dies are optimally positioned to avoid over-swaging the needle-suture bond and, hence, preventing the likelihood of clip-off and to avoid under-swaging the needle-suture bond to prevent the chance of pull-out.

The repeated suture draw, cutting, and swaging operations are controlled by control system thread 1300 (FIG. 4) as now explained with reference to FIGS. 6(e) and 6(f). As indicated at step 1305, FIG. 6(b), a run mode operation is assumed. At step 1310, the swaging servo motor for controlling the location of the fixed servo die is moved to the programmed set point in accordance with the size of the needle to be swaged. FIG. 5 illustrates the swaging die operating under control of the swaging die servo motor 115c and servo controller 116c. At step 1315, a time delay is invoked to ensure that the swage die has moved to its set point. At step 1317, a determination is made as to whether the fixed servo die is at its programmed position. If the servo is not at its run ready position, then the cycle jam bit will be set as indicated at step 1319 and the process will continue until the swage assembly servo is at its ready position. The next step, indicated at step 1320, is to determine whether the swage cylinder 319 is at its home position. The swage cylinder is shown in FIG. 52(a) as operable under control of solenoid valve 803b. If the cylinder is not at its home position, then the cycle jam bit will be set as indicated at step 1321 and the process will continue until the swage cylinder is at its home position. Next, as indicated at step 1322 is to ensure that the first suture pull gripper 232a of suture tower 220 assembly is on, i.e., normally open, and at step 1324, to determine whether the MAG offset is retracted, so as not to interfere with the MAG extension at suture tower. Conceptually, the MAG offset mechanism is actuated by MAG offset cylinder 261 as shown in FIG. 52(*a*) operating under control of solenoid valve 804*r* and control computer 999. If the MAG offset mechanism is not retracted, then the cycle jam hit will be set indicating non-critical fault as indicated at step 1325 and the process will continue until the MAG offset mechanism is retracted. The control system then initiates a signal to close the suture draw gripper 232*b*. The system then performs a check at steps 1327 and 1328 to determine whether the suture gripper 232*b* has closed within the allotted time of the current cycle. If a time-out flag has been generated by the control system indicating a time-out error, the process will be terminated and prompted for re-initialization at step 2010. If the suture draw gripper is closed, then the control system initiates a signal to enable the suture funnel dies to clamp the needle in the manner described above, as indicated at step 1330. If the swage assembly MAG offset is required, then the control system initiates the MAG offset mechanism to adjust the position of the MAG which is carrying the needle, as indicated at step 1333. Then, as indicated at step 1334, the control system generates a control signal to effectuate release of the needle from the MAG 155 as described above with respect to FIG. 14. The process continues as indicated at step 1335 to enable the suture insertion within the clamped needle at the swaging station, as will be described with respect to FIG. 6(*j*).

Specifically, the control process 1335 for inserting the tipped free end 12*a* of the indefinite length suture strand within the suture receiving end 13 of surgical needle 9, is illustrated in FIG. 6(*j*). First, a check is made to ensure that the top suture draw gripper is at its predetermined position along its respective vertical guide rod as indicated at step 1337 in FIG. 6(*j*). This entails receiving a control signal from the tower #1 PLC 116*d* that the tower #1 servo motor 115*d* is ready. Next, as indicated at step 1339 in FIG. 6(*j*), a check is made to ensure that the needle 9 has been clamped in position within the swage die opening 303 as described above. Immediately thereafter, the top suture draw gripper 232*a* is enabled to advance the suture material 12 for a short stroke distance of about 1 to 5 inches, and preferably, 1.9 inches, so that the tipped end 12*a* advances precisely within the suture receiving end 13 for a swaging operation to take place. This is indicated at step 1340 in FIG. 6(*g*).

While the top suture draw gripper is inserting the suture during the short stroke, the system performs a check at step 1341 to determine whether a time-out flag has been generated by the control system indicating a time-out error. If a time-out flag has not been generated, the top suture draw gripper has inserted the tipped end of the indefinite length of suture material within the suture receiving end of the needle and the process continues. If the time-out flag is generated by the control system as a time-out error, the process will be terminated and prompted for reinitialization at step 2010. As the status of the first tower servomotor 115*d* that advances the suture material for the short stroke distance is continuously monitored, then as indicated at steps 1343 and 1344 in FIGS. 6(*g*) and 6(*h*), a decision is made to determine whether it has completed its short stroke cycle within the time period allotted for the cycle. If the short stroke is accomplished within the allotted time, then the current servo cycle ends as indicated at step 1343. If the short stroke is not completed within the time period allotted for the cycle, then a time-out flag is generated by the control system indicating a time-out error and the process will be terminated and prompted for reinitialization at step 2010.

Next, as indicated at step 1345 in FIGS. 6(*g*) and 6(*h*), the control system initiates a command to run the swage air cylinder 319, in essence, by providing air pressure sufficient to actuate cam 315 to bear on lever 307 for thrusting movable swage die 302 toward the fixed swage die to accomplish the swaging of the suture receiving end to the needle placed therebetween. As shown in the pneumatic schematic of FIG. 52(*a*), supply line 808*c* supplies pressurized air through suitable swage regulator 809*a* and solenoid valve 803*b* to provide the swaging pressure of the swage cylinder 319 under the timing and control of the control system 999.

FIG. 23(*f*) shows the completed swage stroke. The swage die 302 has been driven to a fixed stop by the swage cylinder, which exerted sufficient force to deform the suture receiving end 13 of needle 9. In the preferred embodiment, the moveable swage die 302 comes to an automatic stop by a swage stop mechanism herein described.

At step 1347 of FIG. 6(*e*), a check is made to determine if the swage cylinder had been fully extended to its predetermined position as commanded by the control system 999. This is accomplished by a proximity sensors located at the swage assembly (not shown). If the swage cylinder is not fully extended, then the cycle jam bit will be set indicating non-critical fault, as indicated at step 1348, and the process will continue until the swage cylinder is fully extended.

A breakdown of the run swage cylinder process at step 1345 is shown in the flow chart of FIG. 6(*i*), which illustrates specific control for the suture draw/swaging/and cutting steps. Thus, at step 1345*a*, FIG. 6(*i*), the run cylinder process includes extending the swage cylinder, i.e., initiating the swage operation, and waiting until the swage operation is completed at step 1345*b*. Then, at step 1345*c*, appropriate pressure sensing transducers located in the air pressure lines are used to monitor the swage pressure to be applied to the needle-suture assembly by the swage dies and, at step 1345*d*, the system ensures that the minimum swage pressure is reached. Particularly, as the swaging pressure applied to the moveable swage die 302 can be adjusted by the control system 999, then the air pressure supplied to the swaging cylinders will be stepped up until the minimum acceptable swage pressure is achieved.

Referring back to FIGS. 6(*g*) and 6(*h*), after the swage cylinder has been fully extended, and the swaging pressure used to accomplish the swaging is measured, then, at step 1349 in FIGS. 6(*g*) and 6(*h*), a determination is made whether the swage cylinder pressure is sufficient. If the swage pressure was not sufficient, then the cycle jam bit will be set indicating non-critical fault, as indicated at step 1350, and the process will continue. The degree of swage compression imparted on the needle, and resulting strength of grip by the needle on the suture, is adjusted by precise positioning of the fixed die 301 in the manner as explained above.

As indicated at step 1353 in FIGS. 6(*g*) and 6(*h*), immediately after swaging of the suture to the needle, the bottom suture draw gripper 230 engages the suture strand at its home position and the top suture gripper is opened to release its grip of the now swaged definite length suture strand. FIG. 6(*i*) shows the breakdown of this process at steps 1353*a*, which is the command to close the bottom suture draw gripper. The system waits a predetermined amount of time to ensure that the grippers close as indicated at steps 1353*b* and 1353*c*, and, if the gripper bottom does not close within that time period, then the system will generate a time-out error and the machine will terminated and prompted for re-initialization.

At the next step 1356 as shown in FIG. 6(*g*) and 6(*h*), the suture cutter that has been positioned just above the location where the bottom gripper is now gripping the indefinite length suture strand is extended to cut the indefinite length suture strand and then retracted. Note that this process step is broken down as steps 1356a–1356c as shown in FIG. 6(i). As shown at steps 1357 and 1358, a continuous monitoring is performed to determine whether the cutter assembly has performed the cutting operation within the allotted time for the current index cycle. Thus, at step 1358, a check is made to determine whether a time-out flag has been generated by the control system indicating a time-out error. If the time-out flag is detected, the process will be terminated and prompted for reinitialization at step 2010. If a time-out flag has not been generated, then at step 1360, a determination is made as to whether the top suture draw gripper 232a has opened within the time period allotted for the current index cycle. Thus, at step 1361, a check is made to determine whether a time-out flag has been generated by the control system indicating a time-out error. If the time-out flag is detected, the process will be terminated and prompted for reinitialization at step 2010.

If the time-out flag has not been generated at step 1361, then, at step 1363, a determination is made as to whether the swage pressure has been turned off. If the swage cylinder pressure has not been turned off, then the cycle jam bit will be set indicating non-critical fault, as indicated at step 1364, and the process will continue until the swage pressure is off. Then, at step 1366, a determination is made as to whether the swage cylinder has retracted to its home position. If the swage cylinder has not retracted, then the cycle jam bit will be set indicating non-critical fault, as indicated at step 1367, and the process will continue until the swage cylinder has retracted. Next, at step 1369, the now-swaged needle-suture assembly is released to the MAG device indexed at the swage station 200. The control system then waits at step 1370 for a control signal indicating that the tower #2 assembly is OK to enable drawing of the indefinite length suture to the top of the tower for the next suture insertion cycle. Thus, at step 1371, a check is made to determine whether a time-out flag has been generated by the control system indicating a time-out error. If the time-out flag is detected, the process will be terminated and prompted for reinitialization at step 2010. If the time-out flag has not been generated at step 1371, then, at step 1380, a "swap towers" routine is performed to command the single axis movement of the opened top suture draw gripper to a position at the bottom of the tower, and to command the suture engaging bottom gripper to move up the tower to the suture insertion position.

Thus, as shown at step 1382 in FIG. 6(k), the control process 999 for drawing of the indefinite length suture material up the servo tower at the swaging station, first determines that the bottom (Tower#2) and top (Tower#1) servomotors are operational. Additionally, a check is provided to ensure that the bottom and top grippers and their corresponding gripper arm drives are ready. Then, as indicated in FIG. 6(k) at steps 1384 and 1386, the tower #2 servo motor is enabled to drive the top (right) gripper vertically up along right rod 238a to a location just below the suture insertion position located near the top of the drawing tower 220 as shown in FIG. 18. To accomplish this, the tower #2 servomotor advances the bottom indefinite length suture strand engaging bottom gripper for a long stroke distance, which may range from 12 inches to 36 inches depending upon the length of said suture strand desired. The long stroke moves bottom gripper 232b from a home position just below the cutter assembly 234, to the position slightly below swaging assembly 200 as shown in FIG. 18.

Simultaneous with the positioning of the bottom gripper 232b during the long stroke of step 1384, the tower #1 servomotor 236, enables movement of the opened top gripper 232a along left rod 238b to the cut position below the cutter assembly 234 as shown in FIG. 18. The process of advancing suture material 12 by alternating grippers at each cycle eliminates the recycle or return time for retaining the gripper to the original position. This makes faster machine speeds and hence, higher production rates possible.

Finally, as indicated in FIG. 6(k) at step 1388 and 1389, a continuous check is provided to ensure that the top gripper servomotor has drawn the indefinite length suture strand during the long stroke to its vertical destination along its respective guide rod within the time allotted in the current index cycle, as sensed by proximity sensor 270 as shown in FIG. 13. Thus, at step 1389, a check is made to determine whether a time-out flag has been generated by the control system indicating a time-out error. If the time-out flag is detected, the process will be terminated and prompted for reinitialization at step 2010. If a time-out flag has not been generated, then the bottom suture draw gripper has reached its vertical position, and a control signal indicating that all of the swage dial assemblies have been accomplished for the current cycle is generated (step 1244, FIGS. 6(c) and 6(d). After swaging of the needle, the movable die 302 is again retracted by air cylinder 306, and the pin 142 of the multi-axis gripper 155 is actuated to engage the armed needle in the manner described above. Subsequently, the multi-axis gripper 155 is retracted to its position along the swage dial 150 for subsequent indexing to the pull-test station 300 for further processing.

Referring back to FIGS. 23(a) and 23(c)–(f) roller cam 165 is used to provide the compound off-set movement of the multi-axis gripper as it is reciprocated outwardly by the swage dial cam plate 172. Specifically, as shown in FIG. 23(a), after the needle has been swaged to the suture, the multi-axis gripper 155 closes pin 142 on needle barrel end 13 as the drive roller 243 is reciprocated out of engagement with plunger 149. Simultaneously therewith, the moveable swage plate 302 is retracted to enable movement of needle 9 by the multi-axis gripper 155. Before the swage dial 172 is rotated, the offset drive cam roller 165 is again advanced to bear against cam plate 167 and provide egress of the needle 9 from the swage die cavity in fixed swage plate 201. Once the multi-axis gripper 155 and needle 9 have cleared the fixed swage plate 301, the cam dial assembly 172 is rotated advancing cam rollers 185 inwardly to retract the multi-axis grippers 155 in a radial direction and enable rotation of the swage dial 150. Swage dial 150 then rotates the needle and suture assembly to the pull test station 300 for testing.

Automatic Pull Test Station

Figure 29:
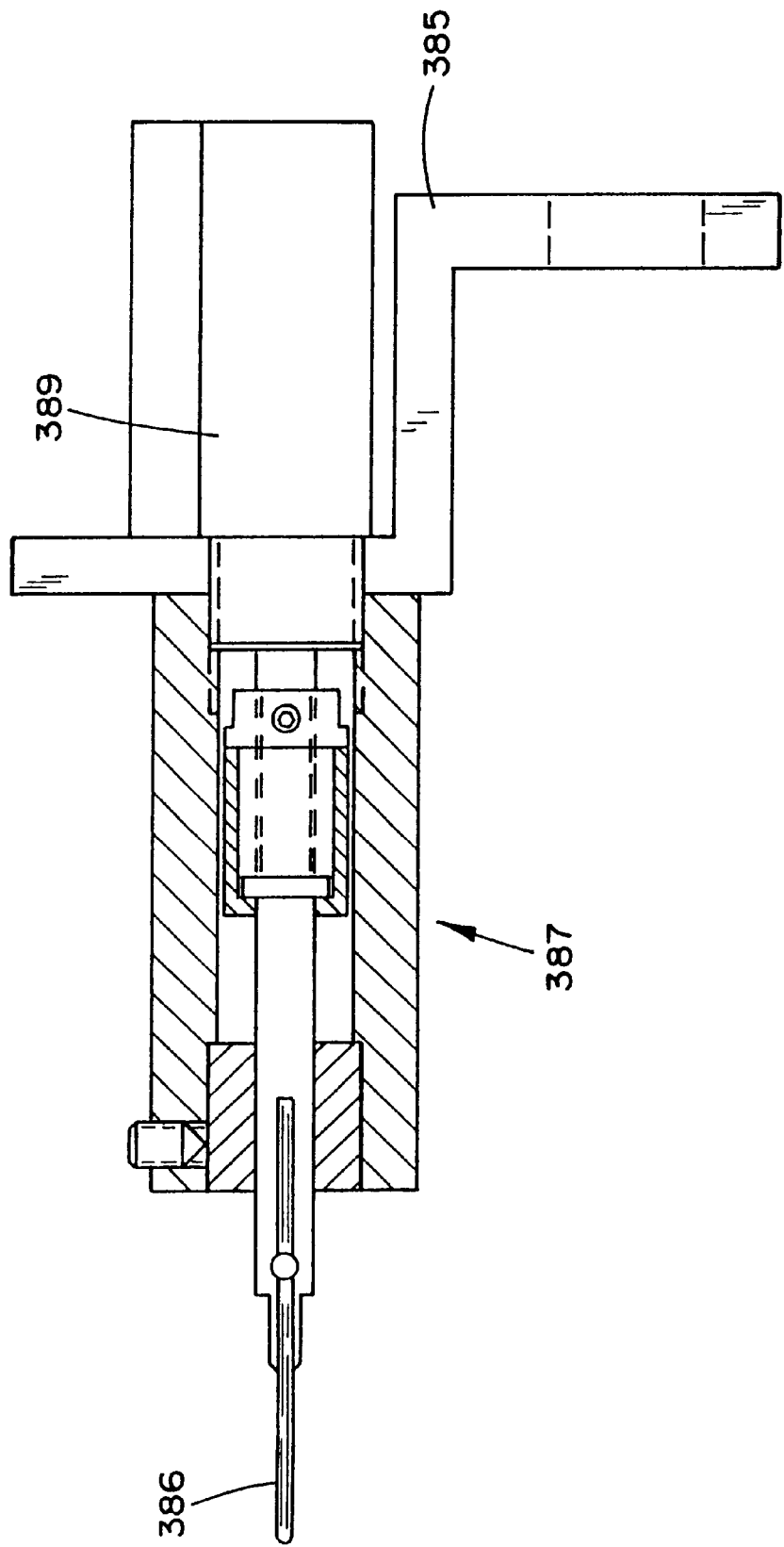
FIG. 29 is a partially cross sectioned top view of the needle stripper assembly used in the present invention.

The automatic pull-test station 300 that provides automatic pull-testing of a surgical needle and suture assembly is shown generally in FIGS. 26 through 29. As illustrated in FIG. 29 the automatic pull-test assembly 300 generally comprises a load cell mounting assembly 330 for mounting a load cell 335 which responds to loading of a V-plate needle arm 336 which receives the armed needle 9 from the multi-axis gripper 155. A needle release solenoid 388 is provided for relaxing the armed needle from the grip of the multi-axis gripper 155 and thereby release the needle so that it is supported by load cell 335. A pull-test fence assembly 340 is provided to prevent the armed needle 9 from tipping over or becoming misaligned when the armed needle is relaxed.

The suture gripping assembly 370 includes two pairs of retractable grippers 333a,b, and 334a,b for gripping the suture during the pull-tests. Grippers 333a,b, are operatively connected to the weighted slide block assembly 372 for performing non-destructive pull-tests as will be described with respect to FIGS. 26 and 27. Two separate pneumatic cylinders are used to drive grippers 334a,b for destructive pull-tests.

A detailed description of each of these assemblies and their interaction will be explained in detail hereinbelow.

As shown in FIG. 26, a surgical needle 9 with attached suture is retained by a multi-axis gripper 155 and, in the manner described above, is indexed to the automatic pull test station 300 by the rotary swage dial 150 to the position illustrated in FIG. 26. To position the armed needle 9 in the load cell 335, the multi-axis gripper 155 is extended from the swage dial 150 from center load "A" to center load "B" so that the end portion 13 of needle 9 is positioned above a corresponding receiving V-plate arm 336(a) of the load cell assembly 330 as shown in FIG. 34.

In the preferred embodiment, as described in greater detail in co-pending U.S. patent application Ser. No. 09/020,085 the load cell 335 is loaded by a pivotally mounted V-plate needle arm 336 having a thin needle supporting blade for supporting the suture receiving end portion 13 of various size surgical needles with the suture material 12 depending therefrom. Different V-plate arms may be provided for different needle suture combinations which accommodate larger and smaller sutures having diameters of approximately 0.009 to 0.017+/−0.001 inches. Depending upon the batch of surgical needles currently being pull tested, the appropriate needle V-plate supporting arm 336 will be positioned to receive the needle from the multi-axis gripper.

Non-destructive pull testing of the armed surgical needle 9 is accomplished as follows:

After positioning the multi-axis gripper 155 in the extended position as heretofore described, grippers 333a,b, of suture gripping assembly 370 are closed from an open position to grip the suture strand slightly below the needle V-plate supporting arm 336 of load cell assembly 330 as shown in FIG. 26. A single pneumatic actuator 372 (illustrated in FIG. 27(a)) is provided for opening and closing gripper arms 333a,b, and the cylinder is actuated by solenoid valve 804j (FIG. 52(c)) under control of control system computer 999.

Figure 27A:
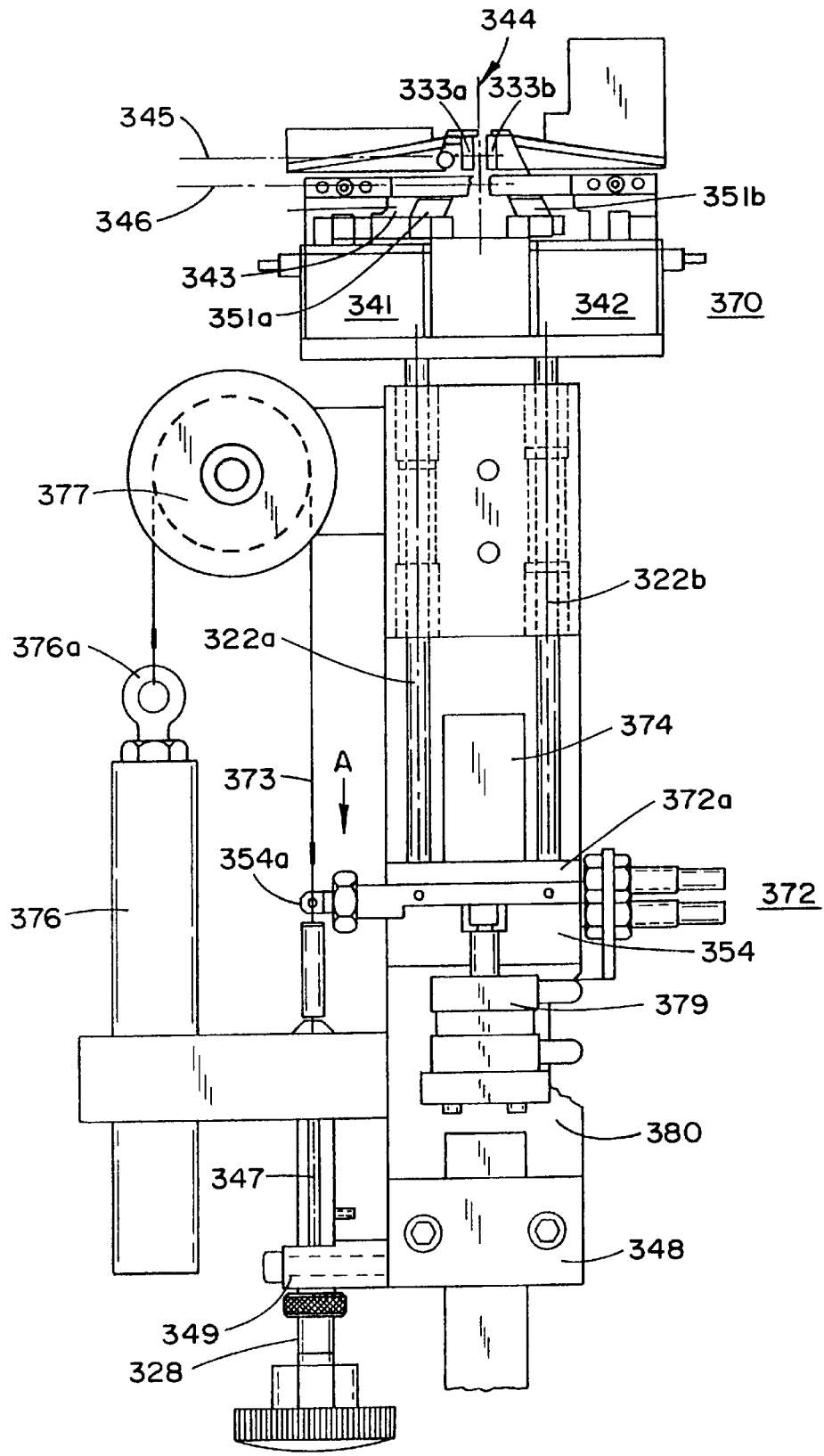
FIG. 27(a) is a front elevation view of the pull test assembly illustrating the gripper assembly and the slide block assembly.
Figure 27B:
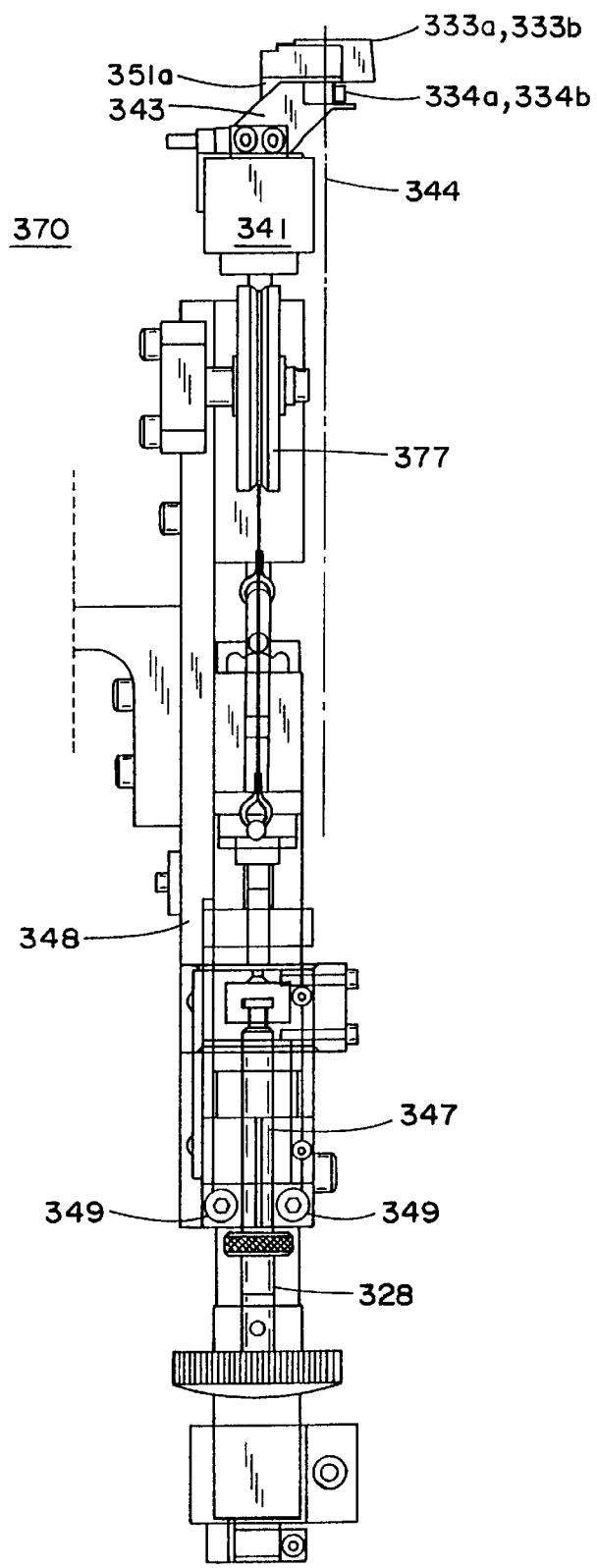
FIG. 27(b) is a side elevation view of the pull test assembly of FIG. 27(a) illustrating the gripper assembly and the slide block assembly.
Figure 28:
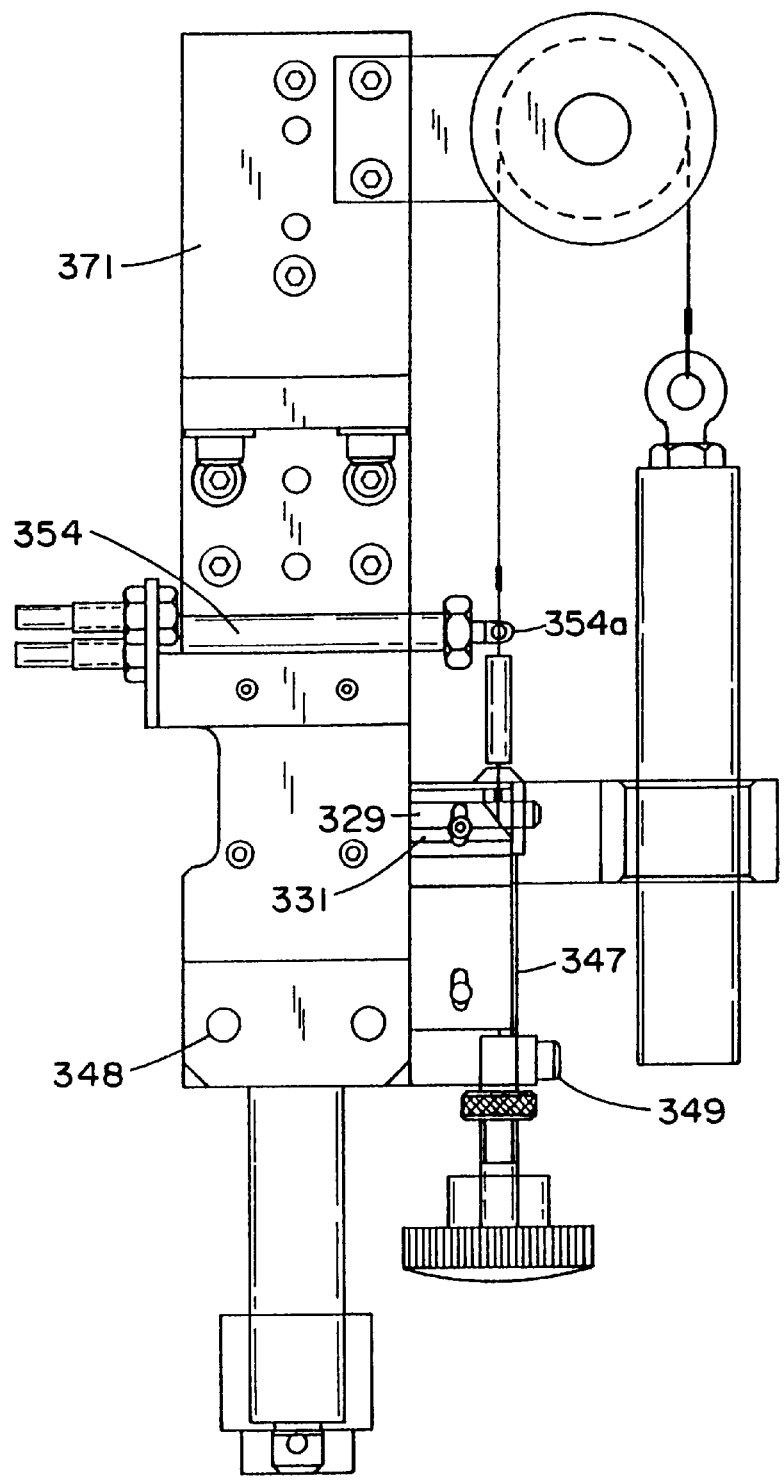
FIG. 28 is a rear elevation view of the pull test assembly illustrating the spring tension assembly used for non-destructive pull tests.

FIGS. 27(a) and 27(b) illustrate the slide block assembly 372 that is composed of slide rods 322a,b and a lower slide block 372a which reciprocates vertically on the slide rods 322a,b. Slide block 372a includes a load balancing plate 354 upon which air cylinders 374, 379, apply respective upward and downward forces depending upon the type of pull-test that is to be performed. As shown in FIG. 27a, air cylinder 379 is shown in an extended position providing an upward force that supports the load balance plate 354 and consequently maintains slide block 372a of slide assembly 372 at a fixed vertical position.

Slide block 372a is counter weighted to a net zero weight by appropriately sized counterweight 376 that is attached to the load balance plate at 354a and acts through cable 373, around pulley 377, and to attachment point 376a. This counterweight 376 acts to balance the net load on slide block 372a to a neutral position. An adjustable net downward force of 2 to 30 oz. is provided by an adjustable spring tension device 347. One end of spring tension device 347 is mounted to fixed position on the frame 348 by a mounting bolts 349 such as clearly shown in FIG. 28. The other end of spring tension device 347 is attached to the load balancing plate 354 at 354a and exerts an adjustable downward loading between the load balance plate 354 and the fixed frame member 348. This adjustable download tension is normally offset by air support cylinder 379 which drives the lower slide block 354 upward to a home position.

The amount of spring tension applied during a non-destructive pull-test can be varied from 2 to 30 oz. by rotation of knob 328 and the effective pull test loading is indicated by pointer 329 on scale 331.

To accomplish the non-destructive pull test, slide block support cylinder 379, mounted on sub frame 380 is relaxed from its extended position (FIG. 27(a)) supporting the load balance plate 354 to remove the upward force on load balancing plate 354 and impose the selected spring tension net weight of 2 to 30 ounces downwardly on slide block 372a and through slide rods 322a,b to the gripper assembly 370 and the gripper jaws 333a,b. This causes a pull force on the suture attached to swage needle 9, in the downwardly direction of arrow "A". The accuracy of this system is enhanced because slide block 372a is suspended on slide rods 322a,b which are mounted in low friction ball bushings, pressed into frame member 371, thereby imposing minimal mechanical drag on the system. Relaxation of the slide block support cylinder 379 is actuated by solenoid valve 804i under control of control system computer 999, as shown in FIG. 52(c).

Note in FIG. 27a, that the fixed slide block frame 348 is positioned parallel to the axis 344 of the suture depending from the needle 9, and is located a distance away from the axis corresponding to the length of the offset arms 351a,b of gripper jaws 333a,b.

Simultaneous with or momentarily before the slide assembly 372 is released, the needle release solenoid 388 is actuated by control system solenoid valve 804k (FIG. 52(d), to enable multi-axis gripper 155 to disengage its grip on the armed needle 9 by depressing MAG gripper plunger 149 in the manner as previously described with respect to FIGS. 23(a–d) . Releasing the armed needle from the grip of the gripper 155 is necessary to ensure that it is firmly positioned on the V-plate needle supporting blade at 336(a). Moreover, to provide an accurate pull-test, the needle must be released so that there is no existing upward force that would cause false results.

Referring to FIG. 26, a needle fence assembly 340 is provided to prevent the needle 9 from becoming misaligned or from tipping over after the multi-axis gripper 155 releases its grip on the needle. The needle fence assembly 340 includes vertical fence plate 342 which can be adjusted to lie a needle's diameter away From the face of gripper 184, and thereby retains the needle in an upright position for the test. The lateral positioning of the vertical fence plate 342 is adjustable by rotating lead screws 343 (shown in FIG. 26) which advances or retracts the fence an appropriate distance to accommodate the configurations of different size needles.

The controlled release of the minimum pull-test is of short duration, preferably ranging in milliseconds. If the test is successful, i.e., the suture meets the minimum pull-test requirements, the needle is re-gripped by the multi-axis gripper 155 by deactuating the needle release solenoid 388 to release the downward force on plunger 149. The suture gripper jaws 333a,b, are then retracted to their open position to release their grip on the suture as controlled by the control system. Subsequently, the multi-axis gripper 155 is retracted and the rotary swage dial 150 and rotated to convey the armed needle downstream for hand-off to the packaging dial 500.

If the suture fails the minimum pull-test, i.e., if the suture is dislodged from the surgical needle 9 as a result of the non-destructive test, the control system computer 999 is flagged so that the disarmed needle 9 will be ejected at the pull-test station. The dislodged suture strand will be drawn into a vacuum assembly (not shown) and the needle 9 will be ejected by a needle stripper assembly 387 that is mounted to the swage dial assembly by mounting bracket 385 shown generally in FIG. 16(a) and in detail in FIG. 29. As shown in FIGS. 29 and 52(c), needle stripper solenoid 804l actuating cylinder 389 will be actuated by a control signal output from the control system computer 999 to extend needle stripper pin 386 to a space between the needle 9 and the face of the multi-axis gripper 155 to remove the needle while relaxed in the multi-axis gripper 155. The needle will fall and be collected by appropriate collection means (not shown) located at the pull-test station.

After the pull test, whether successful or unsuccessful, the apparatus prepares for the next armed needle to be pull-tested. Slide block assembly 372 and retracted gripper jaws 333a,b, are pushed back up with respect to the fixed slide mount frame 326 to the home position by an appropriate upward force supplied by the air cylinder 379 as controlled by the control system computer 999.

In the preferred embodiment, the load cell 335, illustrated in FIG. 26 is a piezoelectric transducer that measures the force applied by the slide block assembly to the needle-suture assembly 9. The transducer load cell 335 can he interfaced with the control system computer 999 by conventional means, and, in the preferred embodiment, is a 25 lb. transducer manufactured by Techniques Co. (Model No. MDB-25PH). The forces applied to the suture 9 and measured by the load cell transducer 335 during the destructive pull-testing may be stored for statistical purposes or for real-time monitoring during a swage die setup routine that may take place when a new batch of surgical needles are to be swaged in the manner to be described. For instance, if the non-destructive pull-tests fail and the force measured by the transducer 335 is determined to be at the low end of a predetermined range, then the control system computer 999 will acknowledge this and may send appropriate signals to the upstream swaging assembly described previously causing the fixed swaging die 301 to be advanced an incremental amount toward the moveable swage die 302, resulting in subsequent swages being stronger. Likewise, if the non-destructive pull-test passes, i.e., the forces measured by the transducer are determined to be between a minimum and maximum load, then no die adjustment need be made.

Destructive pull-testing of the armed surgical needle is performed at a parts change set up and at every nth needle indexed thereafter. The purpose of performing a destructive pull-test is to set the swage dies located at the upstream swaging station for correct maximum swage pull-out value. This is by necessity a destructive test, and the test frequency, which is programmable, is set high enough to maintain control of the operation, but low enough to avoid excessive product waste. In the preferred embodiment, this frequency may be set at every 50th needle, but could be every 75th or 100th needle. As mentioned above, destructive pull testing of the armed surgical needle 9 is accomplished similarly as described herein above with respect to the minimum pull test, but with a second pair of gripper jaws 334a,b and destructive test air cylinder 374. However, the fundamental difference between the tests is a fixed mechanical stroke that is always strong enough to pull the suture out of the needle. This destructive stroke replaces the variable 2 to 30 ounce force of the minimum pull test routine.

Another purpose of the destructive pull test is to aid in installing a new swage die set during a changeover procedure, which is a procedure that is used to prepare the needle swaging apparatus (swage dies) for processing a new batch of needles when they are of a different size from a previously processed batch. Contrary to the non-destructive pull-test described above, the pull-test apparatus is programmed for 100% destructive test of a swaged needle, while the swaging assembly is operating and feeding the armed needles to the pull-test station. The die adjustment system at the upstream swaging assembly will receive a signal from the computer 999 transducer load cell 335, at each machine cycle, and quickly perform a correct adjustment of the swage dies.

Destructive test pull-out values are recorded in the system computer 999 and are used to compute statistical process control information in the manner to be described which is fed back to the machine operator through display screens.

As shown in FIG. 27(a), the second air cylinder 374 located opposite air cylinder 379 is actuated under control of solenoid valve 804k (FIG. 52(c)) which is programmed by control system computer to provide a fixed stroke against load balancing plate 354 from the home position shown in FIG. 27(a). This results in a downward vertical displacement of lower slide block assembly 372 from the position shown in FIG. 27(a). This also results in a downward force upon slide rods 372(a) and (b), which moves the gripper assembly 370 downwardly, including gripper jaws 334a,b and the suture gripped therein, in the direction of the arrow "A" as shown in FIG. 27(a) The air pressure supplied to cylinder 374 is set high enough to always pull the suture out of needle 9. This stroke is limited by the bottom portion of slide assembly 372 striking the top of stationary frame 326 which is sensed by appropriate sensor (not shown) to indicate the end of the test. The destructive pull test jaws 334a,b are serrated on their gripping surface, as shown in FIG. 27(a) to ensure a positive non-slip grip on the suture during the destruct cycle. Further, the destruct gripper jaws 334a,b are driven by a pair of air cylinders 341,342 through angled offset arms 343,344 and are actuated under control of solenoid valve 804q (FIG. 52(c)).

The axis of reciprocation for each of the sets of jaws is illustrated in FIG. 27(a), with the axis for the non-destruct gripper at 345, and the axis of reciprocation for the destructive gripper jaws illustrated in FIG. 27(a) at 346.

The force necessary to accomplish the destructive pull-test is measured by the piezoelectric load cell transducer 335 as discussed above, and data representing this force is sent to the control computer 999. If it is determined by the process control algorithm (described below) that the destructive pull-test forces as measured by the transducer load cell are lower than a predetermined range of pull-test values, the control system computer 999 will send out appropriate control signals to increase the swaging die stroke applied when swaging the suture to the needle at the upstream swaging station. If it is determined that the destructive pull-test forces as measured by the transducer load cell are higher than the predetermined range, the control system computer 999 will send out appropriate control signals to the upstream swaging assembly to move a fixed swage die a small incremental distance away from the moveable swage jaw, thereby decreasing the swaging pressure applied when swaging the suture to the needle.

Figure 6M:
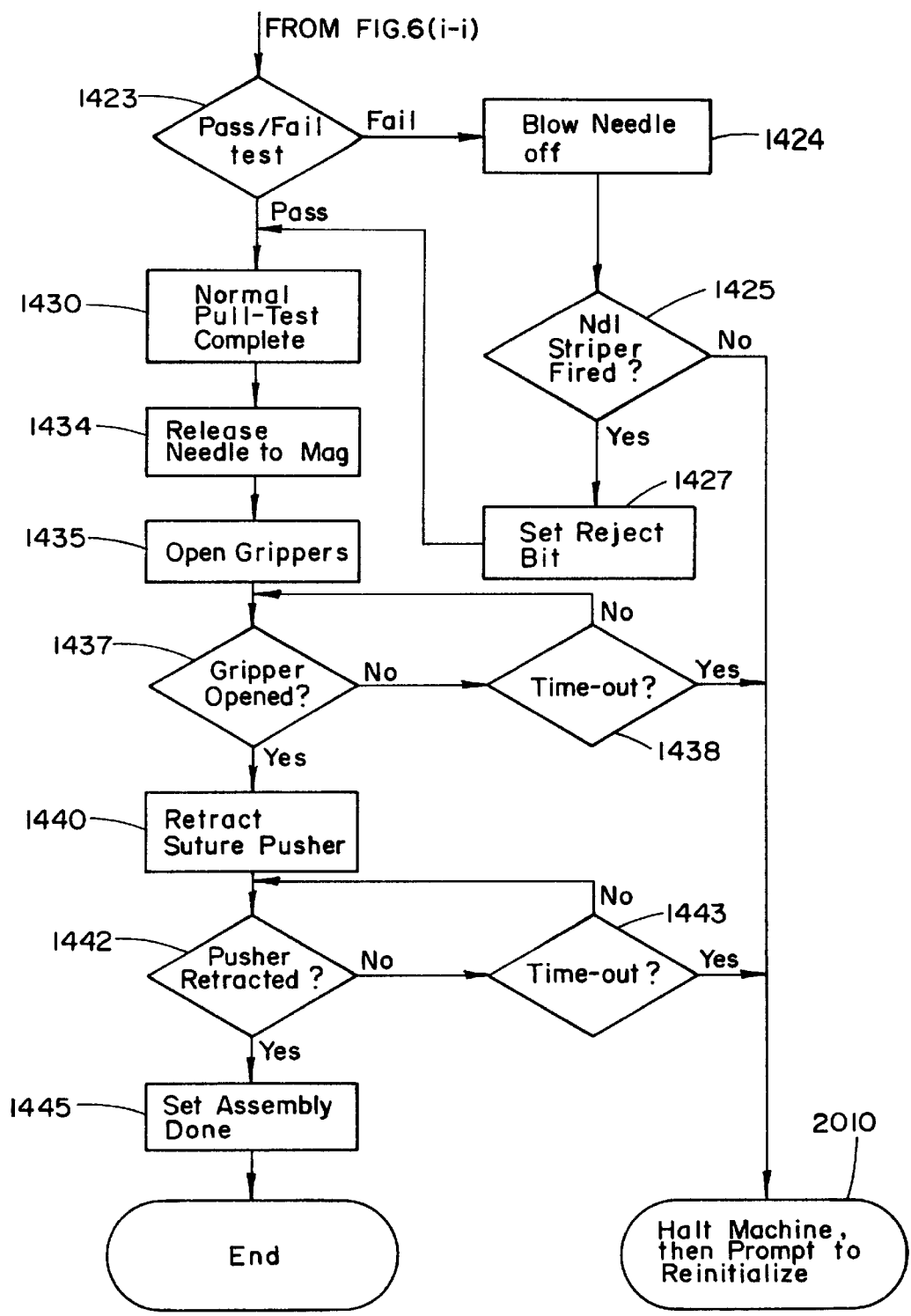

As illustrated in FIGS. 6(l) and 6(m), the control process 1400 at the suture pull-test station 400 comprises a first step 1402 to position the armed needle 9 in the load cell 335, this entails extending the MAG gripper from the swage dial 150 from center load "A" to center load "B" as shown in FIG. 26, so that the end portion 14 of needle 9 is positioned above the corresponding receiving V-plate arm 336(*a*) of the load cell assembly 330. Extension of the MAG gripper into the pull-test assembly is accomplished by virtue of the cam mechanism in the swage dial as described above. Then, as indicated at step 1404, a suture pusher mechanism 337 (FIG. 52(*c*)) actuated under control of solenoid valve 804*p* is extended to position the suture extending from the needle to within the close of the first pair of retractable grippers 333*a,b*, for gripping the suture during the pull-test. Next, as indicated at steps 1406 and 1407, a determination is made as to whether the suture pusher has extended within the time allotted for the current cycle. Thus, at step 1407, a check is made to determine whether a time-out flag has been generated by the control system 999 indicating a time-out error. If the time-out flag is detected, the process will be terminated and prompted for reinitialization at step 2010. If a time-out flag has not been generated, then at step 1408, the control system commands the closing of suture gripper arms 333*a,b*, from an open position to grip the suture strand 12 slightly below the needle supporting blade 336 of load cell 335 as shown in FIG. 26. Next, as indicated at steps 1410 and 1411, a determination is made as to whether the gripper is closed within the time allotted for the current cycle. Thus, at step 1411, a check is made to determine whether a time-out flag has been generated by the control system 999 indicating a time-out error. If the time-out flag is detected, the process will be terminated and prompted for reinitialization at step 2010. If a time-out flag has not been generated, the control system actuates the MAG needle release cylinder 388 to enable multi-axis gripper 155 to disengage its grip on the armed needle 9 as indicated at step 1412. Releasing the armed needle from the grip of the gripper 155 is necessary to ensure that it is firmly positioned on the load cell needle supporting blade 336. Moreover, to provide an accurate pull-test, the needle must be released so that there is no existing upward force that would cause false results. Next, as indicated at steps 1413 and 1414, a determination is made as to whether the release cylinder has been extended within the time allotted for the current cycle. Thus, at step 1414, a check is made to determine whether a time-out flag has been generated by the control system 999 indicating a time-out error. If the time-out flag is detected, the process will be terminated and prompted for reinitialization at step 2010. If a time-out flag has not been generated, the normal support slide cylinder supporting the slide block assembly 372 is released, as indicated at step 1415 to enable the weighted force to perform the pulling of the suture.

As indicated at step 1417, a determination is made as to whether the cylinder has been activated. If the support slide cylinder has not been activated, as indicated at step 1418 then this indicates a fatal pull-test assembly error, the process will be terminated and prompted for reinitialization at step 2010. If the cylinder has been activated, then the pull-test force as applied by the suture gripping assembly to the needle-suture assembly 9 is measured by a transducer as indicated at step 1420 in FIGS. 6(*l*) and 6(*m*). The determination of whether the minimum-pull test has passed, i.e., is within the pre-programmed pull-test limits, or failed, i.e., exceeded the pull test limits, is made at step 1423 as shown in FIG. 6(*i*).

If the suture fails the minimum pull-test, i.e., if the suture 12 is dislodged from the surgical needle 9 as a result of the release, the now dis-armed needle is removed from the MAG by firing a needle reject "stripper" cylinder 389, actuated by a control signal output, to extend needle stripper blade 386 to remove the needle as indicated at steps 1424 and 1425. The needle will fall and be collected by appropriate collection means (not shown) located at the pull-test station. If the needle reject cylinder is not fired, as determined at step 1425, then the process will be terminated and prompted for reinitialization at step 2010. Additionally, if the pull-test fails, the dislodged suture strand is ejected by a suitable blast of air provided by an air jet 392 as controlled by solenoid valve 804*u* (FIG. 52(*c*)) and subsequently sucked into a vacuum assembly (not shown). Finally, a NEEDLE REJECT flag is raised by the control system computer 999 as indicated at step 1427 indicating a failed needle-suture assembly.

If the needle-suture assembly passes the minimum pull-test, i.e., the suture meets the minimum pull-test requirements as indicated at step 1430, the needle is re-gripped by the MAG gripper 155 as indicated at step 1434 in FIGS. 6(*l*) and 6(*m*). This is accomplished by deactuating the needle release solenoid 388 which releases the force on plunger 149. Then, as indicated at step 1435, the suture pull-test grippers 333*a,b*, are retracted to their open position to release their grip on the suture 12. As indicated at steps 1437 and 1438, a continuous check is provided to ensure that the grippers have opened within the time allotted in the current index cycle. Thus, at step 1438, a check is made to determine whether a time-out flag has been generated by the control system 999 indicating a time-out error. If the time-out flag is detected, the process will be terminated and prompted for reinitialization at step 2010. If a time-out flag has not been generated, then the suture pusher cylinder 337 is retracted at step 1440. As indicated at steps 1442 and 1443, a continuous check is provided to ensure that the suture pusher is retracted within the time allotted in the current index cycle. Thus, at step 1443, a check is made to determine whether a time-out flag has been generated by the control system 999 indicating a time-out error.

If the time-out flag is detected, the process will be terminated and prompted for reinitialization at step 2010. If a time-out flag has not been generated, then a flag indicating that the minimum pull-test was successful and that the armed needle may be conveyed downstream for packaging thereof, is set at step 1445 for later use by the control system.

Figure 6N:
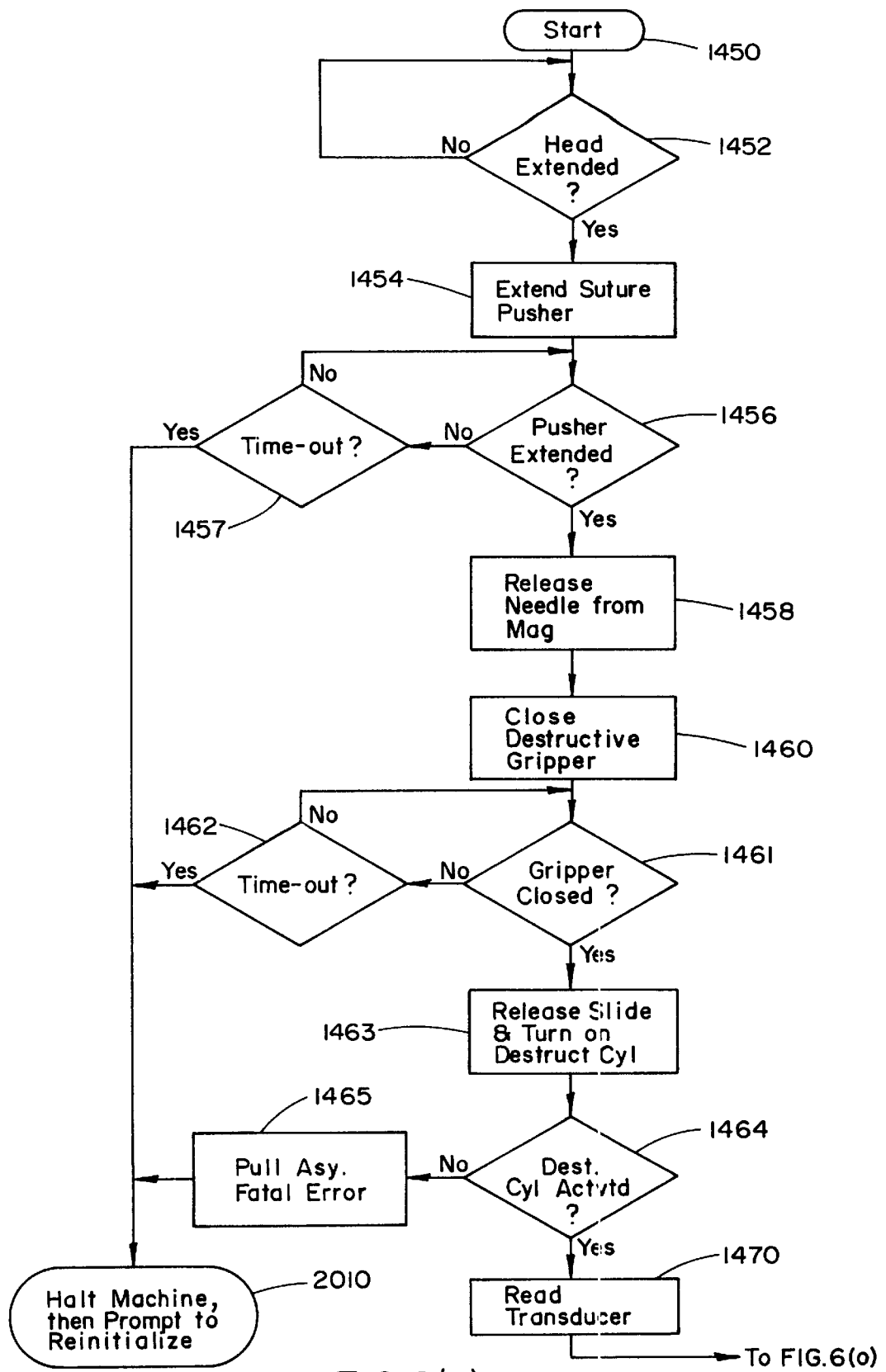
Figure 6O:
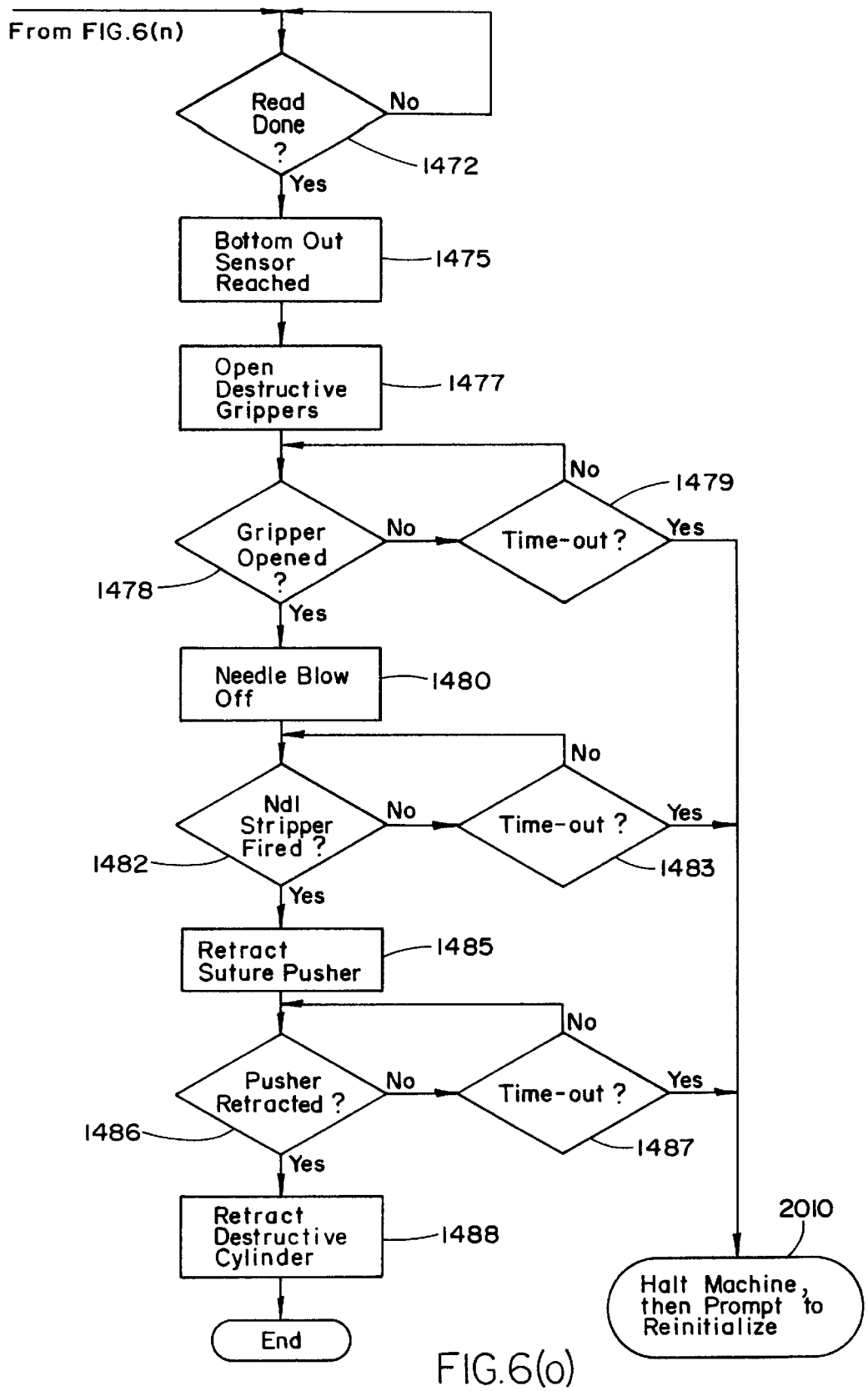

FIGS. 6(*n*) and 6(*o*) illustrates the control process steps 1450 for the destructive needle-suture assembly pull-test. As shown in FIG. 6(*j*), steps 1452–1457 are exactly the same as corresponding steps 1402–1407 as shown and described above with respect to FIGS. 6(*l*) and 6(*m*) for extending the MAG within the station and extending the suture pusher. Then, as indicated at step 1458, the control system actuates the MAG needle release cylinder to enable multi-axis gripper 155 to disengage its grip on the armed needle 9. Releasing the armed needle from the grip of the gripper 155 is necessary to ensure that it is firmly positioned on the load cell needle supporting blade 336. The control system then commands the closing of the destructive suture gripper arms 426*a,b*, from an open position to grip the suture strand 12 slightly below the needle supporting blade 336 of load cell 335 as indicated at step 1460 shown in FIGS. 6(*n*) and 6(*o*). Next, as indicated at steps 1461 and 1462, a determination is made as to whether the gripper is closed within the time allotted for the current cycle. Thus, at step 1462, a check is made to determine whether a time-out flag has been generated by the control system 999 indicating a time-out error. If the time-out flag is detected, the process will be terminated and prompted for reinitialization at step 2010. If a time-out flag has not been generated, then the normal support slide cylinder supporting the slide block assembly 372 is released, as indicated at step 1463 to enable the weighted force to perform the pulling of the suture. As indicated at step 1464, a determination is made as to whether the destructive test cylinder 374 has been activated. If the destructive test cylinder has not been activated, as indicated at step 1465, then this indicates a fatal destructive pull-test assembly error, and the process will be terminated and prompted for reinitialization at step 2010. If the destructive test cylinder has been activated, then the pull-test force as applied by the destructive suture gripping assembly to the needle-suture assembly 9 is measured by a transducer as indicated at steps 1470, 1472 in FIGS. 6(n) and 6(o). Additionally, a control signal is initiated to confirm that the bottom out sensor has been reached during the destructive pull-test, as indicated at step 1475. Then, as indicated at step 1477, the destructive suture pull-test grippers 333a,b, are opened to release their grip on the suture 42 which is then blown away by air jet as described herein with respect to the non-destructive pull test failure. As indicated at steps 1478 and 1479, a continuous check is provided to ensure that the grippers have opened within the time allotted in the current index cycle. Thus, at step 1479, a check is made to determine whether a time-out flag has been generated by the control system 999 indicating a time-out error. If the time-out flag is detected, the process will be terminated and prompted for reinitialization at step 2010. If a time-out flag has not been generated, then the now dis-armed needle is removed from the MAG by firing the needle reject "stripper" cylinder, actuated by a control signal output, to extend needle stripper blade 386 to remove the needle as indicated at steps 1480–1483 for collection thereof by suitable collection means (not shown). If the needle reject cylinder is not fired within the time period allotted for the current index cycle at step 1483, then the process will be terminated and prompted for reinitialization at step 2010. If a time-out flag has not been generated at step 1483, then the suture pusher cylinder 337 is retracted at step 1485. As indicated at steps 1486 and 1487, a continuous check is provided to ensure that the suture pusher has retracted within the time allotted in the current index cycle. Thus, at step 1487, a check is made to determine whether a time-out flag has been generated by the control system 999 indicating a time-out error. If the time-out flag is detected, the process will be terminated and prompted for reinitialization at step 2010. If a time-out flag has not been generated, then the control system commands the retraction of the destructive test cylinder 374, as indicated at step 1488.

FIGS. 6(p)–6(s) are flow charts showing a procedure 810 for analyzing and using the information obtained during the destructive pull tests. Details concerning this procedure can be had to co-pending U.S. Pat. No. 5,793,634 entitled "Method and System For Establishing And Monitoring A Needle Swaging Procedure" assigned to the same assignee as the present invention and the contents and disclosure of which is incorporated by reference herein. This procedure may be performed by the control system computer, or a processing logic unit, which may be located at the pull test station, for processing the results of the non-destructive and destructive suture pull-test results for quality control purposes.

Figure 6P:
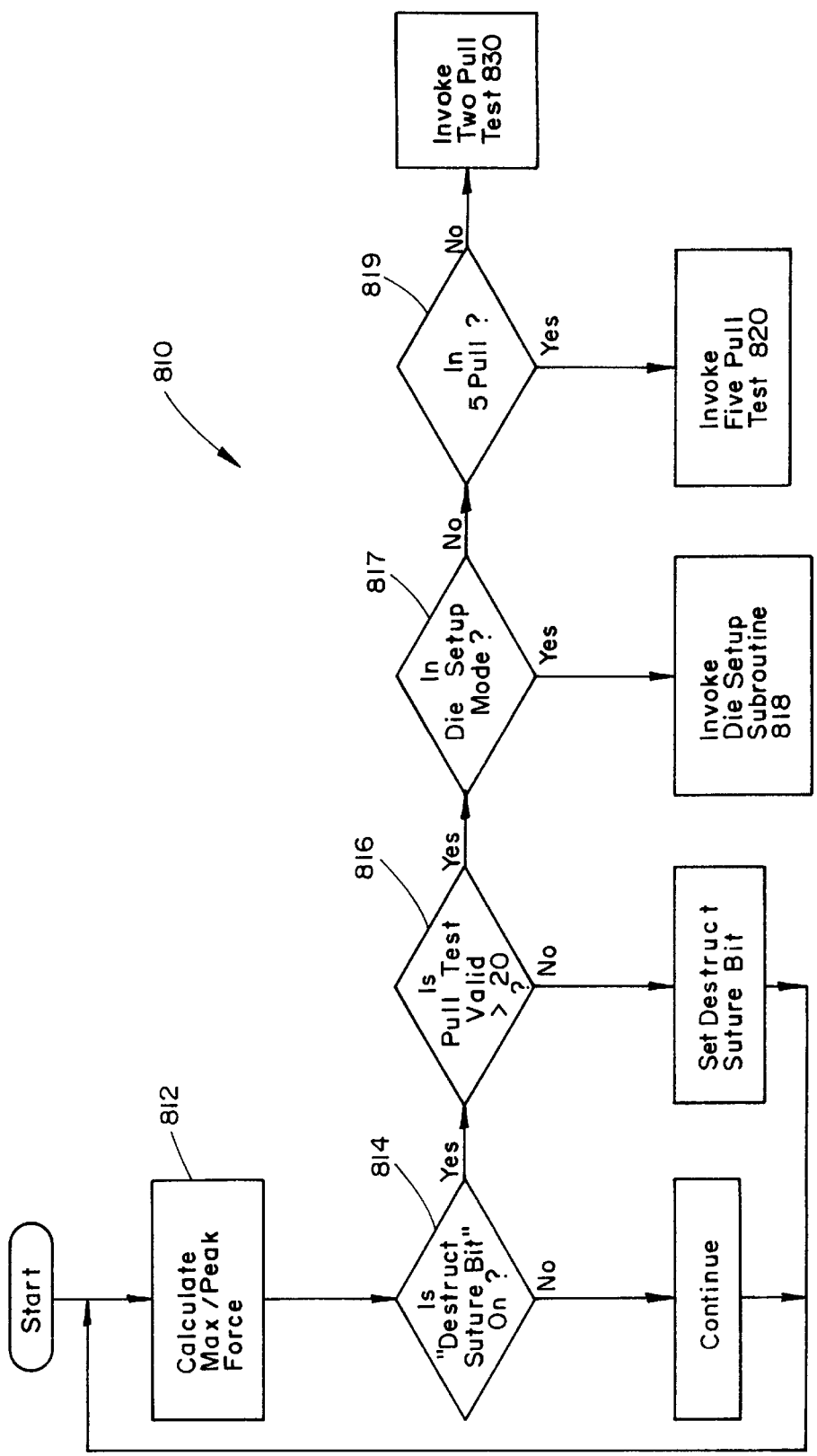
Figure 6Q:
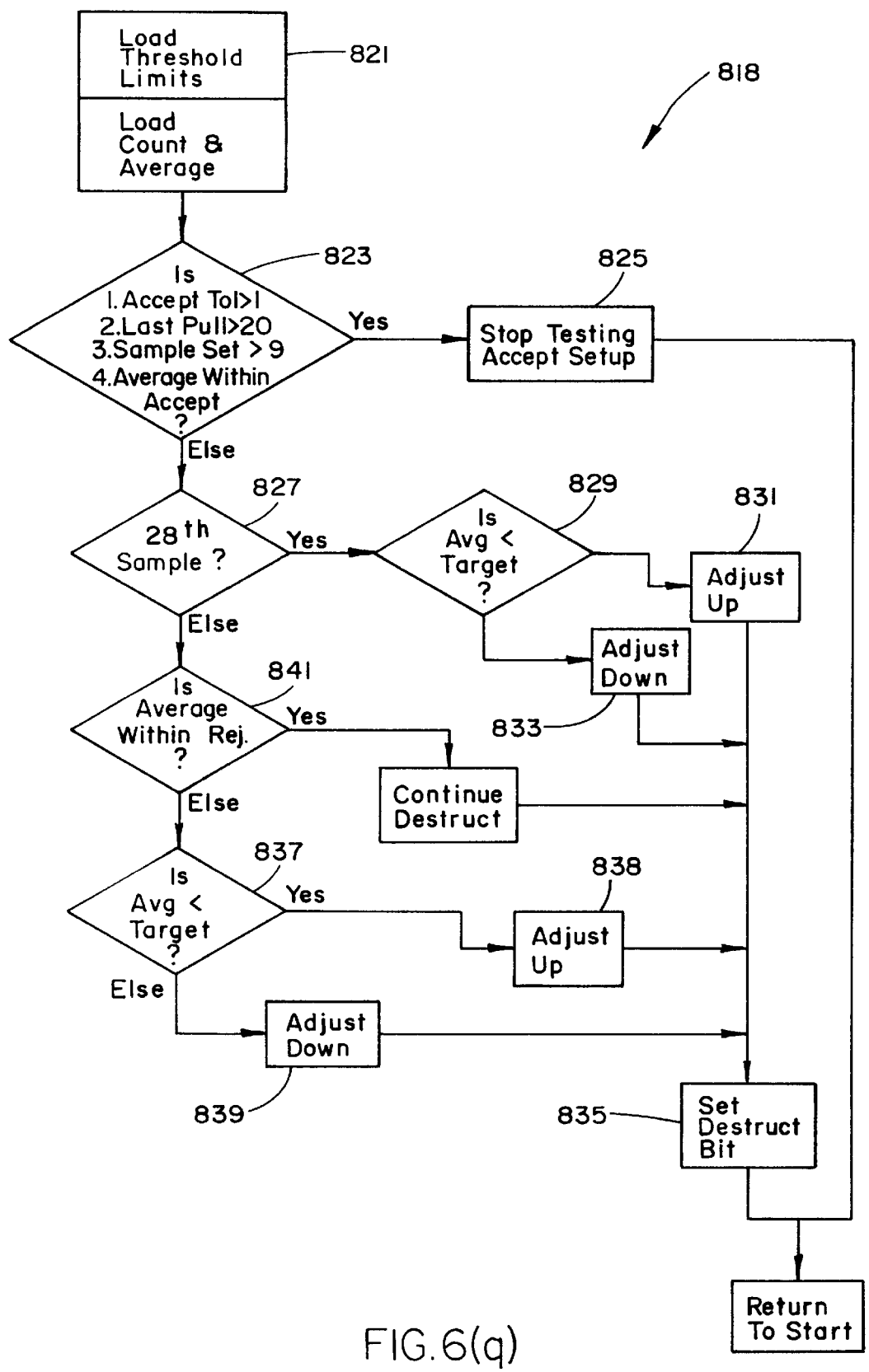

Generally, as shown in FIG. 6(p) at step 812 the procedure implements the supervisor computer 99b for calculating the maximum or peak force applied to the suture during the pull test; and at step 814, the processor checks a bit, referred to as the destruct suture bit, to determine whether this pull test was a destructive pull test. This bit may be part of a status word stored in supervisor 99b that describes various conditions at station 400. In particular, the bit indicates whether the pull test to be applied at station 400 is to be a non-destructive or a destructive pull test. If the last applied pull test was not a destructive pull test, the procedure 810 returns to the start step. If, though, that test was a destructive pull test, the routine proceeds to step 816.

At this step, processor 99b determines whether the pull test was a valid test; and, more specifically, the processor determines this by determining whether the peak force calculated at step 812 is above a lower limit, such as twenty grams. If the calculated force is below that limit, processor 99b sets the destruct suture bit for the next needle arriving at station, so that the destructive pull test is repeated on that next needle, and then the routine returns to the start step. If, however, the pull test is considered to be a valid test, the routine 810 moves on to step 817.

At step 817, the routine checks to determine whether machine 10 is in a mode of operation referred to as a swaging die set-up or initialization mode, in which various adjustments are made, manually, automatically, or both manually and automatically, to work station 200. For example, in this mode, the specific position of a swaging anvil may be adjusted to adjust the swaging pressure applied to the needles at swaging station 200. Machine 25 may enter the set-up mode in a number of ways. For instance, various events that may be sensed or monitored by control system 999 may cause machine 25 to enter the initialization mode.

When the machine does enter the initialization mode, a particular bit or flag is set in the supervisor computer 99b to indicate this fact, and at step 817, the control computer 99b checks to determine whether this bit has been set. If this bit is set, the procedure 810 proceeds through subroutine 818, discussed in detail below. If this die set-up bit is not set, then the procedure 810 moves on to step 819.

At step 819, routine 810 determines which of two analyses, referred to as the two pull and the five pull tests, should be invoked. Generally, the two pull test is a preliminary or screening test and analyzes the results of two successive valid destructive pull tests to determine whether the five pull test should be invoked, and the five pull test is used to determine whether the swaging pressure should be adjusted.

The decision of which of these two tests to invoke is determined by the state of a bit or flag, referred to as the five pull bit, maintained in a control register in control system 999; and at step 819, the processor checks this bit. If the five pull test is to be invoked, the routine then proceeds through subroutine 820; while if the two pull test is to be invoked, the routine proceeds through subroutine 830.

Figure 6R:
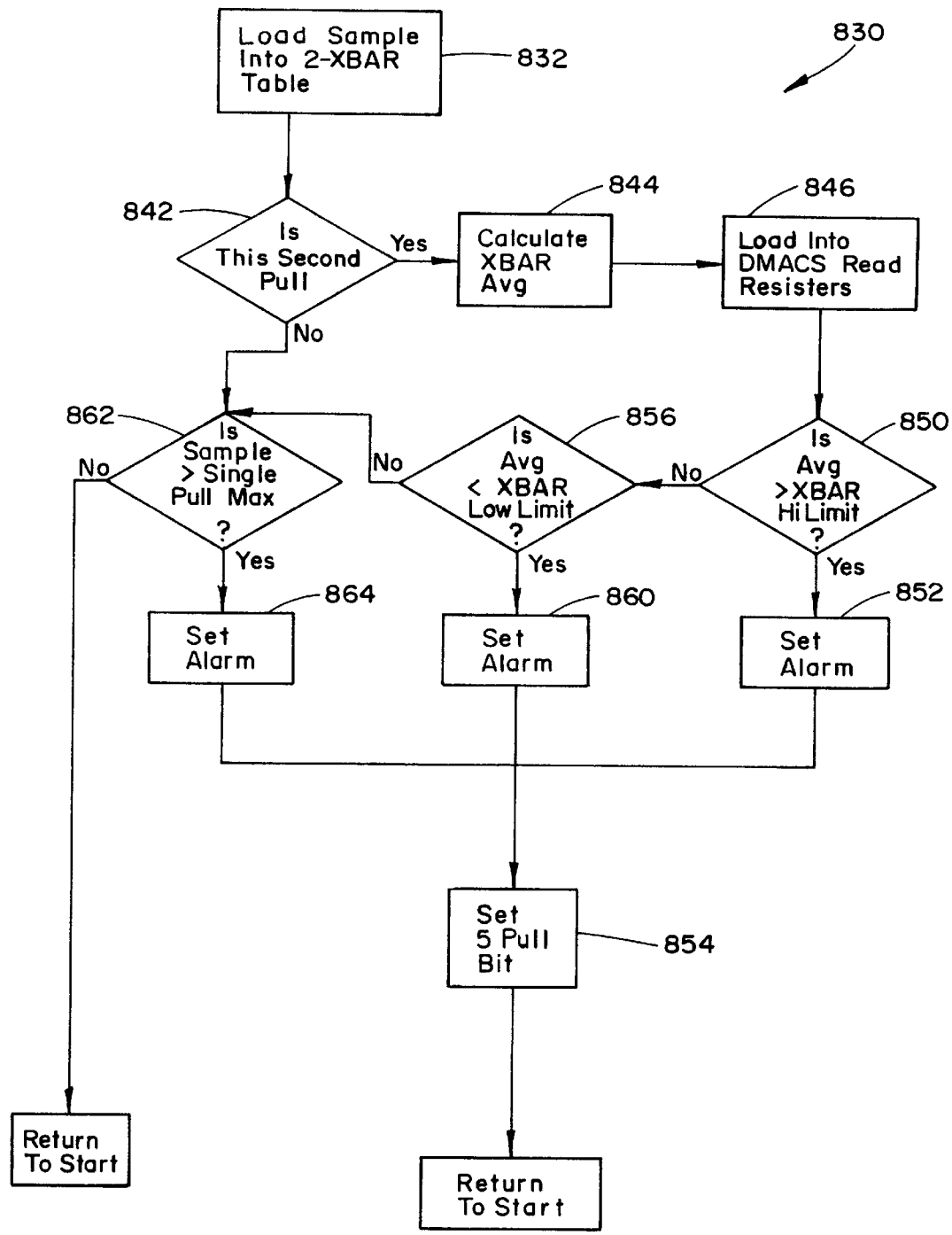
Figure 6S:
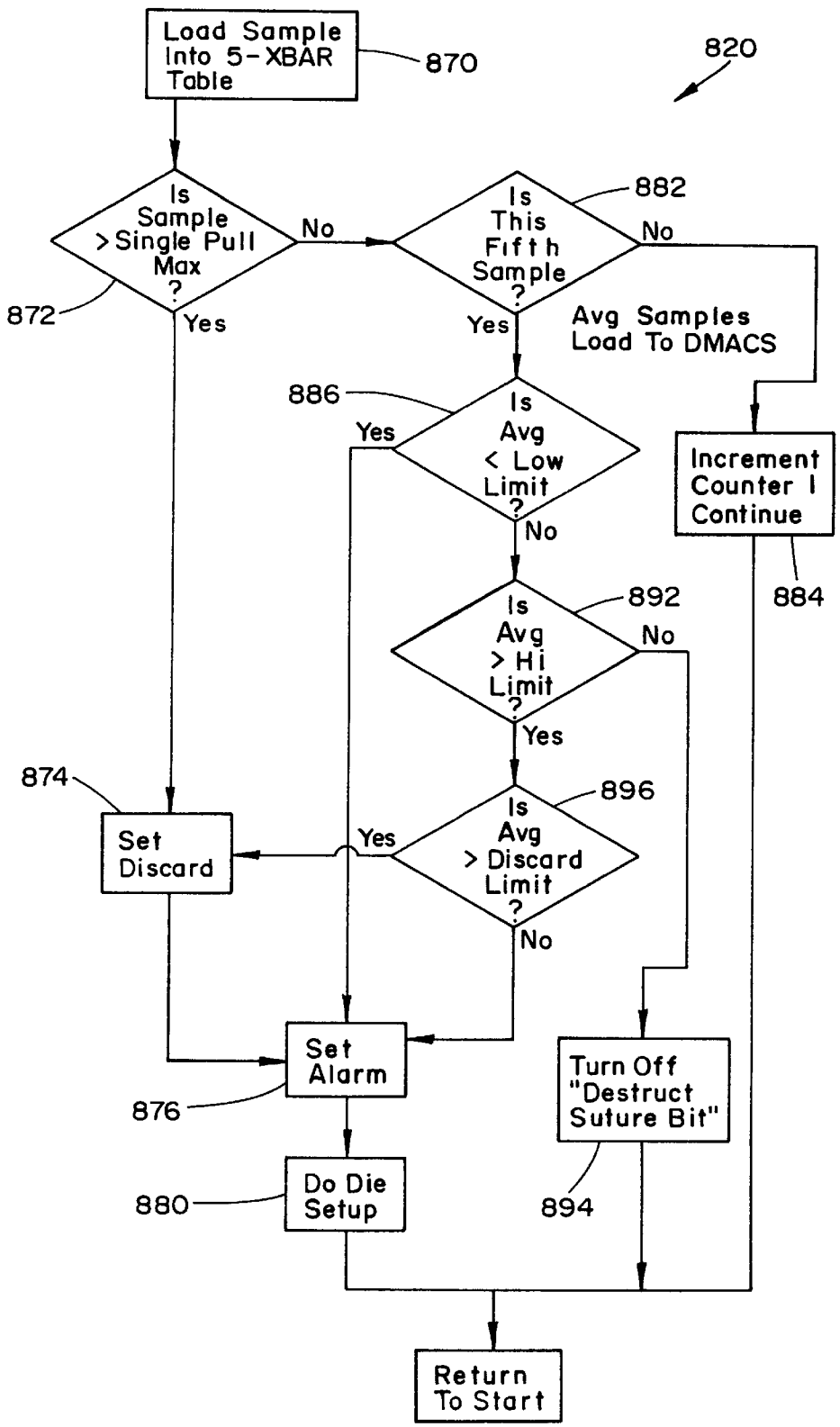
Figure 6T:
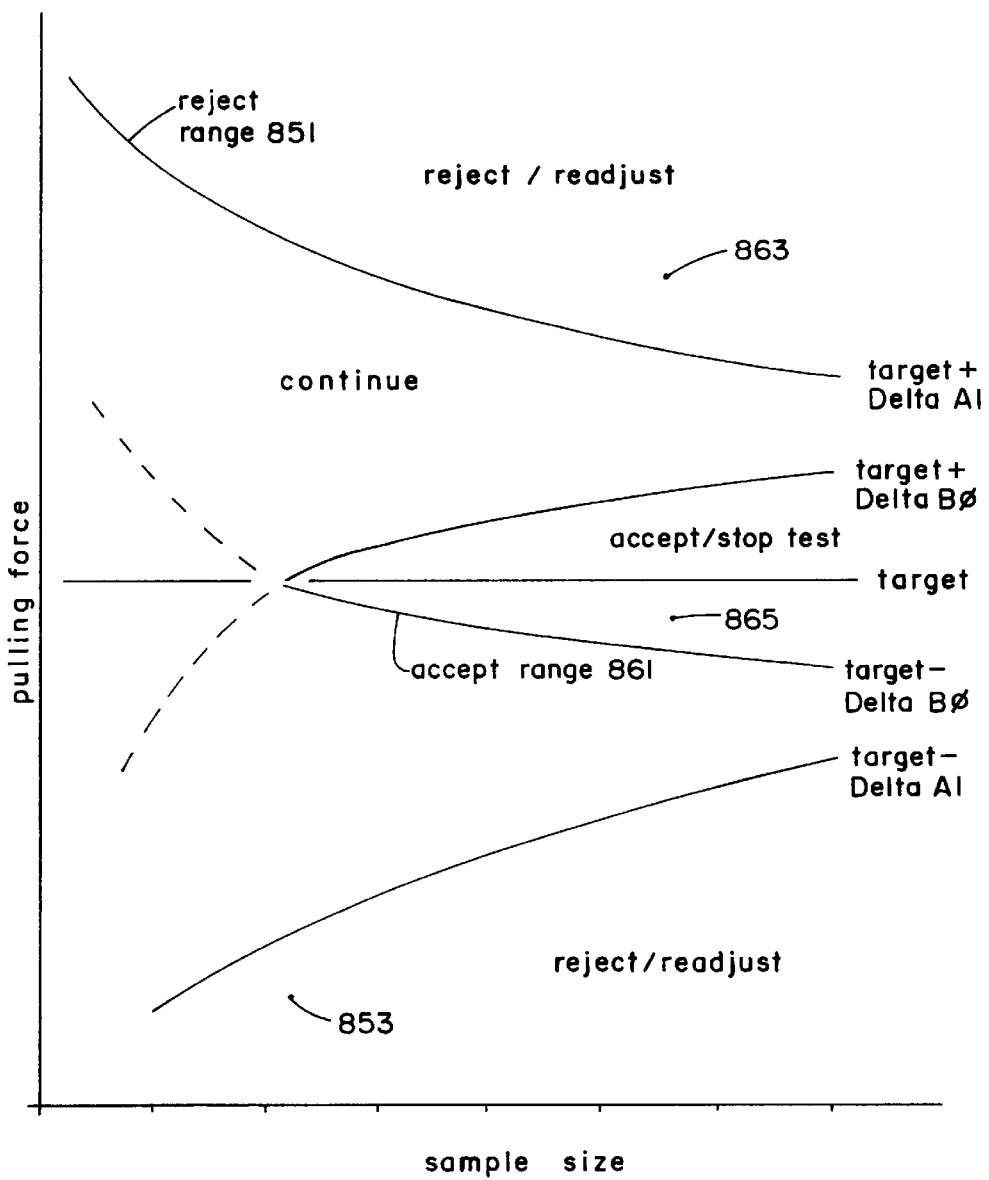

With reference to FIG. 6(r), the first step 832 in subroutine 830 is to record the results of the pull test in a table in a manner that indicates that the results are being used in the two pull test. For instance, FIG. 6(u) shows a table 881 having one column 883 for pull test data used in the two pull test and a second column 885 for pull, test data used in the five pull test; and at step 832, the results of the latest suture pull test are recorded in column 887.

At step 842, the subroutine 830 determines whether the latest suture pull test is the first or the second of the two suture pull tests that are to be used in the two pull test 830. If the subroutine 830 determines that the latest test is the second of these two pull tests, the subroutine proceeds to step 844, where processor 99b determines the average of the pull forces calculated during these two pull tests. That average is then loaded into a register, at step 846, for record keeping purposes, and then the calculated average value is compared to an upper limit at step 850. If the calculated average is above that upper limit, an alarm is set at step 852, the five pull test bit is set at step 854, and the subroutine returns to the start step.

If, at step 850, the calculated average is below the upper limit, that average value is then, at step 856, compared to a lower limit. If the calculated average is also below that lower limit, an alarm is set at step 860, the five pull test bit is set at step 854, and the subroutine returns to the start step. If, at step 856, the calculated average is above the lower limit, then the subroutine 830 proceeds to step 862, where the last calculated pulling force is compared to another upper limit value, referred to as the single pull max. This upper limit represents a preferred maximum allowable value for the force required to break a suture from a needle.

If, at step 862, the last pulling force value is less than that maximum pulling force limit, then the subroutine returns to the start step. In contrast, if that maximum value is exceeded in any pull test, an alarm bit is set at step 864, and the five pull test bit is set at step 854, so that during the next operation of routine 810, the five pull test 820 is invoked. Then, from step 854, the subroutine returns to the start step.

If at step 842 the subroutine 830 determines that the latest suture pull test is the first such pull test to be considered in the two pull test, a bit or flag is set to indicate this fact and the subroutine then proceeds directly to step 862, skipping steps 844, 846, 850 and 856. Again, at step 862, the subroutine compares the latest calculated pulling force to the single pull max. If the pulling force value is less than that maximum value, the subroutine 830 returns to the start step; while if the pulling force value is greater than that maximum value, an alarm bit is set at step 864, and the five pull test hit is set at step 854.

With reference to FIG. 6(*s*), the first step 870 in the five pull test subroutine 820 is to store the latest pulling force value or sample in the five pull test column 885 of table 881. Then, at step 872, the pulling force of the last suture pull test is compared to the single pull max. If this pulling force is greater than that maximum allowable single pulling force value, a discard alarm is generated at step 874. This alarm is intended to advise the operator that a number of needles might have been swaged too tightly and that it might be preferred to discard those needles. Then, at step 876, an internal alarm bit is set; at step 880, the die set up bit is set; and then subroutine 820 returns to the start step.

If at step 872, the calculated pulling force of the latest suture pulling test is not greater than the single pull max value, then subroutine 820 proceeds to step 882, where the control computer 99*b* tests to to determine whether the latest suture pull test is the fifth of the set of five suture pull tests that are to be used for the five pull test. If the latest suture pull test is not that fifth test, a count of the number of valid pull tests in that set is incremented by one at step 884, and then the subroutine returns to the start step.

If, though, at step 882, the latest suture pull test is the fifth of the five suture pull tests that are needed for the five pull test, then the subroutine 820 calculates the average of the pulling forces of those five pull tests; and then the subroutine goes to step 886, where that average is compared to a lower limit value. If the calculated average is below that lower limit, then an internal alarm is set at step 876, the die set-up bit is set at step 880, and the routine returns to the start step. If, at step 886, the calculated average is above the lower limit, then that calculated average is compared to an upper limit at step 892. If the calculated average value is not above this upper limit, then the destruct suture bit is cleared at step 894 so that a non-destructive pull test is applied to the next needle positioned at work station 300; and from step 894, the subroutine returns to the start step.

If at step 892, the calculated average is above the upper limit, then, at step 896, that calculated average value is compared to a higher value, referred to as the discard limit. If this discard limit is exceeded, then, not only is it appropriate to invoke the die set-up subroutine, but also it may be appropriate to discard the most recently sutured needles, as they may have been sutured too tightly. In particular, if that discard limit is exceeded, the discard alarm is set at step 874, an internal alarm flag is set at step 876, and the die set up bit is set at step 880. If the discard limit is not exceeded at step 896, the subroutine directly proceeds to steps 876 and 880, where the internal alarm flag and the die set-up bit are set. From step 880, the subroutine returns to the start step.

Swage Die Setup Procedure

Subroutine 818, shown in FIG. 6(*q*), is the procedure for setting or adjusting the swaging dies; and, as previously mentioned, this subroutine is invoked when, at step 817, the die set-up bit is set. This subroutine 818 is used during set-up or initialization of machine 10 to determine an acceptable swaging pressure, and this subroutine is also used during operation of the machine to adjust or reset that swaging pressure in response to changes or drifts in that pressure.

Generally, in the operation of subroutine 818, the peak forces required to break the sutures during he pull tests are added to a data base; and each time a value, or sample, is added to that data base, an average of all the sample values in the data base is calculated. These calculated average values are compared to first and second ranges, shown at 851 and 861 in FIG. 6(*t*), and referred to as reject and accept ranges, respectively. More specifically, each calculated average value is compared to the reject range, which is relatively broad. If any calculated average value falls outside that reject range, for example as shown at 853 and 863, then the swaging pressure is adjusted and the subroutine 818 is restarted, with a new, or empty, data base.

In addition to the foregoing, once the sample reaches a given size, such as eight or nine samples, the calculated average values are also compared to the accept range 861, which is within and narrow than the reject range 851. If a calculate average value is within this second range, for example as shown at 865 in FIG. 6(*o*), the swaging pressure is considered acceptable and the subroutine 818 terminates immediately. If the number of samples in the data base reaches a preset maximum number, such as twenty-eight, and none of the average values calculated from that data base have been within the accept range, the procedure is restarted with a new, or empty data base.

With reference again to FIG. 6(*q*), at step 821 of subroutine 818, various values are determined. In particular, the current sample size is obtained, the relevant range limits, also referred to as threshold limits, are determined, and the average of the pulling force values in the sample is determined. It should be understood that threshold and range limit values will vary in accordance with the type of surgical needle and the attached suture being processed.

At step 823, control computer 99*b* tests to determine whether several conditions are met. Specifically, the processor determines, first, whether their exist a valid acceptance range (such as greater than 1) for the sample size, and second, whether the last suture pull test was a valid test. Like at step 816 (FIG. 6(*p*)) the processor at step 823 determines whether the suture pull test is valid by determining whether the peak pulling force is greater than a preset value such as twenty grams. At step 823, the processor also determines whether the size of the sample has become larger than a given value such as nine, and whether the calculated average pulling force is within the accept range. If all of these conditions are met, the swaging pressure is acceptable and, as represented by step 825, the destructive pull testing is stopped. Subroutine 818 ends and the subroutine returns to the start step.

However, if at step 823, one of the conditions is not met, then subroutine 818 moves to step 827, where the computer 99b tests to determine if the maximum sample size has been reached; and, specifically, the processor compares the size of the sample to a predetermined value, such as twenty-eight. If the sample has reached the maximum size, the processor then, at step 829, compares the calculated average value for the sample to the accept range. If the calculated average is above or below the accept range, then the swaging pressure is decreased or increased, respectively, at steps 831 or 833. The subroutine then goes to step 835, where the suture destruct bit is set, so that the destructive pull test is applied to the next needle located at station 400, and then the subroutine returns to the starting step.

If, at step 827, the sample size is less than its maximum size, the subroutine 818 proceeds to step 841, and the processor determines whether the calculated average value for the sample is within the reject range. If the calculated average value is within the reject range, subroutine 818 is repeated, as represented by step 843, and the suture destruct bit is set at step 835. As a result, a destructive pull test is performed on the next needle transferred to station 400, the peak pulling force required to break the suture is measured and recorded, and that recorded value is added to the sample, increasing the size of that sample by one.

In contrast, if at step 841 the calculated average value is outside the reject range, the swaging pressure is adjusted and the subroutine 818 is restarted. In particular, at step 837, the calculated average value is compared to a target swaging pressure, and the swaging pressure is either increased or decreased, as represented by steps 838 and 839, depending on whether the calculated average value is, respectively, below or above that target value. Then the suture destruct bit is set at step 835, and the subroutine returns to the start step. The next time a needle is transferred to station 300, a destructive pull test is performed on the needle, the peak pulling force required to break the suture on that needle is measured and recorded, that recorded value becomes the first value in a new sample, and routine 810 again proceeds through subroutine 818.

The subroutine 818 is repeated in this way until either all four of the conditions tested at step 823 are satisfied, or the sample reaches the maximum size. In the former case, the swaging pressure is accepted. in the latter case, the swaging pressure is accepted or adjusted depending on whether the last calculated average value is, respectively, within or outside the accept range. Also, with the above described routine, any appropriate procedure may be used to adjust the swaging pressure. For instance, if it is determined that the swaging pressure should be adjusted, control computer 99b may generate an appropriate signal that is applied to a controller or to an assembly at the swaging station to change the swaging pressure in the desired manner.

The preferred reject and accept ranges may be determined or calculated in any suitable manner, and for example, these ranges may be determined on the basis of statistical analysis, such as described in co-pending U.S. Pat. No. 5,793,634.

As described in FIGS. 6(l) and 6(m) with respect to step 1434, the needle-suture which has passed the non-destructive minimum pull-test is regripped by the MAG gripper while extended at the pull-test station 300. Referring back to step 1229 of FIG. 6(b), the system waits for the various interlock signals indicating that it is safe to retract the MAGs from their extended position and forwardly index the swage dial and each MAG thereof to the next processing station. Thus, the needle having the suture attached thereto gripped by the MAG at station 300 is indexed to the needle/suture load to package station 450 for packaging thereof as will now be described in further detail.

AUTOMATED PACKAGING MACHINE

During the process of arming surgical needles at the needle threading and swaging dial 150, as described above, a simultaneous packaging process occurs at the suture wind and packaging machine 25. In essence, as shown in FIG. 1, the rotary turret (dial) 500 is indexed forwardly in the direction of arrow "B" in FIG. 1 such that each tool nest located on dial 500 is adapted to be advanced in succession to a number of workstations located about the periphery of the rotary turret 500.

The foregoing indexing motions of the rotary turret 500 are implemented in order to produce a completed suture package and are correlated with each other through the program-controlled operation of the machine such that the dwelling-time periods at each of the respective workstations is computed to allow sufficient time for the preceding step to be completed at the preceding workstation or workstations. This enables a smooth and continuous flow of product from the automated packaging machine and provide for high-speed and efficient manufacturing cycles.

SUTURE WIND AND PACKAGE DIAL

As shown in FIGS. 30–32, the automated needle and suture packaging machine 25 comprises a rotary turret or turntable 512 which is essentially a packaging dial supported on an essentially stationary machine frame structure 514 including structural uprights 516 and S18, which are interconnected by horizontal beams 520, 522, 524, with the entire frame structure 514 adapted to be supported on a floor through the intermediary of adjustable leveling footings 526. The frame structure 514 comprises an outer stationary frame arrangement 515, and an inner vertically adjustable frame arrangement 517 supporting the turntable 512 for vertical adjustment relative to the remaining machine components. The vertical adjustment of the frame arrangement 517 is provided for by a central hydraulically-actuated piston structure 541, which also concurrently effectuates the vertical adjustment of all of the operative packaging devices at the various workstations of the machine so as to accommodate the packaging of a wide range of differently sized surgical needles without the necessity for modifying any machine components. Arranged within the frame structure are the various belt drive and operating components for the machine, and the vacuum systems employed in the packaging cycles for the suture packages, as described herein. The turntable 512 is oriented in a horizontal plane, and through the intermediary of a program-controlled drive installation 519, is rotatable in an indexing or incrementally angular advance about a central vertical axis. In this instance, the turntable 512 is rotated in a counter-clockwise direction when viewed from above, as represented by arrow A, in 30° increments.

The rotary turret or turntable 512 is essentially constituted of a circular disk-shaped member or packaging dial which has a plurality of tool nests 530 mounted in a uniform circumferentially spaced array on the upper surface of the package dial or rotary turret 512, with each tool nest 530 having an outer end projecting radially outwardly of the peripheral edge of the turret or dial 512. In the particular construction of the packaging machine 25, by way of example, twelve (12) tool nests 530 are arranged at uniformly distributed annular spacings of 30° from each other about the circumference of the dial or rotary turret 512, the details of which will be described hereinbelow.

In essence, as mentioned hereinbelow, the rotary turret or turntable 512 of the packaging machine 25 is adapted to be indexed forwardly in an angularly incremental or indexed rotational advance, each such incremental advance comprising one-twelfth of the 360° circumferential rotation of the turntable, or basically 30°, along the direction of rotation identified by arrow A in FIG. 30, such that the tool nests 530 which are each adapted to mount a suture tray or package are designed to be advanced in sequence to a number of successive workstations; designated herein as workstations (1) through (12), which are stationarily evenly spaced about the periphery of the rotary turret 512, as illustrated in FIG. 30 of the drawings.

As shown in FIGS. 32 through 34, each tool nest 530 includes a housing 532, fixedly mounted on the upper surface 534 of the rotary turret 512. Each housing 532 includes a horizontal radially extending central bore having a shaft 526 rotatably journaled therein. The shaft is normally secured against rotation within housing 532 by means of a locating pin 533 which engages plate member 531 to prevent rotation of the shaft 526. However at predetermined workstations of the machine, the shaft 526 may be released by means of the locating pin 533 so as to be axially radially inwardly movable within housing 532 against stationary plate 531 mounted centrally on the rotary turret or dial 512 for regulating the rotational displacement which may be imparted to the shaft 526, as discussed hereinbelow in more specific detail.

The outwardly facing structure 540 of a plate element 538, which is secured to the radially outer end of shaft 526, is adapted for supporting the package components and particularly the trays utilized in the production of surgical needle end suture-containing packages. The base of the suture package essentially consists of a generally flat-bottomed, shallow injection-molded plastic tray 45 of oblong parallel-sided straight and convexly round-ended shape, as shown through a plan view thereof in the drawings, and which is adapted to receive and clampingly retain therein a single armed suture, and with a tray cover or label adapted to be ultimately fastened thereon so as to produce a complete needle and suture-containing package.

The radially outer structure of the tool nest housing 530 for mounting the plastic suture tray 45 includes the plate element 538 including plate element 550 having rim structure 536 and sides 537 and ends 539 shaped generally in conformance with the peripheral shape of tray 45 for seating engagement therein. An outer planar surface on the plate member 538 includes protruding perimeter structure for seating engagement with the suture tray, with the plate member 538 being fixedly secured to the radially outer end of the shaft 526 so as to be adapted for rotation therewith. Extending forwardly from the outer planar surface of the rotatable plate element 550 of the tool nest 530 are protuberances or guide pins 552 which align the plastic tray 45 thereon for appropriate positioning on the plate member 538, with the tray 45 retained thereon through the application of a vacuum to the plate member surface 550 through passageways communicating with a vacuum source connected thereto through the tool nest housing 530.

Figure 35:
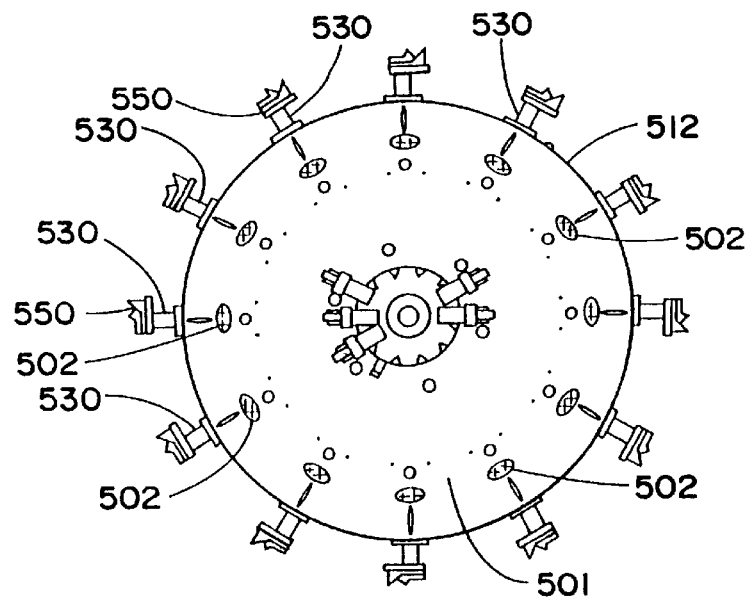
FIG. 35 illustrates a bottom view of the dial or turntable mounting the tool nests, showing vacuum ports for communicating the tool nests with vacuum-generating source means.
Figure 36:
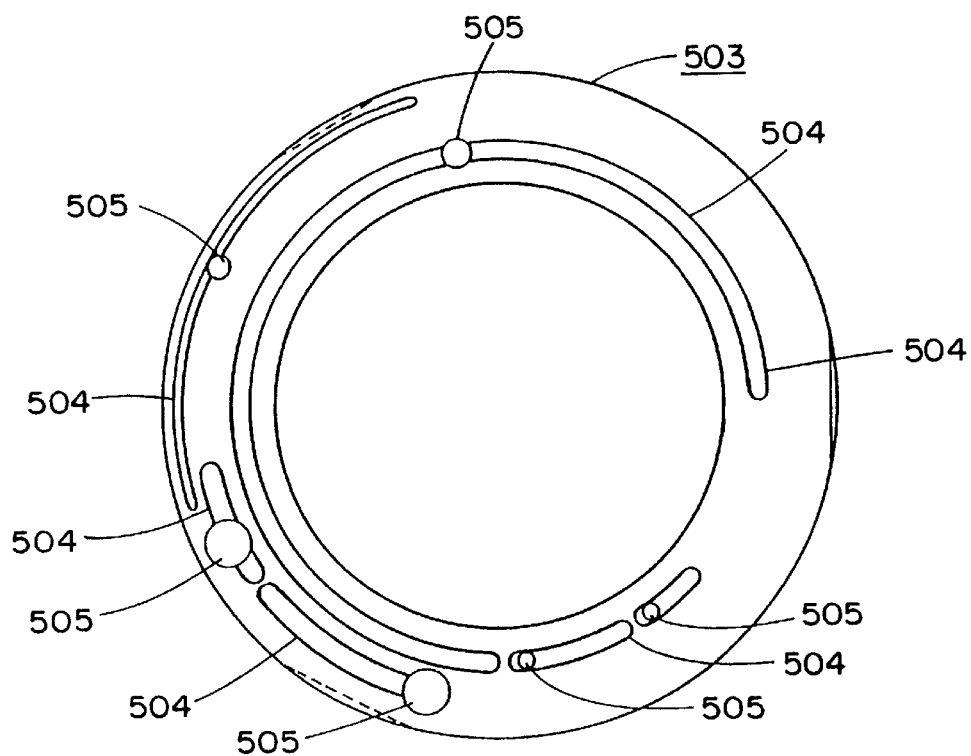
FIG. 36 illustrates a vacuum plenum for supplying the tool nests with controlled vacuum conditions.

The vacuum passageways extend through the lower surface 501 of the dial or turntable 512, as shown in FIG. 35, which includes a plurality of apertures 502 each communicating with, respectively, passageways leading to an associated tool nest 530. Particularly, the vacuum is supplied to the apertures 502 in a selective controlled mode through the intermediary of a stationary vacuum plenum 503 arranged below the dial 512, as shown in FIG. 2 of the drawings. The plenum 503, as shown in FIG. 36 and pneumatic diagrams in FIGS. 50(a), 50(d), includes outlet slots 504 and ports 505 for applying or closing a vacuum to respective tool nests 530 in accordance with the rotational positions of the dial 512 with the aperture or ports 505 in the lower surface 501 being in communication with the vacuum plenum outlet slots or ports. As shown in FIG. 50(d), air supply line 806a supplies the pressurized air for the various vacuum systems as will be described, and, particularly, provides air to a vacuum pump 802a providing the vacuum maintained in the package dial plenum 503. These vacuum systems control the periods of vacuum applied to the tool nests and to the apparatus at the various work stations by means of vacuum apertures or ports 501 provided in a lower portion of the turntable 512, as shown diagrammatically in the drawings, the timing of the applications of which is provided for by a vacuum plenum 503 having predetermined lengths of vacuum outlet openings 504, as illustrated, e.g., in FIG. 36. Thus as the vacuum ports in the turntable work stations travel over the outlet openings 504 of plenum 503, the vacuum to these operative elements is, respectively, either applied or released as required by the applicable packaging cycle in forming the suture packages.

The package dial 500 and rotary turret 512 thereof operates under control of a package dial drive motor 115f and servo controller 116f as shown in FIG. 5 in communication with control system I/O card 999 via communication lines 114f. Indexing of the package dial 500 is controlled by control system thread 1500 (FIG. 4) for controlling the package dial servo motor 115f and hence, package dial indexing, as now explained with reference to FIG. 7(a).

Figure 7A:
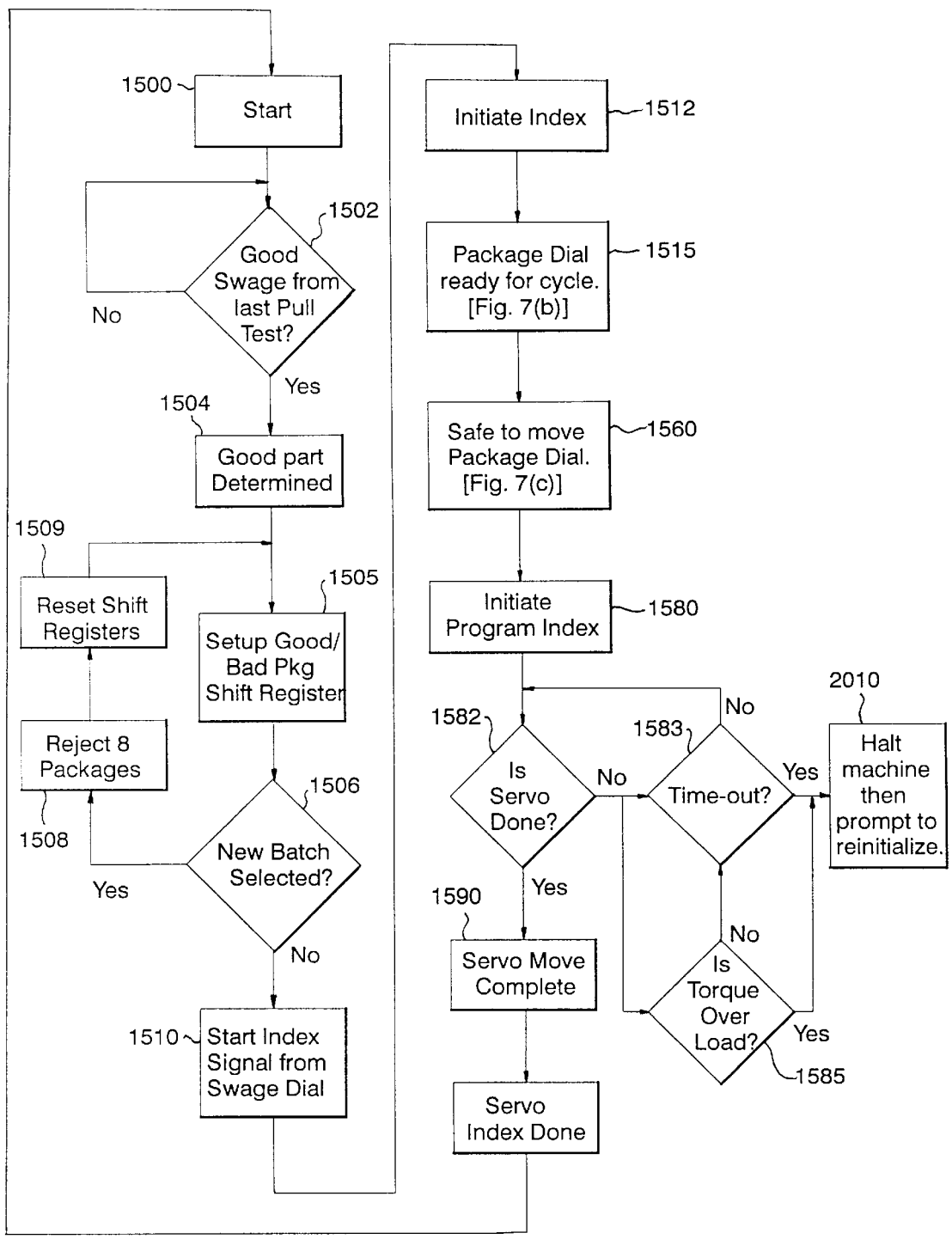
FIGS. 7(a)–7(t) are flow diagrams illustrating the control processes for controlling the indexing of the rotary package dial 500 and each of the suture winding and packaging operations performed at each of the suture winding and packaging stations at the package dial 500.
Figure 7B:
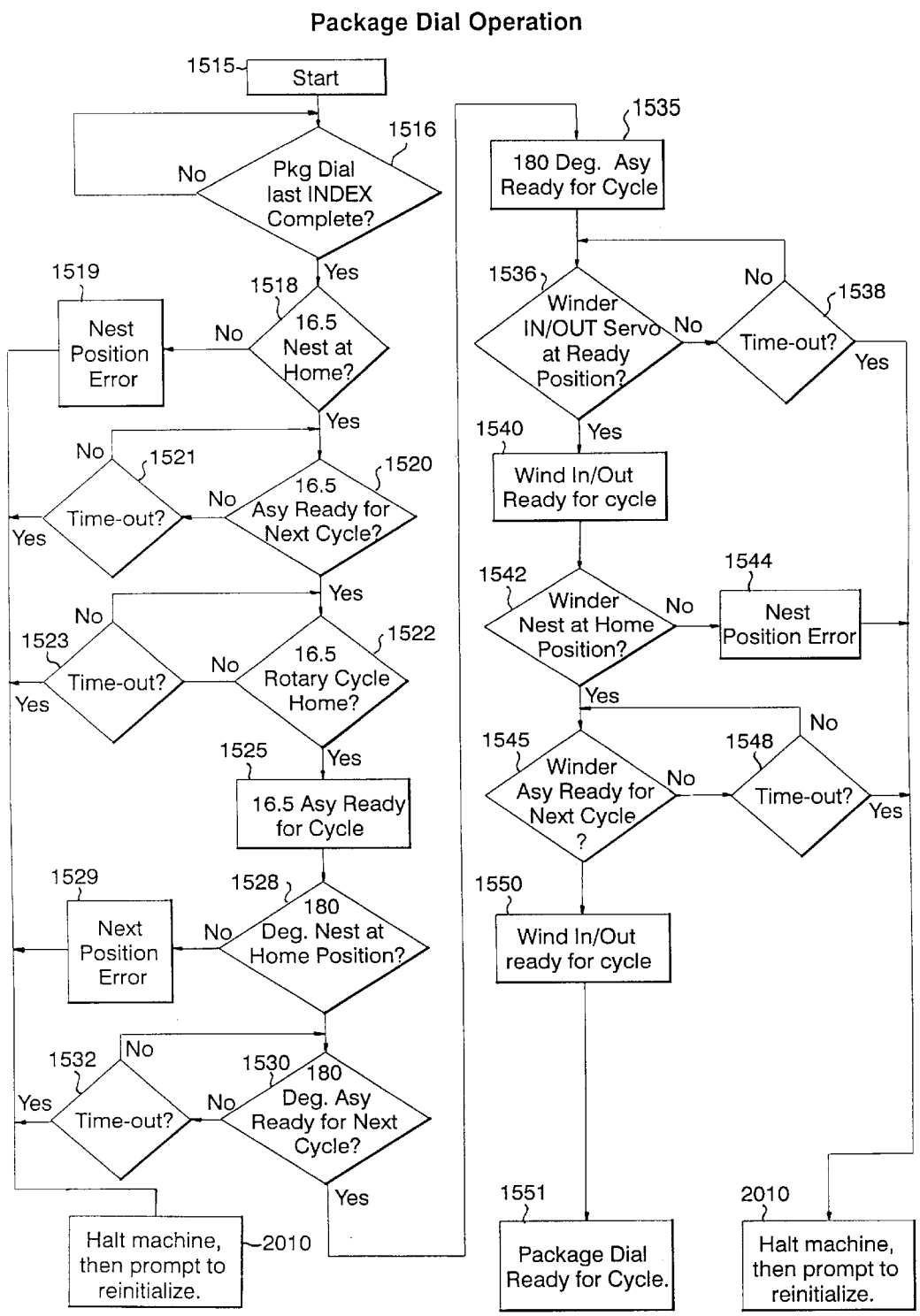
Figure 7C:
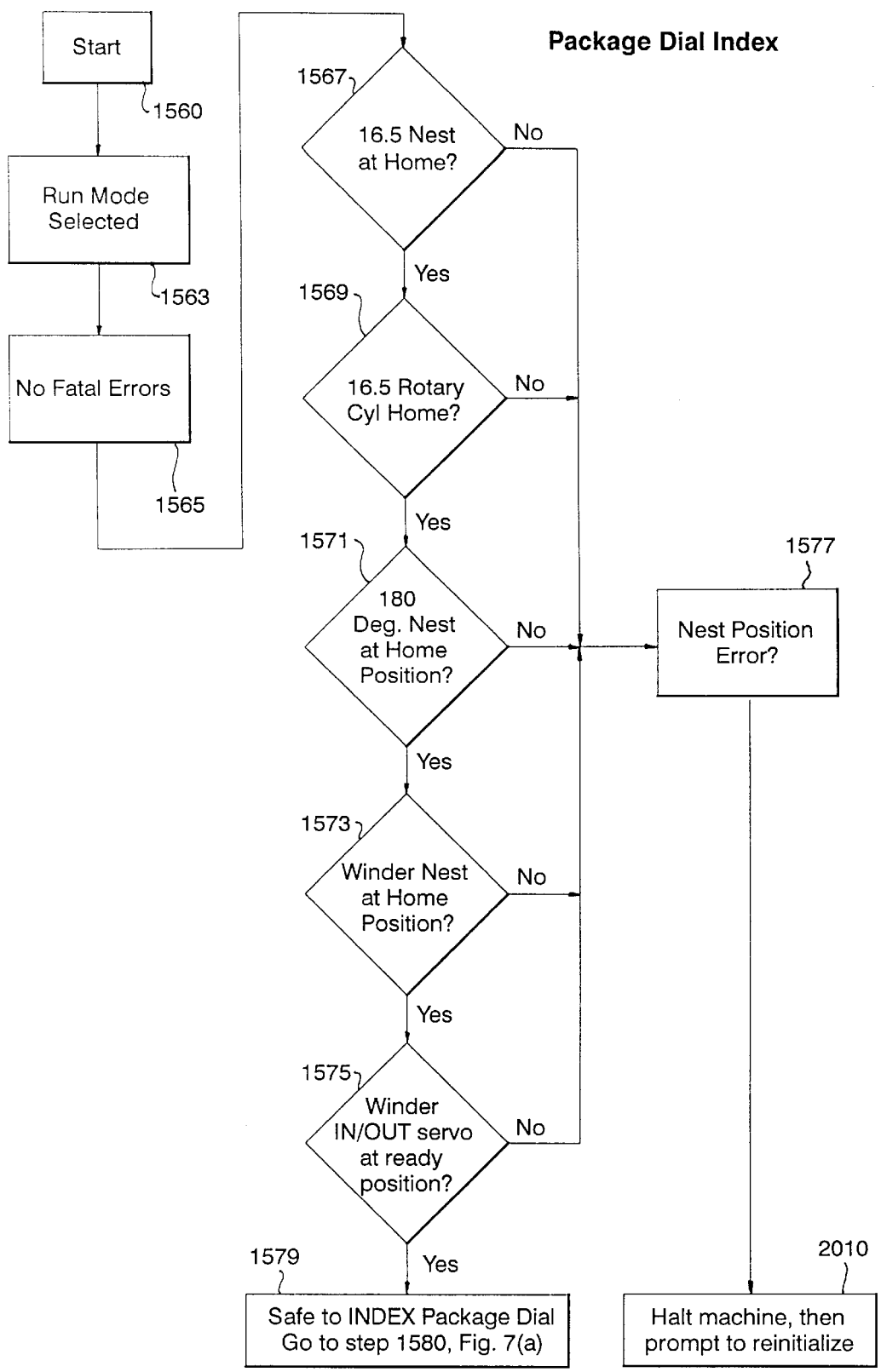
Figure 7D:
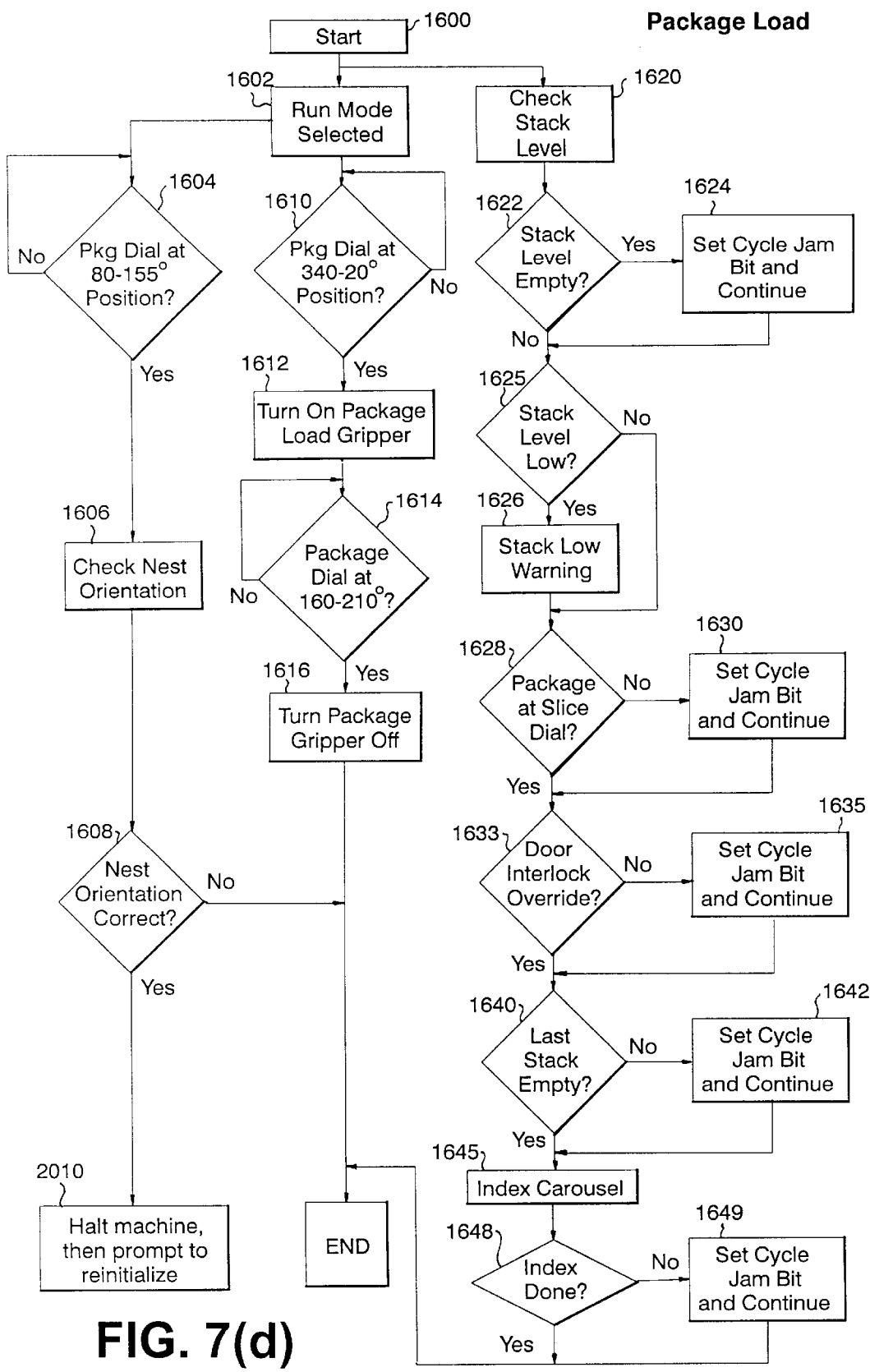

As indicated at step 1502, FIG. 7(a), a first determination is made that the swage from the last pull test at pull-test station 400 was successful, and at step 1504, that the needle and suture assembly is good. Then, as shown at step 1505, a procedure is called to setup the good/bad package shift register which is a memory register maintained to track the number of good and bad packages in a particular batch. At step 1506, a determination is made as to whether the needle suture assemblies being formed at the automatic needle-suture swaging machine are from a new batch, i.e., a new size needle/suture combination, as commanded by manual entry or as a result of initialization at the control system computer. If a new batch has been selected, then the process will initiate the rejection of the eight packages formed at step 1508 and reset all of the package shift registers at step 1509, for the new batch being transferred for automatic packaging. At step 1510, the start package signal index is received from the swage dial as shown with respect to FIG. 3, to initiate the package dial servomotor index process. Thus, as indicated at step 1512, the package dial index is ready for initiation, and at step 1515 performs a process (FIG. 7(b)) that checks whether all of the packaging assemblies at each of the packaging processing stations are at their home and/or initial positions about the packaging dial. Additionally, before indexing, at step 1560, the system performs a process (FIG. 7(c)) to check the various packaging system interlock signals indicating that all of the packaging operations have been successfully performed in the current cycle. Then as indicated at step 1580, the control system will initiate a package dial index. A decision is made at steps 1582, 1583 to determine whether the package dial has been indexed within the time period allotted for the index cycle. Additionally, as indicated at step 1585, a determination is made as to whether there is a package dial servomotor 115f torque overload condition. If there is no torque overload condition detected, then the process returns to step 1583 to determine if the package dial has indexed. If there is a torque overload condition then a critical failure has occurred and the process will be terminated and prompted for reinitialization at step 2010. Additionally, if at step 1583, if the time-out flag is detected, the process will be terminated and prompted for reinitialization at step 2010. If the package dial index is accomplished within the allotted time, then the current servo cycle is complete, as indicated at step 1590 and the package dial index process ends. The package dial servo process repeats for each subsequent cycle by returning to step 1500.

FIG. 7(*b*) particularly relates to the control system process 1515 for determining whether the package dial is ready to cycle. As shown at step 1516, a determination is first made as to whether the last package dial index has been completed and will wait for this control signal. Then, as shown in FIG. 7(*b*), a determination is made as to whether the 16.5° tool nest is at its home position, as indicated at step 1518. If the 16.5° tool nest is not at its home position, then the control system initiates a nest position error at step 1519, and the process will be terminated and prompted for reinitialization at step 2010. If the 16.5° tool nest is at its home position, then a determination is made as to whether the following control system signals have been received: a signal indicating whether the 16.5° turn assembly is ready for the next cycle, as indicated at step 1520; and, a signal indicating whether the 16.5° rotary cylinder is at its home position, as indicated at step 1522. If these signals have not been received, then a check is made at respective steps 1521 and 1523 in FIG. 7(*b*), to determine whether a time-out flag has been generated. If a time out flag is generated indicating that these signals have not been received within the time allotted for the current package dial index, then the process will be terminated and prompted for reinitialization at step 2010. If these signals have been received, then the control system initiates a signal indicating that the 16.5° turn assembly is ready for cycle, as indicated at step 1525.

Then, as shown in FIG. 7(*b*), a determination is made as to whether the 180° tool nest is at its home position, as indicated at step 1528. If the 180° tool nest is not at its home position, then the control system initiates a nest position error at step 1529, and the process will be terminated and prompted for reinitialization at step 2010. If the 180° tool nest is at its home position, then a determination is made as to whether the control system signal indicating whether the 180° turn assembly is ready for the next cycle, as indicated at step 1530. If this control signal has not been received, then a check is made at step 1532 in FIG. 7(*b*), to determine whether a time-out flag has been generated. If a time out flag is generated indicating that this signal has not been received within the time allotted for the current package dial index, then the process will be terminated and prompted for reinitialization at step 2010. If this signal has been received, then the control system initiates a signal indicating that the 180° turn assembly is ready for cycle, as indicated at step 1535. Then, as indicated at step 1536, a determination is made as to whether the control system signal indicating whether the Winder IN/OUT servomotor 115*j* for controlling winding operations (FIG. 43) is at its ready position. If this control signal has not been received within the time period allotted during the current package index cycle, then a check is made at step 1538 in FIG. 7(*b*), to determine whether a time-out flag has been generated. If a time out flag is generated indicating that this signal has not been received within the allotted time, then the process will be terminated and prompted for reinitialization at step 2010. If this signal has been received, then the control system initiates a signal indicating that the Winder IN/OUT servomotor 115*j* is ready for cycle, as indicated at step 1540. Continuing, a determination is then at step 1542 as to whether the Winder tool nest is at its home position. If the Winder tool nest is not at its home position, then the control system initiates a nest position error at step 1544, and the process will be terminated and prompted for reinitialization at step 2010. If the Winder tool nest is at its home position, then a determination is made as to whether the Winder nest assembly is ready for the next cycle, as indicated at step 1545, and whether this signal has been received within the time period allotted for the given package index cycle, as indicated at step 1548. If the control signal indicating whether the Winder tool nest is ready for the next cycle is not received within the time period allotted, then the process will be terminated and prompted for reinitialization at step 2010. If this signal has been received, then the control system initiates a signal indicating that the winder tool nest assembly is ready for cycle, as indicated at step 1550 and that the package dial is ready to cycle, as indicated at step 1551.

FIG. 7(*c*) particularly relates to the control system process 1560 for determining whether the package dial is safe to move (FIG. 7(*a*)) upon receipt of the various system interlock signals in the current indexing cycle. As shown in FIG. 7(*c*), assuming run mode operation has been selected, as indicated at step 1563, and further, that no fatal errors have been detected, as indicated at step 1565, then the control system verifies that the following interlock signals have been received prior to indexing the package dial: 1) a signal indicating the 16.5° tool nest is home, as indicated at step 1567; 2) a signal indicating the 16.5° rotary cylinder is home, as indicated at step 1569; 3) a signal indicating the 1800 tool nest is home, as indicated at step 1571; 4) a signal indicating the Winder tool nest is home, as indicated at step 1573; and, 5) a signal indicating the Winder IN/OUT servo is at ready position, as indicated at step 1575. If any of these signals are not received, then a nest position error signal is generated at step 1577, and the process will be terminated and prompted for reinitialization at step 2010. If all of these signals have been received, then the control system will generate a SAFE to INDEX package dial signal at step 1579, with the system initiating the dial index at step 1580, FIG. 7(*a*).

The successive work stations which collectively constitute the automated machine 25 for the packaging of surgical needles and attached sutures viewed in the direction of rotation of arrow A in FIG. 30, are essentially described as follows: (1) The first work station 400 relates to the operative aspect of empty suture trays being separated from the bottom of stacks of trays 45 contained in a rotary carousel 402 to a rotationally indexed plate 408 under the action of a vacuum, and thereafter picked up and transferred by a cam-controlled pivot arm 412 to the tool nests so as to be retained thereon while being conveyed to subsequent work stations, as set forth hereinbelow.

Figure 37:
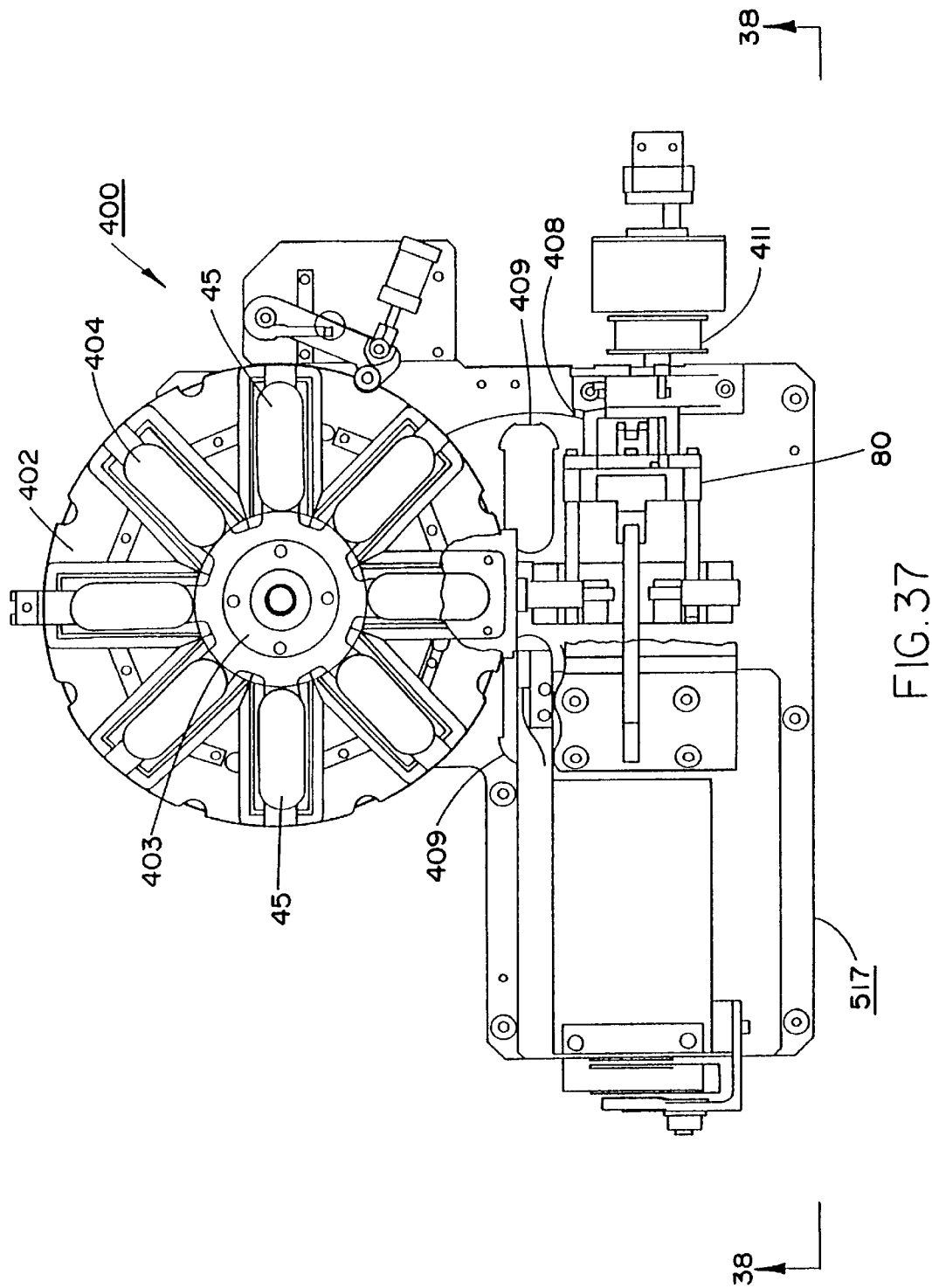
FIG. 37 illustrates a top plan view of the carousel and robotic pivot-arm arrangement of the tray loading and feeding workstation of the packaging station.
Figure 38:
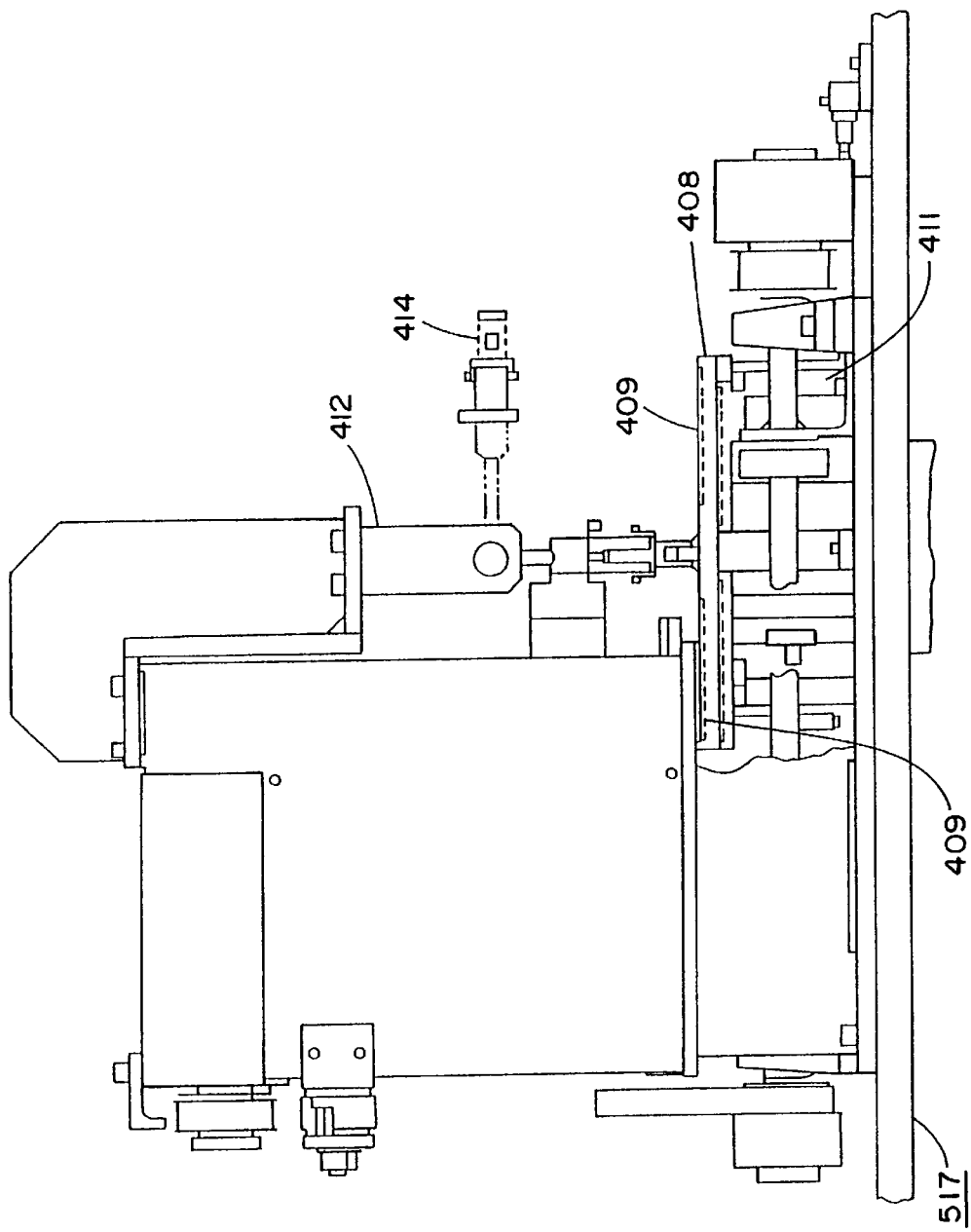
FIG. 38 illustrates an elevational side view taken along line 38—38 in FIG. 37.
Figure 39A:
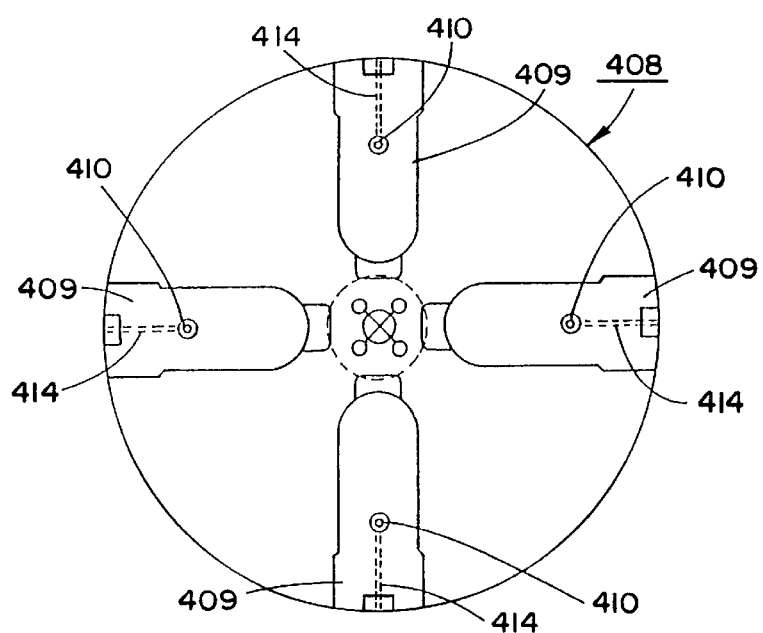
FIGS. 39(a) and 39(b) illustrate, respectively, plan and side views, shown partly in section, of the rotatable plate member for separating trays from the carousel of FIG. 37.
Figure 39B:
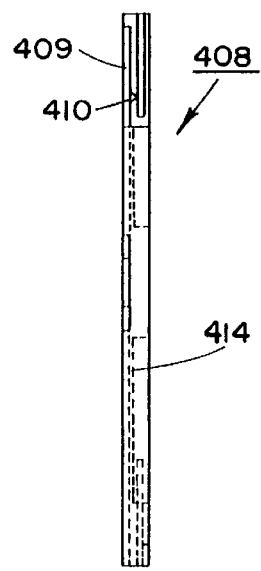

Referring to FIGS. 37 and 38, there is shown a tray loading installation, also mounted on the adjustable frame member 517, that includes rotatable carousel 402 having eight (8) vertical chutes 404 in an adjoining spoke-like array about a vertical control shaft 403. Each chute 404 is adapted to hold a stack of superimposed empty package trays 45. The carousel 402 is adapted to be rotatably indexed about shaft 403 through the intermediary of a suitable drive mechanism (not shown) whereby a chute, which is filled with a stack of the trays 45 is adapted to have the open bottom end thereof located in close proximity above-the upper surface of a circular plate 408 arranged beneath the carousel with a portion thereof extending beneath the bottom end of the chute of the carousel which is adjacent thereto. The circular plate 408, as shown in FIGS. 39(*a*) and 39(*b*), has four (4) radially extending recesses 409 each of a depth essentially corresponding to the height and peripheral shape of the package tray 45, and with each recess 409 extending at a 90° angular spacing relative to an adjacent recess, each having an aperture 410 in the bottom surface thereof communicating with a passageway 414 leading to a controllable vacuum generating arrangement in the machine 25.

When one of the recesses 409 of the rotary plate 408 is in alignment with the bottom of a superimposed tray-containing chute 404 of the carousel 402, a bottommost tray is sliced off or separated from the remaining stack of trays and deposited in the recess 409 located therebeneath under the effect of a vacuum which is applied to the bottom surface of the tray recess 409 through aperture 410.

As the plate 408 is rotatably indexed forwardly by means of a drive unit 411, each successive recess 409 has a respective successive bottommost tray 45 deposited therein from the chute 404 of the carousel 402 which is in superimposed alignment therewith. As the plate 408 continues its indexed rotation, a robotic or cam-controlled pivot arm 412, as shown in FIG. 39, has a gripper attachment 414 at a forward end depending downwardly so as to contact the tray 45 located in recess on plate 408. The vacuum is released in the recess 409, and the gripper atttachment 414 grasps the tray 45. The pivot arm 412 is then pivoted upwardly into a horizontal orientation, as shown in FIG. 39, and then extended forwardly into contact with the tray-mounting vertical plate element 538 on a therewith aligned tool nest 530 of the rotary turntable 512.

Thereupon, the gripper attachment 414 releases the tray while a vacuum is applied to plate element 538 to transfer the tray 45 thereto and retain it on the tool nest. The pivot arm 412 is then retracted and pivoted downwardly to enable gripper attachment 414 to engage a subsequent tray 45 positioned in a successive recess 409 in the plate 408, and in synchronism with the forwardly indexed rotation of the turntable 512, to repeat the foregoing cycle of positioning trays 45 with regard to successive tool nests 530 coming into operative alignment with the robotic pivot arm structure.

As a chute 404 of the carousel 402 empties of trays 45, upon the last remaining tray 45 of the stack of trays in that chute being transferred to rotary plate 408, the carousel 402 is rotatably indexed forwardly to the next or adjacent full chute, so as to have that subsequent tray-filled chute 404 arranged in an alignment with the rotary plate 408, to enable the continued and uninterrupted repetitive supplying of empty trays 45 to the rotary plate 408, and then through the intermediary of the operation of robotic pivot arm 412 member to the tool nests 530 on the turntable 512 of the automated packaging machine 25. The empty chutes on the carousel may be manually refilled with new stacks of package trays 45.

Between the chute 404 and the disc-like plate 408 is a single multi-tray buffer area (not shown) which functions to retain a plurality of trays. Thus, when the current chute is empty, the buffer allows time for the next chute of the rotatable carousel to be indexed into position without stopping the machine. Therefore, trays 45 can be continuously fed into the disc-like plate 408 without interrupting the packaging process.

The tool nest 530 with the tray 45 retained under a vacuum on the radially outwardly facing surface of the plate element 538 at a generally horizontal orientation of the longitudinal axis 45*a* of the tray 45 which is retained thereon is then advanced to work station (2) through the rotation of the turntable 512 (through a rotation of 30° in the direction of arrow A).

The control process 1600 for the tray load station 400 is exemplified in FIG. 7(*d*) which illustrates a first step 1602 indicating that the run mode has been selected. From step 1602, two processing threads are shown in FIG. 7(*d*), with the first thread determining whether the nest orientation is proper for initiating the tray load operation at station 400. This processing thread implements a first step 1604 to ascertain when the package dial has reached a certain predetermined position as the package dial is being indexed, and after the proper orientation has been detected, performs a check as to the nest orientation as detected by proximity detector (not shown), at step 1606. Then, at step 1608, a determination is made as to whether the tool nest orientation is correct. If the tool nest orientation is correct then the tray load operation continues, and if the tool nest orientation is incorrect, then the process will be terminated and prompted for reinitialization at step 2010. Concurrently, a determination is made at step 1610 to ascertain when the package dial has reached a second certain predetermined position during package dial indexing to ensure that the package dial 512 is at an oriented position suitable for receiving the package tray from the robot arm grippers 412 as described above. After the proper package dial orientation has been detected, then, as indicated at step 1612 in FIG. 7(*d*), a control signal is activated to enable the solenoid valve 803*h* (FIG. 52(*e*), that actuates the robot gripper mechanism 414 to place the empty package tray 45 onto the tool nest plate 538 in the manner as described above. After the package is oriented for placing the empty tray at the tool nest plate, a check is made at step 1614 as to whether the package dial is at the predetermined position for receiving the empty tray from the robot gripper. After the proper package dial orientation has been detected, then, as indicated at step 1616 in FIG. 7(*d*), a control signal is activated to turn off (deactuate) the gripper mechanism 414, so that it can be retracted and positioned to receive the next empty tray from the tray stack.

It should be understood that the foregoing operations of transferring the trays 45 from the carousel 402 to the plate 408 under a controlled vacuum applied to the tray recess 409, and, the vacuum for maintaining the trays 45 in position on the tray-mounting plate elements 538 of the tool nests, are controlled by being applied or released in operative interrelationship through vacuum systems installed in the packaging machine 10. For instance, as shown in FIG. 52(*e*), vacuum pump 802*a* through vacuum manifold 417 in communication with the circular plate 408 provides the vacuum for the rotary plate recesses to retain trays sliced from the chute. Air supply line 806*a* feeds solenoid valve 803*h* to actuate the gripper 414 under the timing and control of the control system 999 to actuate and deactuate the gripper when placing the tray upon the tool nest.

Referring back to FIG. 7(*d*), simultaneous with the loading of the package tray on the empty tool nest, a check is made at step 1620 to determine whether the tray stack level is at an acceptable level. Thus, at step 1622, a determination is made as to whether the stack level is empty. If the stack level is empty, then the cycle jam bit will be set indicating non-critical fault, as indicated at step 1624, and the process will continue at step 1625 to determine if the stack level is low. If, at step 1625, it is determined that the stack level is low, then a stack low level warning signal is activated at step 1626 which may involve generating an observable yellow warning light at the control computer display or the machine itself, for example. If it is determined that the stack level is not low, then the process continues at step 1628 to determine whether the package is at the slice dial as determined by a proximity sensor (not shown). If the package is not at the slice dial, then the cycle jam bit will be set indicating non-critical fault, as indicated at step 1630, and the process will continue at step 1633 to determine whether the door interlock has been overridden, e.g., by manual intervention. If the door interlock has not been overridden, then the cycle jam bit will be set indicating non-critical fault, as indicated at step 1635, and the process continues at step 1640 to determine whether the last stack in the carousel is empty. If it is determined that the last stack in the carousel is not empty, then the cycle jam it will be set indicating non-critical fault, as indicated at step 1642, and the process continues at step 1645 to generate a control signal for indexing the package tray carousel. Then, at step 1648, a determination is made as to whether the carousel index is done. If the carousel index is not done, then the cycle jam bit will be set indicating non-critical fault, as indicated at step 1649, and the package load process terminates. If the carousel index is done, then the package load process terminates.

At the next workstation, indicated as 16.5° turn station 415 in FIG. 30, to which the respective tool nest supporting the empty tray 45 thereon has been advanced by the rotational advance of the turntable mounting the tool nest; in effect 30° rotated forwardly; operative structure engages the plate element on the outer end of the tool nest supporting the empty tray under a vacuum, and rotates the plate element and tray counterclockwise within the vertical plane thereof about the axis of the horizontal shaft of the tool nest through an angle of approximately sixteen and one-half (16.5°) degrees so as to be in appropriate angular orientation relative to a horizontal axis for facilitating the subsequent insertion and retention of a surgical needle and attached suture into the tray at the needle-to-package load station 450.

As shown in FIG. 30, an apparatus 419 at work station 415 includes a pair of cooperating arm elements 432 adapted to be activated so as to impart a counterclockwise rotation to the tray 45 and plate element 538 with the vertical plane thereof about the axis of the shaft supporting the plate element 538. The tray 45 is angled counterclockwise relative to the initially horizontal longitudinal axis 45a thereof by an angle of about 16.5° so as to be in position for the insertion of an armed suture at the needle-to-package load workstation 450.

In order to be able to effectuate the rotational movement or angular displacement of the tray 45, operative structure engaging the tool nest enables radially inward retraction of shaft 526 causing cam plate 531 to disengage from the locating pin 533 at the radially inward end rear of housing 532. Thus, the shaft 526 is enabled for rotation until the plate element 538 and tray 45 are tilted by shaft 526 as required, i.e., 16.5° relative to the horizontal. The shaft 526 is then moved axially forwardly, allowing the pin 531 to engage, and locking the plate element 538 and tray 45 into tilted position.

Figure 7E:
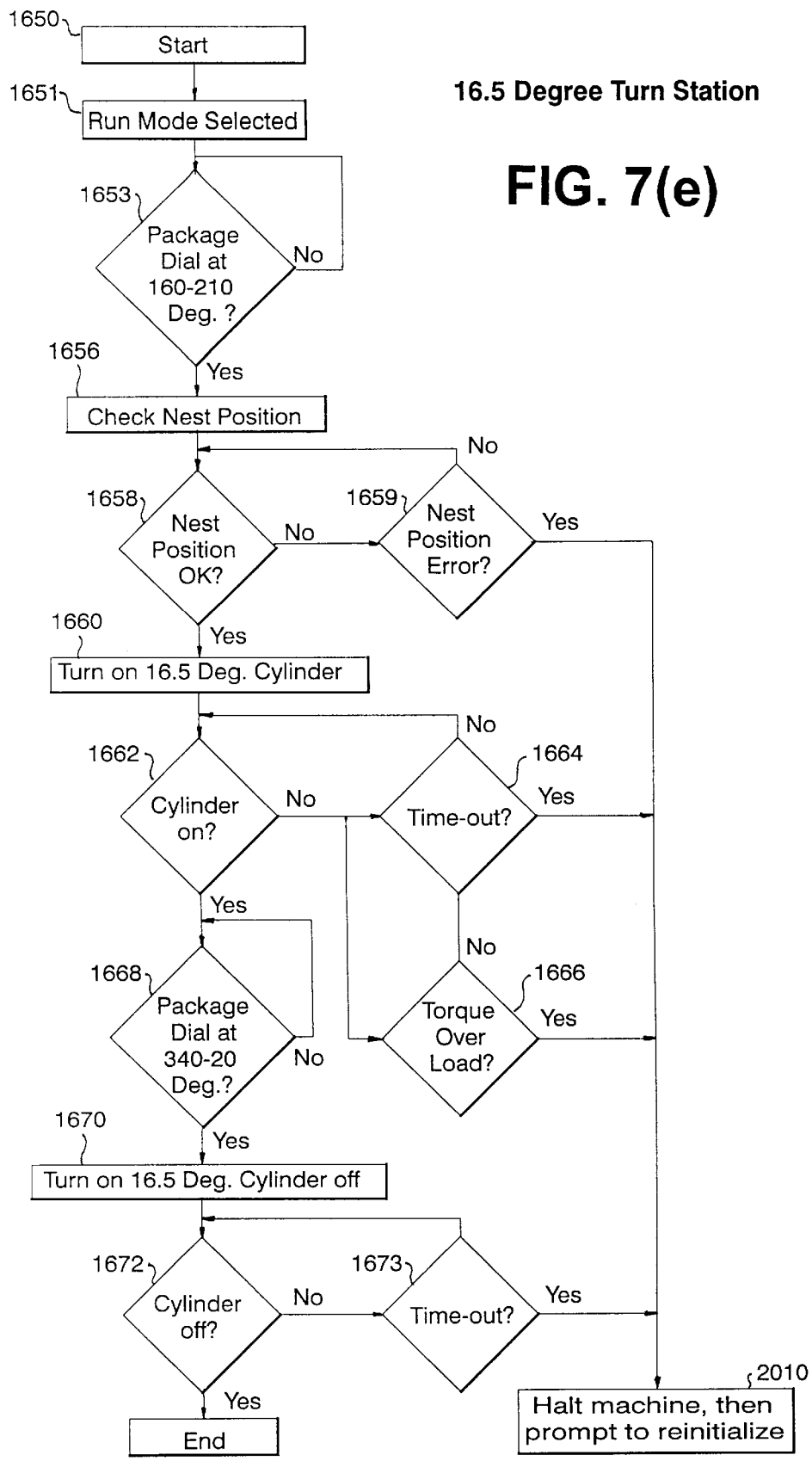
Figure 7F:
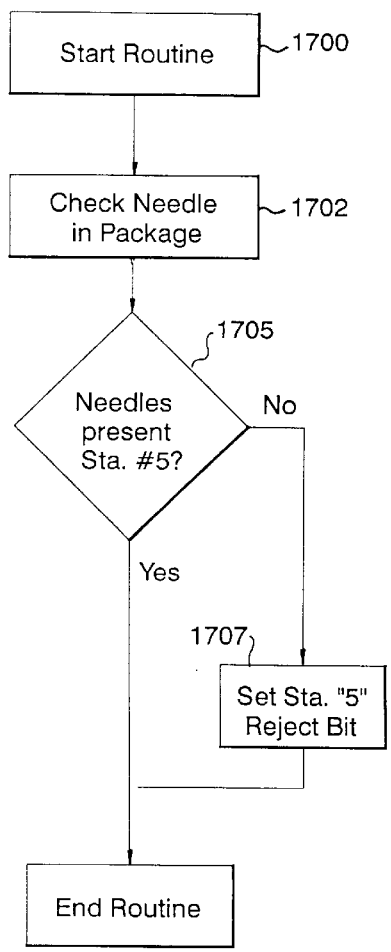

The control process 1650 (FIG. 3) for the tray 16.5° turn station 415 is exemplified in FIG. 7(e) which illustrates a first step 1651 indicating that the run mode has been selected. A second step, indicated as step 1653, ensures that the package dial is at a predetermined orientation for enabling the package tray rotation operation. Then at step 1656, the nest position is checked to ensure that it too is in proper orientation for the package tray rotation operation. At step 1658, a determination is made as to whether the tool nest is positioned for rotation. If there is a nest position error as indicated at step 1659, the process will repeat at step 1658 until the nest position is good. If the nest position is not good, then the process will be terminated and prompted for reinitialization at step 2010. If the nest position is good, then at step 1660, the 16.5° cylinder is actuated to rotate the tool nest. Specifically, as shown in FIG. 50(b), the 16.5° cylinder 432 is actuated by solenoid valve 803w under the timing and control of the control system computer 999.

Next, as indicated at step 1662, the control system performs a check to ensure that the 16.5° cylinder is on, i.e., whether a time-out flag has been generated by the control system indicating a time-out error. If a time-out flag has not been generated, then the cylinder has not completed tray rotation or has not been actuated. The control system performs a two-fold test: first by determining at step 1664 whether the 16.5° cylinder has timed out, and, by determining whether there is a torque overload in the rotation operation, as indicated at step 1666. If the time-out flag is generated by the control system as a time-out error, then the machine will be halted and prompted for reinitialization as indicated at step 2010. If it is determined that there is a torque overload, then the machine will be halted and prompted for reinitialization as indicated at step 2010. Then, at step 1668, a control command is generated to determine whether the package dial has rotated to an orientation for enabling deactivation of the 16.5° cylinder. The control system will wait for this package dial orientation at step 1668 before turning off the 16.5° cylinder at step 1670. Then, at step 1672, a determination is made as to whether the 16.5° cylinder has turned off within the allotted time determined by the control system. If the time-out flag is generated at step 1673 by the control system as a time-out error, then the machine will be halted and prompted for reinitialization as indicated at step 2010. Otherwise, the 16.5 tray rotation cycle at workstation 415 ends.

Thereafter, as shown in FIG. 30, upon the plate element 538 with the tilted tray 45 therein being advanced forwardly through the indexed rotation of the turntable 512, to workstation 435, an upright support structure 441 supports a sensor 445 for detecting and verifying the presence of a tray 45 on the plate element 538 of the tool nest 530; for instance, by scanning a spot formed at a specific location on the tray 45. The package detect process is generally illustrated as control thread process 1680 (FIG. 3) operating concurrently with the other package dial operations described herein.

With the tray 45 in readiness to have a needle and attached suture inserted therein at the at the needle-to-package load workstation 450, the rotary turret 512 is indexed forwardly to workstation (4), i.e., the needle-suture load-to-package station 450 with reference had to co-pending application Ser. No. 09/020,091; 10196.

The needle-suture load-to-package station 450 provides a mechanism for inserting a single surgical needle and attached suture into the suture tray which has been indexed forwardly by the rotary turret so as to be located in operative alignment with the needle-feed mechanism. The needles are conveyed by the mechanism so as to be mounted on suitable clamping or needle "park" structure constituting an integral portion of the tray. Vacuum-controlled suture capture and tensioning devices which are located below each tool nest, become operative at this work station to capture and tension the suture portions depending outwardly of the tray mounting the surgical needle.

Figure 41:
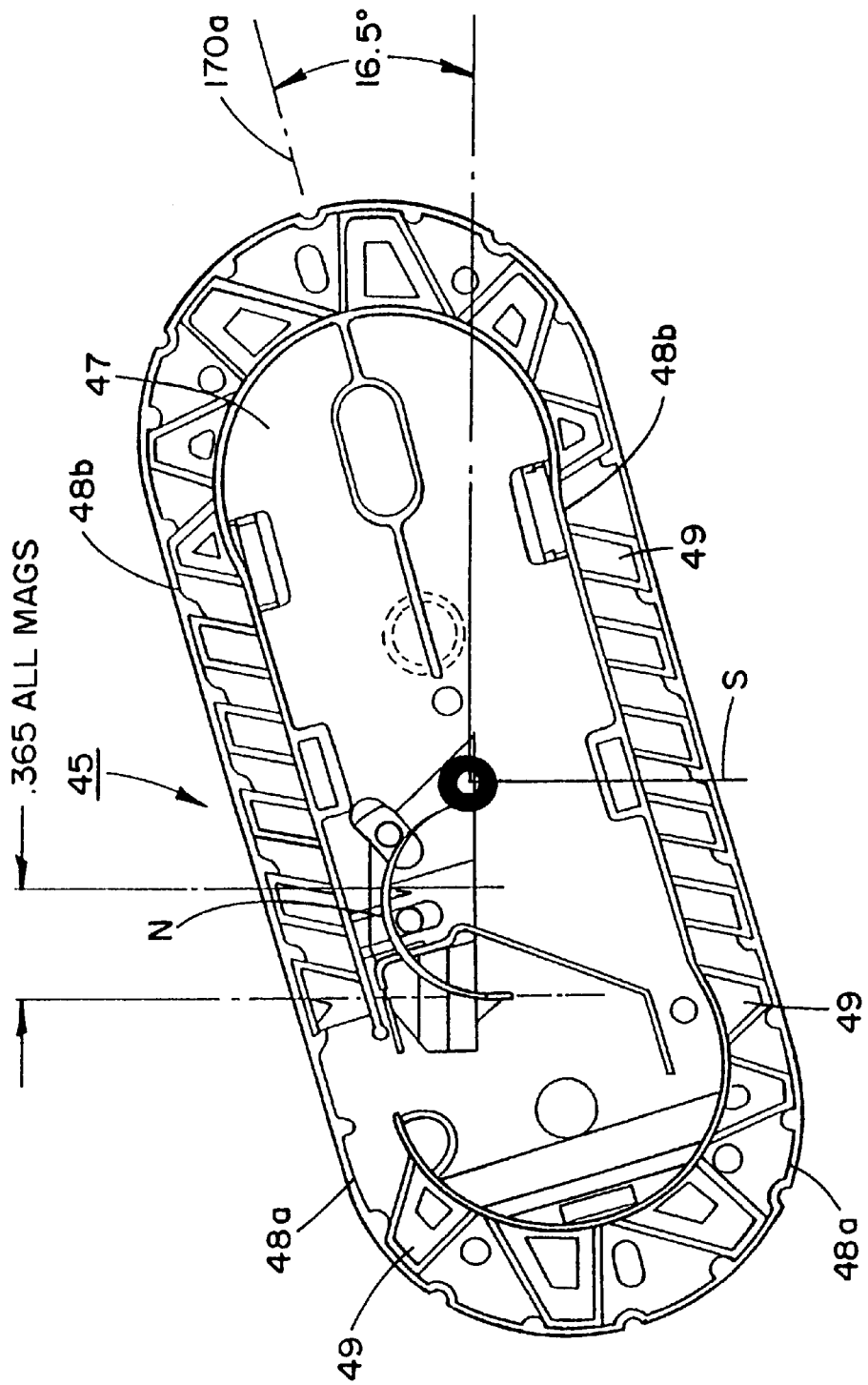
FIG. 41 is a close up view of the armed needle 9 parked within package tray 45.
Figures 42A, 42B, 42C, 42D, 42E, 42F:
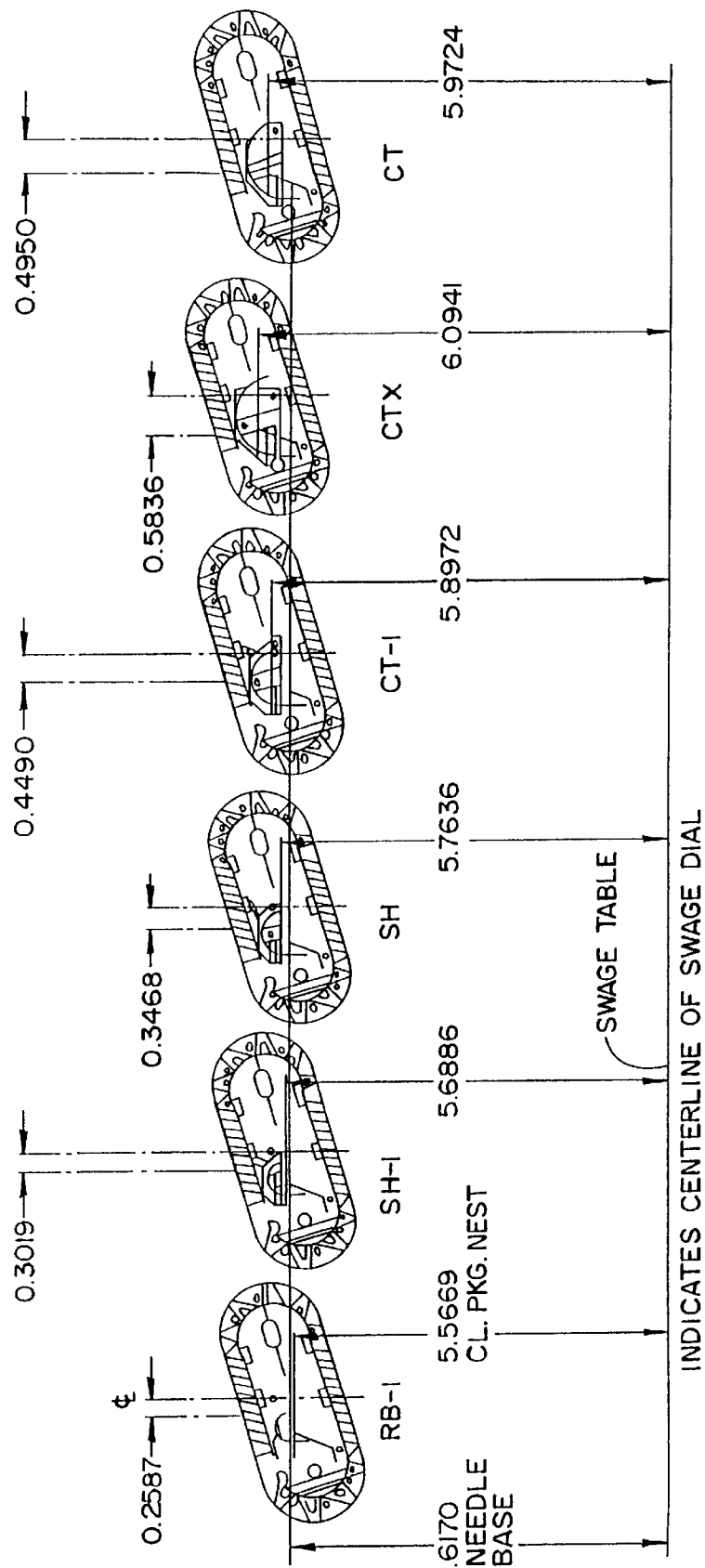
FIGS. 42(a) through 42(f) illustrate the positioning values for differently sized surgical needles by the multi-axis grippers.

Particularly, as shown in FIG. 40, the multi-axis gripper 155 of the rotary swage dial 150 is extended to insert an armed suture into the suture tray 45 indexed by the packaging dial 500 in a confrontingly opposed relation to the multi-axis gripper. The needles are fed by the multi-axis gripper 155 so as to be positioned on a suitable clamping structure formed integrally with the central surface portion of the suture tray 45, as shown in FIG. 41 of the drawings and explained in detail in co-pending patent application Ser. No. 09/020,085 assigned to the same assignee of the present invention and incorporated by reference herein.

Generally, to load the armed needle into the empty package 45, the tool nest 530 is brought to station 450 in its home position as shown in FIG. 40. Simultaneously therewith, the multi-axis gripper 155 is indexed from the pull-test station 300 to station 450 where it is then extended toward the empty, tilted package 45, in the manner described above, to cause the armed surgical needle 9 to engage the clamping groove structure 446 formed in the face 46 of the tray 45. Specifically, after the multi-axis gripper 155 has been extended toward the tray in the manner described above, the control system 1000 actuates solenoid 808k to enable push rod 443 to depress the plunger 149 on the multi-axis gripper so that it may release its grip of the armed needle 9 as described above with respect to FIG. 6(a). Having released the surgical needle, the MAG gripper 155 is retracted away from the packaging tray as the swage dial is indexed.

FIG. 41 of the drawings illustrates packaging tray 45 oriented at the 16.5° angle clampingly engaging needle ("N") and suture ("S") assembly, that is essentially constituted of molded plastic material, and includes a planar base 47 with parallel sides and semi-circular rounded ends. A first vertical wall 48a extends about the perimeter of the tray, while inwardly spaced thereof is a second vertical wall 48b having radially outwardly extending fingers 49 which are flexible at the upper edge reaching close to the outer wall 48a so as to define a hollow channel structure.

In order to adapt the packaging machine 25 to the differently sized surgical needles which are to be packaged in essentially identically-sized packaging trays 45, the latter of which may accommodate a wide range of needle sizes without having to have the suture package modified, the turntable 512 and the tool nests 530 which are mounted thereon, including the various workstation components, are adapted to be adjustable in elevation relative to the needle transfer devices or grippers 155 so as to compensate for changes in needle size, without having to modify the functioning of the packaging machine 25 or the need to replace any of the structural components of the machine at the various workstations.

As illustrated in the drawing FIGS. 42a through 42f differently sized surgical needles, identified by symbols RB-1, SH-1, SH, CT-1, CTX and CT by way of example, may be introduced into basically identical packaging trays 45, and which also indicates the different adjustments of the packaging machine 500 above a fixed reference line of the swage dial apparatus 150 and a swage table (not shown) from which the surgical needles and attached sutures are transferred by the gripper structure 155 to the tray 45 mounted on tool nest 530 of the packaging machine 25.

As indicated in the drawing FIG. 31, arranged within the stationary support arrangement of the frame portion 515 for the machine 25 is the frame portion 517 which is movable relative to stationary frame portion 515, and is adapted to be vertically adjusted through the intermediary of the jack screw unit 541 which is connected to turntable 512, and enables the height of the latter to be adjusted in correlation with the particular size of surgical needle which is to be transferred into the tray 45.

The elevational adjustability of the movable frame 517 and, resultingly, that of the turntable 512 and tool nests 530 may be preprogrammed or otherwise determined and controlled by the operating personnel for the machine 25, e.g., during a set-up or initialization procedure, as will be described hereinbelow.

As may be ascertained from FIG. 50(e) of the drawings, vacuum-controlled clamping structure 466 having supplied a vacuum via supply line 806d through the intermediary of vacuum pump 802d, of which one is mounted on the lower surface of the turntable 512 below each respective tool nest 530, clampingly engages and captures the portion of suture 12 depending outwardly and downwardly from the tray 45 in which the armed needle has been parked, and is able to maintain a predetermined controlled gripping action on the suture in cooperation with a suture tensioning arrangement, as described in more specific detail in co-pending application Ser. No. 09/019,674; 10197), the disclosure of which is incorporated herein by reference.

With respect to the features of the packaging machine 25 which are directed to a provision of arrangements for capturing and tensioning the portion of the suture which depend outwardly of a packaging tray 45 during the cycle portion of machine operation in which the surgical needle and attached suture is transferred into and parked in a tray at needle load to package workstation 450 and until completion of the winding of the entire length of suture into the confines of the packaging tray, appropriate controlled tension is maintained on the outwardly depending suture portion in order to avoid any snagging thereof which would inhibit or adversely affect the unobstructed winding of the suture into a channel formed in the tray 45.

Referring in particular to the drawings, there is illustrated a vacuum-operated clamping arrangement 466, of which one each is mounted beneath each respective tool nest 530 and below the level of turntable 512. Each vacuum-operated clamping arrangement is operatively connected through the vacuum plenum 503 with a vacuum-generating system which is provided in the packaging machine 25 and may be supplied through suitable vacuum ports and passageways as described in co-pending U.S. patent application No. 09/020, 084when a vacuum is adapted to be supplied thereto during predetermined intervals. In this instance, the clamping arrangement 466 which includes a plurality of vacuum nozzles or fingers 456 as illustrated conceptually in FIG. 50(e), is rendered operative when a surgical needle 9 is inserted into the suture tray 45 at workstation 450, which is the needle load to package station. The suture portion 12 which extends outwardly of and downwardly of the tray 45 from its attached end to the surgical needle which is being and has been parked in the tray, is captured by the vacuum operated clamping arrangement 466 through the intermediary of vacuum nozzles 456, and at a location which is below the respective therewith associated tool nest 530.

Figure 45:
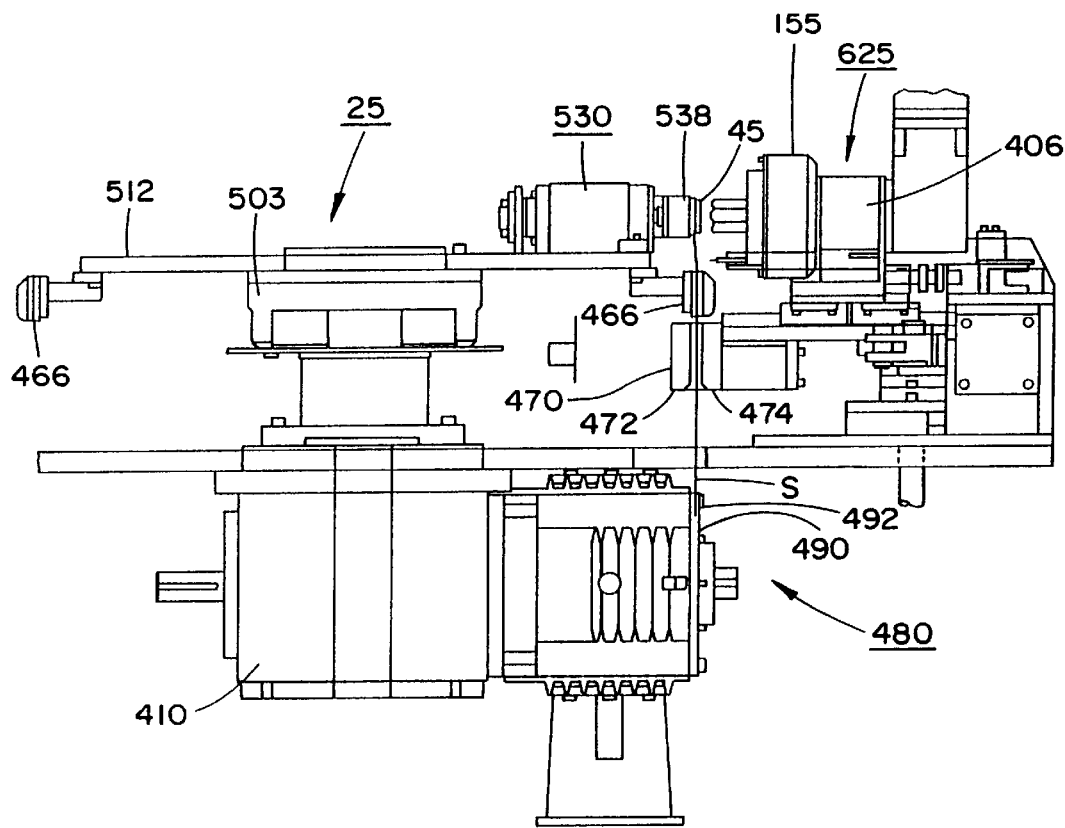
FIG. 45 illustrates a side view of the vacuum tensioning arrangements for the suture.

At the point in time when the surgical needle 9 has been inserted into the tray 45 and the suture portion 12 depends outwardly and downwardly therefrom, it passes through the clamping arrangement 466, as shown in FIG. 45, and extends downwardly through a further vacuum nozzle arrangement 480 for tensioning the suture portion 12, and into a further lower suture tensioning device (not shown) which is also vacuum-operated and tensions the trailing end of the suture portion 12. Upon the tool nest 530 with the tray 45 with the surgical needle 9 and attached suture 12 having been advanced to subsequent winding stations for winding the suture 12 into the confines of the tray 45, the vacuum in the nozzles 456 of clamping arrangement 466 is released, thereby permitting upward movement therethrough of the outwardly extending suture portion towards the tray 45. However, the suture is maintained under tension in that the vacuum is applied by the plurality of a vacuum nozzles 490, 492 which are located below the vacuum clamping arrangement 466. This will facilitate that although tension is maintained on the suture, the latter is still permitted to move relative to the workstation which the needle has been inserted to the tray, and at the workstations wherein the suture is adapted to be wound into the tray, as illustrated in co-pending application Ser. No. 09/020,191; 10198), the disclosure of which is incorporated herein by reference.

Moreover, as shown in FIG. 45, a guide arrangement 470 for the depending suture portion is provided at winding workstation 625 below the clamping unit 480. The guide arrangement 470 may comprises a pair of plates 472, 474 having wing portions (not shown) forming a conveying passageway (not shown) through which the suture is guided towards the winding head.

From the foregoing, it becomes readily apparent that the utilization of the vacuum-operated arrangement 466 for capturing and the vacuum nozzles devices 490 for tensioning the suture portion 12 which depends outwardly of the tray 45 when the latter has the surgical needle and attached suture end portion positioned therein, will clearly facilitate the unhindered winding of the suture at subsequent workstations into the package tray, thus avoiding any snagging of the suture when being wound into the tray.

As shown in FIG. 30, at the first needle detect work station 475, a stationary sensor 476 located radially outwardly of the turntable can be utilized to ascertain the presence of the surgical needle and attached suture having been properly introduced into the tray. Specifically as shown in the control process thread 1700 in FIG. 7(f), the first step 1702 is to check whether the needle is in the package, for instance, by receipt of a control sensor signal indicating the presence of the needle. Then, at step 1705, a determination is made as to whether the needle is present in the package tray at the workstation 475. If the needle is not detected, then the reject bit corresponding to workstation 475 in the bad package shift register is set at step 1707 to indicate to the control system that the current package absent the needle should be rejected at a further workstation in the manner to be described. Whether the needle is detected or not at step 1705, the process ends and the package dial 500 is then indexed to register the tray and parked needle suture assembly therein at the next workstation in the manner as described.

At workstation 600, there is provided operating structure 612 as detailed hereinbelow, for imparting a pivoting displacement to the packaging tray 45. Concurrently, a vacuum-operated clamping unit 480 capturing the suture and vacuum nozzle 490 for tensioning the portion or length of the suture depending outwardly of tray 45 maintain their function, as described above.

A first tray winding mechanism is provided that engages the plate element on the tool nest supporting the tray, while the suture tensioning device ensures that the suture portion depending out of and downwardly from the tray is maintained under tension by the vacuum-operated tensioning device associated therewith, with the tray being rotated within its vertical plane approximately 163.5°, to assume a horizontal orientation which is 180° reversed from its original orientation on the tool nest at the first work station 400, and with the remaining length of the suture being tensioned by the vacuum device externally of the tray.

Figure 43:
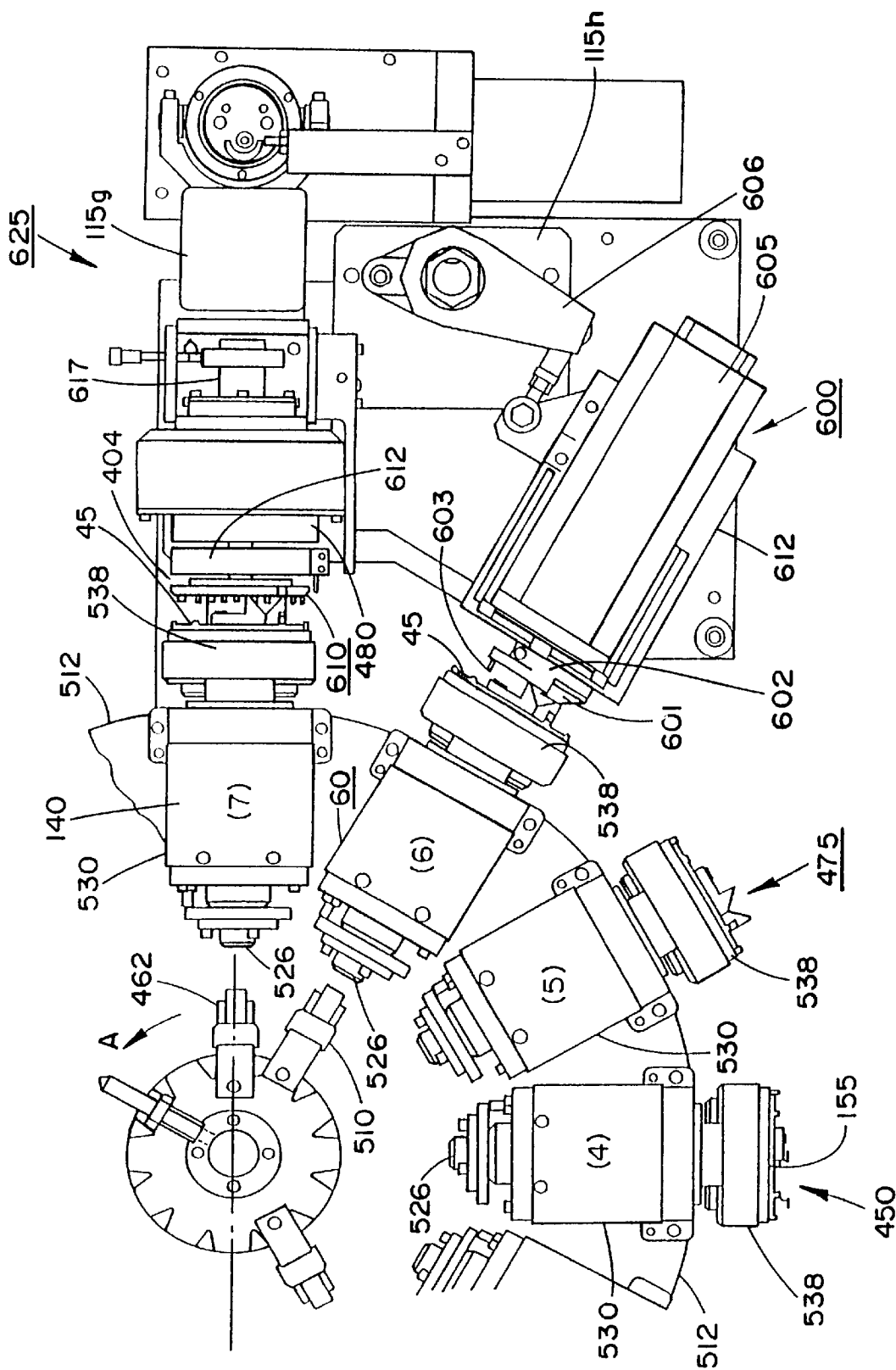
FIG. 43 illustrates a top plan view of the suture winding stations of the packaging station.

As shown in FIG. 43, at the first winding workstation 600, a first winder head 601 of a winding apparatus 612 includes pin structure 603 which upon advance of slide bracket or element 605 engages the support plate 538 on the tool nest on which the tray 45 is mounted, and imparts rotation thereto counterclockwise through an angle of approximately 163.5°. This in effect inverts the longitudinal orientation of the package tray 45 about its axis and of the needle 9 contained therein, while orienting the longitudinal tray axis in a horizontal plane, it previously having been imparted an angular tilt or about 16.5° to facilitate the insertion of the surgical needle 9 and attached suture at the needle feed or transfer workstation 450. The apparatus 602 for effecting the foregoing initial winding includes the rotatable winder head 601 which intermittently advances by means of a slide bracket 604 which is activated by a pivot arm element 606 towards and through pin 603 into engagement with the tool nest 530 to be able to impart rotation to the tray 45, and then retracts after having rotated the tool nest plate member 538 and the package tray 45 mounted thereon through the angle of 163.5°. In this connection, the shaft 526 in the tool nest 530 has been radially inwardly retracted in tool nest housing 532 so as to facilitate rotation thereof. This allows the plate member to rotate with winder head 601, and upon completion of rotation, the shaft 544 is caused to retract, and pin 533 in housing 532 secure the plate member 538 in its rotated position.

Figure 7G:
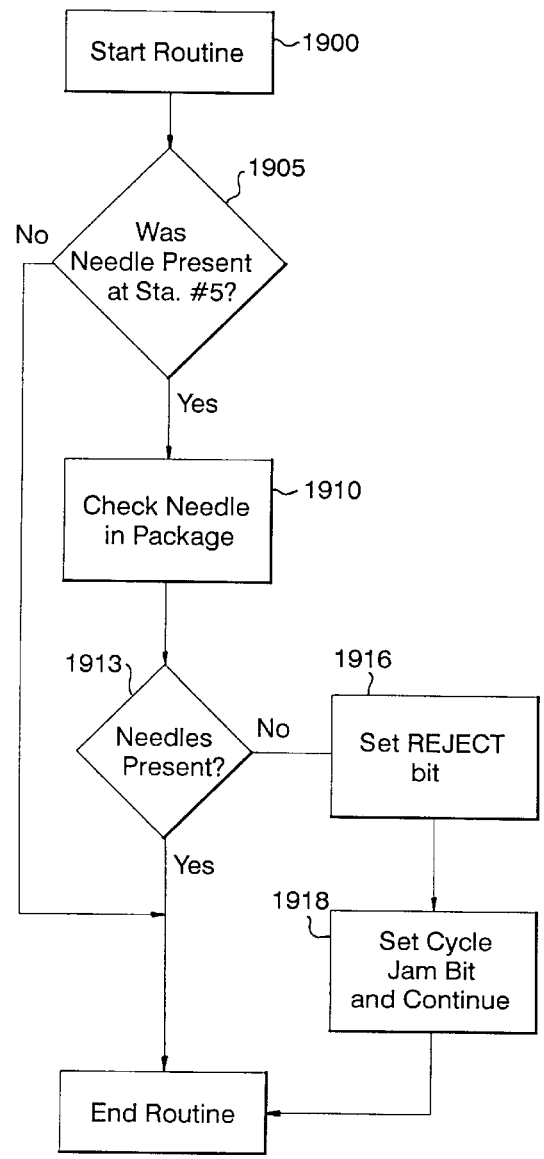
Figure 7H:
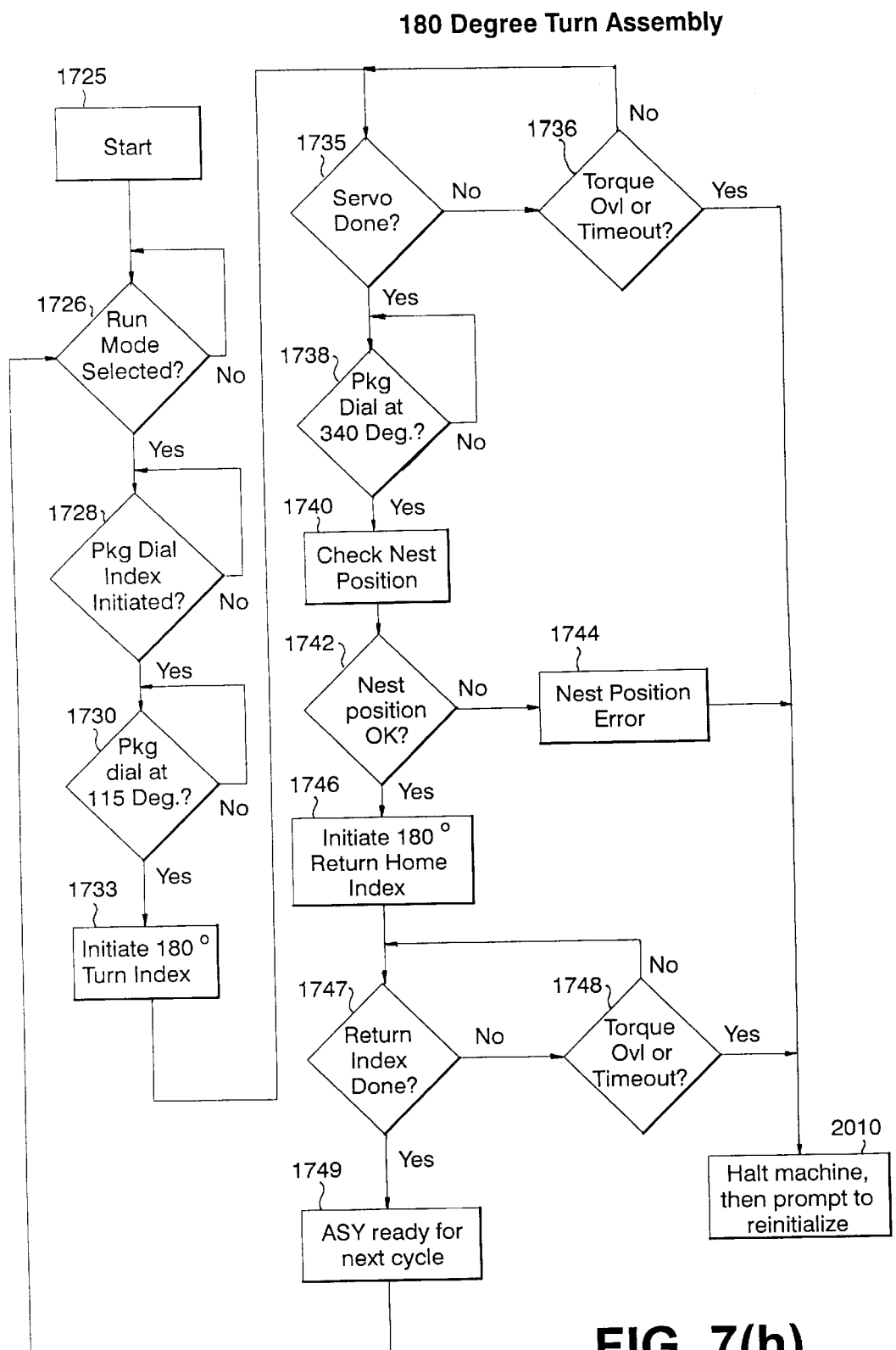

The control process 1725 (FIG. 3) for the package 180° turn station 600 is exemplified in FIG. 7(h) which illustrates a first step 1726 indicating that the run mode has been selected. A second step, indicated as step 1728, ensures that the package dial index has been initiated and will wait until such time that the package dial indexes. Then at step 1730, a check is made to determine that the package dial has reached a predetermined angular orientation before initiating indexing of the 180° wind servo, specifically, by receiving a control signal from the package dial index servo controller 116f through lines 114f. Once this control signal is received, then at step 1733, the 180° turn index is initiated in preparation for the 180° turn operation. As indicated at steps 1735 and 1736, a determination is made as to whether the 180° servo controller for initiating the turn index has timed out or has detected a torque overload condition. If, at step 1736, it is determined that either a time-out flag has been generated by the control system indicating a time-out error, or a torque overload condition exists, then the process will be terminated and prompted for reinitialization at step 2010. If no time-out error or torque overload condition exists, then at step 1738, the control system waits until the package dial has reached a predetermined angular orientation for enabling the 180° package rotation operation, specifically, by receiving an control signal from the package dial index servo controller 116f. Once the package dial and package tray is determined to be in the proper orientation, a check of the tool nest position is made at step 1740 to ensure that it too is in proper orientation for the package tray rotation operation. At step 1742, a determination is made as to whether the tool nest is positioned for rotation. If there is a nest position error as indicated at step 1744, the process will be terminated and prompted for reinitialization at step 2010. If the nest position is good, then the 180° wind operation is performed at step 1746, in the manner described above. Then, at step 1747, a check is made to determine whether the 180° wind index has completed within the time allotted in the current package index cycle. Thus, at step 1748 a determination is made as to whether a time-out flag has been generated by the control system indicating a time-out error, or a torque overload condition exists. If any of these condition are detected, then the process will be terminated and prompted for reinitialization at step 2010. Otherwise, a control signal is generated indicating that the assembly is ready for the next cycle, as indicated at step 1749, which, as described herein, is necessary to initiate the indexing of the package dial and the package trays to the next work station. FIG. 5 illustrates the 180° turn servo motor 115h operating under control of servo controller 116h in communication with control system I/O card 999 to which it communicates any of the above control signals via lines 114h.

At a subsequent work station, indicated as workstation 625 in FIG. 30 and 43, a further winding mechanism is provided to engage the tool nest and the tray mounted thereon, and impart rapid rotation to the tray so as to enable tray structure-engaging portions of the mechanism to completely wind the entire remaining length of the suture into a peripheral groove extending about the confines of the tray.

Figure 44A:
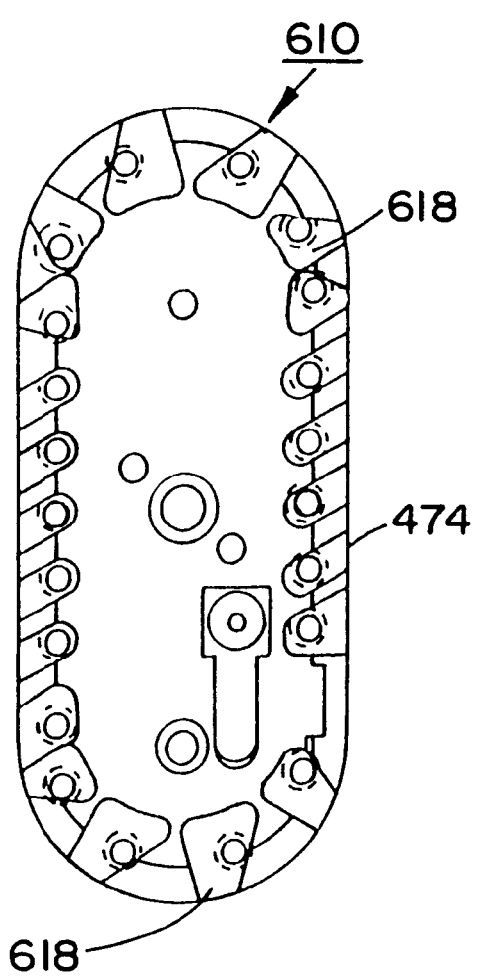
FIGS. 44(a) and 44(b) illustrate, respectively, front and side views of a winding head for winding the sutures into the trays.
Figure 44B:
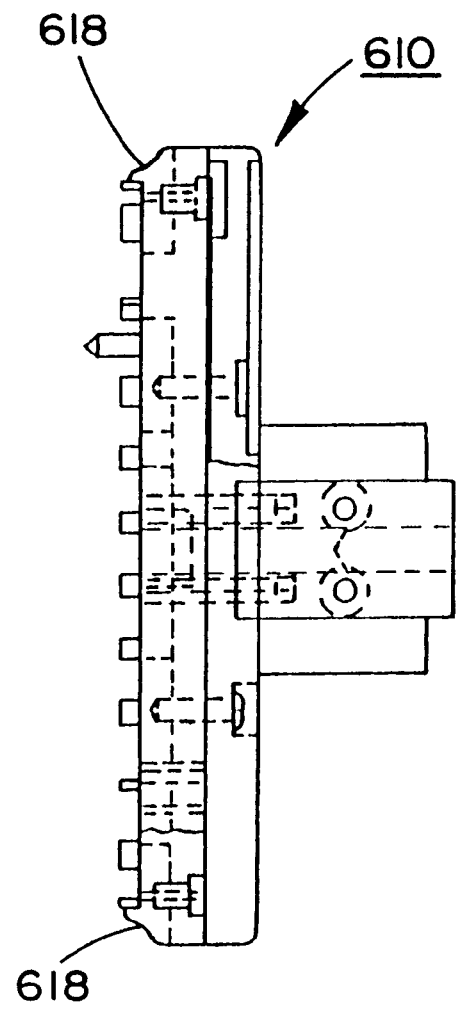

Thus, upon the now invertedly oriented package tray 45 and the parked needle 9 having been advanced by turntable 512 to the second winding station (625), with the major portion of the suture 12 still depending downwardly and engaged by the clamping unit 580 and tensioned by the vacuum nozzles 490 and 492, as described hereinabove, a second winder head 610 of a winding apparatus 612 engages the tool nest and package tray. The shaft 526 is released as in the first winding workstation 600 and retracted to contact cam 510 on dial 512, as described above, to allow plate 538 to rotate with the tray 45. As shown in FIGS. 44(a),44(b), a plurality of lifting surfaces 618 on the winder head 610 are adapted to cooperatively engage finger structure extending over the peripheral channel in the tray 45. Accordingly, during rotation of the plate member 538 and tray 45 on the tool nest, the raised fingers 618 of the tray 45 will allow for guiding the suture into the peripheral tray channel. A so-called "zipper" winding mechanism of generally this type is described in U.S. Pat. No. 5,660,024 the disclosure of which is incorporated by reference. This winding rotation is imparted by winding servo motor 115g operating under the control of servo controller 116g as shown in FIG. 5 in communication with control system I/O card 999 to which it receives commands via lines 114g to rotate the package tray at a high speed over a plurality of rotations commensurate with the length of the particular suture portion 12 extending therefrom, so as to cause the entire length of suture to be wound in one or more circumferential windings into a peripheral channel formed in the package tray 45. Thereafter, the winder head 610 is retracted from the tool nest 530, and the shaft 526 and plate 531 is axially forwardly released back into contact with locating pin 531.

A wind IN/OUT slide mechanism operating under the control of winding In/Out servo motor 115j and servo controller 116j as shown in FIG. 5 in communication with control system I/O card 999, is cooperatively actuated to advance the winding head for engagement with the tool nest.

The control process 1750 (FIG. 3) for the package wind mechanism is exemplified in FIG. 7(i) which illustrates a first step 1752 indicating that the run mode has been selected. A second step, indicated as step 1754, is to determine from the DMACS control program the particular suture length that is to be wound in the package. As mentioned, the winding amount to be performed is commensurate with the length of the particular suture portion 12 extending from the needle. Thus, at steps 1760, 1763 and 1766, a determination is made as to whether the suture length is 18", 27"–30" or 36", respectively. Correspondingly, in accordance with the programmed length, the servo index, i.e., the amount of winding turns, is selected as indicated at respective steps 1770, 1773, and 1776.

The next step, as indicated at step 1780 in FIG. 7(i), is to first verify the actual presence of a suture attached to the parked needle, as will be described, and to verify the actual suture length as determined by a sensor control signal (not shown). At step 1782, a determination is made as to whether the suture length is in fact the correct length as programmed. If the suture length is not correct as indicated at step 1783, then a critical fault condition exists, and the machine will be halted and prompted for reinitialization as indicated at step 2010. Otherwise, the selected servo wind index bit is set, as indicated at step 1785.

Figure 7J:
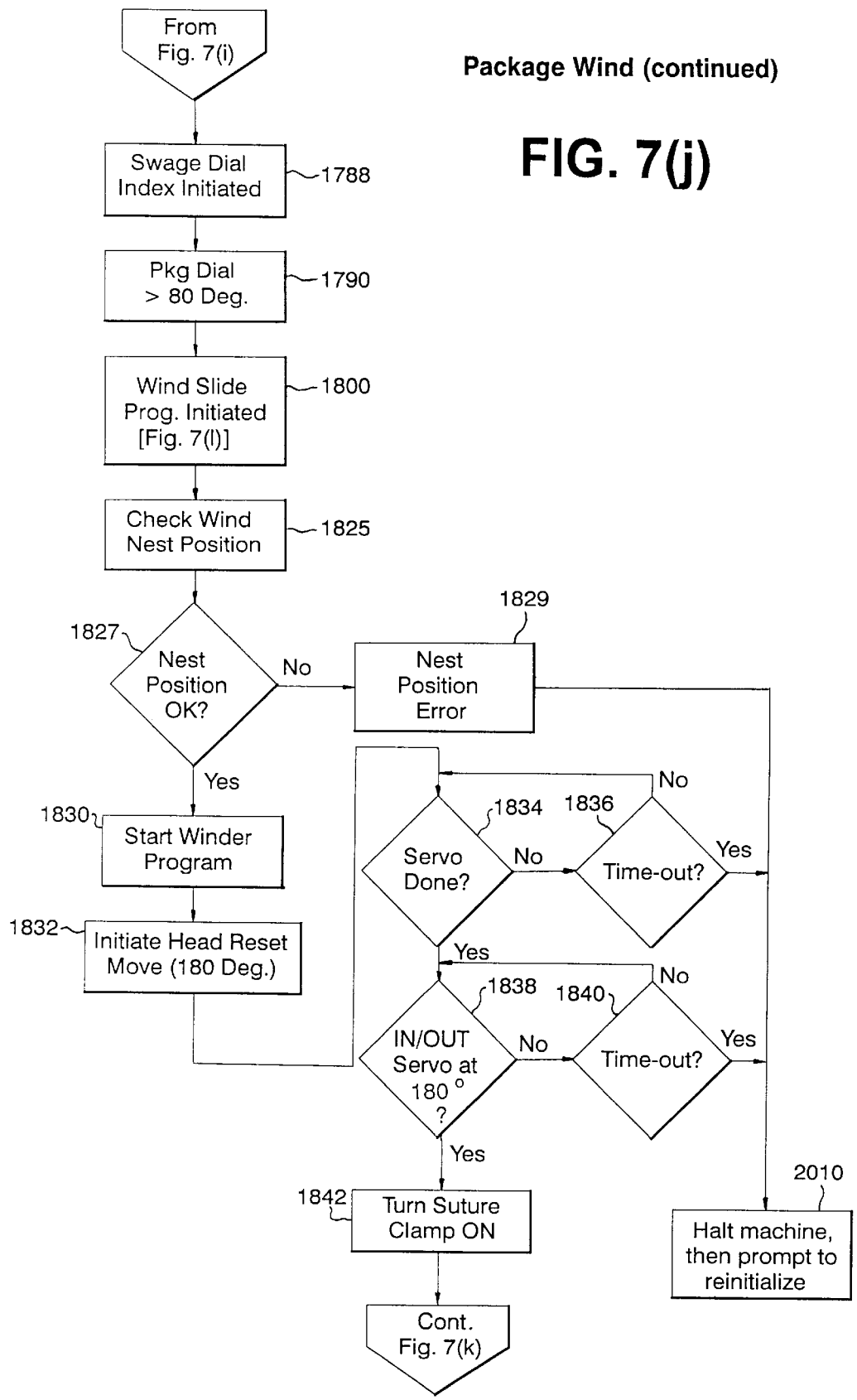
Figure 7K:
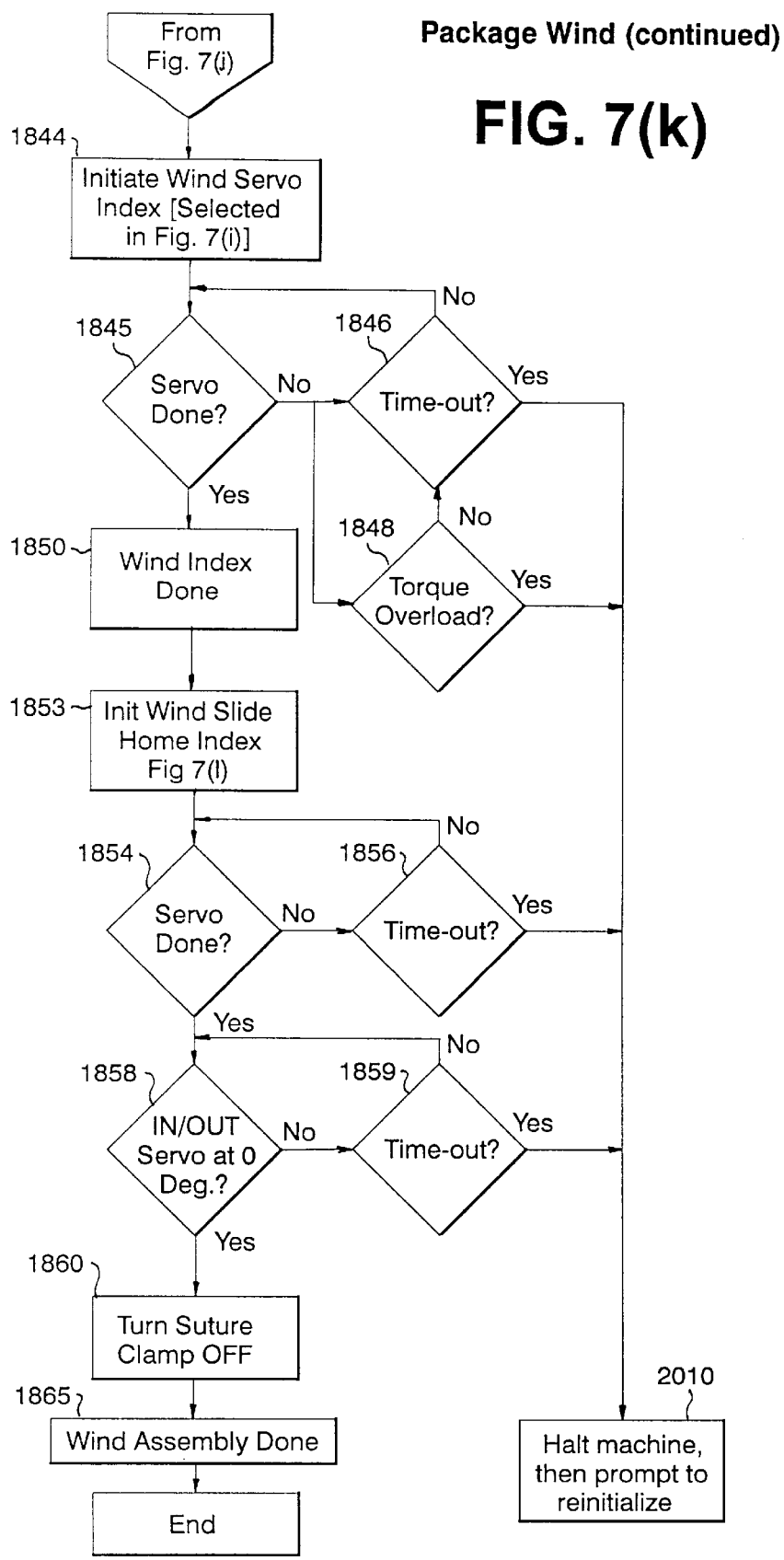

Then, as indicated at step 1788 in FIG. 7(j), the swage dial index is initiated in the manner as described above with respect to FIG. 6(b). Next, at step 1790, a check is made to determine that the package dial has reached a predetermined angular orientation before initiating wind IN/OUT slide operation (FIG. 7(1)), specifically, by checking a control signal from the package dial index servo controller 116f. Once this control signal is received, then at step 1800, the wind IN/OUT slide operation is initiated as described below with respect to FIG. 7(1). Then, as shown at step 1825, a check of the tool nest to be wound is made to ensure that it too is in proper orientation. At step 1827, a determination is made as to whether the tool nest is positioned for winding. If there is a nest position error as indicated at step 1829, the process will be terminated and prompted for reinitialization at step 2010. If the nest position is good, then the winding servo operation is initiated at step 1830, in the manner described above, to rotate the package at high-speed for the predetermined number of turns in accordance with the suture length of the armed needle.

The winding operation comprises a first step 1832 to reset the position of the winding head to a 180° orientation. Then, at step 1834, a determination is made as to whether the wind head servo has completed its reset operation within the allotted time determined by the control system. If the time-out flag is generated at step 1836 by the control system as a time-out error, then the machine will be halted and prompted for reinitialization as indicated at step 2010. Then, as indicated at step 1838, a check is made as to whether the wind IN/OUT slider servo 115j has completed its operation to extend the winding head. If the control signal indicating the completed wind IN/OUT slider servo operation is not received within the period of time allotted by the control system, then the time-out flag is generated at step 1840 by the control system as a time-out error, and the machine will be halted and prompted for reinitialization as indicated at step 2010. Otherwise, the winding process continues at step 1842, to turn the suture clamp on, prior to winding, which is a spring loaded pressure pad mounted to an air cylinder which is activated for tensioning the suture. Particularly, a control signal is activated to enable the solenoid valve 803v (FIG. 52(e), to enable winder clamp to clamp the suture prior to winding. Then, at step 1844, FIG. 7(k), the next step is to initiate the wind servo index, for the suture length selected at steps 1760–1766, FIG. 7(i), to rotate the package at high-speed for the predetermined number of turns in accordance with the selected suture length. Then, at steps 1845 and 1846, the control system performs a two-fold test: first, determining at step 1845 whether the winding servo motor operation has been completed, i.e., not timed out, as indicated at step 1846, and, by determining at step 1848 whether there is a torque overload in the winding operation. If the time-out flag is generated by the control system as a time-out error at step 1846, then the machine will be halted and prompted for reinitialization as indicated at step 2010. If it is determined at step 1848 that there is a torque overload, then the machine will be halted and prompted for reinitialization as indicated at step 2010. Then, at step 1850 the package wind servo controller will generate a wind index done signal. Next, as indicated at step 1853, a control signal is sent to retract the wind head slider to its home position as controlled by IN/OUT servo motor 115k, and a control signal is received at step 1854 indicating that the wind IN/OUT servo motor is done. If a control signal is not received within a predetermined time period, as indicated at step 1856 then a time-out condition occurs and the machine will be halted and prompted for reinitialization as indicated at step 2010.

Then, as indicated at step 1858, the package wind control process waits for a signal from the wind IN/OUT slide control process indicating that the IN/OUT servo motor 115k is back to its home position. If the signal is not received within a predetermined time, then a time-out condition occurs, as indicated at step 1859, and the machine will be halted and prompted for reinitialization as indicated at step 2010. Thereinafter, at step 1860, the suture clamp is turned off, and a control signal indicating that the wind assembly operation is done for the current package index cycle is generated at step 1865.

Figure 7M:
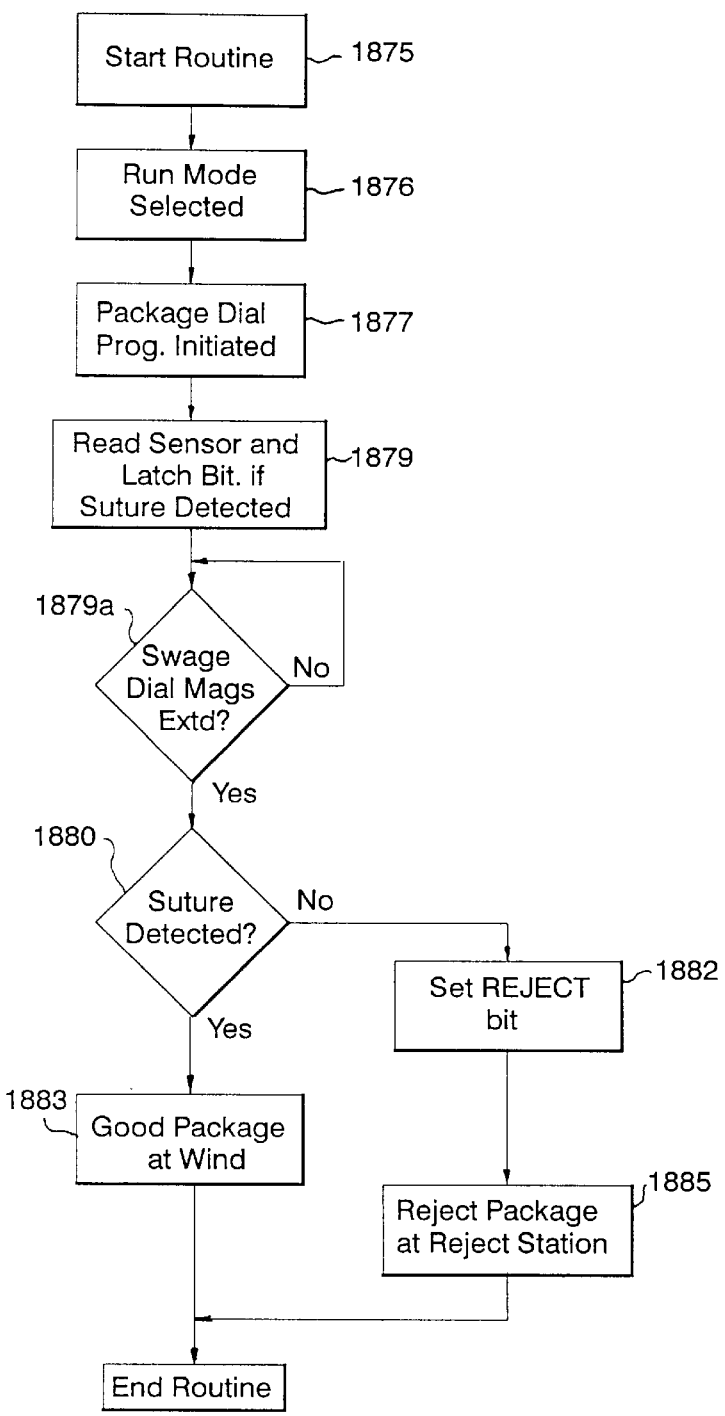

As mentioned above, the detection of the suture is performed prior to the winding operation described above, and the control process 1875 for the suture detect operation is now described with reference to FIG. 7(m) which illustrates a first step 1876 indicating that the run mode has been selected. A second step, indicated as step 1877, is to determine when the package dial has been orientated to a certain position to enable the detection of the suture, as indicated at step 1879. Particularly, two right-angled fiber optic sensors (KEYENCE #FU-32) are mounted below the suture guide nozzles, which detect the presence of the suture when it is indexed to the winding station. As shown at step 1879a, before confirming the presence of the suture, the system waits for an interlock signal indicating that the swage dial MAGs have been extended. After receiving such interlock signal, if it is determined that the suture is detected at step 1880, a bit is set to indicate that the package is good at the winding station as indicated at step 1883. Otherwise, if the suture was not detected, a package reject bit is set in the good/bad package register at step 1882 and the package will be rejected at the package reject station as indicated at step 1885, FIG. 7(m).

The control process 1800 for the package wind In/Out servo mechanism is exemplified in FIG. 7(l) which illustrates a first step 1802 indicating that the run mode has been selected. A second step, indicated as step 1804, is to determine when the package dial has been orientated to a certain position by receipt of a control signal from package dial servo motor controller 116f. Once the package dial and package tray is determined to be in the proper orientation, a check of the tool nest to be wound is made at step 1806 to ensure that it too is in proper orientation. At step 1808, a determination is made as to whether the tool nest is positioned for rotation. If there is a nest position error as indicated at step 1810, the process will be terminated and prompted for reinitialization at step 2010. If the nest position is good, then the wind IN/OUT servo operation is performed at step 1812, in the manner described above, to move the slide forward to push back the tool nest disengaging the positioning plate. Then, at step 1814, a determination is made as to whether the wind IN/OUT servo has completed its operation within the allotted time determined by the control system. If the time-out flag is generated at step 1816 by the control system as a time-out error, then the machine will be halted and prompted for reinitialization as indicated at step 2010. Otherwise, the system waits until the winding operation performed by winding servo 115g, is done, as indicated at step 1818, at which time a control signal is initiated by the winding servo motor controller indicating winding completion. Upon, receipt of this control signal, the control system commands the wind IN/OUT servo 115k to return the slide back to its home position, as indicated at step 1820. Then, at step 1822, a determination is made as to whether the wind IN/OUT servo has returned to its home position within the allotted time determined by the control system. If the time-out flag is generated at step 1824 by the control system as a time-out error, then the machine will be halted and prompted for reinitialization as indicated at step 2010. Otherwise, the control process for the wind IN/OUT servo terminates.

Upon retraction of the winder head from the tool nest 530 at the rapid-winding station 625, the tray is adapted to be advanced towards cover-applying workstation 675. Intermediate the rapid-winding station 625 and the cover-applying workstation 675 (FIG. 30), there can be arranged a workstation 650 comprising a sensor which is adapted to ascertain the presence of the surgical needle in the package tray. Particularly, a stationary sensor 651 at work station 650 is located radially outwardly of the turntable is adapted to ascertain the positioning of the surgical needle in the tray.

The control process 1900 (FIG. 3) for verifying the presence of the needle in the package after suture winding within the package at station 625, is exemplified in FIG. 7(g) which illustrates a first step 1905 to determine whether the needle was present at the last needle check at station 475. If the needle was not present at the last needle check station, then the routine ends. If the needle was present at the last needle check, then at step 1910, a second check is made by a sensor, e.g., OMRON retro reflective sensor #E3C-VM35R, which issues a control signal verifying the presence of the needle in the package. At step 1913, a determination is made whether the control sensor signal had been received, i.e., presence of the needle is detected, and at step 1916 a reject bit is set if the needle was not detected for subsequent rejection of the package. Then, at step 1918, the cycle jam bit is set indicating non-critical fault and the needle detect process ends.

Figure 46:
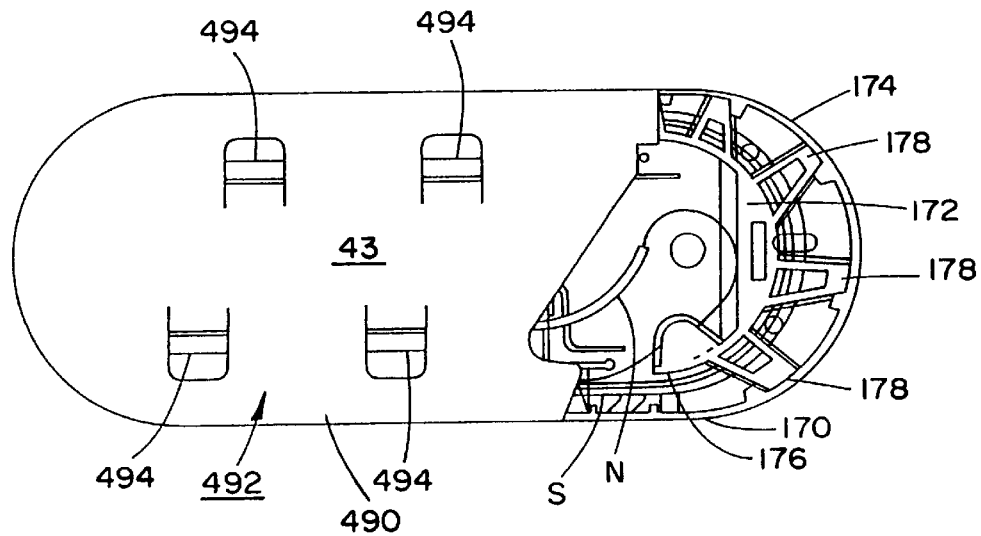
FIG. 46 illustrates a completed suture package with the cover applied thereto.

The next workstation 675 provides apparatus for the application and attachment of a cover or label to the tray containing the surgical needle and attached suture to produce a complete suture package. As shown in FIG. 46, interengageable latching structure 494, such as cut-outs and flaps, formed on the cover and package tray ensure their latched engagement upon application of the cover 43 to the packaging tray 45.

A rotatably indexed disc-like plate 680 includes a plurality, e.g., four, equidistantly circumferentially spaced cover-receiving areas, wherein these are rotated below a vertical stack of covers or labels such that, under the action of a vacuum, the bottommost covers of the stack are sequentially sliced off or separated and deposited into a respective area under the influence of the vacuum present therebeneath, and thereafter is rotated into radial alignment with the tool nest mounting the tray containing the surgical needle and attached wound suture. A cam-controlled pivot arm structure lifts the cover from its plate, while a subsequent area receives a further cover from the stack for transfer onto a following tray, and swings upwardly and horizontally forwardly so as to position the cover into latching engagement with the tray, thereby forming a completed suture package.

Figure 47:
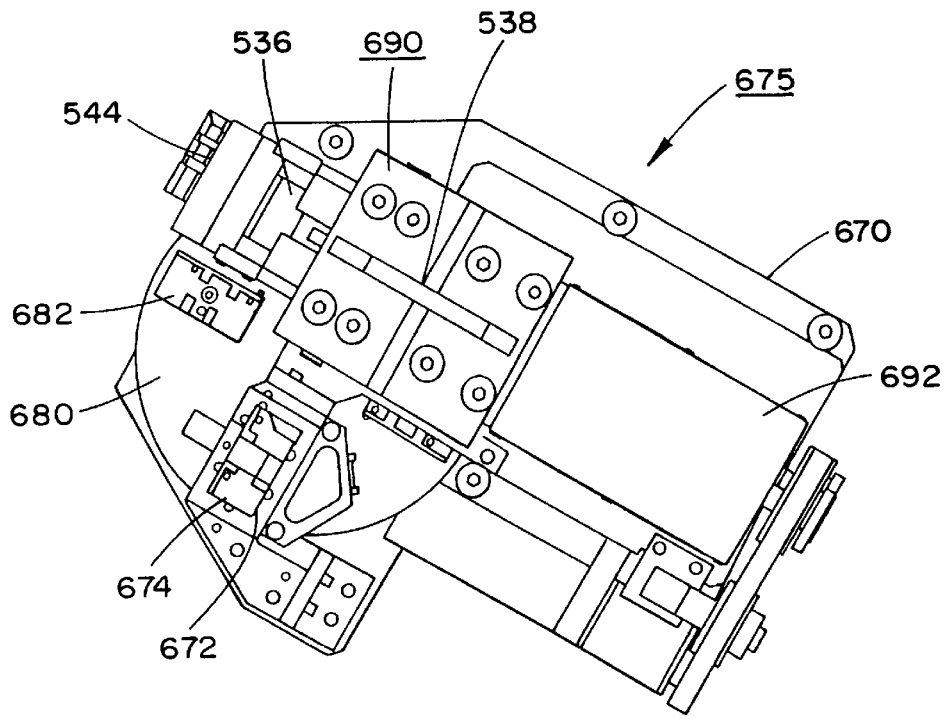
FIG. 47 is a top plan view of the cover load station.

Referring to the drawings which are more specifically directed to the workstation 675 in which a cover 43 or label is applied onto a respective package tray 45 containing a surgical needle 9 and therein wound suture 12, there is disclosed a platform arrangement 670 on which there is mounted a stationary vertical structure 672, as shown in FIG. 47, comprising an open-bottomed chute 674 for the positioning therein of a stack of superimposed lay flat covers 43, such as are shown in FIG. 46.

The lower end 676 of the chute 674 containing the stack of covers 43 is located in close proximity above a rotatable disc-like plate element 680 which is adapted to be driven by a suitable drive arrangement 115i. The disc-like plate element 680 has a plurality of surface areas 682, e.g., four areas at 90° radial and annular spacings from each other, which each conform to respectively the shape of the cover 43.

Between the chute end 676 and the rotatable disc-like plate element 680 is a single multi-cover buffer area (not shown) containing a stack of buffer trays. The buffer area allows the chute 674 to be removed and reloaded with covers 490 without stopping the machine. Therefore, covers 43 can be continuously loaded into the disc-like plate element 680 from the tray stack in the buffer area while loading more covers into the chute 674 without interrupting the packaging process.

During the indexed rotational movement of the plate element 680, a bottommost cover 43 of the stack in chute 674 is sliced off or separated and deposited onto respectively a surface area 682 located therebelow on the upper surface of the plate member 680 which is in alignment therewith. This transfer of the covers 43 from the chute is implemented through the intermediary of applying a vacuum by means of a vacuum pump 802c and vacuum plenum 679 as depicted generally in FIG. 50(e), to the applicable surface area by means of a suitable channel (not shown) which is in communication with the vacuum source. Accordingly, each time a surface area 682 of plate element 680 passes beneath the bottom of the chute 674 containing the stack of covers 43, one cover 43 is sliced off or separated from the bottom of the stack and deposited on the rotatable plate member. At a point in time when a cover 43 on the surface area 682 is located opposite a program-controlled robotic pivot arm 690 which is located rotationally 180° offset from the chute 674 containing the stack of covers 43, as shown in FIGS. 47 and 48, one of the covers 43 is picked up from plate element 680 for transfer and placement on a packaging tray 45 located on a tool nest 530.

As shown in drawing FIGS. 47 and 48, the pivot arm structure 690 includes a housing 692 which is mounted on the platform arrangement 699, and with a portion of plate element 680 rotating below the housing 692. The housing 692 contains actuating and robotically-controlled driving devices (now shown) for operating a pivot arm mechanism 690 which is movably attached to housing portion 692.

Figure 48:
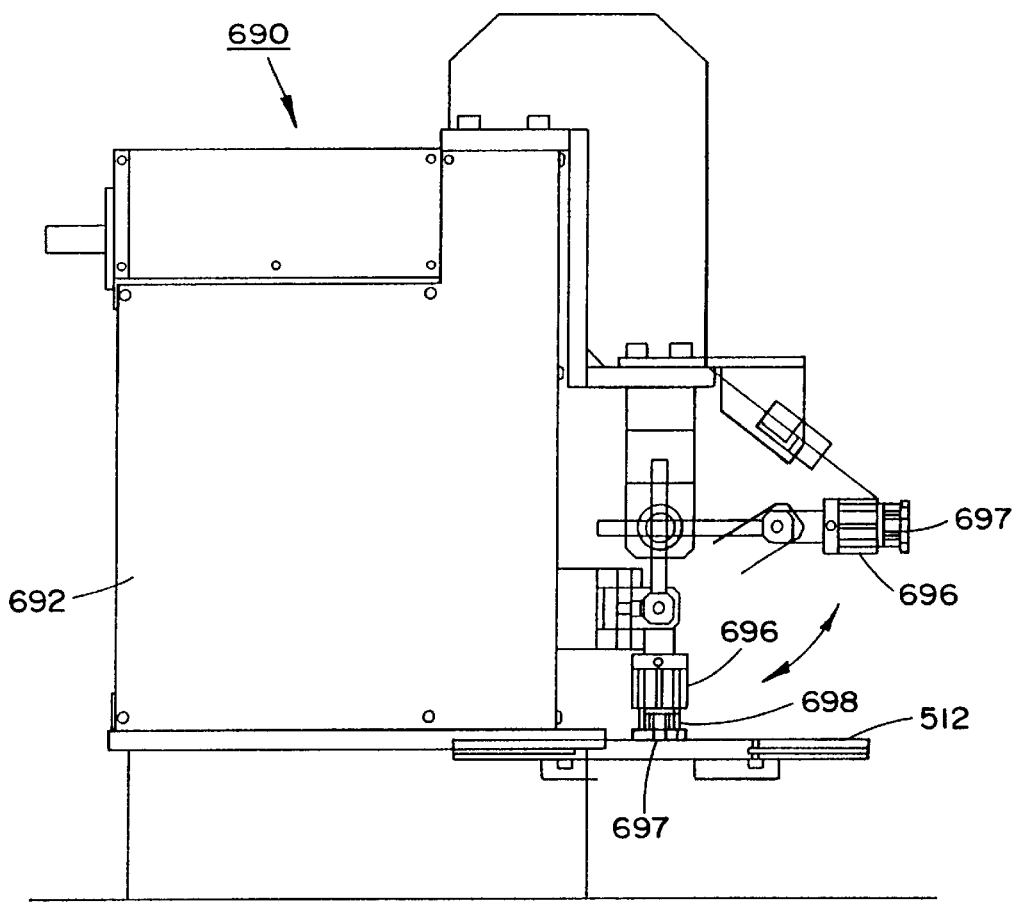
FIG. 48 illustrates the robotic pivot arm shown in two operative positions at the cover load station.

Referring to FIG. 48, the pivot arm is in two operative positions, the free end 696 of the pivot arm 690 includes a surface 697 forming a suction device which is adapted to pick up a cover 43 through the intermediary of suction passages 698 communicating with a vacuum-generating source. While connected to a vacuum source, the arm 690 is pivoted downwardly to enable the pick-up of the cover 45 by the suction device 697 under the aspirating action of the vacuum, while a vacuum acting on the plate surface area 682 of plate element 680 at that location is released. This causes the cover 43 to adhere to the pivot arm suction device 697. Thereafter the pivot arm 690 is swung upwardly into the horizontal orientation shown in FIG. 48 so as to align the cover 43 with a needle and suture-containing package tray 43 located on the plate element 532 of a tool nest 530 which is in operative alignment therewith. The pivot arm 690 with the cover 43 thereon at 697 is then extended forwardly so as to cause the cover 43, to be pressed into latching engagement with the package tray 43, as shown in FIG. 46, thereby forming a complete suture package. At this time, the vacuum in the suction device 697 is released, and this completes the application of the cover 43 to the tray 45. This will then enable the robotic pivot arm 690 to be retracted and pivoted downwardly so as to be able to repeat the operative sequence described above with regard to a successive cover which has been rotated into position therebeneath on the plate element 680, while the tool nest 530 with the completed suture package is advanced forwardly to a package unloading workstation. A successive tool nest 530 having a package tray 45 with a surgical needle and wound suture arranged therein is concurrently indexed into position opposite the robotic pivot arm 690 by the indexed advance of turntable 512 so as to enable the foregoing cycle of applying a cover 43 onto a tray 45 to be repeated.

Figure 7N:
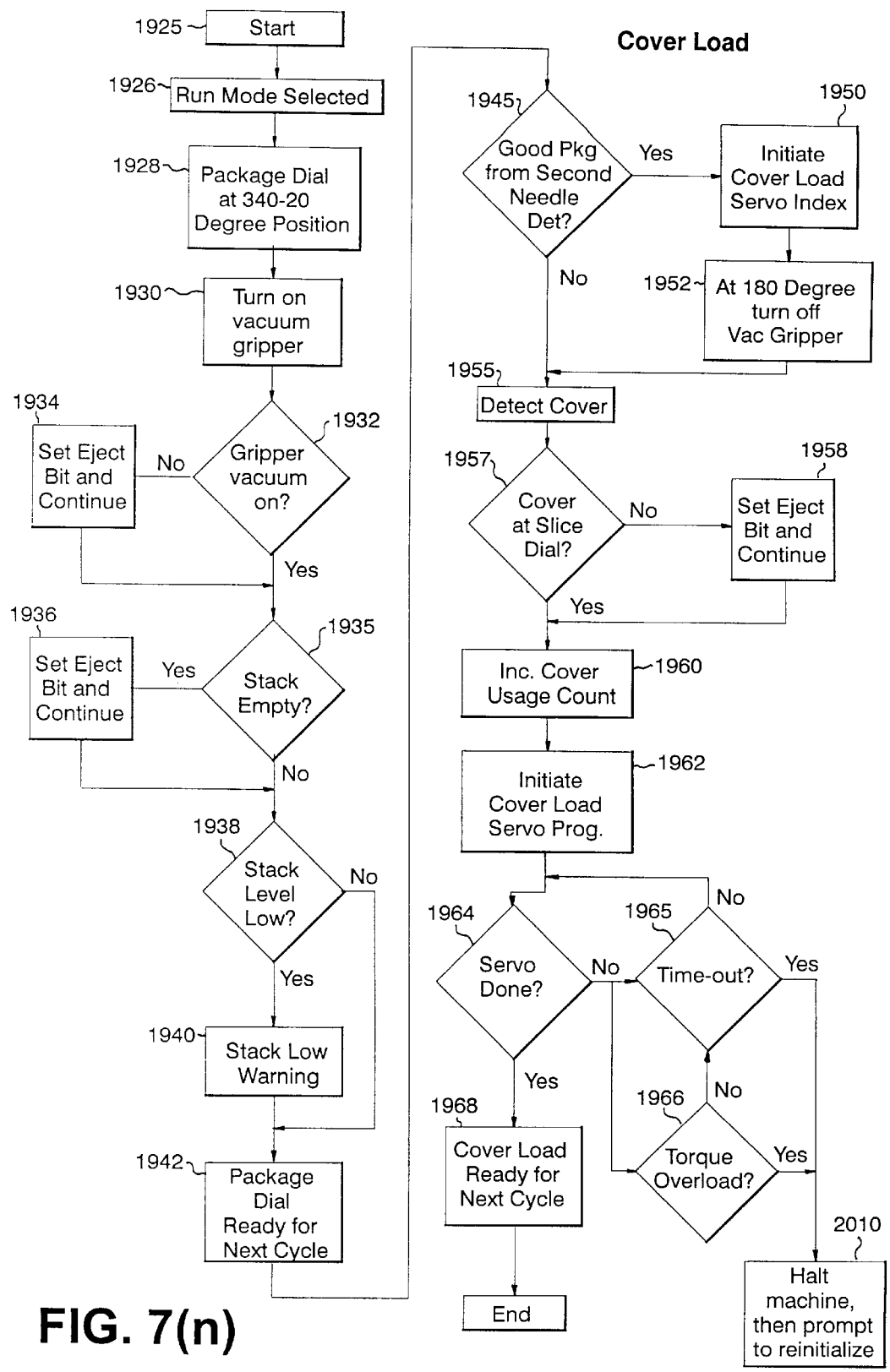

The control process 1925 (FIG. 3) for the cover load station 675 is exemplified in FIG. 7(n) which illustrates a first step 1926 indicating that the run mode has been selected. A second step, indicated as step 1928, awaits the receipt of a package dial position signal from the package dial index servo controller 116f to ensure that the package dial has reached a predetermined angular orientation. Then, at step 1930, a control system signal is initiated to turn on a vacuum gripper adapted for gripping the cover at the cover load station. Once this control signal is received, the cover load gripper arm solenoid valve 803t, as shown in FIG. 50(e), is actuated for controlling the cover load arm 690 that grips each package cover 43 from the cover stack prior to loading it onto the tray. A check is then made at step 1932 to determine if the gripper vacuum is on, and if not, sets an eject bit at step 1934 and continues. Then, a check is made at step 1935 to determine whether the stack of package covers (not shown) is empty, and if so, sets an eject bit at step 1936 and continues. If the cover stack is not empty, then a determination is made at step 1938 to ensure that the stack level is not too low. If it is determined that the stack of package covers is too low, then the control system will either generate a stack low warning signal at step 1940 and continue, or proceed to step 1942 to determine whether the package dial is ready for the next cycle. If the package dial is ready, then at step 1945, a check is made as to whether the package is a good package as determined from the needle detect station 650. If the package is a good package, then at step 1950, the cover load servo index is initiated to rotate the robotic pivot arm from the cover pick area to the cover place area where the cover is extended and latched onto the tray. Immediately thereafter, the vacuum applied to the gripper is turned off, as indicated at step 1952. The controlled movement of the cover load plate is implemented by cover load servo motor 115i and servo controller 116i as shown in FIG. 5 in communication with control system I/O card 999.

Then, at step 1955, FIG. 7(n), a detect cover program is initiated to detect the presence of the cover now latched onto the package tray. Then, at step 1957, a determination is made as to whether the next cover to be loaded is at the slice dial, and, if not, an eject bit is set at step 1958 and the process continues. Then, at step 1960, the current over usage count is incremented for quality control purposes. Then, at step 1962, the cover load servo program is initiated to retract the vacuum gripper arm at its home position. The control system then performs a two-fold test: first by determining at steps 1964 and 1965 whether the cover load servo motor 115i has not completed its program within the allotted time period, i.e., has timed out, and, by determining whether there is a torque overload in the rotation operation, as indicated at step 1966. If the time-out flag is generated by the control system as a time-out error, then the machine will be halted and prompted for reinitialization as indicated at step 2010. If it is determined that there is a torque overload, then the machine will be halted and prompted for reinitialization as indicated at step 2010. Finally, at step 1968, a control signal is generated to indicate that the cover load is ready for the next cycle.

At the next workstation 700, a gripper arm is provided to remove the completed package from the tool nest, and swings downwardly so as to deposit the completed suture package into receiving bins or compartments within an elongated tray member whereby upon a certain amount of trays being deposited, the latter is indexed to align a further empty compartment with the tool nests. The tray member having the various filled compartments is then conveyed away and replaced automatically by another empty tray member.

Figure 49:
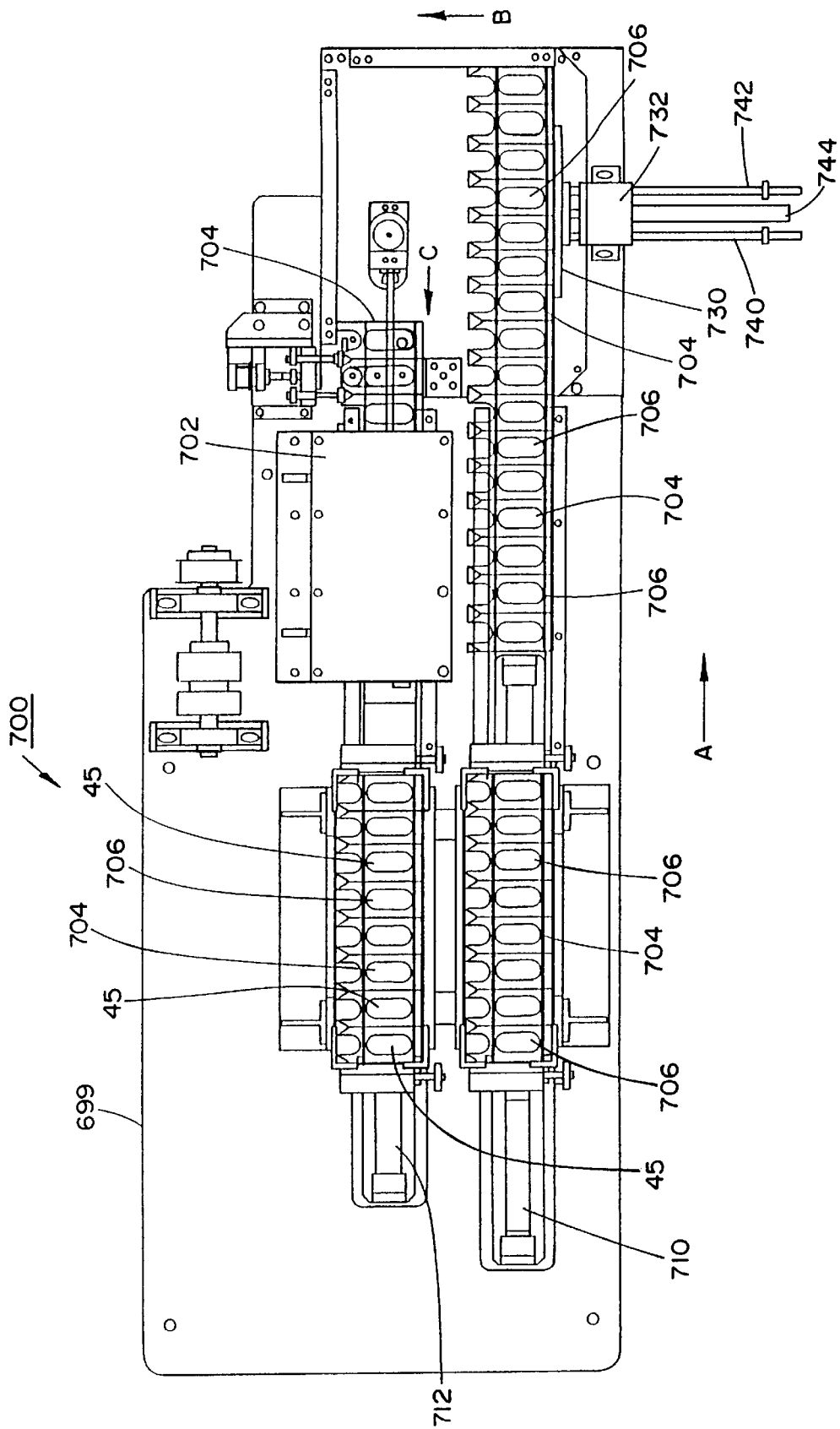
FIG. 49 illustrates a diagrammatic plan view of the suture package unloading arrangement.
Figure 50:
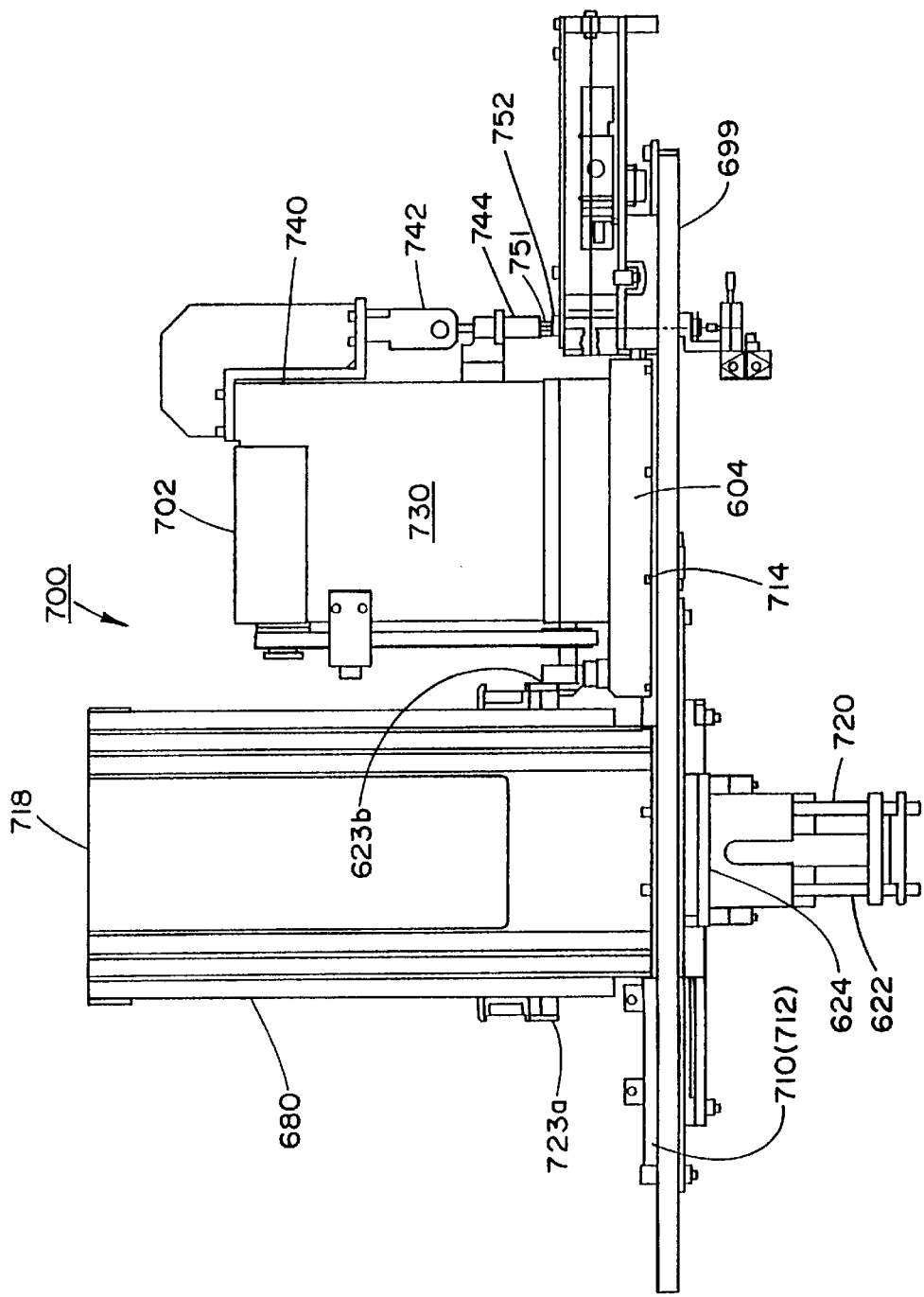
FIG. 50 illustrates a side elevational view of the suture package unloading arrangement of FIG. 49.

Reverting now more specifically to the description of the suture package unloading workstation 700, reference may be had to drawing FIGS. 49 and 50. Basically, the components of the workstation 700 are supported on a stationary horizontal platform 699. The major components, as detailed hereinbelow are a robotic arm arrangement 702; elongate parallel movable racks comprising compartmented trays 704 each possessing a plurality of compartments 706, which are adapted to each receive and stack a predetermined quantity of completed suture packages 45 which have been removed in succession by means of the robotic arm arrangement 702 from tool nests 530 on the turntable 512 of the packaging machine 25.

The compartmented trays 704 are each mounted so as to be slidable along parallel supports 710, 712 radially extending into proximity with and below the turntable 512 of the packaging machine.

As can be ascertained from the Figures, each compartmented tray 704 is movable along its longitudinal axis by means of tray-engaging elements 714 spaced along the bottom of each of the supports 710, 712. The slidable support 710 is adapted to convey empty of the compartmented trays 704 towards the turntable 512. The slidable support 712, conversely, is adapted to index compartmented trays beneath the robotic arm arrangement 702 for filling the compartments 706 with stacks of suture packages and then conveying the suture package-filled compartmented trays away from the turntable 512 for stacking in a storage 708 through the intermediary of an elevator mechanism 720.

As shown in FIG. 49, the longitudinal or axial conveyance of slidable support 710 is implemented by a drive unit, whereas the indexing motion and conveyance of slidable support 712 is carried out through an indexing and drive unit 724 which is located below the platform 699.

As shown in FIG. 50, the robotic arm arrangement 702 is located above the slidable support 712 and includes a housing 730 straddling the support 712, with the housing being arranged intermediate the compartmented tray storage 708 and the turntable 512 of the packaging machine 25, in effect along the path of axial movement or travel of the compartmented trays 704 which are being filled with suture packages 45 and transported to the storage 718.

In essence, a continuous sequence of empty compartmented trays 704 are adapted to be advanced forwardly along a path of travel towards turntable 512 (not shown) as shown by arrow A in FIG. 49 so that a forwardmost compartmented tray 704 is in position adjacent a pusher plate 730 of drive mechanism 732 for displacing the forwardmost compartmented tray 704 laterally in the direction of arrow B. When a compartmented tray 704 has its most rearward compartment 706 located in alignment with the robotic pivot arm arrangement 702, the compartment is successively supplied with a predetermined quantity of suture packages 45; i.e., such as ten (10) packages. At that point, the compartmented tray is indexed in the direction of arrow C by a distance of one compartment 706 so as to enable the following compartment to be filled with suture packages 45. This sequence is repeated until all of the compartments have been filled with suture packages, whereupon the filled compartmented tray is advanced towards the storage 718, as described hereinbelow. At that time, the forwardmost compartmented tray 704 on the slidable support 710 is laterally displaced by the pusher plate 730 which slides along support rods 740, 742 adjacent a piston unit 744 of the drive mechanism 732 so as to locate the rearwardmost compartment 706 thereof below the robotic pivot arm arrangement 702. Thereupon, the filling cycle for the compartmented tray 704 is repeated as heretofore, while a successive empty compartmented tray 704 is advanced forwardly along arrow A so as to be positioned in readiness adjacent the retracted pusher plate 740.

Reverting to the construction of the robotic pivot arm arrangement 702, the housing 730 incorporates driving mechanism (not shown) located in housing portion 740 having a depending arm 742 with a pivotable arm device 744 for conveying suture packages 45 from therewith aligned tool nests 530 (not shown) into the compartments 706 of the compartmented trays 704.

The robotic pivot arm arrangement 702 has pivot arm device 744 hinged for swinging and axial movements at a hinge point so as to be oriented downwardly, as shown in FIG. 50 for depositing suture packages 45 into the compartments of the compartmented trays 704, or extended horizontally for reciprocation. During that horizontally oriented axial reciprocatory movement, the pivot arm device is adapted to remove suture trays 45 from the plate element 538 on a therewith aligned tool nest 530. The free or distal end 751 of the pivot arm device 744 includes a gripper mechanism 752, such that, upon a suture package 45 being arranged on the tool nest 530 which is located at this workstation of the turntable 512, the arm 744 is horizontally oriented and extended towards the tool nest 530 so as to have the gripper mechanism 752 engage the suture package, and, while the vacuum retaining the suture package 45 on the tool nest 530 is concurrently released, the engaged suture package 45 is withdrawn from the tool nest 530 by the pivot arm 744.

The pivot arm 744, with the suture package 45 gripped by gripper mechanism 752, is then retracted and pivoted downwardly, as shown in FIG. 45, whereupon the gripper is deactuated to release the suture package 45 and drop it into a compartment 706 located therebeneath. The turntable 512 is concurrently indexed forwardly, as shown in FIG. 30, so as to permit a successive tool nest 530 mounting a completed suture package 45 to be positioned at the package unloading workstation, and the pivot arm 744, which has already released the previous suture package 45 is swung upwardly into its horizontal position and extended forwardly so as to contact the suture package 45 located on that tool nest 530 while the vacuum in tool nest 530 is released as heretofore. Then, as previously, the pivot arm is retracted, swung downwardly and the mechanical gripper is deactuated so as to enable the suture package 45 to drop into the compartment 706 therebelow in superposition on the previous suture package or, alternatively, if the compartment is full and the compartmented tray 704 has been indexed forwardly by one compartment in the direction B, to cause the suture package to drop into an empty compartment.

As described in greater detail in co-pending U.S. patent application No. 09/020,084, the filled compartmented trays are conveyed by slidable support 712 to position below the storage unit 708. The storage 708 consists of an open housing structure 718 having two adjacently arranged vertically-extending chutes one of which is adapted to have empty compartmented trays stacked therein, and the other receives filled compartmented trays. The housing structure itself has a vertical lifting arrangement connected therewith, which may be a pneumatic cylinder and push rods 622, 720 connected to a push plate 624 for raising the filled compartmented trays in sequence, or lowering the empty trays. In the instance of raising filled trays within the storage chute, pivotable fingers 623a,b, as shown in FIG. 50, each pivot about pivot points under the biasing action of tension springs which hold the filled compartmented trays in position after elevation by the push plate so as to enable positioning of further trays therebelow. The stacks of filled compartmented trays 704 may then be manually removed from the open side of housing structure; in effect, from one of the chutes, and empty trays 704 inserted into adjacent chute so as to be lowered onto slidable support 712.

Figure 7O:
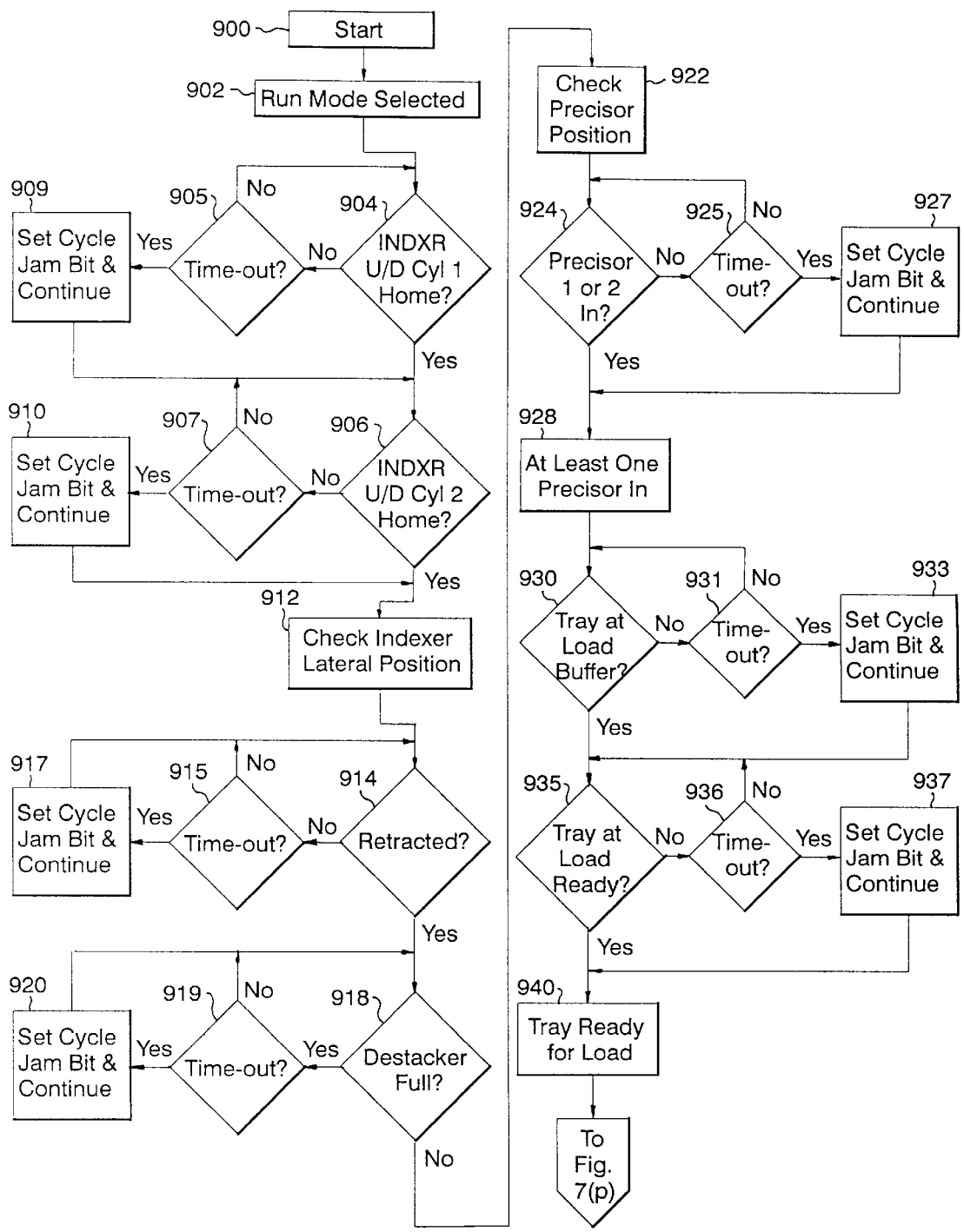

The control process 900 (FIG. 3) for the package unload apparatus is exemplified in FIG. 7(o) which illustrates a first step 902 indicating that the run mode has been selected. Then, at respective steps 904 and 906, a determination is made as to whether respective first and second tray load/unload cylinders 743, 747 as shown in FIG. 52(b) and respectively actuated by solenoid valves 803j and 803l for controlling respective tray stack loading and tray destack unloading operations in storage housing 721, are at their home position. If either one of the load/unload cylinders are not sensed at their home positions within a predetermined time period, as indicated at respective steps 905 and 907 respectively, then the cycle jam bit is set indicating a non-critical fault, at respective steps 909 and 910, and the process continues at step 912. At step 912, a check is made to determine if the tray transfer lateral thruster 730 is in its home (retracted) position. The tray transfer lateral thruster 730 is shown in FIG. 52(b) actuable by solenoid valve 803m under control of the control computer 999. As shown at steps 914 and 915, FIG. 7(o), the control system waits a predetermined amount of time for lateral transfer cylinder to retract, and will set a cycle jam bit at step 917, if a time-out condition occurs. Either way, the process resumes until full retraction is achieved. Next, at step 918, a check is made to determine if the destacker is full, i.e., the tray load destacker is full indicating that there is no more room to unload full trays. If the destacker is full, the system waits at step 919 until a signal is generated indicating that the destacker is not full, and as indicated at step 920, will set a cycle jam bit if a time-out condition occurs. Either way, the process resumes until the destacker can receive an empty tray. Continuing at step 922, FIG. 7(o), the control system checks the position of the first and second precisors, which help control the indexing movement of the tray under the package pick and place tooling area as it is being filled with completed packages. A check is thus made at step 924 to determine if signals indicating whether the precisor 1 or precisor 2 pins have been inserted, and, at step 925, the system waits until a signal is received indicating that one of the precisor pins are engaging a pocket of an empty tray. If the pins have not been inserted within the predetermined period of time, then a time out condition exists, and as indicated at step 927, a cycle jam bit is set. Either way, the process resumes until at least one precisor pin is in, as shown at step 928. Next at step 930, a determination is made as to whether the tray package load sensor has determined that a tray is at the load package buffer, to be loaded with good packages. At step 931, the system waits until a signal is received indicating that the tray is at the package load buffer. If the tray is not loaded at the buffer within the predetermined period of time, then a time out condition exists, and as indicated at step 933, a cycle jam bit is set. Either way, the process resumes at step 935 to determine whether the tray is ready to receive a good package at the load package buffer. At step 936, the system waits until a signal is received indicating that the tray is ready to receive a package at the package load buffer. If the tray is not ready at the buffer within a predetermined period of time, then a time out condition exists, and as indicated at step 937, a cycle jam bit is set. Either way, the process continues to step 942, FIG. 7(p) when a tray is ready for loading of good packages as indicated at step 940, FIG. 7(o).

Figure 7P:
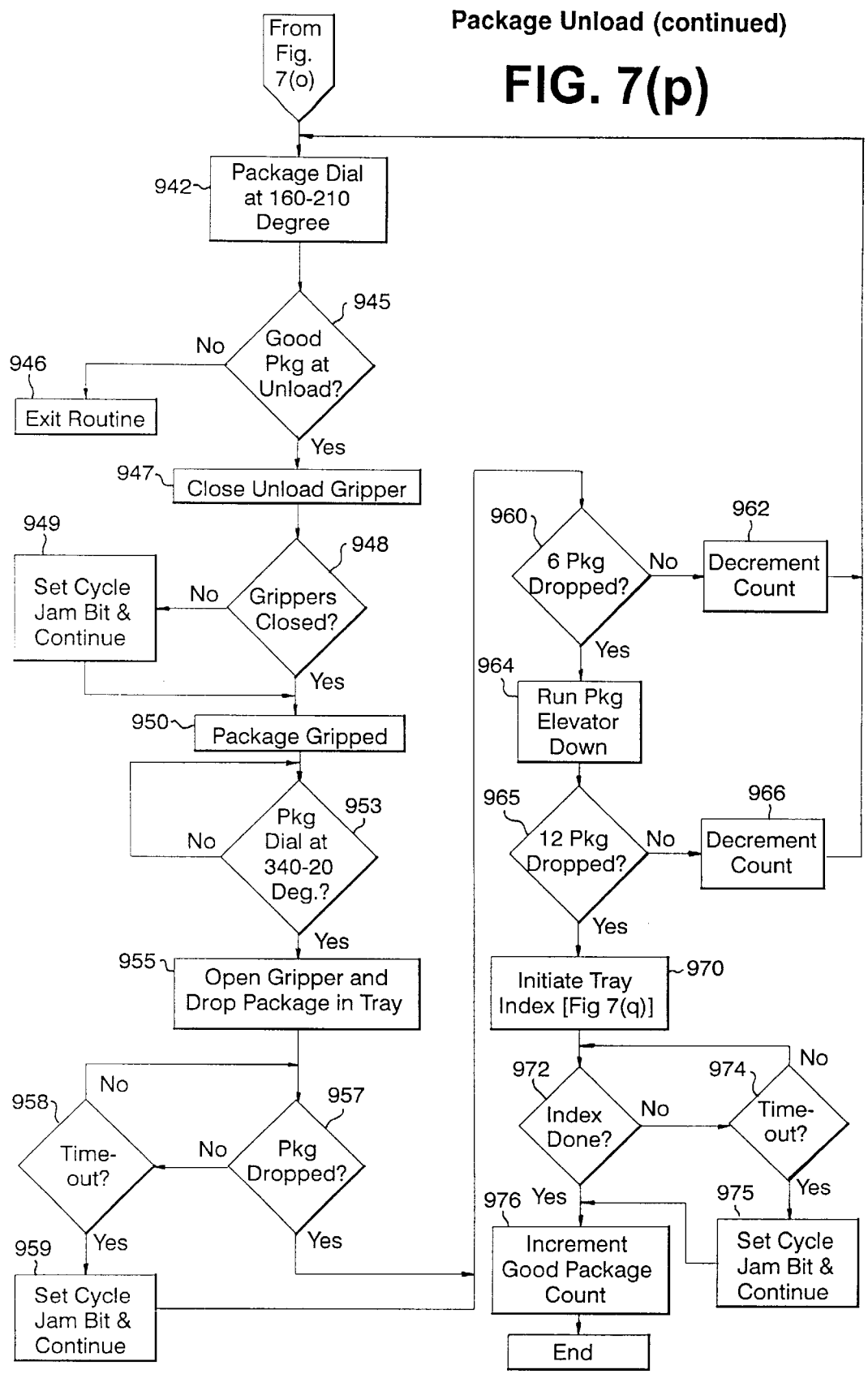
Figure 7Q:
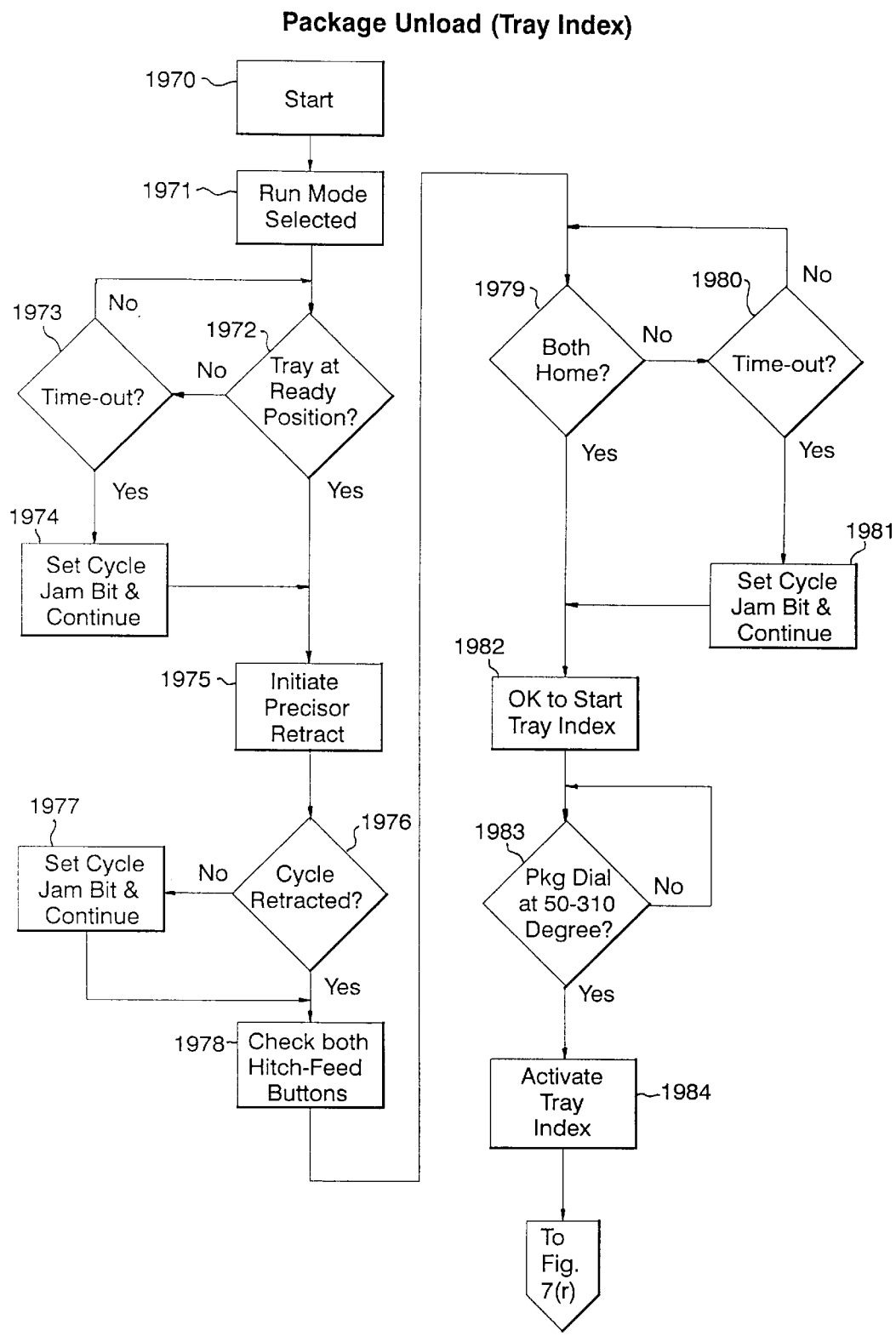
Figure 7S:
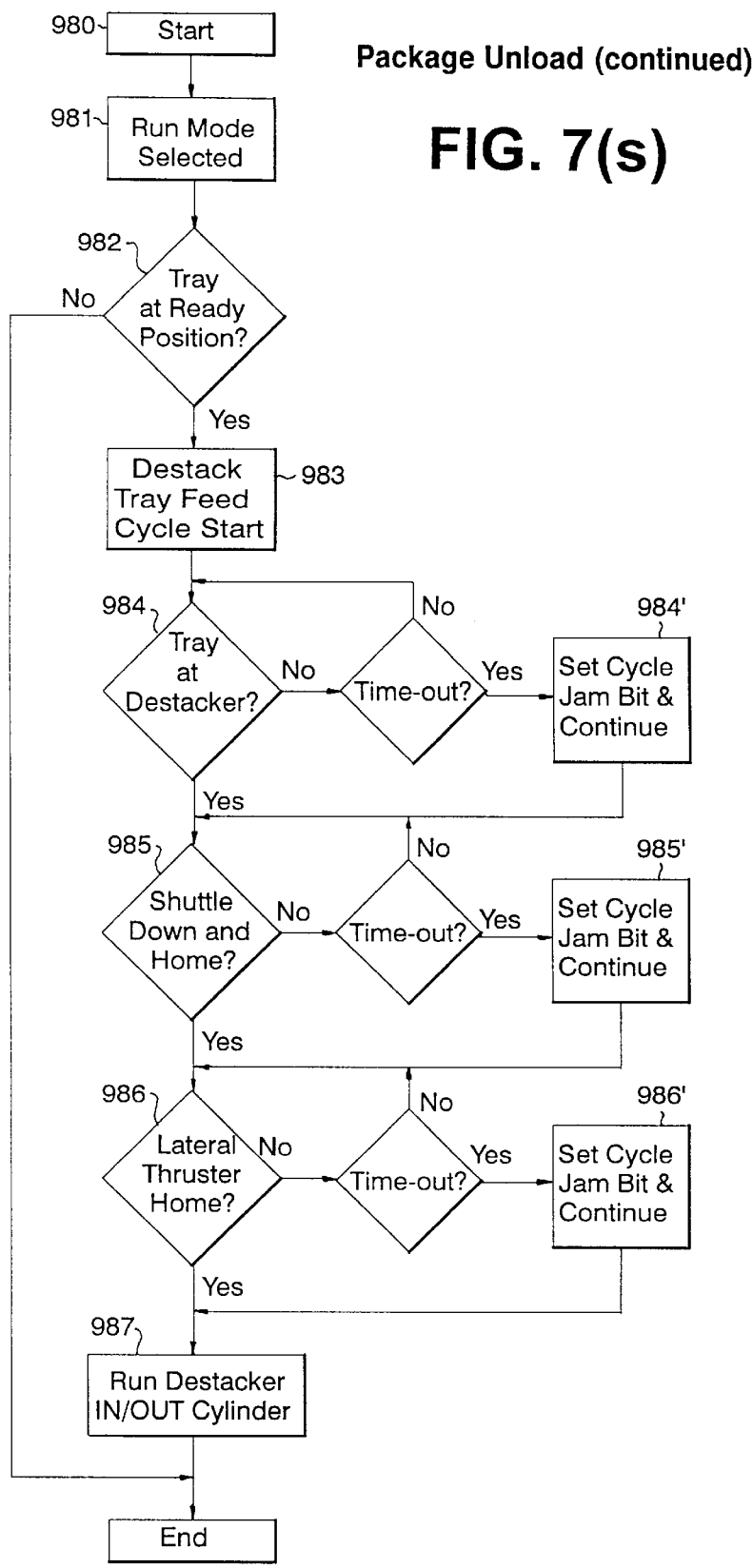
Figure 7T:
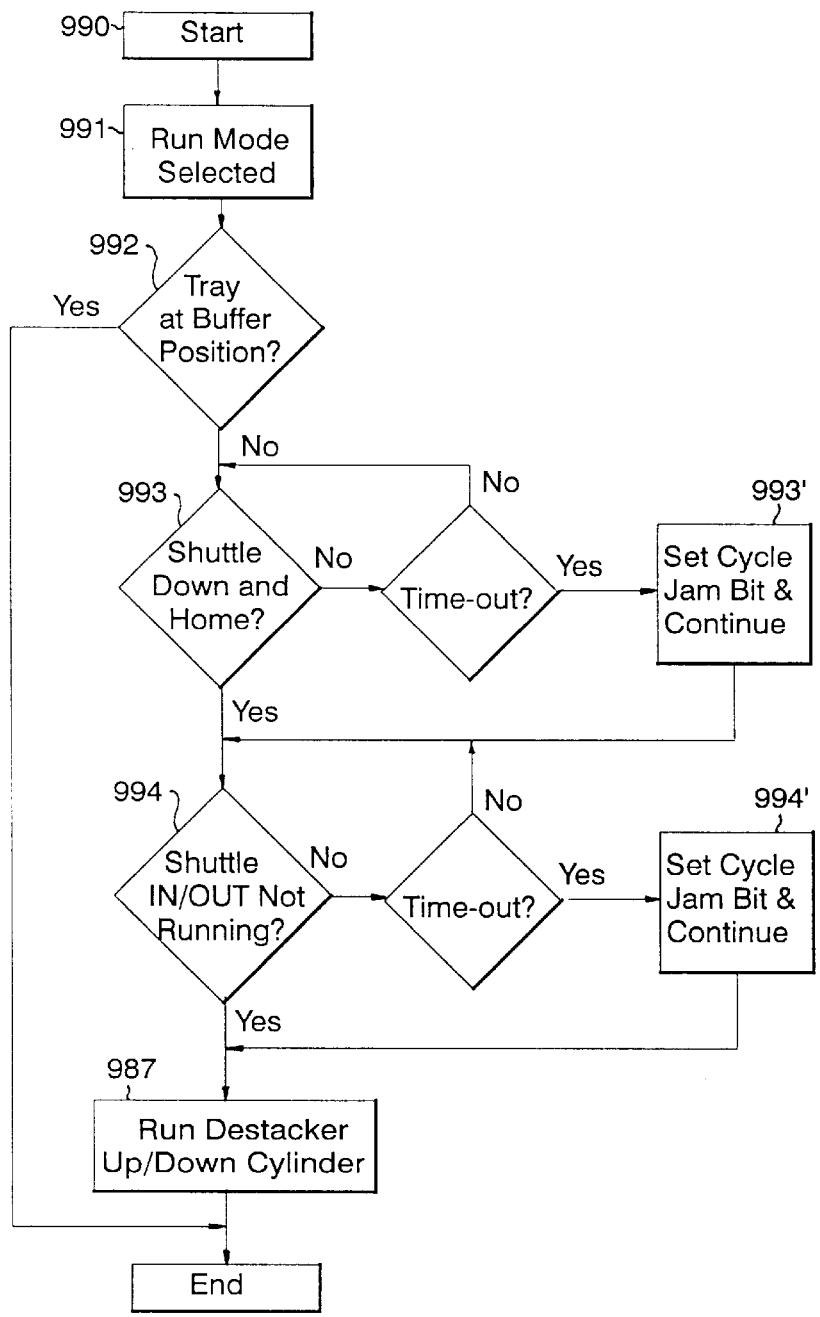

Then, as indicated at step 942, FIG. 7(p), the control system waits for a signal from the package dial servo controller 116f to indicate when the package dial has reached a certain predetermined position during package dial indexing to ensure that the package dial 512 is at an oriented position suitable for enabling robot arm 744 of pivot arm assembly 702 to suction grip the completed package tray from the tool nest. As shown in FIG. 52(e), the gripper mechanism 752 is adapted for extended and retracted movement through solenoid valve 803f under control of control system computer 999. After the proper package dial orientation has been detected, then, as indicated at step 945, a determination is made as to whether the current package at that unload station is a good package, i.e., a check is made of bits in the good/bad package register. If it is determined at step 945 that the package is no good, then an exit routine is performed at step 946 to reject the package. If the package is a good package, then at step 947 in FIG. 7(p), a control signal applied to the solenoid valve 803f (FIG. 50(e)), enables the gripper 752 to grip the completed package tray 45. At step 948, a determination is made as to whether the package gripper has closed upon the good package to be unloaded loaded from the tool nest plate 538 in the manner as described above. If the grippers do not close, as indicated at step 949, then the cycle jam bit is set indicating a non-critical fault error and the process continues at step 950 where a control signal is generated to indicate that the package has been gripped. At step 953, the control system waits for a signal from the package dial. servo 116f to indicate when the package dial has reached a certain predetermined position during package dial indexing to enable the robot gripper arm and gripper element 752 to deactuate its grip hold of the completed package and drop the package in the registered tray, as indicated at step 955. Then, at step 957, a decision is made as to whether the package has dropped within an allotted time period, and will wait until the package is dropped, or issue a time out signal at step 958 indicating non-critical time-out error. If the time-out error condition exists, then a cycle jam bit is set at step 959, and the process continues at step 960.

Once it is determined that the package has been dropped into the tray, a decision is made at step 960 to determine whether the good package dropped is the sixth consecutive packet to be dropped in a single tray pocket. If the just-dropped package is not the sixth package, then a counter (not shown) is decremented to account for the just-dropped package at step 962 and the process returns to step 942 to await indexing of the next completed package on a tool nest for unloading at station 700. If the package is the sixth package dropped, then a control signal is generated to run the package elevator down as indicated at step 964, which controls the platform vertically movable within the pocket tray for receiving the dropped packages. As mentioned herein, the package elevator platform 749 is actuated by solenoid valve 803$q$ for movement up through the bottom of the tray compartment providing a platform for the good packages to rest on as they are being deposited by the robotic arm assembly. Then, at step 965, a decision is made as to whether the just-dropped package is the 12th package to be dropped indicating a filled tray pocket. If the just-dropped pocket is not the twelfth, then a counter (not shown) is decremented to account for the just-dropped package at step 966 and the process returns to step 942 to await the next good package to be unloaded from the next tool nest indexed at package unload station 700. If the package is the twelfth package dropped, then a control signal is generated to initiate the tray pocket indexing at step 970 as discussed below with respect to FIG. 7($q$). Next, at step 972, a decision is made as to whether tray indexing is achieved without a time out error, as detected at step 974. Particularly, if a time out condition exists at step 974, then the cycle jam bit will be set indicating non-critical fault, as indicated at step 976, and the process will continue at step 975 to increment the good package count, and the package unload control process ends.

As mentioned above with respect to step 970, the tray index is initiated when it is necessary to provide a new pocket or new tray, for the tray unload process. FIG. 7($q$) illustrates a control system flow diagram 1970, for controlling the tray indexing processes. As shown in FIG. 7($q$), assuming run mode operation has been selected, as indicated at step 1971, the first step is to verify that the tray is in the ready position as described above with respect to step 940, FIG. 7($o$) by waiting for the tray ready control signal, as indicated at steps 1972 and 1973. If the tray ready control signal is not received within a predetermined time period, then the cycle jam bit is set at step 1974, and the process continues at step 1975. Once the tray ready position is verified, then at step 1975, the precisor cylinder 751 is retracted by actuating solenoid valve 803$g$, as shown in FIG. 52($e$). At step 1976, FIG. 7($q$), a check is made to determine that the cylinder has retracted, and at step 1977, will set the cycle jam bit indicating non-critical fault if the cylinder controlling the precisor is not retracted. If the cylinder is retracted, then the process proceeds to steps 1978 and 1979 to determine if both hitch feed buttons located at the ends of the end of the indexing cylinder, are home, i.e., at their disengaged position prior to indexing. If both corresponding hitch feed button home signals are received without the occurrence of a time out condition at step 1980, then a signal is generated at step 1982 to initiate the tray indexing. If, at step 1980, a time out condition occurs, then a cycle jam bit is set at step 1981 and the process continues at step 1982. Once a signal is received that it is OK to start the tray index, then, at step 1983, the control system waits for a signal from the package dial servo 116$f$ to indicate when the package dial has reached a certain predetermined position during package dial indexing to enable activation of the tray index, as indicated at step 1984. The process for activating the tray index begins at step 1985, FIG. 7($r$), which comprises a first step of running both hitch feed buttons up, i.e., to their engaging positions. Once both hitch feed buttons are run up, as indicated at step 1986, either with or without a time out condition error, in which case the cycle jam bit signal is set at step 1986', the process proceeds to step 1987 to initiate forward indexing of the tray load index advance cylinder 724 as controlled by solenoid valve 803$n$, shown in FIG. 50($b$), to initiate movement for one pocket distance as an empty pocket in the loading position. Referring back to FIG. 7($r$), at step 1988, a determination is made as to when the cylinder is done advancing which can be done either with or without a time out error condition in which case the cycle jam bit is set at step 1988'. Once the cylinder is done indexing forward, both hitch feed buttons are run down to their home positions as indicated at step 1989. Once both hitch feed buttons are run down, as indicated at step 1990, either with or without a time out condition error, in which case the cycle jam bit signal is set at step 1990', the process proceeds to step 1991 to initiate reverse indexing of the cylinder as controlled by solenoid valve 803$n$, shown in FIG. 50($b$). At step 1992, FIG. 7($r$), a determination is made as to when the cylinder is done reversing which can be done either with or without a time out error condition in which case the cycle jam bit is set at step 1992'. Once with cylinder is done reverse indexing, a determination is made at step 1994 indicating that the tray index is done. If the tray index is not achieved within a predetermined amount of time for the current package dial index cycle, then a time-out error occurs at step 1995 and the process is halted for re-initialization, as indicated at step 2010. Otherwise, a control signal indicating that the tray index is complete is initiated at step 1997, and the control process ends.

The control process 980 for controlling the package destack shuttle In/Out operation is now described with respect to FIG. 7($s$). Assuming run mode operation has been selected, as indicated at step 981 the first step is to verify that the tray is in the ready position as described above with respect to step 940, FIG. 7($o$) by waiting for the receipt of the tray ready control signal. If the tray is not in a tray ready position, the process will end. If the tray is in a tray ready position, then, as indicated at steps 983, the destack tray feed cycle is begun to start the empty tray destacking process. Particularly, at step 984, a determination is made as to whether the tray is at the destacker location, as sensed by a proximity sensor (not shown). This determination may be made either with or without a time out error condition, the latter case prompting the setting of the cycle jam bit at step 984'. Regardless of whether a time out constraint is violated, the process continues at step 985 to ascertain whether the shuttle destacker 745 is in a down and home position being readied to move a new empty tray along the first conveyor to the lateral transfer position. This determination may be made either with or without a non-critical time out error condition, the latter case prompting the setting of the cycle jam bit at step 985'. Either way the process continues at step 986 to ascertain whether the lateral thruster is in a home position, e.g., when a new empty tray has been transferred to the second conveyor for receiving completed packages from the robot gripper arm. This determination may be made either with or without a non-critical time out error condition, the latter case prompting the setting of the cycle jam bit at step 986'. Finally, at step 987, a control signal is generated to solenoid valve 803$l$, as shown in FIG. 50($b$), for controlling the actuation of the Destacker unload cylinder 747 to move the next empty tray into the lateral transfer position, with one empty tray waiting in queue to be moved into the ready position.

The control process 990 for controlling the package unload destack shuttle Up/Down operation is now described with respect to FIG. 7($t$). Assuming run mode operation has been selected, as indicated at step 991, the first step is to verify that the tray is in the buffer position, as shown at step 992 receiving empty packages. If the tray is at the buffer position, then this indicates that the package unload process will be continuing for at least the next cycle and the process will end. If the tray is not at the buffer position, then, as indicated at step 993, a determination is made as to whether the shuttle 745 is in a down and home position being readied to move an empty tray along the first conveyor to the queue position. This determination may be made either with or without a non-critical time out error condition, the latter case prompting the setting of the cycle jam bit at step 993'. Either way the process continues at step 994 to ascertain whether the destacker In/Out shuttle is not running. This determination may be made either with or without a non-critical time out error condition, the latter case prompting the setting of the cycle jam bit at step 994'. Finally, at step 995, a control signal is generated to solenoid valve 803*k*, as shown in FIG. 50(*b*), for controlling the actuation of the Destacker Up/Down cylinder 747 to remove the empty tray from the stack of empty trays from the storage chute.

In the event that reject bits in the package shift registers have been set indicating that the suture package 45 located on a tool nest 530 is either incomplete or defective, e.g., having a cover lacking or misplaced, and the resultant package has accordingly not been removed at the preceding package unloading work station, then the defective suture package 45 is advanced on its tool nest 530 by the turntable 512 to a subsequent reject workstation 750, at which a reject arrangement 752 is adapted to remove the defective or incomplete suture package 45 from the packaging machine 25.

Figure 51:
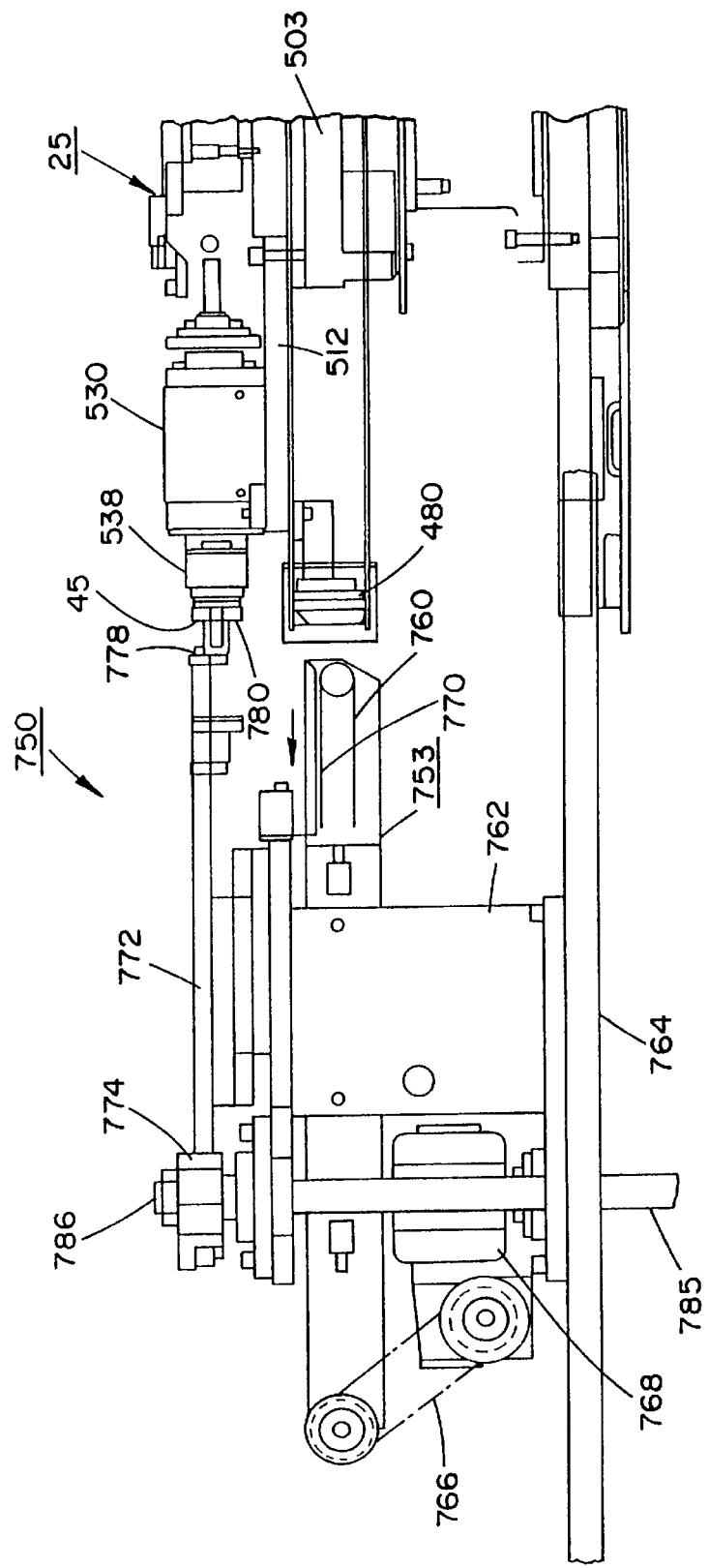
FIG. 51 illustrates a side elevational view of the package reject station.

As shown in FIG. 51, the arrangement 753 for removing defective suture packages 45 comprises a conveyor belt 760 supported on a stationary frame structure 762 having a base plate 764. The conveyor belt 760 is connected to a belt drive 766 operated by a driving motor 768 which imparts a continuous motion to the conveyor belt so that the upper run 770 thereof travels in the direction of the arrow; in effect, radially outwardly away from turntable 512 and tool nest 530 mounting a rejected suture package 45 on plate element 538.

Located above the conveyor belt 760 is an axially slidable member 772 which is reciprocable towards and away from the suture package 45 responsive to the pivoting action of a pivot arm 774 connected thereto at pivot point. A vertical shaft 785 has the upper end 786 connected to the pivot arm 772 and at its lower end 785 is connected to a drive unit (not shown) for imparting oscillatory rotational movement thereto.

At the forward end 778 of slidable member 772, there is connected a head portion 780 having gripper elements adapted to engage the suture package 45 in the forwardly advance position of slidable member 772. Upon engaging the suture package 45, the vacuum in the tool nest 530 is released, thereby enabling the gripper elements to grasp the package 45, the slidable member 772 to retract by means of the pivoting of shaft 785 to swing pivot arm 774 backwards. The elements on head portion 780 then release the suture package 45 so that the latter drops onto the upper run 770 of the conveyor belt 760 so as to be conveyed towards a waste disposal location. The foregoing operation is continually repeated for each tool nest 530 coming into alignment with workstation 750, even if no suture package 45 is located at that workstation, so as to ensure that any suture package will be prevented from passing this workstation, and thereby the machine will always be ready to continue in the complete packaging sequence or cycle for producing suture packages.

The final work station 775 (FIG. 1) on the packaging machine retains a sensor 776 which checks for the presence of a package that may not have been removed at prior stations 700 and 750. This is a further safegard built into the packaging machine to ensure that the tool nest at the first station 400 is empty and ready to accept an empty package tray.

During the operation of the machine, and as described herein, several non-critical faults may occur which can necessitate the intervention of an operator for possible corrective action, e.g., when a time-out error occurs and the process being performed could not be completed within the allotted time. This has herein been referred to as a cycle jam. As illustrated in FIG. 53(*a*), when a cycle jam procedure 2000 is initiated, the current machine cycle is stopped as indicated at step 2002. At step 2004, the DMACS software is employed for displaying the nature of the particular error or fault condition that has occurred on the operator display 992 and instructing an operator to take appropriate remedial action, if possible. Thus, at step 2003, an operator may manually investigate and correct the particular problem or error. When the operator is through correcting the problem, the control system will initiate a command to clear the error as shown at step 2004 in FIG. 53(*a*). At step 2005, the control system will make a determination of whether the particular error has cleared, or, whether the particular problem has been solved. If not, the display error message is again initiated at step 2002. If the problem was solved, a determination is made at step 2006 as to whether the doors of the machine housing (not shown) are shut. If not, an appropriate display error message is again initiated at step 2002. If the doors of the machine housing have been shut and the error solved, then the operator will be prompted to continue the present machine cycle by enabling start button (not shown) as shown at step 2007 in FIG. 53(*a*).

The initialization or reinitialization routine, shown in FIGS. 53(*b*) to 53(*i*) describe the steps necessary to ensure proper running of the automatic needle swaging and automatic packaging machines either before a first run is made, or when reinitialization is called for during run-time after a run time error is displayed.

The procedure is entered into at step 2010 and begins by displaying various menu displays as indicated at steps 2012–2014 prompting the operator to enter into initialization routines. As part of the display shown at step 2014 of FIG. 53(*c*), the operator is first prompted to thread the suture, i.e., wind the suture through the tensioner and around the plurality of pulleys located at the swaging tower as indicated at step 2016. Next, at step 2018, a determination is made as to whether all error flags that might have been set, are cleared. If all the errors are cleared, a start initialization message is displayed at step 2022 of FIG. 53(*c*) that prompts the operator to enter the appropriate key (step 2019) to begin system initialization. Else, the current error message is displayed at step 2019 and the operator is prompted to thread the suture again at step 2014, i.e., wind the suture through the tensioner and around the plurality of pulleys located at the swaging tower as indicated at steps 2014 and 2016.

At step 2024 in FIG. 53(*d*), both left and right grippers are then returned to their home positions. At steps 2025*a,b*, a verification is made to ensure that each tower #1 servo and tower #2 servos controlling gripper movement are placed in their initial (home) positions without the occurrence of a time out error which will prompt the display error message at step 2019 FIG. 53(*c*). The next step is to move the top or lead gripper to its suture insertion position along the suture tower as indicated at step 2026 in FIG. 53(*d*). At steps 2027*a,b*, a verification is made to ensure that the top gripper is positioned within the allotted time as programmed. If not, an appropriate message is displayed at step 2019 of FIG. 53(*c*). The gripper is then moved to its clamping position at step 2028 in FIG. 53(*d*) and a verification is made at step 2029*a,b*, to ensure that the gripper is correctly positioned at the clamp position within the allotted time as programmed. If not, an appropriate message is displayed at step 2019 of FIG. 49(*a*). At step 2030 in FIG. 53(*e*), the bottom gripper is closed so as to engage the indefinite length suture strand just below the position of the cutter assembly. Next, the cutter assembly is reciprocated from a retracted position to the cutting position as shown as step 2032 and back to the retracted position as shown as step 2035 in FIG. 53(*e*). The extended movement of the cutter assembly is verified at steps 2034*a,b* to ensure that it is accomplished within the allotted time as programmed. Likewise, the retracted movement is verified at steps 2036*a,b*, to ensure that it is accomplished within the allotted time as programmed.

At steps 2038, 2038*a*, and 2038*b* in FIG. 53(*e*), the check is again made to place the top or lead gripper at its home position along the tower. The bottom or second gripper, now engaging the indefinite length strand, is then positioned at the clamping position along the servo tower at step 2040 in FIG. 53(*f*). The positioning of the second gripper is verified at steps 2041*a,b* to ensure that it is accomplished within the allotted time as programmed.

Next, as indicated at step 2042 of FIG. 53(*f*), a determination is made as to whether the swage adjust servo is in its home position. If not, the appropriate error message is displayed by returning to step 2019. Then, at step 2043, the swage die servo, specifically for controlling the positioning of the fixed swage die 301, is enabled to its normal, unbiased position and a verification is made at steps 2045*a,b*, to ensure that it is initialized within the allotted time.

The initialization routine 2010 also includes a pull-test check as described herein as indicated at step 2046. Then, a determination is made at step 2047 as to whether the pull-test was good. If the pull test was not good, then an error message will be displayed by returning to step 2019, FIG. 53(*c*). Else, the process continues at step 2050 by determining whether a new batch of needles is being loaded, necessitating the employment of the package dial table lift routine 2200 for indexing the movable frame portion of the package assembly machine to ensure that the horizontal axis of the packaging dial turret 512 is at the proper height for receiving the new sized needle at the needle load to package station 450.

FIG. 53(*b*) illustrates the flow control process 2200 for the package dial table lift routine. Specifically, as shown in FIG. 53(*b*), it is assumed that a new batch of needles to be swaged and packaged are to be run that are of a different size than the previous run, as indicated at step 2205. Then, as indicated at step 2210, the control system will obtain the table parameters for controlling the package dial table height adjustment in accordance with the size of the needles in the new batch to be swaged. At steps 2212, an audible warning is sounded to alert any operator that the package dial table is to be adjusted, and, at step 2215, various high-speed counters are initialized. At step 2220, the package dial table is brought to its home position by means of a jack screw operating under control of the package dial table servo motor 115*j* and servo controller 116*j* shown in FIG. 5 in communication with control system I/O card 999. The high-speed counters are used to ensure very small increments of advance, preferably ranging on the order of tens of thousandths of an inch, as exemplified by the table height adjustment distances shown in the FIGS. 42*a*–42*f*. Only this way can the accuracy of the package dial height adjustment of such small magnitude be assured. At step 2225 and 2226, a decision is made as to whether the package dial table servo has reached its home position within the time period allotted. The machine will be halted and prompted for reinitialization if the package dial table servo does not reach its home position within the time allotted. Based upon the table parameters read at step 2210, a table position is calculated at step 2227 and converted to commands for controlling the servo motor 115*j* to initiate positioning of the package dial table at the adjusted calculated height based on the needle size, as shown at step 2230. A determination is made at step 2231 and 2232 to ensure that the table lift index occurs without the generation of a time-out error which would prompt the halting of the machine and a further reinitialization.

Referring back to FIG. 53(*g*), the next step 2252 is to activate the swage dial servomotor 115*b* to index the swage dial at its home position, i.e., with a first multi-axis gripper facing the needle sorting station 100. A verification is made at steps 2253,2254 to ensure that the swage dial servomotor is indexed to its home position before the generation of a system time-out error which would prompt reinitialization by returning to step 2019, FIG. 53(*c*). Next, as indicated at step 2255, the Camco servo motor controlling the movement of the precision conveyor boats at the needle feed station 100 is initialized to its home position. A verification is made at steps 2257,2258 to ensure that the Camco servomotor is indexed to its home position before the generation of a system time-out error which would prompt reinitialization by returning to step 2019, FIG. 53(*a*). Continuing, at step 2260 in FIG. 53(*h*), the Winder IN/OUT servo motor 115*k* is activated to index the Winder assembly to its home position. A verification is made at steps 2263,2264 to ensure that the Winder IN/OUT servo motor 115*k* is indexed to its home position before the generation of a system time-out error which would prompt reinitialization by returning to step 2019, FIG. 53(*c*). Then, at step 2270 in FIG. 53(*h*), the package load servomotor is activated to index the package load servo to its home position. A verification is made at steps 2273,2274 to ensure that the package load servo is indexed to its home position before the generation of a system time-out error which would prompt reinitialization by returning to step 2019, FIG. 53(*c*). Then, at step 2280 in FIG. 53(*h*), a check is made to determine if all the package load cylinders are at their home positions, and a verification is made at step 2283 to ensure that the package load assembly is home before the generation of a system time-out error which would prompt reinitialization by returning to step 2019, FIG. 53(*c*). Then, at step 2285, a check is made to determine if the 16.5° turn assembly cylinders are at their home positions, and a verification is made at step 2287 to ensure that the 16.5° turn assembly is home before the generation of a system time-out error which would prompt reinitialization by returning to step 2019, FIG. 53(*c*). Then, at step 2288, a check is made to determine if the 180° turn assembly cylinders are at their home positions, and a verification is made at step 2289 to ensure that the 180° turn assembly is home before the generation of a system time-out error which would prompt reinitialization by returning to step 2019, FIG. 53(*c*). Continuing, at step 2290 in FIG. 53(*h*), the Winder servo motor 115*g* is activated to index the Winder assembly to its home position. A verification is made at steps 2293,2294 to ensure that the Winder servo motor 115*g* is indexed to its home position before the generation of a system time-out error which would prompt reinitialization by returning to step 2019, FIG. 53(*c*). Then, at step 2295 in FIG. 53(*i*), the package unload assembly mechanisms are indexed to their home positions, and a verification is made at steps 2296,2297 to ensure that the package unload assembly mechanisms are indexed to their home positions before the generation of a system time-out error which would prompt reinitialization by returning to step 2019, FIG. 53(*c*). Next, a verification is made at steps 2302,2304 to ensure that the package tray load assembly mechanisms are indexed to their home positions before the generation of a system time-out error which would prompt reinitialization by returning to step 2019, FIG. 53(*c*).

Then, at step 2305, a command is initiated to place a tray at the load position, and a verification is made at steps 2306,2307 to ensure that the tray has been made available before the generation of a system time-out error which would prompt reinitialization by returning to step 2019, FIG. 53(*c*).

Next, at step 2310 of FIG. 53(*i*), the package dial servomotor 115*f* is activated to its home position. A verification is made at steps 2315,2316 to ensure that the package dial servomotor is indexed to its home position without the generation of a system time-out error which would prompt reinitialization by returning to step 2019, FIG. 53(*c*). Additionally, as indicated at step 2317, a verification is made at step 2317 to ensure that an overload condition does not occur during indexing of the package dial.

Finally, at step 2319, if all the above initialization routines are verified, the operator is prompted with a new menu, e.g., for setting up the swage die, and, at step 2320, the operator is presented with a message indicating that the system is ready to run.

While the invention has been particularly shown and described with respect to the preferred embodiments thereof, it will be understood by those skilled in the art that the foregoing and other changes in form and details may be made therein without departing from the spirit and scope of the invention, which should be limited only by the scope of the appended claims.

What is claimed:

1. A method for automatically forming armed surgical needles and for automatically packaging the same in a packaging tray, said automatic forming and packaging operations taking place in a needle-suture assembly and packaging machine operating under control of a control computer, each said armed surgical needle comprising a surgical needle having a suture receiving opening formed in a barrel end of said needle for attachment of a definite length suture material thereto at said needle-suture assembly machine, said method comprising the steps of:

(a) singulating a plurality of needles and depositing them on an indexing conveyor in random un-oriented positions;

(b) determining an acceptable needle location for picking up a needle, said acceptable needle location including a barrel end of said needle;

(c) enabling a robot gripper means to sequentially pick up said needles at said barrel end and place a said picked needle in a precision conveyor device for automatic sequential conveyance to a first station, said needle being conveyed in an oriented position;

(d) utilizing a first indexing device for sequentially indexing said needle in said oriented position from said first station to a second station to form said armed needle, said first indexing device being elevated in height for movement along a first horizontal axis;

(e) at said second station, automatically inserting a free end of an indefinite length suture strand into said suture receiving opening of said needle, swaging the needle about said free end of said suture, and cutting said indefinite length suture strand to a predetermined definite length to form said armed needle;

(f) indexing said first indexing device to a subsequent station and sequentially inserting a single formed armed needle from said second station to a respective single packaging tray at said subsequent station; and, (g) prior to inserting said armed needle in said packaging tray, the step of utilizing a second indexing device for sequentially indexing a said single packaging tray at said subsequent station for receiving a respective single armed needle, an elevation of said second indexing device being adjusted relative to the first horizontal axis so as to accommodate the transferring of differently sized surgical needles into said tray without substantially modifying any components of the machine.

2. The method as claimed in claim 1, further including the step of enabling said control computer to provide needle size and suture length parameters to said automatic needle-suture assembly and packaging machine for automatically height adjusting said second indexing device in accordance with the needle size parameters.

3. The method as claimed in claim 2, further including the step of determining an orientation of said singulated needle deposited upon said indexing means.

4. The method as claimed in claim 2, wherein the step e) of automatically inserting a free end of an indefinite length suture strand into said suture receiving opening at said second station further comprises the steps of:

feeding a flexible indefinite length suture strand to a drawing axis for drawing thereof;

enabling a first reciprocating suture drawing means to grip said indefinite length suture strand and draw said indefinite length strand along said drawing axis for insertion of a suture tip within said suture-receiving opening of said needle;

enabling a second reciprocating suture drawing means to grip said indefinite length suture material at a predetermined position along said drawing axis and located below a cutting position, said second suture drawing means gripping said indefinite length suture after said first gripping means inserts said suture tip into said needle; and cutting said indefinite length suture with a cutting device along said drawing axis at said cutting position in accordance with the suture length parameters provided.

5. The method as claimed in claim 4, wherein said first and second suture drawing means further includes retractable gripping elements adapted for movement in a first engaged position gripping said suture strand, and a second retracted position, said control computer controlling simultaneous reciprocation of said first and second suture drawing means wherein said first suture drawing means traverses the drawing axis to said suture insertion position with said gripping elements in said suture engaged position, while said second suture drawing means simultaneously traverses said drawing axis with the gripping elements in said retracted position to below said cutting position.

6. The method as claimed in claim 4, wherein said step (e) of swaging said indefinite length suture to said suture receiving opening comprises the steps of indexing said extendable gripper means to position said suture receiving end of said surgical needle at a swage die opening substantially formed between adjacently positioned first and second swaging dies, said first swaging die being adjustably fixed in position and said second swaging die being movable relative to said first die.

7. The method as claimed in claim 6, further including the steps of retracting said second swage die to a position for enabling placement of said suture receiving opening of said needle substantially within said swage die opening and, extending said second swage die back into an engagement position for gripping the suture receiving end of a needle prior to suture insertion and swaging thereof.

8. The method as claimed in claim 7, further including the step of supplying air pressure to move said second swaging die toward said first swaging die to swage said needle gripped therebetween.

9. The method as claimed in claim 8, further including the step of adjusting the position of said first swaging die relative to said second swaging die to adjust the amount of swage die travel applied to said surgical needle.

10. The method as claimed in claim 9, wherein said first swaging die includes a wedge follower located at one end thereof and a wedge assembly positioned transverse to said wedge follower and adapted for transverse movement relative thereto, said adjusting step further including the step of moving said wedge assembly a predefined distance in accordance with said needle and suture size parameters to laterally move said wedge follower and said first swaging die into a fixed position prior to swaging.

11. The method as claimed in claim 1, wherein said first indexing device includes a first rotatable indexing dial having one or more extendable gripper means peripherally spaced apart for simultaneous registration at each said first, second, and subsequent stations, each gripper means adapted for engaging a said needle in an oriented position for processing at each said first, second and subsequent stations, said method further comprising the step of simultaneously extending each gripper means located on said indexing dial to each of said first, second and subsequent stations during an indexing cycle, whereby oriented needles are simultaneously transferred from said precision conveyor to a said gripper means extended at said first station, a gripper means carrying a said oriented needle is extended at said second station to form a said armed needle, and, a gripper means holding a said armed needle is extended at said subsequent station for inserting said armed needle into said packaging tray registered thereat during said single indexing cycle.

12. The method as claimed in claim 11, wherein said gripper means includes a plurality of pins for engaging said surgical needle, one of said plurality of pins capable of moving between needle engaging and needle relaxing positions, wherein said step of extending said gripper during said indexing cycle further comprising the step of moving said movable pin to said needle relaxing position to facilitate simultaneous needle transfer to said gripper at said first station, armed needle assembly at said second station, and armed needle insertion into a packaging tray at said subsequent station.

13. The method as claimed in claim 11, further comprising prior to step (f), the step of indexing said formed armed needle to a pull-test station for pull testing each needle, said pull-testing step comprising the steps of:

extending said gripper means to a support device for supporting said formed armed needle;

extending a suture pushing means for orienting said suture portion of said armed needle to a predetermined suture-gripping location;

gripping said associated suture of said armed needle with a suture gripping means, said suture gripping means including means for applying a force of predetermined value to said suture portion, said force being of a value sufficient not to break a needle-suture swage bond;

applying said force of predetermined value to said suture while being gripped;

measuring said force applied to said suture; and determining if said force is within acceptable limits; and performing step (f) if said needle-suture swage bond is not broken.

14. The method as claimed in claim 13, wherein said force causes said needle-suture bond to be broken, said method including the step of enabling a needle stripper to remove said needle from said support device.

15. The method as claimed in claim 11, wherein said second indexing means includes a second rotatable indexing dial having a plurality of tool nests peripherally spaced apart on said dial and each for supporting a said single package tray, said indexing dial adapted for indexed advancement for simultaneously registering each said tool nest at a plurality of workstations stationarily arranged proximate said second indexing dial, said method further comprising:

(a) at a first workstation, mounting an empty said tray on a support surface located on said at least one tool nest;

(b) at a second workstation, imparting a predetermined angular displacement to said tray and support surface on said at least one tool nest mounting said tray to facilitate subsequent insertion of a surgical needle into said tray;

(c) at said third workstation, positioning said gripper means engaging a said armed surgical needle in operative relationship opposite said support surface at a predetermined angular displacement relative thereto;

(d) at a said fourth workstation, imparting a predetermined rotational movement to the tray which has a surgical needle retained therein with an attached suture having a portion extending outwardly and downwardly from said tray;

(e) at a fifth workstation, imparting rapid rotational movement to said previously rotated tray so as to completely wind said depending suture portion into the confines of said tray;

(f) at a sixth workstation applying a cover to a tray containing a surgical needle and attached suture, said tray being positioned on a support surface located on said at least one tool nest; and (g) at a seventh workstation, enabling motive means for engaging said suture package located on the support surface of said at least one tool nest; a compartmented tray having a plurality of compartments being positionable at said workstation below said motive means, said motive means being actuable to disengage said suture package from said support surface and convey said suture package into a respective said compartment.

16. The method as claimed in claim 15, wherein said step of mounting an empty said tray on said support surface includes the steps of:

stacking a supply of said empty trays;

arranging a rotary plate beneath said tray stack, said rotary plate being adapted to receive an individual one of said trays from the bottom of said stack;

indexing said rotary plate forwardly at redetermined angular increments; and, engaging said tray on said rotary plate and transferring said tray to the support surface on said one tool nest.

17. The method as claimed in claim 16, wherein said rotary plate is in communication with a vacuum-generating source for imparting a vacuum to the upper surface of said rotary plate to retain said tray thereon during at least the indexing advance of said rotary plate.

18. The method as claimed in claim 17, wherein said first workstation includes pivotable arm structure having tray-engaging means for lifting said tray from said rotary plate and transferring said tray to the support surface on said at least one tool nest indexed thereat.

19. The method as claimed in claim 18, wherein said rotary plate communicates with a vacuum-generating source for imparting a vacuum thereto for retaining said tray on said plate, said vacuum being released upon said tray-engaging means contacting said tray, said tray-engaging means including mechanical gripper means for gripping said tray and transporting said tray to the support surface on said at least one tool nest.

20. The method as claimed in claim 19, wherein upon said tray-engaging means mounting said tray on the support surface of said at least one tool nest, said mechanical gripper releases its grip on said tray and a vacuum is concurrently applied to the support surface of said at least one tool nest so as to retain said tray thereon.

21. The method as claimed in claim 15, wherein said robotic arm structure comprises a cam-controlled robotic pivot arm adapted to swing between a vertical orientation to a horizontal and forward motion for transferring said tray from said rotary plate to said support surface on said at least one tool nest.

22. The method as claimed in claim 15, wherein said means for imparting said angular displacement in said imparting step comprises structure for engageable contact with said support surface.

23. The method as claimed in claim 22, wherein said structure comprises a slidable element having contact means for engaging said support surface, and pivot arm means for imparting movement to said contact means towards said support surface to impart said angular displacement thereto.

24. The method as claimed in claim 23, wherein said angular displacement of said tray and support surface on said at least one tool nest subtends an angle of about 16.5° with a horizontal axis of said tray.

25. The method as claimed in claim 15, wherein adjusting an elevation of said second indexing device includes adjusting the elevation of said second rotatable indexing dial relative to said gripper means mounted on said first indexing dial.

26. The method as claimed in claim 25, wherein said packaging machine includes servo driven lifting means being connected to said second indexing dial for adjusting the elevation thereof.

27. The method as claimed in claim 15, wherein suture clamping means are located proximate said at least one tool nest, said suture method further comprising activating said clamping means to clampingly engage a portion of a suture attached to a surgical needle retained in a tray mounted on said support surface and depending therefrom at said third workstation while transferring said armed needle to said tray, said suture clamping means including a first vacuum-generating means for imparting a tension to said depending suture portion, and second vacuum-generating means for imparting tension to the trailing end of said depending suture portion.

28. The method as claimed in claim 27, further including de-activating said suture clamping means at said third workstation of said packaging machine to release said suture portion upon said tool nest having advanced towards a subsequent fourth workstation.

29. The method as claimed in claim 28, wherein said first and second vacuum-generating means maintain tension on said depending suture portion during advance of said tool nest mounting said needle-containing tray towards a subsequent workstation.

30. The method as claimed in claim 29, wherein said second vacuum-generating means continually imparts tension to the trailing end of said depending suture portion until the latter is wound into said tray.

31. The method as claimed in claim 15, further including the step of utilizing rotation-imparting means at said fourth workstation for rotating said tray so as to assume an orientation which is 180° inverted relative to the initial orientation of said tray on said at least one tool nest.

32. The method as claimed in claim 31, wherein said rotation-imparting means comprises a winder head reciprocable towards and away from said tray on the support surface of said at least one tool nest, said winder head being engageable with said support surface in the forwardly extended position of the winder head; and drive means for imparting rotation to said winder head for rotating said tray.

33. The method as claimed in claim 32, wherein the support surface on said at least one tool nest is fastened to a rotatable shaft extending through said at least one tool nest; means normally securing said shaft against relative rotation, said means releasing said shaft for axial movement and rotation to facilitate said winder head imparting the rotational movement to said tray and support surface.

34. The method as claimed in claim 15, wherein said rapid rotation imparting means at said fifth workstation comprises a winder head structure engage able with said tray and support surface for winding the extending portion of the suture into said tray.

35. The method as claimed in claim 34, wherein said winder head structure at said second workstation comprises protruding means which are engageable with surface structure on said tray so as to facilitate winding of said depending suture portion into a peripheral channel formed in said tray.

36. The method as claimed in claim 35, wherein said winder head structure at said fifth workstation is rapidly rotated a predetermined number of times in accordance with the suture length parameters downloaded from said computer.

37. The method as claimed in claim 36, wherein the support surface on said at least one tool nest is fastened to a rotatable shaft extending through said at least one tool nest; means normally securing said shaft against relative rotation, said means releasing said shaft for axial movement and rotation to facilitate said winder head imparting the rotational movement to said tray and support surface.

38. The method as claimed in claim 15, wherein suture tensioning means imparts tension to the depending suture portion prior to and during the winding of the suture into said tray at said fourth and fifth workstations.

39. The method as claimed in claim 38, wherein said suture tensioning means comprises a plurality of vacuum nozzles.

40. The method as claimed in claim 39, wherein further vacuum tensioning means impart tension to a trailing end of said depending suture portion until said suture is completely wound into said tray.

41. The method as claimed in claim 15, wherein said step of applying a cover to said tray at said sixth workstation includes the steps of:

stacking a supply of said covers; arranging a rotary plate beneath said tray stack, said rotary plate being adapted to receive an individual one of said covers from the bottom of said cover stack, indexing said rotary plate forwardly at predetermined angular increments; and engaging said cover on said rotary plate and transferring said cover for application to the tray which is mounted on the support surface of said at least one tool nest.

42. The method as claimed in claim 41, wherein said cover stacking means at said sixth workstation comprises an open-bottomed chute having a vertical stack of said covers arranged therein, said rotary plate being horizontally oriented and extending closely below the bottom of said chute so as to receive the bottommost cover therefrom on an upper surface of said rotary plate.

43. The method as claimed in claim 42, wherein said rotary plate is in communication with a vacuum-generating source for imparting a vacuum to the upper surface of said rotary plate so as to retain said cover thereon during at least the indexing advance of said rotary plate.

44. The method as claimed in claim 43, wherein said motive means comprises pivotable arm structure having cover-engaging means for lifting said cover from said rotary plate and transferring said cover for application onto the tray on the support surface of said at least one tool nest.

45. The method as claimed in claim 44, wherein said rotary plate communicates with a vacuum-generating source for imparting a vacuum thereto for retaining said cover on said plate, said vacuum being released upon said cover-engaging means contacting said cover, and a vacuum in said cover-engaging means retaining said cover thereon to facilitate transporting said cover for application to the tray on the support surface of said at least one tool nest.

46. The method as claimed in claim 45, further including the step of applying said cover to said tray retained on the support surface of said at least one tool nest, and, upon application of said cover to said tray, the step of releasing said vacuum in said cover-engaging means while vacuum is being applied to the support surface of said at least one tool nest so as to retain said formed suture package in vacuum engagement thereon.

47. The method as claimed in claim 46, wherein said motive means comprises a cam-controlled robotic pivot arm adapted to swing between a vertical orientation to a horizontal and forward motion for transporting said cover from said rotary plate to said tray on the support surface of said at least one tool nest.

48. The method as claimed in claim 15, wherein said plurality of compartments at said seventh workstation are located in a linear array on said compartmented tray, said motive means introducing a predetermined quantity of said suture packages into each said compartment; and means for indexing said compartmented tray responsive to a compartment being filled with said predetermined quantity of suture packages so as to align an adjacent said compartment of said compartmented tray for the conveyance thereto of suture packages by said motive means.

49. The method as claimed in claim 48, wherein drive means replaces the compartmented tray having the compartments thereof filled with said suture packages with a second empty compartmented tray.

50. The method as claimed in claim 49, wherein said drive means shifts said second compartmented tray means laterally perpendicularly to a longitudinal indexing axis for said compartmented tray.

51. The method as claimed in claim 50, wherein said motive means comprise a cam-controlled pivot arm.

52. The method as claimed in claim 51, wherein drive means activate said pivot arm between an elevated horizontal orientation for movement towards and away from said suture package to a downwardly pivoted position above a respective one of the compartments of said compartmented tray means.

53. The method as claimed in claim 52, wherein an outer end of said pivot arm includes a mechanical gripper.

54. The method as claimed in claim 53, further including the step of actuating said mechanical gripper to grip the suture package on the support surface on said at least one tool nest to transfer the suture package to said pivot arm from said support surface while releasing a vacuum in said tool nest, pivoting said pivot arm downwardly over one said compartment and releasing the grip of said mechanical gripper to release the suture package into a compartment located therebelow.

55. The method as claimed in claim 15, wherein a rejected suture package is retained on the support surface of said at least one tool nest for conveyance to a further workstation, and means at said further workstation being provided for withdrawing said rejected suture package from the support surface of said tool nest.

56. The method as claimed in claim 55, wherein said withdrawing means includes a reciprocating member for movement towards and away from said at least one tool nest; and gripper means on the leading and of said reciprocating member for graspingly engaging and withdrawing a rejected suture package from said tool nest.

57. The method as claimed in claim 56, wherein a conveyor belt is located below said reciprocating member, said gripper means releasing said rejected suture package onto said conveyor belt for transport to a disposal site.

* * * * *